(12) United States Patent
Xiang et al.

(10) Patent No.: US 12,281,098 B2
(45) Date of Patent: Apr. 22, 2025

(54) FIVE-MEMBERED-FUSED SIX-MEMBERED COMPOUND, PREPARATION METHOD, PHARMACEUTICAL COMPOSITION AND USE

(71) Applicant: HANGZHOU POLYMED BIOPHARMACEUTICALS, INC., Zhejiang (CN)

(72) Inventors: Jason Shaoyun Xiang, Zhejiang (CN); Lei Wu, Zhejiang (CN); Rui Xu, Zhejiang (CN); Qiang Zhang, Zhejiang (CN); Gang Yang, Zhejiang (CN); Michael Xiang, Zhejiang (CN); Mixue Tong, Zhejiang (CN); Camille Xiang, Zhejiang (CN); Suyue Wang, Zhejiang (CN); Rui Yang, Zhejiang (CN)

(73) Assignee: HANGZHOU POLYMED BIOPHARMACEUTICALS, INC., Zhejiang (CN)

( * ) Notice: Subject to any disclaimer, the term of this patent is extended or adjusted under 35 U.S.C. 154(b) by 0 days.

(21) Appl. No.: 18/632,351

(22) Filed: Apr. 11, 2024

(65) Prior Publication Data
US 2024/0294502 A1    Sep. 5, 2024

Related U.S. Application Data

(63) Continuation-in-part of application No. PCT/CN2022/141624, filed on Dec. 23, 2022.

(30) Foreign Application Priority Data

Dec. 23, 2021 (CN) .......................... 202111634357.1

(51) Int. Cl.
| | | |
|---|---|---|
| C07D 401/14 | (2006.01) |
| A61K 31/4545 | (2006.01) |
| A61K 31/496 | (2006.01) |
| C07D 417/14 | (2006.01) |
| C07D 471/10 | (2006.01) |

(52) U.S. Cl.
CPC ........ C07D 401/14 (2013.01); A61K 31/4545 (2013.01); A61K 31/496 (2013.01); C07D 417/14 (2013.01); C07D 471/10 (2013.01)

(58) Field of Classification Search
CPC .. C07D 401/14; C07D 417/14; C07D 471/10; A61K 31/4545; A61K 31/496
USPC ....................................................... 514/210
See application file for complete search history.

(56) References Cited

U.S. PATENT DOCUMENTS

| | | | |
|---|---|---|---|
| 11,065,231 B2 * | 7/2021 | Crew | A61P 37/06 |
| 2023/0069104 A1 * | 3/2023 | Mainolfi | C07D 407/14 |
| 2023/0101353 A1 * | 3/2023 | Mainolfi | C07D 471/10 |
| | | | 514/210.16 |
| 2023/0192655 A1 * | 6/2023 | Feng | A61P 29/00 |
| | | | 514/253.09 |

FOREIGN PATENT DOCUMENTS

| | | | | |
|---|---|---|---|---|
| CN | 114437035 A | 5/2022 | | |
| WO | WO-2019099926 A1 * | 5/2019 | .......... | A61K 31/422 |
| WO | WO-2020264499 A1 * | 12/2020 | .......... | A61K 31/4545 |
| WO | WO-2021011868 A1 * | 1/2021 | .......... | A61K 47/55 |
| WO | 2022088551 A1 | 5/2022 | | |
| WO | WO-2022147465 A1 * | 7/2022 | .......... | A61K 47/545 |

OTHER PUBLICATIONS

Mar. 13, 2023 International Search Report issued in International Patent Application No. PCT/CN2022/141624.
Mar. 13, 2023 Written Opinion of the International Searching Authority issued in International Patent Application No. PCT/CN2022/141624.
Mark C Field et al., "First and last ancestors: reconstructing evolution of the endomembrane system with ESCRTs vesicle coat proteins, and nuclear pore complexes", Current Opinion in Cell Biology, vol. 21, pp. 4-13, Feb. 7, 2009.

(Continued)

*Primary Examiner* — Jared Barsky
*Assistant Examiner* — Liyuan Mou
(74) *Attorney, Agent, or Firm* — Houston Beshining Law Office PLLC; Liangang Ye

(57) ABSTRACT

A five-membered-fused six-membered compound, a preparation method, a pharmaceutical composition, and the use. The penta-fused hexa-heterocyclic compound is a compound represented by formula (II) or (III). The compound has an inhibition or/and degradation effect on IRAK4.

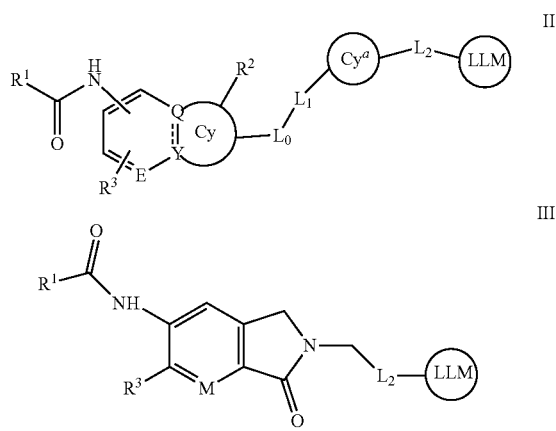

3 Claims, No Drawings

(56) References Cited

OTHER PUBLICATIONS

Zhaodan Cao et al., "IRAK: A Kinase Associated with the Interleukin-I Receptor", Science, vol. 271(5252):1128-1131, Feb. 23, 1996.
Dominic De Nardo et al., "Interleukin-1 receptor-associated kinase 4 (IRAK4) plays a dual role in myddosome formation and Toll-like receptor signaling", J. Biol. Chem. Vol. 293(39), pp. 15195-15207, 2018.
Mahesh Chandra Patra et al., "Recent Progress in the Molecular Recognition and Therapeutic Importance of Interleukin-1 Receptor-Associated Kinase 4", Molecules vol. 21(11), 1529, pp. 1-15, 2016.
Jing Zhang et al., "Assessing IRAK4 Functions in ABC DLBCL by IRAK4 Kinase Inhibition and Protein Degradation", Cell Chemical Biology vol. 27, pp. 1-10, Dec. 17, 2020.
Xiaoxia Li, "IRAK4 in TLR/IL-1R signaling: Possible clinical applications", Eur. J. Immunol. vol. 38: 614-618, 2008.
William T. McElroy, "Interleukin-1 receptor-associated kinase 4 (IRAK4) inhibitors: an updated patent review (2016-2018)", Expert Opinion on Therapeutic Patents, 2019.
Asher Mullard, "IRAK4 degrader to take on innate immunity", Nature Biotechnology vol. 38, pp. 1221-1223, Nov. 3, 2020.
Joao Nunes et al., "Targeting IRAK4 for Degradation with PROTACs", ACS Med. Chem. Lett. Vol. 10, pp. 1081-1085, Jun. 14, 2019.
Chinese Priority Application No. 2021116343571 (not published).

* cited by examiner

FIVE-MEMBERED-FUSED SIX-MEMBERED COMPOUND, PREPARATION METHOD, PHARMACEUTICAL COMPOSITION AND USE

CROSS-REFERENCE TO RELATED APPLICATIONS

The present application is a Continuation-in-part Application of International Application No. PCT/CN2022/141624, filed on Dec. 23, 2022, which claims the right of the priority of Chinese patent application 202111634357.1 filed on Dec. 23, 2021. The contents of the above Chinese patent application are incorporated herein by reference in their entireties.

TECHNICAL FIELD

The present disclosure relates to a five-membered-fused six-membered compound, a preparation method therefor, a pharmaceutical composition thereof, and a use thereof.

BACKGROUND

Kinases have always been important therapeutic targets for the development of anti-inflammatory drugs (Current Opinion in Cell Biology 2009 21, 1-8). Interleukin-1 receptor-associated kinases (IRAKs) are serine/threonine protein kinases that belong to the tyrosine-like kinase (TLK) family. IRAKs are located downstream of the toll like receptor and IL-1R pathways, among which IRAK1 and IRAK4 have kinase activity. IRAK4 acts upstream of the IRAK family kinase activation pathway and plays an important role in innate immune signaling (Science 1996, 271(5252): 1128-31). Stimulation of TLR recruits myeloid differentiation primary response 88 (MYD88) and activates the receptor to form a complex, Myddosome, which then forms a complex with IRAK4 to activate IRAK1. Subsequently, TRAF6 is activated by IRAK1, leading to the activation of the NF-κB and AMPK signaling pathways, which ultimately results in the expression of inflammatory cytokines (Molecules 2016, 21, 1529, J Biol Chem. 2018 Sep. 28; 293(39): 15195-15207, Eur J. Immunol. 2008. 38: 614-618).

A very important feature of IRAK4 is that it has both scaffolding and kinase phosphorylation functions in the TLR and IL-1R signaling pathways. The kinase domain (KD) provides the kinase function, and the death domain (DD) provides the scaffolding function for Myddosome (Molecules 2016, 21(11), 1529). Myddosome is associated with a variety of diseases, not only autoimmune and inflammatory diseases, but also cancer. For example, MYD88 mutations account for 39% of patients with active B-cell-like diffuse large B-cell lymphoma (ABC DLBCL) and 86% to 100% of patients with several other types of B-cell malignancies and primary central nervous system lymphomas (Cell Chemical Biology 27, 1-10, Dec. 17, 2020).

IRAK4 knockout mice and clinicopathologic studies have shown that IRAK4 deficiency itself is not lethal, and that individuals with IRAK4 mutations have a protective effect on chronic lung disease and inflammatory bowel disease (Eur. J. Immunol. 2008. 38: 614-618). IRAK4 inhibitors have been considered as targets for the treatment of immune diseases such as the autoimmune diseases rheumatoid arthritis (RA), systemic lupus erythematosus (SLE), and psoriasis (Expert Opinion on Therapeutic Patents Volume 29, 2019-Issue 4). At the same time, IRAK4 is also a popular target for the treatment of tumors, and a few IRAK4 kinase inhibitors have entered the clinical stage. However, these investigational drugs in clinical stages are all inhibitors with the kinase function (KD) of IRAK4 and have no direct inhibitory effect on the scaffolding function of IRAK4. The IRAK4-targeted protein degrading agent (PROTAC) is expected to simultaneously eliminate its kinase activity and scaffolding function, resulting in better and broader efficacy (Nature Biotechnology 2020, volume 38, pages 1221-1223, ACS Med Chem Lett. 2019 Jul. 11; 10(7): 1081-1085).

BRIEF SUMMARY OF THE INVENTION

The present disclosure provides a five-membered-fused six-membered compound, a preparation method therefor, a pharmaceutical composition thereof, and a use thereof. The compound of the present disclosure has an inhibitory or/and degrading effect on IRAK4 as well as potential clinical application value, and is expected to improve the prognosis of patients and reduce the likelihood of drug resistance.

The present disclosure provides a compound of formula II or III or a pharmaceutically acceptable salt;

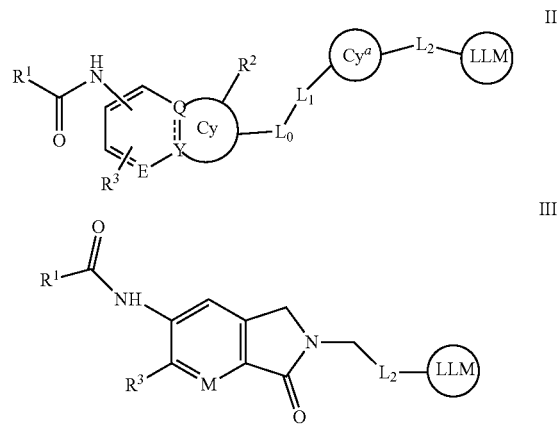

ring Cy is a 5-membered heterocyclic ring, an oxo-5-membered heterocyclic ring, or a 5-membered heteroaromatic ring; the heteroatom of the 5-membered heterocyclic ring is selected from one or two of N and O, and the number of heteroatoms is 1 or 2; the heteroatom of the oxo-5-membered heterocyclic ring is N, and the number of heteroatoms is 1 or 2; the heteroatom of the 5-membered heteroaromatic ring is selected from one or more than one of N, S, and O, and the number of heteroatoms is 1, 2, or 3;

$\lvert\lvert$ is $\lvert$ or $\rVert$;

Q is C or N;

E is CH or N;

Y is C or N;

M is CH or N;

$R^1$ is unsubstituted 5- to 10-membered heteroaryl, 5- to 10-membered heteroaryl substituted by one or more than one $R^{1-1}$, unsubstituted 6- to 10-membered aryl, or 6- to 10-membered aryl substituted by one or more than one $R^{1-2}$; the heteroatom of the 5- to 10-membered heteroaryl is selected from one or more than one of N, S, and O, and the number of heteroatoms is 1, 2, or 3;

$R^{1-1}$ and $R^{1-2}$ are each independently halogen, hydroxyl,

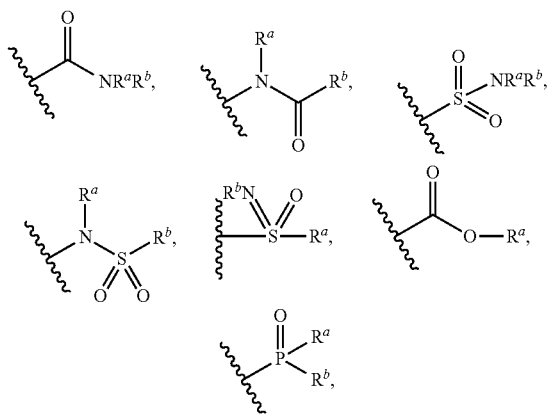

—SO$_2$—R$^a$, —SO—R$^a$, cyano, nitro, unsubstituted 3- to 11-membered heterocycloalkyl, 3- to 11-membered heterocycloalkyl substituted by one or more than one R$^{1-1-1}$, unsubstituted C$_1$-C$_6$ alkoxy, C$_1$-C$_6$ alkoxy substituted by one or more than one R$^{1-1-3}$, unsubstituted C$_1$-C$_6$ alkyl, C$_1$-C$_6$ alkyl substituted by one or more than one R$^{1-1-4}$,

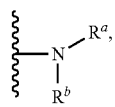

unsubstituted 3- to 10-membered cycloalkyl, 3- to 10-membered cycloalkyl substituted by one or more than one R$^{1-1-5}$, unsubstituted 6- to 10-membered aryl, 6- to 10-membered aryl substituted by one or more than one R$^{1-1-8}$, unsubstituted 5- to 10-membered heteroaryl, or 5- to 10-membered heteroaryl substituted by one or more than one R$^{1-1-7}$; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

R$^{1-1-1}$, R$^{1-1-3}$, R$^{1-1-4}$, R$^{1-1-5}$, R$^{1-1-7}$, and R$^{1-1-8}$ are each independently halogen, oxo, hydroxyl,

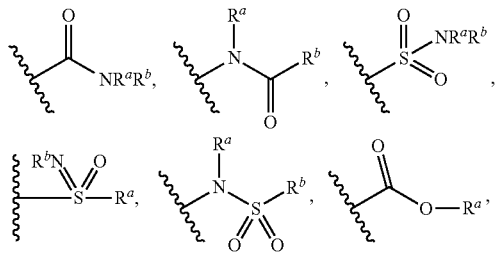

—SO$_2$—R$^a$, —SO—R$^a$, unsubstituted C$_1$-C$_6$ alkoxy, C$_1$-C$_6$ alkoxy substituted by one or more than one halogen, cyano, nitro, unsubstituted 3- to 11-membered heterocycloalkyl, 3- to 11-membered heterocycloalkyl substituted by one or more than one R$^{1-1-1-1}$, unsubstituted C$_1$-C$_6$ alkyl, C$_1$-C$_6$ alkyl substituted by one or more than one halogen, 3- to 10-membered cycloalkyl, unsubstituted 6- to 10-membered aryl, 6- to 10-membered aryl substituted by one or more than one R$^{1-1-1-2}$, unsubstituted 5- to 10-membered heteroaryl, or 5- to 10-membered heteroaryl substituted by one or more than one R$^{1-1-1-3}$; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

R$^{1-1-1-1}$, R$^{1-1-1-2}$, and R$^{1-1-1-3}$ are each independently halogen, oxo, hydroxyl, C$_1$-C$_6$ alkoxy, or C$_1$-C$_6$ alkyl;

R$^2$ is hydrogen, hydroxyl, cyano, halogen, unsubstituted C$_1$-C$_6$ alkyl, C$_1$-C$_6$ alkyl substituted by one or more than one R$^{2-3}$, unsubstituted C$_1$-C$_6$ alkoxy, C$_1$-C$_6$ alkoxy substituted by one or more than one R$^{2-2}$,

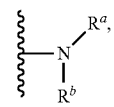

unsubstituted 5- to 10-membered heteroaryl, 5- to 10-membered heteroaryl substituted by one or more than one R$^{2-1}$, unsubstituted 4- to 10-membered heterocycloalkyl, or 4- to 10-membered heterocycloalkyl substituted by one or more than one R$^{2-4}$; the heteroatom of the 5- to 10-membered heteroaryl is selected from one or more than one of N, S, and O, and the number of heteroatoms is 1, 2, or 3; the heteroatom of the 4- to 10-membered heterocycloalkyl is selected from one or more than one of N, S, and O, and the number of heteroatoms is 1, 2, or 3;

R$^{2-1}$, R$^{2-2}$, R$^{2-3}$, and R$^{2-4}$ are each independently halogen, hydroxyl, cyano, nitro, unsubstituted C$_1$-C$_6$ alkyl, C$_1$-C$_6$ alkyl substituted by one or more than one halogen,

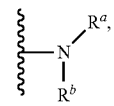

unsubstituted C$_1$-C$_6$ alkoxy, or C$_1$-C$_6$ alkoxy substituted by one or more than one halogen;

R$^3$ is hydrogen, halogen, cyano, hydroxyl, nitro,

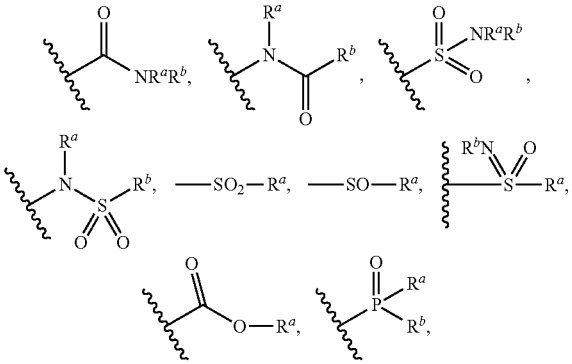

unsubstituted 3- to 11-membered heterocycloalkyl, 3- to 11-membered heterocycloalkyl substituted by one or more than one $R^{3-1}$, unsubstituted 3- to 10-membered cycloalkyl, 3- to 10-membered cycloalkyl substituted by one or more than one $R^{3-2}$,

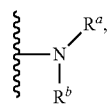

unsubstituted $C_1$-$C_6$ alkyl, $C_1$-$C_6$ alkyl substituted by one or more than one $R^{3-4}$, unsubstituted 6- to 10-membered aryl, 6- to 10-membered aryl substituted by one or more than one $R^{3-5}$, unsubstituted 5- to 10-membered heteroaryl, 5- to 10-membered heteroaryl substituted by one or more than one $R^{3-6}$, hydroxyl substituted by $R^{3-8}$, unsubstituted $C_1$-$C_6$ alkoxy, $C_1$-$C_6$ alkoxy substituted by one or more than one $R^{3-7}$, or —O—COR$^a$; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

$R^{3-1}$, $R^{3-2}$, $R^{3-4}$, $R^{3-5}$, $R^{3-6}$, and $R^{3-7}$ are each independently deuterium, halogen, oxo, hydroxyl, unsubstituted 3- to 11-membered heterocycloalkyl, 3- to 11-membered heterocycloalkyl substituted by one or more than one $R^{3-1-1}$,

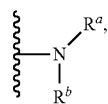

cyano, unsubstituted alkoxy, alkoxy substituted by one or more than one $R^{3-1-3}$,

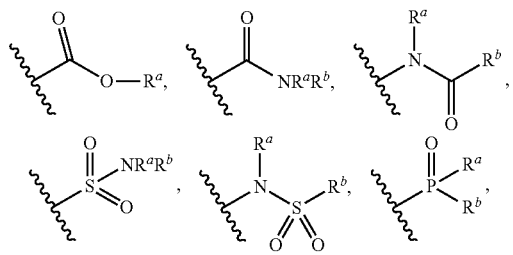

unsubstituted $C_1$-$C_6$ alkyl, $C_1$-$C_6$ alkyl substituted by one or more than one $R^{3-1-4}$, unsubstituted 3- to 10-membered cycloalkyl, 3- to 10-membered cycloalkyl substituted by one or more than one $R^{3-1-5}$, —SO$_2$—R$^a$, —SO—R$^a$,

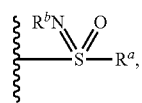

6- to 10-membered aryl, or 5- to 10-membered heteroaryl; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

$R^{3-8}$ is 3- to 10-membered cycloalkyl, 6- to 10-membered aryl, 3- to 11-membered heterocycloalkyl, or 5- to 10-membered heteroaryl; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

$R^{3-1-1}$, $R^{3-1-3}$, $R^{3-1-4}$, and $R^{3-1-5}$ are each independently unsubstituted $C_1$-$C_6$ alkyl, $C_1$-$C_6$ alkyl substituted by one or more than one halogen, halogen, oxo, or hydroxyl;

$R^a$ and $R^b$ are each independently H, unsubstituted $C_1$-$C_6$ alkyl, $C_1$-$C_6$ alkyl substituted by one or more than one $R^{a-1}$, unsubstituted 3- to 10-membered cycloalkyl, 3- to 10-membered cycloalkyl substituted by one or more than one $R^{a-2}$, unsubstituted 3- to 11-membered heterocycloalkyl, 3- to 11-membered heterocycloalkyl substituted by one or more than one $R^{a-3}$, unsubstituted 6- to 10-membered aryl, 6- to 10-membered aryl substituted by one or more than one $R^{a-4}$, unsubstituted 5- to 10-membered heteroaryl, or 5- to 10-membered heteroaryl substituted by one or more than one $R^{a-5}$; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

or, $R^a$ and $R^b$, together with the atom to which they are attached, form a 3- to 11-membered heterocycloalkyl; the heteroatom of the 3- to 11-membered heterocycloalkyl is selected from one or more than one of N, S, and O, and the number of heteroatoms is 1, 2, or 3;

$R^{a-1}$, $R^{a-2}$, $R^{a-3}$, $R^{a-4}$, and $R^{a-5}$ are each independently halogen, cyano, hydroxyl, nitro, $C_1$-$C_6$ alkyl, $C_1$-$C_6$ alkoxy, 3- to 10-membered cycloalkyl, 3- to 11-membered heterocycloalkyl, 6- to 10-membered aryl, or 5- to 10-membered heteroaryl; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

$L_0$ is unsubstituted

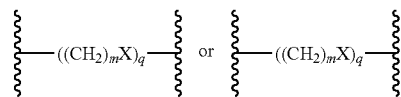

substituted by one or more than one $L_0^{-1}$, m is an integer from 1 to 4, q is an integer from 1 to 6, and X is absent or O; $L_0^{-1}$ is independently halogen, unsubstituted $C_1$-$C_6$ alkyl, or $C_1$-$C_6$ alkyl substituted by one or more than one halogen;

$L_1$ is absent, unsubstituted

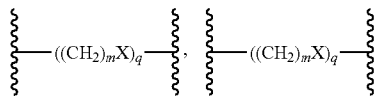

substituted by one or more than one $L_1^{-1}$, or

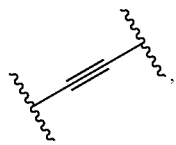 [SMILES: *C#C*]

m is an integer from 1 to 4, q is an integer from 1 to 6, and X is absent or O; each $L_1^{-1}$ is independently halogen, unsubstituted $C_1$-$C_6$ alkyl, or $C_1$-$C_6$ alkyl substituted by one or more than one halogen;

ring $Cy^a$ is unsubstituted

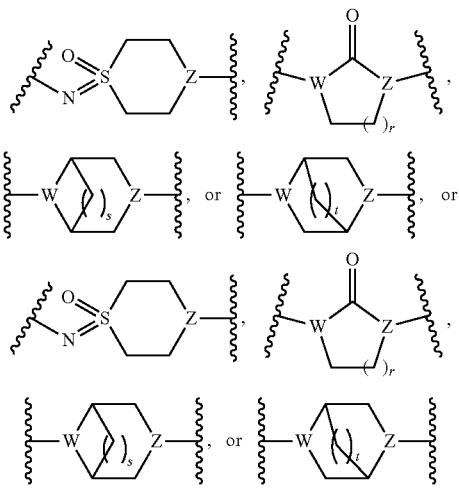

substituted by a substituent; s and t are independently 0, 1, 2, or 3; r is 1, 2, or 3; W and Z are each independently N or CH; when ring $Cy^a$ is substituted by a substituent, the number of the substituents is one or more than one, and each substituent is independently halogen, hydroxyl, or $C_1$-$C_6$ alkyl;

$L_2$ is absent or is a linker unit (linking LLM to $Cy^a$ or

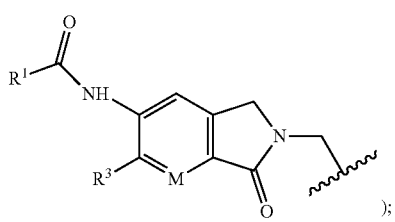

LLM is

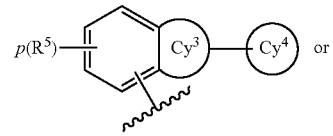

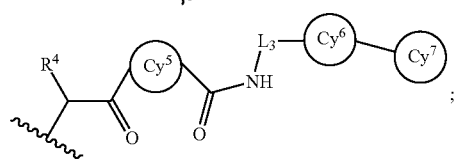

ring $Cy^3$ is an unsubstituted 5- to 12-membered heterocyclic ring or a 5- to 12-membered heterocyclic ring substituted by one or more than one $Cy^{3-1}$; the heteroatom of the 5- to 12-membered heterocyclic ring is selected from one or more than one of N, S, and O, and the number of heteroatoms is 1, 2, or 3; $Cy^{3-1}$ is independently $C_1$-$C_6$ alkyl, halogen, hydroxyl, or oxo;

ring $Cy^4$ is unsubstituted 5- to 12-membered heterocycloalkyl or 5- to 12-membered heterocycloalkyl substituted by one or more than one $Cy^{4-1}$; the heteroatom of the 5- to 12-membered heterocycloalkyl is selected from one or more than one of N, S, and O, and the number of heteroatoms is 1, 2, or 3; $Cy^{4-1}$ is independently $C_1$-$C_6$ alkyl, halogen, hydroxyl, or oxo;

ring $Cy^5$ is an unsubstituted 5- to 12-membered heterocyclic ring or a 5- to 12-membered heterocyclic ring substituted by one or more than one $Cy^{5-1}$; the heteroatom of the 5- to 12-membered heterocyclic ring is selected from one or more than one of N, S, and O, and the number of heteroatoms is 1, 2, or 3; $Cy^{5-1}$ is independently $C_1$-$C_6$ alkyl, hydroxyl, or oxo;

ring $Cy^6$ is an unsubstituted 6- to 10-membered aromatic ring or a 6- to 10-membered aromatic ring substituted by one or more than one $Cy^{6-1}$; $Cy^{6-1}$ is independently $C_1$-$C_6$ alkyl, hydroxyl, or halogen;

ring $Cy^7$ is an unsubstituted 5- to 9-membered heteroaromatic ring or a 5- to 9-membered heteroaromatic ring substituted by one or more than one $Cy^{7-1}$; the heteroatom of the 5- to 9-membered heteroaromatic ring is selected from one or more than one of N, S, and O, and the number of heteroatoms is 1, 2, or 3; $Cy^{7-1}$ is independently $C_1$-$C_6$ alkyl, hydroxyl, or halogen;

$R^4$ is independently hydrogen, halogen, hydroxyl, unsubstituted $C_1$-$C_6$ alkyl, or $C_1$-$C_6$ alkyl substituted by one or more than one halogen;

p is 0, 1, 2, or 3;

each $R^5$ is independently halogen;

$L_3$ is unsubstituted

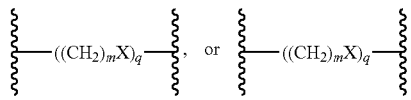

substituted by one or more than one $L_3^{-1}$; wherein m is an integer from 1 to 4, q is an integer from 1 to 6, and X is absent or O; $L_3^{-1}$ is independently halogen, unsubstituted $C_1$-$C_6$ alkyl, or $C_1$-$C_6$ alkyl substituted by one or more than one halogen.

The present disclosure provides a compound of formula II or III or a pharmaceutically acceptable salt;

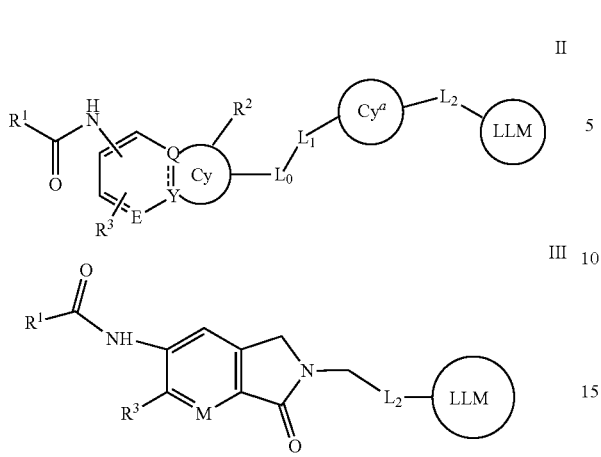

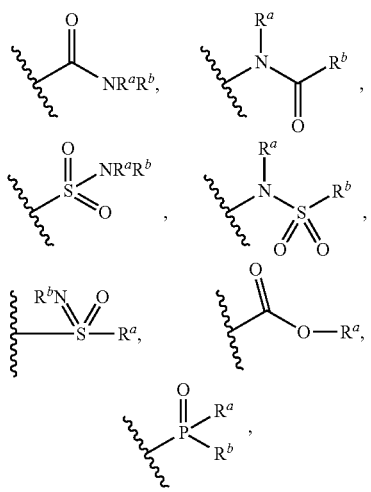

ring Cy is a 5-membered heterocyclic ring, an oxo-5-membered heterocyclic ring, or a 5-membered heteroaromatic ring; the heteroatom of the 5-membered heterocyclic ring is selected from one or two of N and O, and the number of heteroatoms is 1 or 2; the heteroatom of the oxo-5-membered heterocyclic ring is N, and the number of heteroatoms is 1 or 2; the heteroatom of the 5-membered heteroaromatic ring is selected from one or more than one of N, S, and O, and the number of heteroatoms is 1, 2, or 3;

| is | or ||;

Q is C or N;

E is CH or N;

Y is C or N;

M is CH or N;

$R^1$ is unsubstituted 5- to 10-membered heteroaryl, 5- to 10-membered heteroaryl substituted by one or more than one $R^{1-1}$, unsubstituted 6- to 10-membered aryl, or 6- to 10-membered aryl substituted by one or more than one $R^{1-2}$; the heteroatom of the 5- to 10-membered heteroaryl is selected from one or more than one of N, S, and O, and the number of heteroatoms is 1, 2, or 3;

$R^{1-1}$ and $R^{1-2}$ are each independently halogen, hydroxyl,

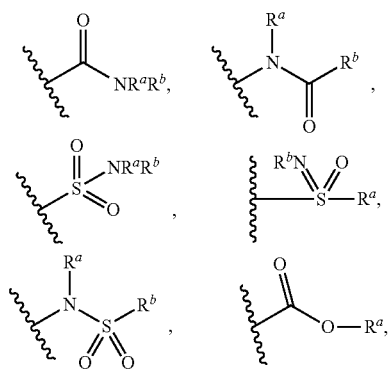

—$SO_2$—$R^a$, —SO—$R^a$ cyano, nitro, unsubstituted 3- to 11-membered heterocycloalkyl, 3- to 11-membered heterocycloalkyl substituted by one or more than one $R^{1-1-1}$, unsubstituted $C_1$-$C_6$ alkoxy, $C_1$-$C_6$ alkoxy substituted by one or more than one $R^{1-1-3}$, unsubstituted $C_1$-$C_6$ alkyl, $C_1$-$C_6$ alkyl substituted by one or more than one $R^{1-1-4}$,

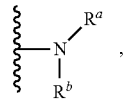

unsubstituted 3- to 10-membered cycloalkyl, 3- to 10-membered cycloalkyl substituted by one or more than one $R^{1-1-5}$, unsubstituted 6- to 10-membered aryl, 6- to 10-membered aryl substituted by one or more than one $R^{1-1-8}$, unsubstituted 5- to 10-membered heteroaryl, or 5- to 10-membered heteroaryl substituted by one or more than one $R^{1-1-7}$; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

$R^{1-1-1}$, $R^{1-1-3}$, $R^{1-1-4}$, $R^{1-1-5}$, $R^{1-1-7}$, and $R^{1-1-8}$ are each independently halogen, oxo, hydroxyl, —$SO_2$—$R^a$, —SO—$R^a$, unsubstituted $C_1$-$C_6$ alkoxy, $C_1$-$C_6$ alkoxy substituted by one or more than one halogen, cyano, nitro, unsubstituted 3- to 11-membered heterocycloalkyl, 3- to 11-membered heterocycloalkyl substituted by one or more than one $R^{1-1-1-1}$, unsubstituted $C_1$-$C_6$ alkyl, $C_1$-$C_6$ alkyl substituted by one or more than one halogen, 3- to 10-membered cycloalkyl, unsubstituted 6- to 10-membered aryl, 6- to 10-membered aryl substituted by one or more than one $R^{1-1-1-2}$, unsubstituted 5- to 10-membered heteroaryl, or 5- to 10-membered heteroaryl substituted by one or more than one $R^{1-1-1-3}$; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

$R^{1-1-1-1}$, $R^{1-1-1-2}$, and $R^{1-1-1-3}$ are each independently halogen, oxo, hydroxyl, $C_1$-$C_6$ alkoxy, or $C_1$-$C_6$ alkyl;

$R^2$ is hydrogen, hydroxyl, cyano, halogen, unsubstituted $C_1$-$C_6$ alkyl, $C_1$-$C_6$ alkyl substituted by one or more than one $R^{2-3}$, unsubstituted $C_1$-$C_6$ alkoxy, $C_1$-$C_6$ alkoxy substituted by one or more than one $R^{2-2}$,

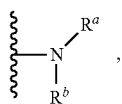

unsubstituted 5- to 10-membered heteroaryl, 5- to 10-membered heteroaryl substituted by one or more than one $R^{2-1}$, unsubstituted 4- to 10-membered heterocycloalkyl, or 4- to 10-membered heterocycloalkyl substituted by one or more than one $R^{2-4}$; the heteroatom of the 5- to 10-membered heteroaryl is selected from one or more than one of N, S, and O, and the number of heteroatoms is 1, 2, or 3; the heteroatom of the 4- to 10-membered heterocycloalkyl is selected from one or more than one of N, S, and O, and the number of heteroatoms is 1, 2, or 3;

$R^{2-1}$, $R^{2-2}$, $R^{2-3}$, and $R^{2-4}$ are each independently halogen, hydroxyl, cyano, nitro, unsubstituted $C_1$-$C_6$ alkyl, $C_1$-$C_6$ alkyl substituted by one or more than one halogen,

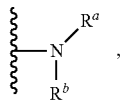

unsubstituted $C_1$-$C_6$ alkoxy, or $C_1$-$C_6$ alkoxy substituted by one or more than one halogen;

$R^3$ is hydrogen, halogen, cyano, hydroxyl, nitro,

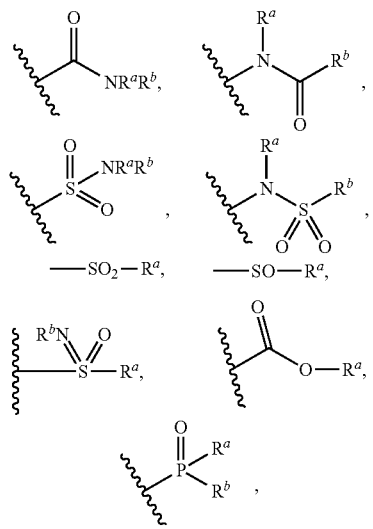

unsubstituted 3- to 11-membered heterocycloalkyl, 3- to 11-membered heterocycloalkyl substituted by one or more than one $R^{3-1}$, unsubstituted 3- to 10-membered cycloalkyl, 3- to 10-membered cycloalkyl substituted by one or more than one $R^{3-2}$,

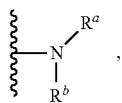

unsubstituted $C_1$-$C_6$ alkyl, $C_1$-$C_6$ alkyl substituted by one or more than one $R^{3-4}$, unsubstituted 6- to 10-membered aryl, 6- to 10-membered aryl substituted by one or more than one $R^{3-5}$, unsubstituted 5- to 10-membered heteroaryl, 5- to 10-membered heteroaryl substituted by one or more than one $R^{3-6}$, hydroxyl substituted by $R^{3-8}$, unsubstituted $C_1$-$C_6$ alkoxy, $C_1$-$C_6$ alkoxy substituted by one or more than one $R^{3-7}$, or —O—$COR^a$; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

$R^{3-1}$, $R^{3-2}$, $R^{3-4}$, $R^{3-5}$, $R^{3-6}$, and $R^{3-7}$ are each independently halogen, oxo, hydroxyl, unsubstituted 3- to 11-membered heterocycloalkyl, 3- to 11-membered heterocycloalkyl substituted by one or more than one $R^{3-1-1}$,

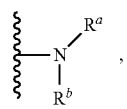

cyano, unsubstituted alkoxy, alkoxy substituted by one or more than one $R^{3-1-3}$,

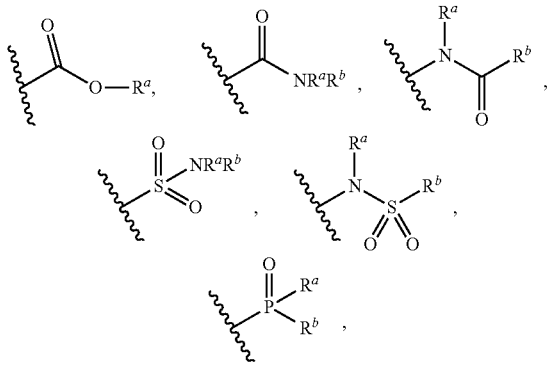

unsubstituted $C_1$-$C_6$ alkyl, $C_1$-$C_6$ alkyl substituted by one or more than one $R^{3-1-4}$, unsubstituted 3- to 10-membered cycloalkyl, 3- to 10-membered cycloalkyl substituted by one or more than one $R^{3-1-5}$, —$SO_2$—$R^a$, —SO—$R^a$,

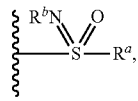

6- to 10-membered aryl, or 5- to 10-membered heteroaryl; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

$R^{3-8}$ is 3- to 10-membered cycloalkyl, 6- to 10-membered aryl, 3- to 11-membered heterocycloalkyl, or 5- to 10-membered heteroaryl; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

$R^{3-1-1}$, $R^{3-1-3}$, $R^{3-1-4}$, and $R^{3-1-5}$ are each independently unsubstituted $C_1$-$C_6$ alkyl, $C_1$-$C_6$ alkyl substituted by one or more than one halogen, halogen, oxo, or hydroxyl;

$R^a$ and $R^b$ are each independently H, unsubstituted $C_1$-$C_6$ alkyl, $C_1$-$C_6$ alkyl substituted by one or more than one $R^{a-1}$, unsubstituted 3- to 10-membered cycloalkyl, 3- to 10-membered cycloalkyl substituted by one or more than one $R^{a-2}$, unsubstituted 3- to 11-membered heterocycloalkyl, 3- to 11-membered heterocycloalkyl substituted by one or more than one $R^{a-3}$, unsubstituted 6- to 10-membered aryl, 6- to 10-membered aryl substituted by one or more than one $R^{a-4}$, unsubstituted 5- to 10-membered heteroaryl, or 5- to 10-membered heteroaryl substituted by one or more than one $R^{a-5}$;

or, $R^a$ and $R^b$, together with the atom to which they are attached, form a 3- to 11-membered heterocycloalkyl; the heteroatom of the 3- to 11-membered heterocycloalkyl is selected from one or more than one of N, S, and O, and the number of heteroatoms is 1, 2, or 3;

$R^{a-1}$, $R^{a-2}$, $R^{a-3}$, $R^{a-4}$, and $R^{a-5}$ are each independently halogen, cyano, hydroxyl, nitro, $C_1$-$C_6$ alkyl, $C_1$-$C_6$ alkoxy, 3- to 10-membered cycloalkyl, 3- to 11-membered heterocycloalkyl, 6- to 10-membered aryl, or 5- to 10-membered heteroaryl; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

$L_0$ is unsubstituted

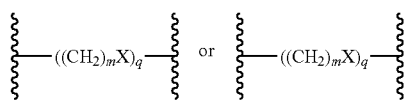

substituted by one or more than one $L_0^{-1}$, m is an integer from 1 to 4, q is an integer from 1 to 6, and X is absent or O; $L_0^{-1}$ is independently halogen, unsubstituted $C_1$-$C_6$ alkyl, or $C_1$-$C_6$ alkyl substituted by one or more than one halogen;

$L_1$ is absent, unsubstituted

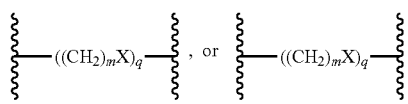

or substituted by one or more than one $L_1^{-1}$, m is an integer from 1 to 4, q is an integer from 1 to 6, and X is absent or O; each $L_1^{-1}$ is independently halogen, unsubstituted $C_1$-$C_6$ alkyl, or $C_1$-$C_6$ alkyl substituted by one or more than one halogen;

ring $Cy^a$ is unsubstituted

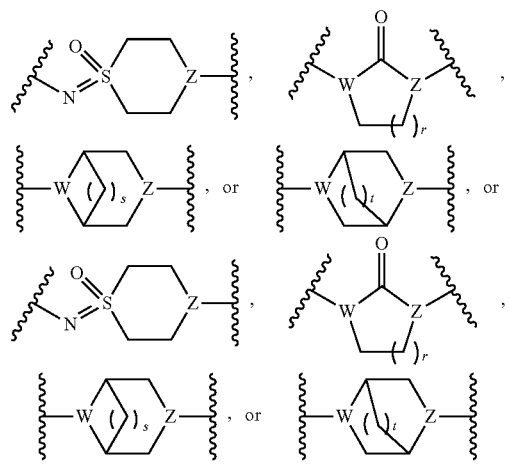

substituted by a substituent; s and t are independently 0, 1, 2, or 3; r is 1, 2, or 3; W and Z are each independently N or CH; when ring $Cy^a$ is substituted by a substituent, the number of the substituents is one or more than one, and each substituent is independently halogen, hydroxyl, or $C_1$-$C_6$ alkyl;

$L_2$ is absent or is a linker unit (linking LLM to $Cy^a$ or

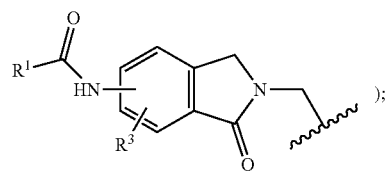

);

LLM is

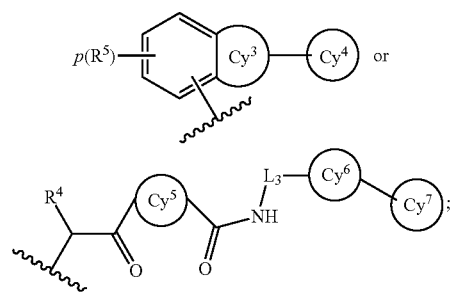

ring $Cy^3$ is an unsubstituted 5- to 12-membered heterocyclic ring or a 5- to 12-membered heterocyclic ring substituted by one or more than one $Cy^{3-1}$; the heteroatom of the 5- to 12-membered heterocyclic ring is selected from one or more than one of N, S, and O, and the number of heteroatoms is 1, 2, or 3; $Cy^{3-1}$ is independently $C_1$-$C_6$ alkyl, halogen, hydroxyl, or oxo;

ring $Cy^4$ is unsubstituted 5- to 12-membered heterocycloalkyl or 5- to 12-membered heterocycloalkyl substituted by one or more than one $Cy^{4-1}$; the heteroatom of the 5- to 12-membered heterocycloalkyl is selected from one or more than one of N, S, and O, and the number of heteroatoms is 1, 2, or 3; $Cy^{4-1}$ is independently $C_1$-$C_6$ alkyl, halogen, hydroxyl, or oxo;

ring Cy⁵ is an unsubstituted 5- to 12-membered heterocyclic ring or a 5- to 12-membered heterocyclic ring substituted by one or more than one Cy⁵⁻¹; the heteroatom of the 5- to 12-membered heterocyclic ring is selected from one or more than one of N, S, and O, and the number of heteroatoms is 1, 2, or 3; Cy⁵⁻¹ is independently $C_1$-$C_6$ alkyl, hydroxyl, or oxo;

ring Cy⁶ is an unsubstituted 6- to 10-membered aromatic ring or a 6- to 10-membered aromatic ring substituted by one or more than one Cy⁶⁻¹; Cy⁶⁻¹ is independently $C_1$-$C_6$ alkyl, hydroxyl, or halogen;

ring Cy⁷ is an unsubstituted 5- to 9-membered heteroaromatic ring or a 5- to 9-membered heteroaromatic ring substituted by one or more than one Cy⁷⁻¹; the heteroatom of the 5- to 9-membered heteroaromatic ring is selected from one or more than one of N, S, and O, and the number of heteroatoms is 1, 2, or 3; Cy⁷⁻¹ is independently $C_1$-$C_6$ alkyl, hydroxyl, or halogen;

R⁴ is independently hydrogen, halogen, hydroxyl, unsubstituted $C_1$-$C_6$ alkyl, or $C_1$-$C_6$ alkyl substituted by one or more than one halogen;

p is 0, 1, 2, or 3;

each R⁵ is independently halogen;

L₃ is unsubstituted

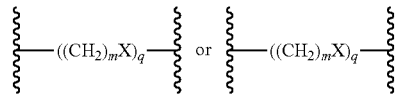

substituted by one or more than one $L_3^{-1}$; wherein m is an integer from 1 to 4, q is an integer from 1 to 6, and X is absent or O; $L_3^{-1}$ is independently halogen, unsubstituted $C_1$-$C_6$ alkyl, or $C_1$-$C_6$ alkyl substituted by one or more than one halogen.

In a certain preferred embodiment, in the five-membered-fused six-membered compound of formula II or III or the pharmaceutically acceptable salt thereof, some groups can be defined as follows, and other groups can be described in any one of the above embodiments (hereinafter referred to as "in a certain embodiment"): the compound of formula II or III is not

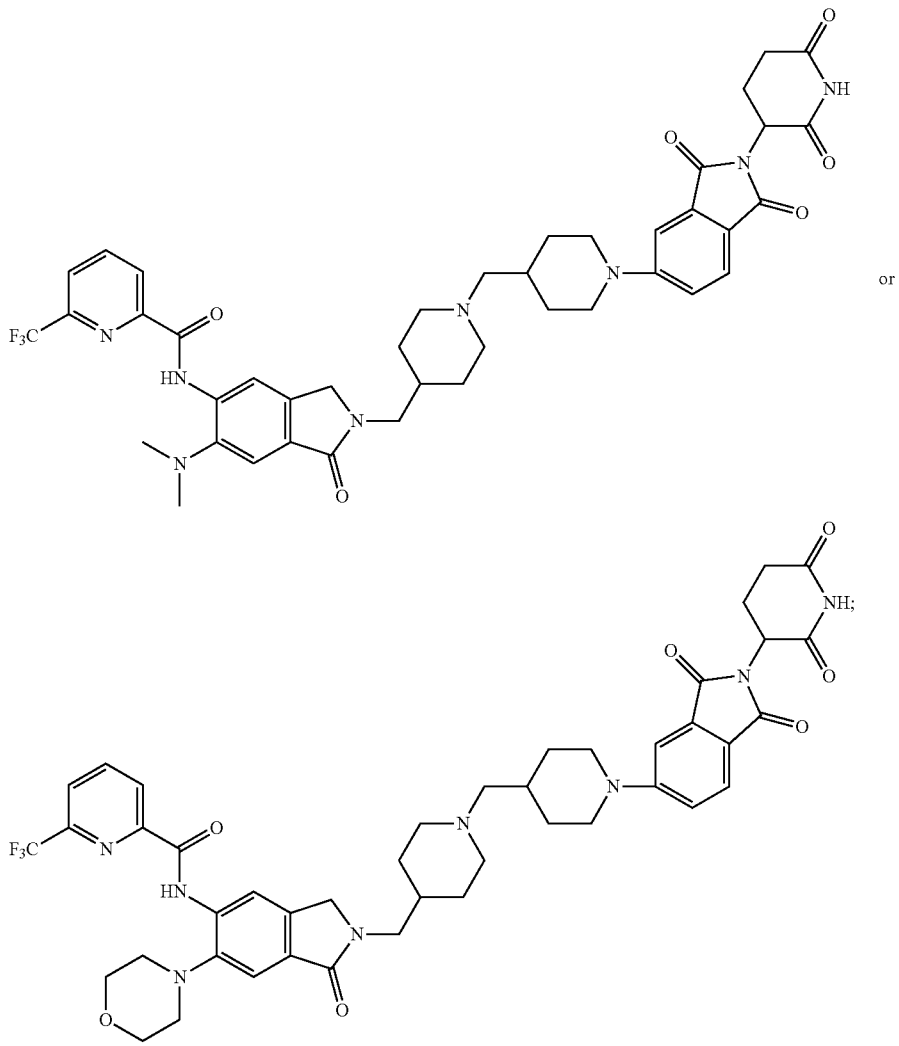

LLM is a ligase binding moiety; the ligase may be an E3 ligase, preferably VHL, CRBN, MDM2, cIAP, Cereblon, XIAP, E3A, APC, UBR5 (EDD1), SOCS/BC-box/eloBC/CUL5/RING, LNXp80, CBX4, CBLL1, HACE1, HECTD1, HECTD2, HECTD3, HECW1, HECW2, HERC1, HERC2, HERC3, HERC4, HUWE1, ITCH, NEDD4, NEDD4L, PPIL2, PRPF19, PIAS1, PIAS2, PIAS3, PIAS4, RANBP2, RNF4, RBX1, SMURF1, SMURF2, STUB1, TOPORS, TRIP12, UBE3A, UBE3B, UBE3C, UBE4A, UBE4B, UBOX5, UBR5, WWP1, WWP2, Parkin, A20/TNFAIP3, AMFR/gp78, ARA54, β-TrCP1/BTRC, BRCA1, CBL, CHIP/STUB1, E6, E6AP/UBE3A, F-box protein 15/FBX015, FBXW7/Cdc4, GRAIL/RNF128, HOIP/RNF31, cIAP-1/HIAP-2, cIAP-2/HIAP-1, cIAP (pan), ITCH/AIP4, KAP1, MARCH8, Mind Bomb 1/MIB1, Mind Bomb 2/MIB2, MuRF1/TRIM63, NDFIP1, NEDD4, NieL, Parkin, RNF2, RNF4, RNF8, RNF168, RNF43, SART1, Skp2, SMURF2, TRAF-1, TRAF-2, TRAF-3, TRAF-4, TRAF-5, TRAF-6, TRIM5, TRIM21, TRIM32, UBR5, or ZNRF3, more preferably VHL, CRBN, MDM2, or cIAP.

In a certain preferred embodiment, the linker unit may be a conventional linker unit in the art, preferably, $L_2$ is $-L_2^{-1}-L_2^{-2}-L_2^{-3}-L_2^{-4}-$; $L_2^{-1}$, $L_2^{-2}$, $L_2^{-3}$, and $L_2^{-4}$ are independently absent, unsubstituted

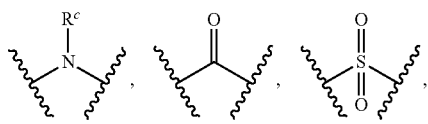

substituted by one or more than one $L_2^{1-1}$, unsubstituted

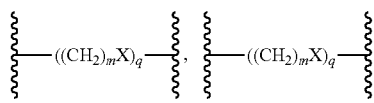

substituted by one or more than one $L_2^{1-2}$, unsubstituted

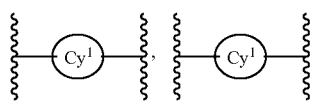

or substituted by one or more than one $L_2^{1-3}$; m is an integer from 1 to 4, q is an integer from 1 to 6, and X is absent or O; ring $Cy^1$ is a 4- to 12-membered heterocyclic ring or a 3- to 12-membered cycloalkyl ring; ring $Cy^2$ is a 5- to 10-membered heteroaromatic ring or a 6- to 10-membered aromatic ring; the heteroatom of the 4- to 12-membered heterocyclic ring is selected from one or more than one of N, S, and O, and the number of heteroatoms is 1, 2, or 3; the heteroatom of the 5- to 10-membered heteroaromatic ring is selected from one or more than one of N, S, and O, and the number of heteroatoms is 1, 2, or 3.

In a certain preferred embodiment, the linker unit may be a conventional linker unit in the art, preferably, $L_2$ is $-L_2^{-1}-L_2^{-2}-L_2^{-3}-L_2^{-4}-L_2^{-5}-L_2^{-6}-L_2^{-7}$; $L_2^{-1}$, $L_2^{-2}$, $L_2^{-3}$, $L_2^{-4}$, $L_2^{-5}$, $L_2^{-6}$, and $L_2^{-7}$ are independently absent,

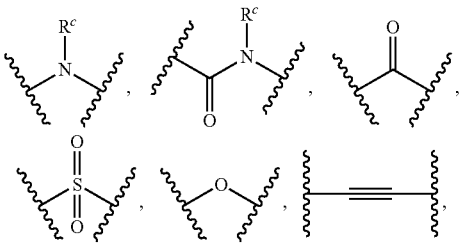

unsubstituted

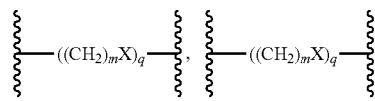

substituted by one or more than one $L_2^{1-1}$, unsubstituted

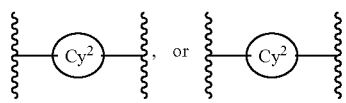

substituted by one or more than one $L_2^{1-2}$, unsubstituted substituted by one or more than one $L_2^{1-3}$; m is an integer from 1 to 4, q is an integer from 1 to 6, and X is absent or O; ring $Cy^1$ is a 4- to 12-membered heterocyclic ring or a 3- to 12-membered cycloalkyl ring; ring $Cy^2$ is a 5- to 10-membered heteroaromatic ring or a 6- to 10-membered aromatic ring; the heteroatom of the 4- to 12-membered heterocyclic ring is selected from one or more than one of N, S, and O, and the number of heteroatoms is 1, 2, or 3; the heteroatom of the 5- to 10-membered heteroaromatic ring is selected from one or more than one of N, S, and O, and the number of heteroatoms is 1, 2, or 3;

$L_2^{1-1}$ and $L_2^{1-2}$ are independently halogen, unsubstituted $C_1$-$C_6$ alkyl, $C_1$-$C_6$ alkyl substituted by one or more than one halogen, hydroxyl, oxo, or

$L_2^{1-3}$ is independently halogen, unsubstituted $C_1$-$C_6$ alkyl, $C_1$-$C_6$ alkyl substituted by one or more than one halogen, unsubstituted $C_1$-$C_6$ alkoxy, $C_1$-$C_6$ alkoxy substituted by one or more than one halogen, cyano,

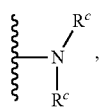

unsubstituted 3- to 10-membered cycloalkyl, 3- to 10-membered cycloalkyl substituted by one or more than one $L_2^{1-3-1}$, unsubstituted 3- to 11-membered heterocycloalkyl, 3- to 11-membered heterocycloalkyl substituted by one or more than one $L_2^{1-3-2}$, or hydroxyl; the heteroatom of the 3- to 11-membered heterocycloalkyl is selected from one or more than one of N, S, and O, and the number of heteroatoms is 1, 2, or 3;

$L_2^{1-3-1}$ and $L_2^{1-3-2}$ are each independently halogen, unsubstituted $C_1$-$C_6$ alkyl, $C_1$-$C_6$ alkyl substituted by one or more than one halogen, hydroxyl, oxo, or

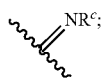

each $R^c$ is independently H, unsubstituted $C_1$-$C_6$ alkyl, $C_1$-$C_6$ alkyl substituted by one or more than one $R^{c-1}$, unsubstituted 3- to 10-membered cycloalkyl, 3- to 10-membered cycloalkyl substituted by one or more than one $R^{c-2}$, unsubstituted 3- to 11-membered heterocycloalkyl, 3- to 11-membered heterocycloalkyl substituted by one or more than one $R^{c-3}$, unsubstituted 6- to 10-membered aryl, 6- to 10-membered aryl substituted by one or more than one $R^{c-4}$, unsubstituted 5- to 10-membered heteroaryl, or 5- to 10-membered heteroaryl substituted by one or more than one $R^{c-5}$; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

$R^{c-1}$, $R^{c-2}$, $R^{c-3}$, $R^{c-4}$, and $R^{c-5}$ are each independently halogen, cyano, hydroxyl, nitro, $C_1$-$C_6$ alkyl, $C_1$-$C_6$ alkoxy, 3- to 10-membered cycloalkyl, 3- to 11-membered heterocycloalkyl, 6- to 10-membered aryl, or 5- to 10-membered heteroaryl; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3.

In a certain preferred embodiment, when ring Cy is a 5-membered heterocyclic ring, the heteroatom of the 5-membered heterocyclic ring is O, and the number of heteroatoms is 1; the 5-membered heterocyclic ring is preferably a tetrahydrofuran ring.

In a certain preferred embodiment, when ring Cy is an oxo-5-membered heterocyclic ring, the heteroatom of the 5-membered heterocyclic ring is N, and the number of heteroatoms is 1; the 5-membered heterocyclic ring is preferably a tetrahydropyrrole ring.

In a certain preferred embodiment, when ring Cy is a 5-membered heteroaromatic ring, the heteroatom of the 5-membered heteroaromatic ring is selected from one or two of N, S, and O, and the number of heteroatoms is 1 or 2; the 5-membered heteroaromatic ring is preferably a pyrrole ring, a pyrazole ring, a thiazole ring, an oxazole ring, or an imidazole ring.

In a certain preferred embodiment, when $R^1$ is unsubstituted 5- to 10-membered heteroaryl or 5- to 10-membered heteroaryl substituted by one or more than one $R^{1-1}$, the heteroatom of the 5- to 10-membered heteroaryl is selected from one or two of N, S, and O, and the number of heteroatoms is 1, 2, or 3; the 5- to 10-membered heteroaryl may be oxazolyl, pyrazolyl, thiazolyl, imidazolyl, pyridyl, pyridazinyl, pyrazinyl, pyrimidinyl, or triazinyl, for example, pyridyl.

In a certain preferred embodiment, when $R^1$ is unsubstituted 6- to 10-membered aryl or 6- to 10-membered aryl substituted by one or more than one $R^{1-2}$, the 6- to 10-membered aryl is preferably phenyl or naphthyl.

In a certain preferred embodiment, when $R^{1-1}$ and $R^{1-2}$ are each independently halogen, the halogen may be fluorine, chlorine, bromine, or iodine; for example, fluorine.

In a certain preferred embodiment, when $R^{1-1}$ and $R^{1-2}$ are each independently unsubstituted 3- to 11-membered heterocycloalkyl or 3- to 11-membered heterocycloalkyl substituted by one or more than one $R^{1-1-1}$, the 3- to 11-membered heterocycloalkyl may be 4- to 8-membered heterocycloalkyl, the heteroatom of the 3- to 11-membered heterocycloalkyl is selected from one or two of N, S, and O, and the number of heteroatoms is 1 or 2; preferably, the heteroatom of the 3- to 11-membered heterocycloalkyl is N, S, or O, and the number of heteroatoms is 1 or 2; each $R^{1-1-1}$ is independently and preferably halogen, hydroxyl, unsubstituted $C_1$-$C_6$ alkoxy, $C_1$-$C_6$ alkoxy substituted by one or more than one halogen, unsubstituted $C_1$-$C_6$ alkyl, or $C_1$-$C_6$ alkyl substituted by one or more than one halogen; the 3- to 11-membered heterocycloalkyl is preferably piperazinyl, piperidinyl, tetrahydropyrrolyl, oxetanyl, azabicyclo[2.2.2]octyl, azabicyclo[3.2.1]octyl, azaspiro[3.3]heptyl, or azabicyclo[2.2.1]heptyl, for example,

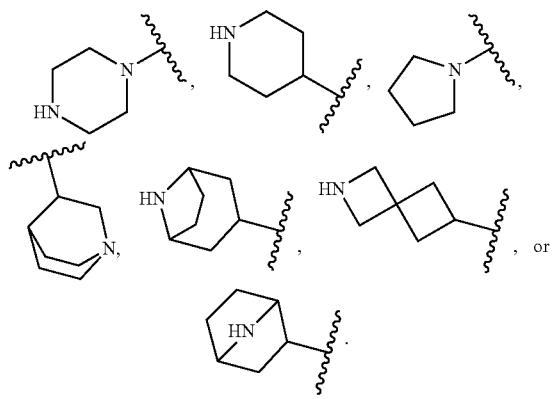

In a certain preferred embodiment, when $R^{1-1}$ and $R^{1-2}$ are each independently unsubstituted $C_1$-$C_6$ alkoxy or $C_1$-$C_6$ alkoxy substituted by one or more than one $R^{1-1-3}$, the $C_1$-$C_6$ alkoxy may be $C_1$-$C_4$ alkoxy, for example, methoxy, ethoxy, n-propoxy, isopropoxy, n-butoxy, isobutoxy, sec-butoxy, or tert-butoxy; each $R^{1-1-3}$ is independently and preferably halogen, hydroxyl, unsubstituted $C_1$-$C_6$ alkoxy, $C_1$-$C_6$ alkoxy substituted by one or more than one halogen, unsubstituted $C_1$-$C_6$ alkyl, or $C_1$-$C_6$ alkyl substituted by one or more than one halogen.

In a certain preferred embodiment, when $R^{1-1}$ and $R^{1-2}$ are each independently unsubstituted $C_1$-$C_6$ alkyl or $C_1$-$C_6$ alkyl substituted by one or more than one $R^{1-1-4}$, the $C_1$-$C_6$ alkyl may be $C_1$-$C_4$ alkyl, for example, methyl, ethyl, n-propyl, isopropyl, n-butyl, isobutyl, sec-butyl, or tert-butyl; each $R^{1-1-4}$ is independently and preferably halogen, hydroxyl, unsubstituted $C_1$-$C_6$ alkoxy, $C_1$-$C_6$ alkoxy substituted by one or more than one halogen, unsubstituted $C_1$-$C_6$ alkyl, or $C_1$-$C_6$ alkyl substituted by one or more than one halogen.

In a certain preferred embodiment, when $R^{1-1}$ and $R^{1-2}$ are each independently unsubstituted 3- to 10-membered cycloalkyl or 3- to 10-membered cycloalkyl substituted by one or more than one $R^{1-1-5}$, the 3- to 10-membered cycloalkyl may be 3- to 6-membered cycloalkyl, for example, cyclopropyl, cyclobutyl, cyclopentyl, or cyclohexyl; each $R^{1-1-5}$ is independently and preferably halogen, hydroxyl, unsubstituted $C_1$-$C_6$ alkoxy, $C_1$-$C_6$ alkoxy substituted by one or more than one halogen, unsubstituted $C_1$-$C_6$ alkyl, or $C_1$-$C_6$ alkyl substituted by one or more than one halogen.

In a certain preferred embodiment, when $R^{1-1}$ and $R^{1-2}$ are each independently unsubstituted 5- to 10-membered heteroaryl or 5- to 10-membered heteroaryl substituted by one or more than one $R^{1-1-7}$, the heteroatom of the 5- to 10-membered heteroaryl is N, and the number of heteroatoms is 1, 2, or 3; each $R^{1-1-7}$ is independently and preferably halogen, hydroxyl, unsubstituted $C_1$-$C_6$ alkoxy, $C_1$-$C_6$ alkoxy substituted by one or more than one halogen, unsubstituted $C_1$-$C_6$ alkyl, or $C_1$-$C_6$ alkyl substituted by one or more than one halogen; the 5- to 10-membered heteroaryl may be pyridyl, pyridazinyl, pyrazinyl, pyrimidinyl, or triazinyl, for example, pyridyl.

In a certain preferred embodiment, when $R^{1-1}$ and $R^{1-2}$ are each independently unsubstituted 6- to 10-membered aryl or 6- to 10-membered aryl substituted by one or more than one $R^{1-1-8}$, the 6- to 10-membered aryl is preferably phenyl or naphthyl; each $R^{1-1-8}$ is independently and preferably halogen, hydroxyl, unsubstituted $C_1$-$C_6$ alkoxy, $C_1$-$C_6$ alkoxy substituted by one or more than one halogen, unsubstituted $C_1$-$C_6$ alkyl, or $C_1$-$C_6$ alkyl substituted by one or more than one halogen.

In a certain preferred embodiment, when $R^{1-1-1}$, $R^{1-1-3}$, $R^{1-1-4}$, $R^{1-1-5}$, $R^{1-1-7}$, and $R^{1-1-8}$ are each independently halogen, the halogen may be fluorine, chlorine, bromine, or iodine, for example, fluorine.

In a certain preferred embodiment, when $R^2$ is halogen, the halogen may be fluorine, chlorine, bromine, or iodine, for example, fluorine or chlorine.

In a certain preferred embodiment, when $R^2$ is unsubstituted 5- to 10-membered heteroaryl or 5- to 10-membered heteroaryl substituted by one or more than one $R^{2-1}$, the heteroatom of the 5- to 10-membered heteroaryl is N, and the number of heteroatoms is 1, 2, or 3; the 5- to 10-membered heteroaryl is preferably pyridyl, pyridazinyl, pyrazinyl, pyrimidinyl, or triazinyl, for example, pyridyl.

In a certain preferred embodiment, when $R^2$ is unsubstituted $C_1$-$C_6$ alkoxy or $C_1$-$C_6$ alkoxy substituted by one or more than one $R^{2-2}$, the $C_1$-$C_6$ alkoxy may be $C_1$-$C_4$ alkoxy, for example, methoxy, ethoxy, n-propoxy, isopropoxy, n-butoxy, isobutoxy, sec-butoxy, or tert-butoxy.

In a certain preferred embodiment, when $R^2$ is unsubstituted $C_1$-$C_6$ alkyl or $C_1$-$C_6$ alkyl substituted by one or more than one $R^{2-3}$, the $C_1$-$C_6$ alkyl may be $C_1$-$C_4$ alkyl, for example, methyl, ethyl, n-propyl, isopropyl, n-butyl, isobutyl, sec-butyl, or tert-butyl.

In a certain preferred embodiment, when $R^2$ is unsubstituted 4- to 10-membered heterocycloalkyl or 4- to 10-membered heterocycloalkyl substituted by one or more than one $R^{2-4}$, the 4- to 10-membered heterocycloalkyl may be 5- to 8-membered heterocycloalkyl, the heteroatom of the 4- to 10-membered heterocycloalkyl is selected from one or two of N, S, and O, and the number of heteroatoms is 1 or 2; preferably, the heteroatom of the 4- to 10-membered heterocycloalkyl is N, S, or O, and the number of heteroatoms is 1 or 2; the 4- to 10-membered heterocycloalkyl is preferably piperazinyl, piperidinyl, tetrahydropyrrolyl, azabicyclo[2.2.2]octyl, azabicyclo[3.2.1]octyl, azaspiro[3.3]heptyl, or azabicyclo[2.2.1]heptyl, for example

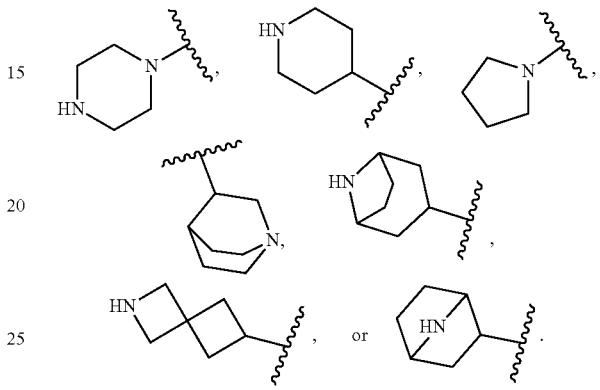

In a certain preferred embodiment, when $R^{2-1}$, $R^{2-2}$, $R^{2-3}$, and $R^{2-4}$ are each independently halogen, the halogen may be fluorine, chlorine, bromine, or iodine; for example, fluorine.

In a certain preferred embodiment, when $R^{2-1}$, $R^{2-2}$, $R^{2-3}$, and $R^{2-4}$ are each independently unsubstituted $C_1$-$C_6$ alkyl or $C_1$-$C_6$ alkyl substituted by one or more than one halogen, the $C_1$-$C_6$ alkyl may be $C_1$-$C_4$ alkyl, for example, methyl, ethyl, n-propyl, isopropyl, n-butyl, isobutyl, sec-butyl, or tert-butyl; the halogen may be fluorine, chlorine, bromine, or iodine; for example, fluorine.

In a certain preferred embodiment, when $R^{2-1}$, $R^{2-2}$, $R^{2-3}$, and $R^{2-4}$ are each independently unsubstituted $C_1$-$C_6$ alkoxy, or $C_1$-$C_6$ alkoxy substituted by one or more than one halogen, the $C_1$-$C_6$ alkoxy in unsubstituted $C_1$-$C_6$ alkoxy and $C_1$-$C_6$ alkoxy substituted by one or more than one halogen may be $C_1$-$C_4$ alkoxy, for example, methoxy, ethoxy, n-propoxy, isopropoxy, n-butoxy, isobutoxy, sec-butoxy, or tert-butoxy, for another example, methoxy; the halogen may be fluorine, chlorine, bromine, or iodine; for example, fluorine.

In a certain preferred embodiment, when $R^3$ is halogen, the halogen may be fluorine, chlorine, bromine, or iodine, for example, bromine.

In a certain preferred embodiment, when $R^3$ is unsubstituted 3- to 11-membered heterocycloalkyl or 3- to 11-membered heterocycloalkyl substituted by one or more than one $R^{3-1}$, the 3- to 11-membered heterocycloalkyl may be 3- to 8-membered heterocycloalkyl, the heteroatom of the 3- to 11-membered heterocycloalkyl is preferably N and/or O, and the number of heteroatoms is 1 or 2; the 3- to 11-membered heterocycloalkyl is preferably piperidinyl, tetrahydropyrrolyl, 2-azaspiro[3.3]heptyl, 2-oxaspiro[3.3]heptyl, morpholinyl, tetrahydropyranyl, oxetanyl, azabicyclo[2.2.1]heptyl, or diazabicyclo[2.2.1]heptyl; each $R^{3-1}$ is independently and preferably halogen, oxo, or hydroxyl, and the unsubstituted 3- to 8-membered heterocycloalkyl or the 3- to 8-membered heterocycloalkyl substituted by one or more than one $R^{3-1}$ is preferably

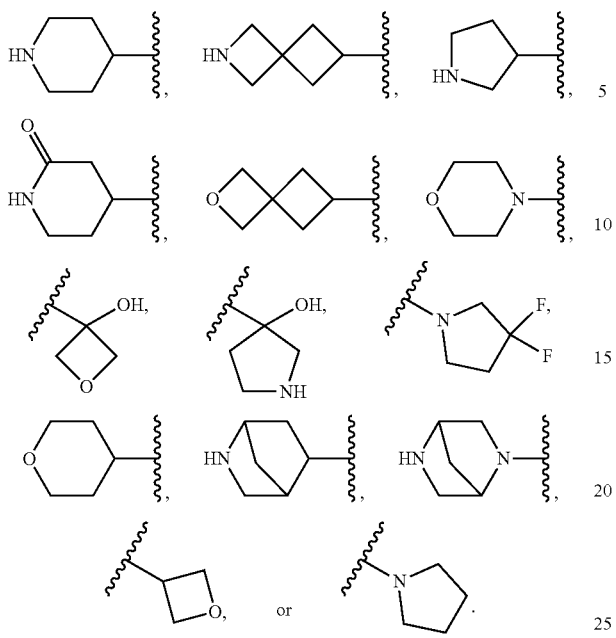

In a certain preferred embodiment, when $R^3$ is unsubstituted 3- to 10-membered cycloalkyl or 3- to 10-membered cycloalkyl substituted by one or more than one $R^{3-2}$, the 3- to 10-membered cycloalkyl may be $C_3$-$C_6$ cycloalkyl, and may also be cyclopropyl, cyclobutyl, cyclopentyl, or cyclohexyl, for example, cyclopropyl, cyclobutyl, or cyclohexyl; each $R^{3-2}$ is independently and preferably halogen or hydroxyl; the unsubstituted 3- to 10-membered cycloalkyl or the 3- to 10-membered cycloalkyl substituted by one or more than one $R^{3-2}$ is preferably

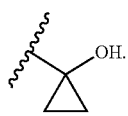

In a certain preferred embodiment, when $R^3$ is unsubstituted $C_1$-$C_6$ alkyl or $C_1$-$C_6$ alkyl substituted by one or more than one $R^{3-4}$, the $C_1$-$C_6$ alkyl may be methyl, ethyl, n-propyl, isopropyl, n-butyl, isobutyl, sec-butyl, tert-butyl, n-pentyl, isopentyl, primary pentyl, sec-pentyl, tert-pentyl, or neopentyl, and may also be methyl, ethyl, n-propyl, isopropyl, or isopentyl; each $R^{3-4}$ is independently and preferably halogen, hydroxyl, —$SO_2$—$R^a$, or

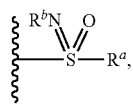

$R^a$ is $C_1$-$C_6$ alkyl, and $R^b$ is hydrogen; the unsubstituted $C_1$-$C_6$ alkyl or $C_1$-$C_6$ alkyl substituted by one or more than one $R^{3-4}$ may be

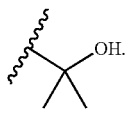 [SMILES: *C(C)(C)O]

In a certain preferred embodiment, when $R^3$ is unsubstituted $C_1$-$C_6$ alkoxy or $C_1$-$C_6$ alkoxy substituted by one or more than one $R^{3-7}$, the $C_1$-$C_6$ alkoxy may be $C_1$-$C_4$ alkoxy, and may also be methoxy, ethoxy, n-propoxy, isopropoxy, n-butoxy, isobutoxy, sec-butoxy, or tert-butoxy, and may also be methoxy, ethoxy, or isopropoxy; each $R^{3-7}$ is independently and preferably halogen; the unsubstituted $C_1$-$C_6$ alkoxy or $C_1$-$C_6$ alkoxy substituted by one or more than one $R^{3-7}$ is preferably methoxy, isopropoxy, or trifluoromethoxy.

In a certain preferred embodiment, when $R^3$ is hydroxyl substituted by $R^{3-8}$, $R^{3-8}$ may be 3- to 6-membered cycloalkyl or 3- to 6-membered heterocycloalkyl, the heteroatom of the 3- to 6-membered heterocycloalkyl is O, and the number of heteroatoms is 1; the hydroxyl substituted by $R^{3-8}$ is preferably

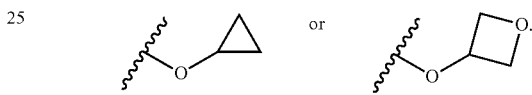

In a certain preferred embodiment, when $R^{3-1}$, $R^{3-2}$, $R^{3-4}$, $R^{3-5}$, $R^{3-6}$, and $R^{3-7}$ are each independently halogen, the halogen may be fluorine, chlorine, bromine, or iodine, for example, fluorine.

In a certain preferred embodiment, when $R^{3-1}$, $R^{3-2}$, $R^{3-4}$, $R^{3-5}$, $R^{3-6}$, and $R^{3-7}$ are each independently unsubstituted 3- to 11-membered heterocycloalkyl or 3- to 11-membered heterocycloalkyl substituted by one or more than one $R^{3-1-1}$, the 3- to 11-membered heterocycloalkyl may be 5- to 8-membered heterocycloalkyl, the heteroatom of the 3- to 11-membered heterocycloalkyl is preferably N and/or O, and the number of heteroatoms is 1 or 2; the unsubstituted 3- to 11-membered heterocycloalkyl or 3- to 11-membered heterocycloalkyl substituted by one or more than one $R^{3-1-1}$ is preferably tetrahydropyrrolyl, oxetanyl, or spiroheptyl containing one oxygen atom and/or one nitrogen atom, for example,

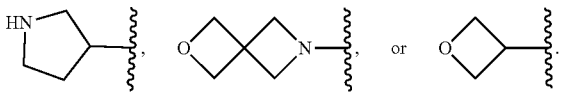

In a certain preferred embodiment, when $R^{3-1-1}$, $R^{3-1-3}$, $R^{3-1-4}$, and $R^{3-1-5}$ are each independently unsubstituted $C_1$-$C_6$ alkyl or $C_1$-$C_6$ alkyl substituted by one or more than one halogen, the $C_1$-$C_6$ alkyl may be $C_1$-$C_4$ alkyl, and may also be methyl, ethyl, n-propyl, isopropyl, n-butyl, isobutyl, sec-butyl, or tert-butyl, and may also be methyl or ethyl; the halogen may be fluorine, chlorine, bromine, or iodine; for example, fluorine.

In a certain preferred embodiment, when $R^{3-1-1}$, $R^{3-1-3}$, $R^{3-1-4}$, and $R^{3-1-5}$ are each independently halogen, the halogen may be fluorine, chlorine, bromine, or iodine, for example, fluorine.

In a certain preferred embodiment, when each $L_0^{-1}$ is independently unsubstituted $C_1$-$C_6$ alkyl or $C_1$-$C_6$ alkyl substituted by one or more than one halogen, the $C_1$-$C_6$ alkyl may be $C_1$-$C_4$ alkyl, and may also be methyl, ethyl, n-propyl, isopropyl, n-butyl, isobutyl, sec-butyl, or tert-butyl, and may also be methyl, ethyl, or isopropyl; the halogen may be fluorine, chlorine, bromine, or iodine, for example, fluorine.

In a certain preferred embodiment, when each $L_0^{-1}$ is independently halogen, the halogen may be fluorine, chlorine, bromine, or iodine, for example, fluorine.

In a certain preferred embodiment, when each $L_1^{-1}$ is independently unsubstituted $C_1$-$C_6$ alkyl or $C_1$-$C_6$ alkyl substituted by one or more than one halogen, the $C_1$-$C_6$ alkyl may be $C_1$-$C_4$ alkyl, and may also be methyl, ethyl, n-propyl, isopropyl, n-butyl, isobutyl, sec-butyl, or tert-butyl, and may also be methyl, ethyl, or isopropyl; the halogen may be fluorine, chlorine, bromine, or iodine, for example, fluorine.

In a certain preferred embodiment, when each $L_1^{-1}$ is independently halogen, the halogen may be fluorine, chlorine, bromine, or iodine, for example, fluorine.

In a certain preferred embodiment, when $R^a$ and $R^b$ are each independently unsubstituted $C_1$-$C_6$ alkyl or $C_1$-$C_6$ alkyl substituted by one or more than one $R^{a-1}$, the $C_1$-$C_6$ alkyl may be $C_1$-$C_4$ alkyl, and may also be methyl, ethyl, n-propyl, isopropyl, n-butyl, isobutyl, sec-butyl, or tert-butyl, and may also be methyl, ethyl, or isopropyl.

In a certain preferred embodiment, when $R^a$ and $R^b$ are each independently unsubstituted 3- to 10-membered cycloalkyl or 3- to 10-membered cycloalkyl substituted by one or more than one $R^{a-2}$, the 3- to 10-membered cycloalkyl may be 3- to 6-membered cycloalkyl, for example, cyclopropyl, cyclobutyl, cyclopentyl, or cyclohexyl.

In a certain preferred embodiment, when $R^a$ and $R^b$ are each independently unsubstituted 3- to 11-membered heterocycloalkyl or 3- to 11-membered heterocycloalkyl substituted by one or more than one $R^{a-3}$, the 3- to 11-membered heterocycloalkyl may be 5- to 8-membered heterocycloalkyl, the heteroatom of the 3- to 11-membered heterocycloalkyl is selected from one or two of N, S, and O, and the number of heteroatoms is 1 or 2; preferably, the heteroatom of the 3- to 11-membered heterocycloalkyl is N, S, or O, and the number of heteroatoms is 1 or 2; the 3- to 11-membered heterocycloalkyl is preferably piperazinyl, piperidinyl, tetrahydropyrrolyl, azabicyclo[2.2.2]octyl, azabicyclo[3.2.1]octyl, azaspiro[3.3]heptyl, or azabicyclo[2.2.1]heptyl, for example,

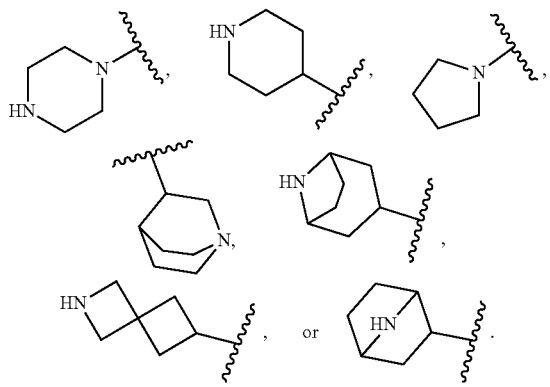

In a certain preferred embodiment, when $R^a$ and $R^b$ are each independently unsubstituted 6- to 10-membered aryl or 6- to 10-membered aryl substituted by one or more than one $R^{a-4}$, the 6- to 10-membered aryl may be a benzene ring or a naphthalene ring.

In a certain preferred embodiment, when $R^a$ and $R^b$ are each independently unsubstituted 5- to 10-membered heteroaryl or 5- to 10-membered heteroaryl substituted by one or more than one $R^{a-5}$, the 5- to 10-membered heteroaryl may be 5-membered heteroaryl or 6-membered heteroaryl; the 6-membered heteroaryl is preferably pyridyl, pyridazinyl, pyrazinyl, pyrimidinyl, or triazinyl; the 5-membered heteroaryl is preferably pyrazolyl, thiazolyl, or imidazolyl.

In a certain preferred embodiment, in ring $Cy^3$, the 5- to 12-membered heterocyclic ring may be a 5- to 6-membered heterocyclic ring, the heteroatom of the 5- to 12-membered heterocyclic ring is preferably N, S, or O, and the number of heteroatoms is 1 or 2; the 5- to 12-membered heterocyclic ring may be a tetrahydropyrrole ring, a piperidine ring, a tetrahydrofuran ring, or a tetrahydrothiophene ring, for example, a tetrahydropyrrole ring.

In a certain preferred embodiment, in $Cy^{3-1}$, the $C_1$-$C_6$ alkyl may be $C_1$-$C_4$ alkyl, and may also be methyl, ethyl, n-propyl, isopropyl, n-butyl, isobutyl, sec-butyl, or tert-butyl, and may also be methyl, ethyl, or isopropyl.

In a certain preferred embodiment, in ring $Cy^4$, the 5- to 12-membered heterocyclic ring may be a 5- to 6-membered heterocyclic ring, the heteroatom of the 5- to 6-membered heterocyclic ring is preferably N, S, or O, and the number of heteroatoms is 1 or 2; the 5- to 12-membered heterocyclic ring may be a tetrahydropyrrole ring, a piperidine ring, a tetrahydrofuran ring, or a tetrahydrothiophene ring, for example, a piperidine ring.

In a certain preferred embodiment, in $Cy^{4-1}$, the $C_1$-$C_6$ alkyl may be $C_1$-$C_4$ alkyl, and may also be methyl, ethyl, n-propyl, isopropyl, n-butyl, isobutyl, sec-butyl, or tert-butyl, and may also be methyl, ethyl, or isopropyl.

In a certain preferred embodiment, in ring $Cy^5$, the 5- to 12-membered heterocyclic ring may be a 5- to 6-membered heterocyclic ring, the heteroatom of the 5- to 12-membered heterocyclic ring is preferably N, S, or O, and the number of heteroatoms is 1 or 2; the 5- to 12-membered heterocyclic ring may be a tetrahydropyrrole ring, a piperidine ring, a tetrahydrofuran ring, or a tetrahydrothiophene ring, for example, a tetrahydropyrrole ring.

In a certain preferred embodiment, in $Cy^{5-1}$, the $C_1$-$C_6$ alkyl may be $C_1$-$C_4$ alkyl, and may also be methyl, ethyl, n-propyl, isopropyl, n-butyl, isobutyl, sec-butyl, or tert-butyl, and may also be methyl, ethyl, or isopropyl.

In a certain preferred embodiment, in $Cy^6$, the 6- to 10-membered aromatic ring may be a benzene ring or a naphthalene ring.

In a certain preferred embodiment, in $Cy^{6-1}$, the halogen may be fluorine, chlorine, bromine, or iodine, for example, fluorine or chlorine.

In a certain preferred embodiment, in $Cy^{6-1}$, the $C_1$-$C_6$ alkyl may be $C_1$-$C_4$ alkyl, and may also be methyl, ethyl, n-propyl, isopropyl, n-butyl, isobutyl, sec-butyl, or tert-butyl, and may also be methyl, ethyl, or isopropyl.

In a certain preferred embodiment, in ring $Cy^7$, the 5- to 9-membered heteroaromatic ring may be a 5-membered heteroaromatic ring or a 6-membered heteroaromatic ring; the 6-membered heteroaromatic ring is preferably a pyridine ring, a pyridazine ring, a pyrazine ring, a pyrimidine ring, or a triazine ring; the 5-membered heteroaromatic ring is preferably a pyrazole ring, an oxazole ring, a thiazole ring, or an imidazole ring, for example,

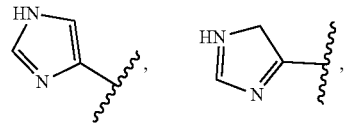

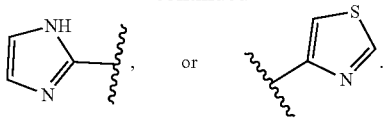

In a certain preferred embodiment, in $Cy^{7-1}$, the halogen may be fluorine, chlorine, bromine, or iodine, for example, fluorine or chlorine.

In a certain preferred embodiment, in $Cy^{7-1}$, the $C_1$-$C_6$ alkyl may be $C_1$-$C_4$ alkyl, and may also be methyl, ethyl, n-propyl, isopropyl, n-butyl, isobutyl, sec-butyl, or tert-butyl, and may also be methyl.

In a certain preferred embodiment, in $R^4$, the $C_1$-$C_6$ alkyl may be $C_1$-$C_4$ alkyl, and may also be methyl, ethyl, n-propyl, isopropyl, n-butyl, isobutyl, sec-butyl, or tert-butyl, and may also be tert-butyl.

In a certain preferred embodiment, in $R^4$, the halogen may be fluorine, chlorine, bromine, or iodine, for example, fluorine or chlorine.

In a certain preferred embodiment, in $R^5$, the halogen may be fluorine, chlorine, bromine, or iodine, for example, fluorine or chlorine.

In a certain preferred embodiment, in $L_{31}$, the $C_1$-$C_6$ alkyl may be $C_1$-$C_4$ alkyl, and may also be methyl, ethyl, n-propyl, isopropyl, n-butyl, isobutyl, sec-butyl, or tert-butyl.

In a certain preferred embodiment, when ring $Cy^1$ is a 5- to 12-membered heterocyclic ring, the heteroatom of the 5- to 12-membered heterocyclic ring is N, S, or O, and the number of heteroatoms is 1 or 2; the 5- to 12-membered heterocyclic ring may be a tetrahydrofuran ring, a piperidine ring, a piperazine ring, diazaspiro[3.5]nonane, azaspiro[3.3]heptane, diazaspiro[3.3]heptane, diazaspiro[5.5]undecane, azaspiro[3.5]nonane, or an azaspiro[5.5]undecane.

In a certain preferred embodiment, when ring $Cy^2$ is a 5- to 10-membered heteroaromatic ring, the heteroatom of the 5- to 10-membered heteroaromatic ring is selected from one or two of N, S, and O, and the number of heteroatoms is 1 or 2; the 5- to 10-membered heteroaromatic ring is preferably a 5-membered heteroaromatic ring or a 6-membered heteroaromatic ring; the 6-membered heteroaromatic ring is preferably a pyridine ring, a pyridazine ring, a pyrazine ring, a pyrimidine ring, or a triazine ring; the 5-membered heteroaromatic ring is preferably a pyrazole ring, a thiazole ring, or an imidazole ring.

In a certain preferred embodiment, when ring $Cy^2$ is a 6- to 10-membered aromatic ring, the 6- to 10-membered aromatic ring is a benzene ring.

In a certain preferred embodiment, in $L_2^{1-1}$ and $L_2^{1-2}$, the $C_1$-$C_6$ alkyl may be $C_1$-$C_4$ alkyl, and may also be methyl, ethyl, n-propyl, isopropyl, n-butyl, isobutyl, sec-butyl, or tert-butyl, and may also be methyl, ethyl, or isopropyl.

In a certain preferred embodiment, in $L_2^{1-3}$, the halogen may be fluorine, chlorine, bromine, or iodine, for example, fluorine or chlorine.

In a certain preferred embodiment, in $L_2^{1-3}$, in the unsubstituted $C_1$-$C_6$ alkyl or $C_1$-$C_6$ alkyl substituted by one or more than one halogen, the $C_1$-$C_6$ alkyl may be $C_1$-$C_4$ alkyl, and may also be methyl, ethyl, n-propyl, isopropyl, n-butyl, isobutyl, sec-butyl, or tert-butyl, and may also be methyl, ethyl, or isopropyl; the halogen is preferably fluorine, chlorine, bromine, or iodine, for example, fluorine or chlorine.

In a certain preferred embodiment, in $L_2^{1-3}$, in the unsubstituted $C_1$-$C_6$ alkoxy or $C_1$-$C_6$ alkoxy substituted by one or more than one halogen, the $C_1$-$C_6$ alkoxy may be $C_1$-$C_4$ alkoxy, and may also be methoxy, ethoxy, n-propoxy, isopropoxy, n-butoxy, isobutoxy, sec-butoxy, or tert-butoxy, and may also be methoxy, ethoxy, or isopropoxy; the halogen is preferably fluorine, chlorine, bromine, or iodine, for example, fluorine or chlorine.

In a certain preferred embodiment, in $L_2^{1-3}$, in the unsubstituted 3- to 10-membered cycloalkyl or 3- to 10-membered cycloalkyl substituted by one or more than one $L_2^{1-3-1}$, the 3- to 10-membered cycloalkyl may be $C_3$-$C_6$ cycloalkyl, and may also be cyclopropyl, cyclobutyl, cyclopentyl, or cyclohexyl, for example, cyclopropyl, cyclobutyl, or cyclohexyl; each $L_2^{1-3-1}$ is independently and preferably halogen or hydroxyl.

In a certain preferred embodiment, in $L_2^{1-3}$, in the unsubstituted 3- to 11-membered heterocycloalkyl or 3- to 11-membered heterocycloalkyl substituted by one or more than one $L_2^{1-3-2}$, the 3- to 11-membered heterocyclic ring may be a 4- to 9-membered heterocyclic ring, the heteroatom of the 4- to 9-membered heterocyclic ring is preferably one or two of N, S, and O, and the number of heteroatoms is 1 or 2; the 3- to 11-membered heterocyclic ring may be a tetrahydropyrrole ring, a piperidine ring, a tetrahydrofuran ring, or a tetrahydrothiophene ring, for example, a piperidine ring.

In a certain preferred embodiment, when $R^c$ is unsubstituted $C_1$-$C_6$ alkyl or $C_1$-$C_6$ alkyl substituted by one or more than one $R^{c-1}$, the $C_1$-$C_6$ alkyl may be $C_1$-$C_4$ alkyl, and may also be methyl, ethyl, n-propyl, isopropyl, n-butyl, isobutyl, sec-butyl, or tert-butyl, and may also be methyl, ethyl, or isopropyl.

In a certain preferred embodiment, when $R^c$ is unsubstituted 3- to 10-membered cycloalkyl or 3- to 10-membered cycloalkyl substituted by one or more than one $R^{c-2}$, the 3- to 10-membered cycloalkyl may be 3- to 6-membered cycloalkyl, for example, cyclopropyl, cyclobutyl, cyclopentyl, or cyclohexyl.

In a certain preferred embodiment, when $R^c$ is unsubstituted 3- to 11-membered heterocycloalkyl or 3- to 11-membered heterocycloalkyl substituted by one or more than one $R^{c-3}$, the 3- to 11-membered heterocycloalkyl may be 5- to 8-membered heterocycloalkyl, the heteroatom of the 3- to 11-membered heterocycloalkyl is selected from one or two of N, S, and O, and the number of heteroatoms is 1 or 2; preferably, the heteroatom of the 3- to 11-membered heterocycloalkyl is N, S, or O, and the number of heteroatoms is 1 or 2; the 3- to 11-membered heterocycloalkyl is preferably piperazinyl, piperidinyl, tetrahydropyrrolyl, azabicyclo[2.2.2]octyl, azabicyclo[3.2.1]octyl, azaspiro[3.3]heptyl, or azabicyclo[2.2.1]heptyl, for example,

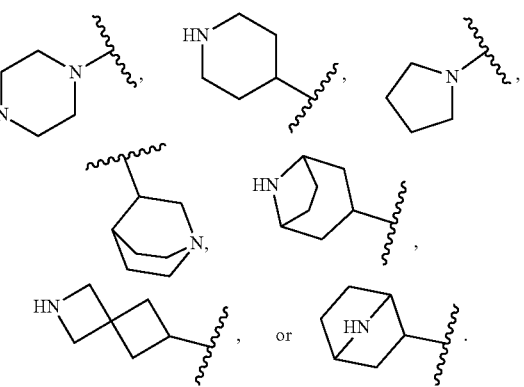

In a certain preferred embodiment, when $R^c$ is unsubstituted 6- to 10-membered aryl or 6- to 10-membered aryl substituted by one or more than one $R^{c-4}$, the 6- to 10-membered aryl may be a benzene ring or a naphthalene ring.

In a certain preferred embodiment, when $R^c$ is unsubstituted 5- to 10-membered heteroaryl or 5- to 10-membered heteroaryl substituted by one or more than one $R^{c-5}$, the 5- to 10-membered heteroaryl may be 5-membered heteroaryl or 6-membered heteroaryl; the 6-membered heteroaryl is preferably pyridyl, pyridazinyl, pyrazinyl, pyrimidinyl, or triazinyl; the 5-membered heteroaryl is preferably pyrazolyl, thiazolyl, or imidazolyl.

In a certain preferred embodiment, in $L_0$, m is 1 or 2.
In a certain preferred embodiment, in $L_0$, q is 1 or 2.
In a certain preferred embodiment, in $L_1$, m is 1 or 2.
In a certain preferred embodiment, in $L_1$, q is 1 or 2.
In a certain preferred embodiment, in ring $Cy^a$, s is 0, 1, or 2.
In a certain preferred embodiment, in ring $Cy^a$, t is 0, 1, or 2.
In a certain preferred embodiment, in ring $Cy^a$, r is 1 or 2.
In a certain preferred embodiment, in LLM, p is 0 or 1.
In a certain preferred embodiment, in $L_2$, m is 1 or 2.
In a certain preferred embodiment, in $L_2$, q is 1 or 2.
In a certain preferred embodiment, in $L_3$, m is 1 or 2.
In a certain preferred embodiment, in $L_3$, q is 1 or 2.
In a certain preferred embodiment, when ring $Cy^a$ is substituted by a substituent and the substituent is halogen, then the halogen may be fluorine, chlorine, bromine, or iodine, for example, fluorine or chlorine.

In a certain preferred embodiment, when ring $Cy^a$ is substituted by a substituent and the substituent is $C_1$-$C_6$ alkyl, then the $C_1$-$C_6$ alkyl may be $C_1$-$C_4$ alkyl, for example, methyl, ethyl, n-propyl, isopropyl, n-butyl, isobutyl, sec-butyl, or tert-butyl.

In the present disclosure, in $R^{1-1-1}$, $R^{1-1-3}$, $R^{1-1-4}$, $R^{1-1-5}$, $R^{3-1-1}$, $R^{3-1-4}$, $R^{3-1-5}$, $R^{1-1-1-1}$, $R^{1-1-1-2}$, $R^{1-1-1-3}$, $R^{a-1}$, $R^{a-2}$, $R^{a-3}$, $R^{a-4}$, and $R^{a-5}$, the 6- to 10-membered aryl may be independently phenyl or naphthyl.

In the present disclosure, in $R^{1-1-1}$, $R^{1-1-3}$, $R^{1-1-4}$, $R^{1-1-5}$, $R^{3-1-1}$, $R^{3-1-4}$, $R^{3-1-5}$, $R^{1-1-1-1}$, $R^{1-1-1-2}$, $R^{1-1-1-3}$, $R^{a-1}$, $R^{a-2}$, $R^{a-3}$, $R^{a-4}$, and $R^{a-5}$, the $C_1$-$C_6$ alkoxy may be independently $C_1$-$C_4$ alkoxy, for example, methoxy, ethoxy, n-propoxy, isopropoxy, n-butoxy, isobutoxy, sec-butoxy, or tert-butoxy, for another example, methoxy.

In the present disclosure, in $R^{1-1-1}$, $R^{1-1-3}$, $R^{1-1-4}$, $R^{1-1-5}$, $R^{3-1-1}$, $R^{3-1-4}$, $R^{3-1-5}$, $R^{1-1-1-1}$, $R^{1-1-1-2}$, $R^{1-1-1-3}$, $R^{a-1}$, $R^{a-2}$, $R^{a-3}$, $R^{a-4}$, and $R^{a-5}$, the halogen may be independently fluorine, chlorine, bromine, or iodine, for example, fluorine or chlorine.

In the present disclosure, in $R^{1-1-1}$, $R^{1-1-3}$, $R^{1-1-4}$, $R^{1-1-5}$, $R^{3-1-1}$, $R^{3-1-4}$, $R^{3-1-5}$, $R^{1-1-1-1}$, $R^{1-1-1-2}$, $R^{1-1-1-3}$, $R^{a-1}$, $R^{a-2}$, $R^{a-3}$, $R^{a-4}$, and $R^{a-5}$, the $C_1$-$C_6$ alkyl may be independently $C_1$-$C_4$ alkyl, and may also be methyl, ethyl, n-propyl, isopropyl, n-butyl, isobutyl, sec-butyl, or tert-butyl, and may also be methyl, ethyl, or isopropyl.

In the present disclosure, in $R^{1-1-1}$, $R^{1-1-3}$, $R^{1-1-4}$, $R^{1-1-5}$, $R^{3-1-1}$, $R^{3-1-4}$, $R^{3-1-5}$, $R^{1-1-1-1}$, $R^{1-1-1-2}$, $R^{1-1-1-3}$, $R^{a-1}$, $R^{a-2}$, $R^{a-3}$, $R^{a-4}$, and $R^{a-5}$, the 3- to 11-membered heterocycloalkyl may be independently 6-membered heterocycloalkyl, 5-membered heterocycloalkyl, 8-membered heterocycloalkyl, or 7-membered heterocycloalkyl, the heteroatom of the 3- to 11-membered heterocycloalkyl is selected from one or two of N and O, and the number of heteroatoms is 1 or 2; the 6-membered heterocycloalkyl is preferably piperazinyl, morpholinyl, or piperidinyl, for example,

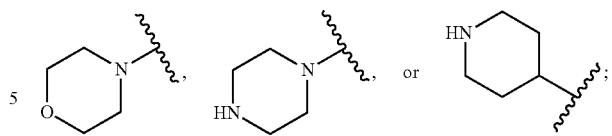

the 5-membered heterocycloalkyl is preferably tetrahydropyrrolyl, for example,

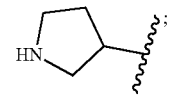

the 8-membered heterocycloalkyl is preferably azabicyclo[2.2.2]octyl or azabicyclo[3.2.1]octyl, for example,

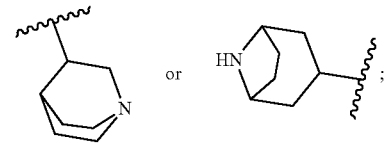 [SMILES: *C1CN2CCC1CC2 ; *C1CC2CCC(C1)N2]

the 7-membered heterocycloalkyl is preferably azaspiro[3.3]heptyl or azabicyclo[2.2.1]heptyl, for example, or

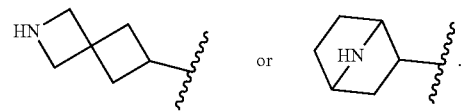 [SMILES: *C1CC2(CNC2)C1 ; *C1CC2CCC1N2]

In the present disclosure, in $R^{1-1-1}$, $R^{1-1-3}$, $R^{1-1-4}$, $R^{1-1-5}$, $R^{3-1-1}$, $R^{3-1-4}$, $R^{3-1-5}$, $R^{1-1-1-1}$, $R^{1-1-1-2}$, $R^{1-1-1-3}$, $R^{a-1}$, $R^{a-2}$, $R^{a-3}$, $R^{a-4}$, and $R^{a-5}$, the 3- to 10-membered cycloalkyl may be independently 3- to 6-membered cycloalkyl, for example, cyclopropyl, cyclobutyl, cyclopentyl, or cyclohexyl.

In the present disclosure, in $R^{1-1-1}$, $R^{1-1-3}$, $R^{1-1-4}$, $R^{1-1-5}$, $R^{3-1-1}$, $R^{3-1-4}$, $R^{3-1-5}$, $R^{1-1-1-1}$, $R^{1-1-1-2}$, $R^{1-1-1-3}$, $R^{a-1}$, $R^{a-2}$, $R^{a-3}$, $R^{a-4}$, and $R^{a-5}$, the 5- to 10-membered heteroaryl may be independently 5-membered heteroaryl, 6-membered heteroaryl, or 5-membered-fused 5-membered heteroaryl; the 6-membered heteroaryl is preferably pyridyl, pyridazinyl, pyrazinyl, pyrimidinyl, or triazinyl; the 5-membered heteroaryl is preferably pyrazolyl, oxazolyl, thiazolyl, or imidazolyl, for example,

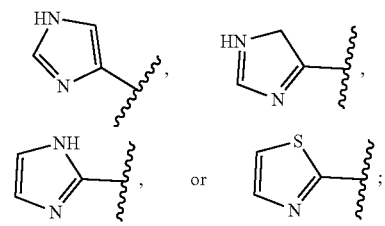

the 5- to 10-membered heteroaryl is preferably pyrazolyl, thiazolyl, imidazolyl, tetrahydropyrrolothiazolyl, or tetrahydropyrrolopyrazolyl, for example,

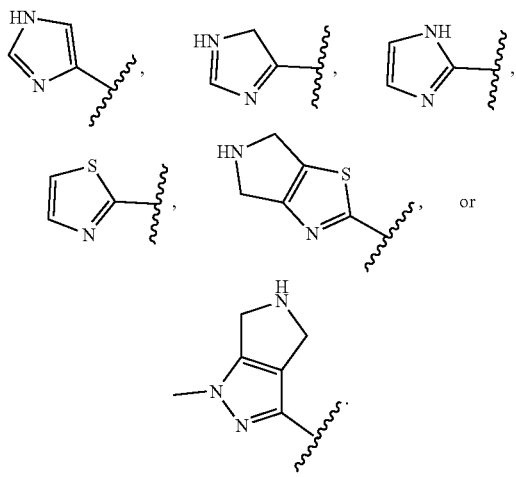

In a certain preferred embodiment, ring Cy is a 5-membered heterocyclic ring or a 5-membered heteroaromatic ring; the heteroatom of the 5-membered heterocyclic ring is selected from one or two of N and O, and the number of heteroatoms is 1 or 2; the heteroatom of the 5-membered heteroaromatic ring is selected from one or more than one of N, S, and O, and the number of heteroatoms is 1, 2, or 3.

In a certain preferred embodiment, $R^1$ is unsubstituted 5- to 10-membered heteroaryl, 5- to 10-membered heteroaryl substituted by one or more than one $R^{1-1}$, unsubstituted 6- to 10-membered aryl, or 6- to 10-membered aryl substituted by one or more than one $R^{1-2}$; the heteroatom of the 5- to 10-membered heteroaryl is selected from one or two of N, S, and O, and the number of heteroatoms is 1 or 2. $R^1$ is preferably unsubstituted 5- to 6-membered heteroaryl, 5- to 6-membered heteroaryl substituted by one or more than one $R^{1-1}$, unsubstituted 6- to 10-membered aryl, or 6- to 10-membered aryl substituted by one or more than one $R^{1-2}$; the heteroatom of the 5- to 6-membered heteroaryl is selected from one or two of N, S, and O, and the number of heteroatoms is 1 or 2. $R^1$ is preferably unsubstituted 5- to 6-membered heteroaryl or 5- to 6-membered heteroaryl substituted by one or more than one $R^{1-1}$, the heteroatom of the 5- to 6-membered heteroaryl is N, and the number of heteroatoms is 1 or 2; the 5- to 6-membered heteroaryl is preferably pyridyl.

In a certain preferred embodiment, $R^{1-1}$ and $R^{1-2}$ are each independently halogen, hydroxyl,

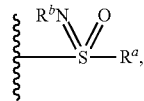

—$SO_2$—$R^a$, —SO—$R^a$, unsubstituted $C_1$-$C_6$ alkyl, $C_1$-$C_6$ alkyl substituted by one or more than one $R^{1-1-4}$, unsubstituted 5- to 10-membered heteroaryl, or 5- to 10-membered heteroaryl substituted by one or more than one $R^{1-1-7}$; the heteroatom of the 5- to 10-membered heteroaryl is selected from one or two of N, S, and O, and the number of heteroatoms is 1 or 2. $R^{1-1}$ and $R^{1-2}$ are each independently and preferably halogen, unsubstituted 5- to 6-membered heteroaryl, 5- to 6-membered heteroaryl substituted by one or more than one $R^{1-1-7}$, unsubstituted $C_1$-$C_6$ alkyl, or $C_1$-$C_6$ alkyl substituted by one or more than one $R^{1-1-4}$; the heteroatom of the 5- to 6-membered heteroaryl is selected from one or two of N, S, and O, and the number of heteroatoms is 1 or 2. $R^{1-1}$ and $R^{1-2}$ are each independently and preferably unsubstituted $C_1$-$C_6$ alkyl or $C_1$-$C_6$ alkyl substituted by one or more than one $R^{1-1-4}$.

In a certain preferred embodiment, each $R^{1-1-4}$ is independently halogen, for example, fluorine.

In a certain preferred embodiment, each $R^{1-1-7}$ is independently halogen, hydroxyl, unsubstituted $C_1$-$C_6$ alkoxy, or $C_1$-$C_6$ alkoxy substituted by one or more than one halogen, cyano, nitro, unsubstituted $C_1$-$C_6$ alkyl, or $C_1$-$C_6$ alkyl substituted by one or more than one halogen, unsubstituted 6- to 10-membered aryl, or 6- to 10-membered aryl substituted by one or more than one $R^{1-1-1-2}$, or unsubstituted 5- to 10-membered heteroaryl, or 5- to 10-membered heteroaryl substituted by one or more than one $R^{1-1-1-3}$; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3. Each $R^{1-1-7}$ is independently and preferably unsubstituted $C_1$-$C_6$ alkyl or $C_1$-$C_6$ alkyl substituted by one or more than one halogen.

In a certain preferred embodiment, $R^{1-1-1-1}$, $R^{1-1-1-2}$, and $R^{1-1-1-3}$ are each independently halogen or $C_1$-$C_6$ alkyl.

In a certain preferred embodiment, $R^2$ is hydrogen.

In a certain preferred embodiment, $R^3$ is hydrogen, hydroxyl, halogen, cyano, unsubstituted 3- to 10-membered heterocycloalkyl, 3- to 10-membered heterocycloalkyl substituted by one or more than one $R^{3-1}$, unsubstituted 3- to 8-membered cycloalkyl, 3- to 8-membered cycloalkyl substituted by one or more than one $R^{3-2}$, unsubstituted $C_1$-$C_6$ alkyl, $C_1$-$C_6$ alkyl substituted by one or more than one $R^{3-4}$, unsubstituted $C_1$-$C_6$ alkoxy, $C_1$-$C_6$ alkoxy substituted by one or more than one $R^{3-7}$, or hydroxyl substituted by $R^{3-8}$; the heteroatom of the 3- to 10-membered heterocycloalkyl is selected from one or two of N and O, and the number of heteroatoms is 1, 2, or 3. $R^3$ is preferably halogen, unsubstituted 3- to 6-membered heterocycloalkyl, 3- to 6-membered heterocycloalkyl substituted by one or more than one $R^{3-1}$, unsubstituted $C_3$-$C_6$ cycloalkyl, $C_3$-$C_6$ cycloalkyl substituted by one or more than one $R^3$ unsubstituted $C_1$-$C_6$ alkoxy, $C_1$-$C_6$ alkoxy substituted by one or more than one $R^{3-7}$ unsubstituted $C_1$-$C_6$ alkyl, $C_1$-$C_6$ alkyl substituted by one or more than one $R^{3-4}$, or hydroxyl substituted by $R^{3-8}$; the heteroatom of the 3- to 6-membered heterocycloalkyl is selected from one or two of N and O, and the number of heteroatoms is 1 or 2. $R^3$ is preferably unsubstituted 3- to 6-membered heterocycloalkyl, 3- to 6-membered heterocycloalkyl substituted by one or more than one $R^{3-1}$, unsubstituted $C_3$-$C_6$ cycloalkyl, $C_3$-$C_6$ cycloalkyl substituted by one or more than one $R^{3-2}$, unsubstituted $C_1$-$C_6$ alkoxy, $C_1$-$C_6$ alkoxy substituted by one or more than one $R^{3-7}$, unsubstituted $C_1$-$C_6$ alkyl, $C_1$-$C_6$ alkyl substituted by one or more than one $R^{3-4}$, or hydroxyl substituted by $R^{3-8}$; the heteroatom of the 3- to 6-membered heterocycloalkyl is selected from one or two of N and O, and the number of heteroatoms is 1 or 2. $R^3$ is preferably unsubstituted $C_1$-$C_6$ alkoxy, unsubstituted $C_1$-$C_6$ alkyl, or $C_1$-$C_6$ alkyl substituted by one or more than one $R^{3-4}$.

In a certain preferred embodiment, $R^{3-1}$, $R^{3-2}$, $R^{3-4}$, and $R^{3-7}$ are each independently oxo, hydroxyl, halogen, 3- to 6-membered cycloalkyl, 3- to 6-membered heterocycloalkyl, unsubstituted $C_1$-$C_6$ alkyl, or $C_1$-$C_6$ alkyl substituted by one or more than one halogen; the heteroatom of the 3- to 6-membered heterocycloalkyl is selected from one or two of N, S, and O, and the number of heteroatoms is 1 or 2. Each $R^{3-1}$ is independently and preferably hydroxyl or halogen. Each $R^{3-2}$ is independently and preferably hydroxyl. Each $R^{3-4}$ is independently and preferably hydroxyl; each $R^{3-7}$ is independently and preferably halogen.

In a certain preferred embodiment, $R^{3-8}$ is 3- to 6-membered cycloalkyl or 3- to 6-membered heterocycloalkyl; the heteroatom of the 3- to 6-membered heterocycloalkyl is selected from one or more than one of N, S, and O, and the number of heteroatoms is 1, 2, or 3. $R^{3-8}$ is preferably 3- to 6-membered cycloalkyl or 3- to 6-membered heterocycloalkyl; the heteroatom of the 3- to 6-membered heterocycloalkyl is selected from one or two of N and O, and the number of heteroatoms is 1.

In a certain preferred embodiment, $R^a$ and $R^b$ are each independently H, unsubstituted $C_1$-$C_6$ alkyl, or $C_1$-$C_6$ alkyl substituted by one or more than one $R^{a-1}$. $R^a$ and $R^b$ are each independently and preferably H.

In a certain preferred embodiment, $L_1$ is absent or

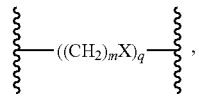

m is an integer from 1 to 4, q is an integer from 1 to 6, and X is absent or O. Preferably, $L_1$ is

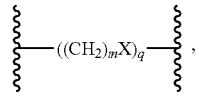

m is an integer from 1 to 4, q is an integer from 1 to 2, and X is absent.

In a certain preferred embodiment, $L_1$ is absent,

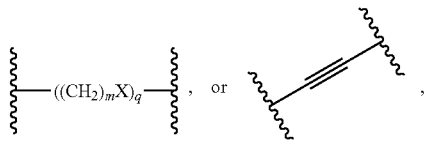

m is an integer from 1 to 4, q is an integer from 1 to 6, and X is absent or O. Preferably, $L_1$ is

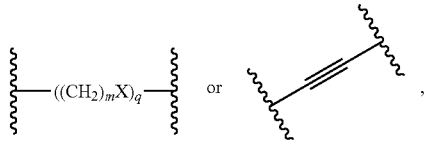

m is an integer from 1 to 4, q is an integer from 1 to 2, and X is absent.

In a certain preferred embodiment, $L_2^{-1}$, $L_2^{-2}$, $L_2^{-3}$, and $L_2^{-4}$ are independently absent,

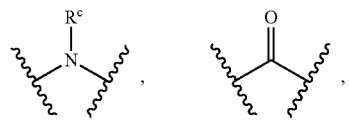

unsubstituted

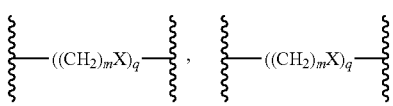

substituted by one or more than one $L_1^{1-1}$, unsubstituted

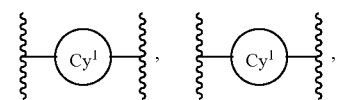

substituted by one or more than one $L_1^{1-2}$, unsubstituted

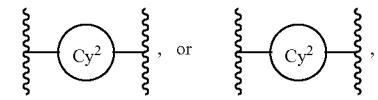

or substituted by one or more than one $L_1^{1-3}$; m is an integer from 1 to 4, q is an integer from 1 to 6, and X is absent or O; ring $Cy^1$ is a 3- to 11-membered heterocyclic ring or a 4- to 11-membered cycloalkyl ring; ring $Cy^2$ is a 5- to 10-membered heteroaromatic ring or a 6- to 10-membered aromatic ring; the heteroatom of the 3- to 11-membered heterocyclic ring is selected from one or more than one of N, S, and O, and the number of heteroatoms is 1, 2, or 3; the heteroatom of the 5- to 10-membered heteroaromatic ring is selected from one or more than one of N, S, and O, and the number of heteroatoms is 1, 2, or 3. Preferably, in a certain preferred embodiment, $L_2^{-1}$, $L_2^{-2}$, $L_2^{-3}$, and $L_2^{-4}$ are independently absent,

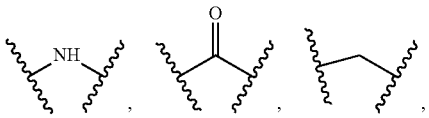

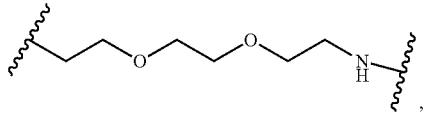

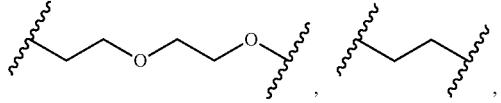

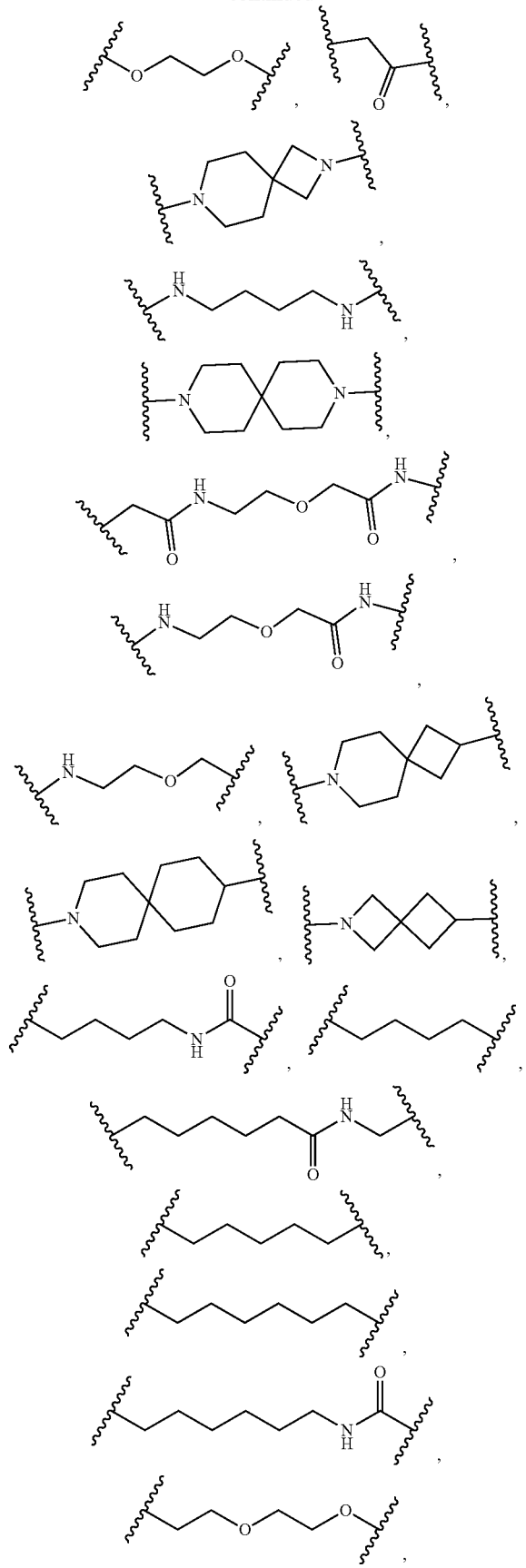
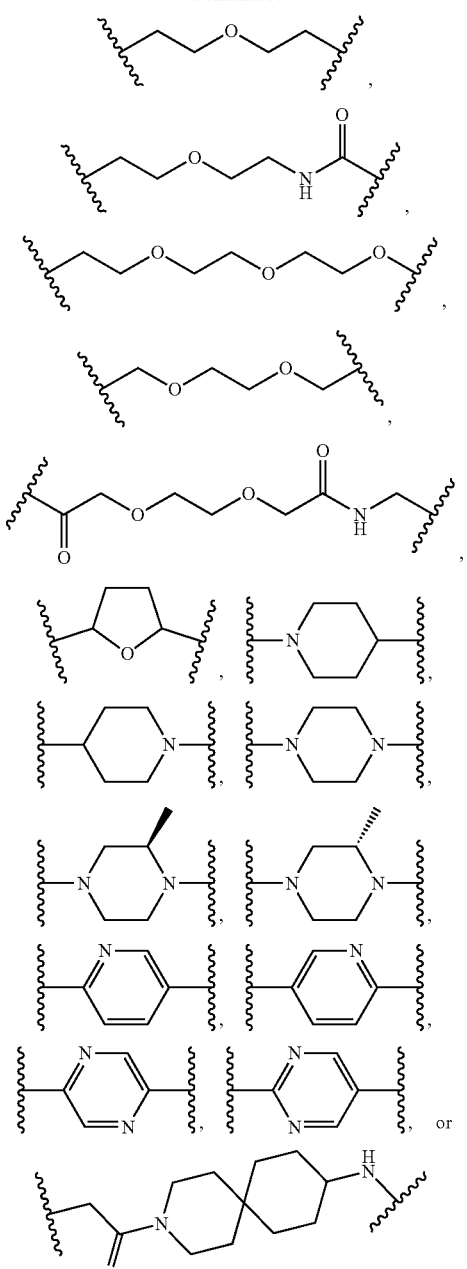
In a certain preferred embodiment $L_2^{-1}$, $L_2^{-2}$, $L_2^{-3}$, $L_2^{-4}$, $L_2^{-5}$, $L_2^{-6}$, and $L_2^{-7}$ are independently absent,
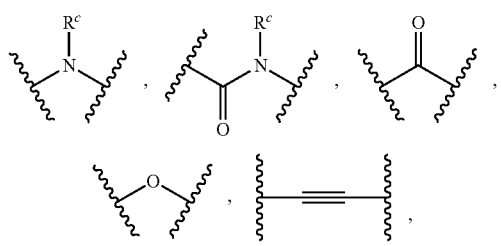

unsubstituted

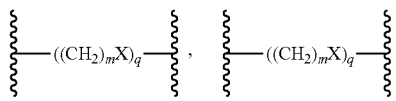

substituted by one or more than one $L_1^{1-1}$, unsubstituted

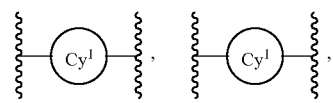

substituted by one or more than one $L_1^{1-2}$, unsubstituted

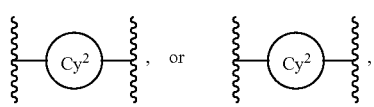

or substituted by one or more than one $L_1^{1-3}$; m is an integer from 1 to 4, q is an integer from 1 to 6, and X is absent or O; ring $Cy^1$ is a 3- to 11-membered heterocyclic ring or a 4- to 11-membered cycloalkyl ring; ring $Cy^2$ is a 5- to 10-membered heteroaromatic ring or a 6- to 10-membered aromatic ring; the heteroatom of the 3- to 11-membered heterocyclic ring is selected from one or more than one of N, S, and O, and the number of heteroatoms is 1, 2, or 3; the heteroatom of the 5- to 10-membered heteroaromatic ring is selected from one or more than one of N, S, and O, and the number of heteroatoms is 1, 2, or 3. Preferably, in a certain preferred embodiment, $L_2^{-1}$, $L_2^{-2}$, $L_2^{-3}$, $L_2^{-4}$, $L_2^{-5}$, $L_2^{-6}$, and $L_2^{-7}$ are independently absent O

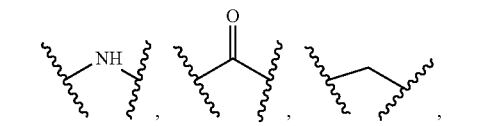

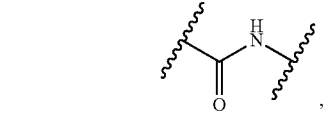

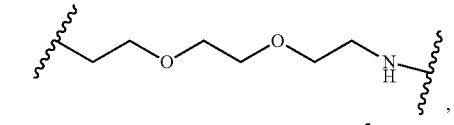

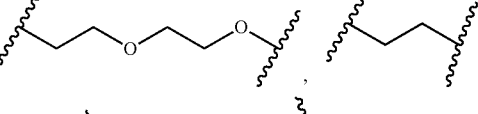

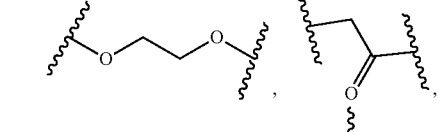

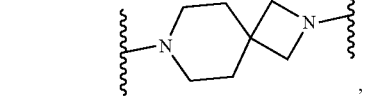

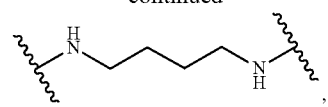

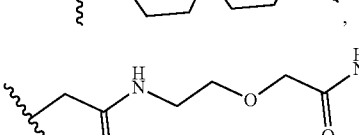

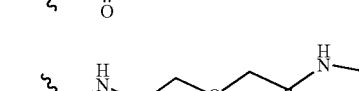

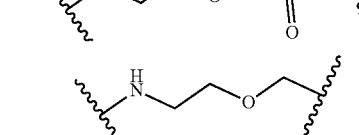

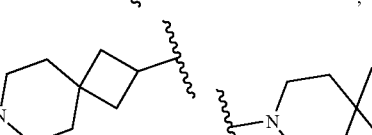

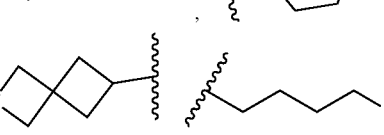

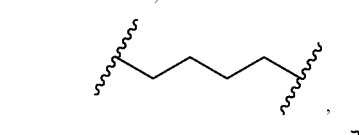

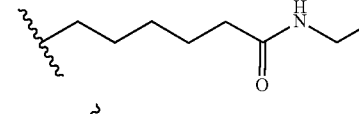

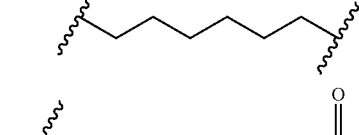

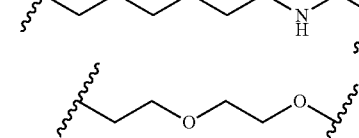

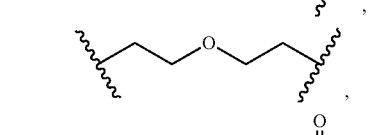

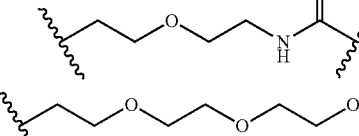

-continued

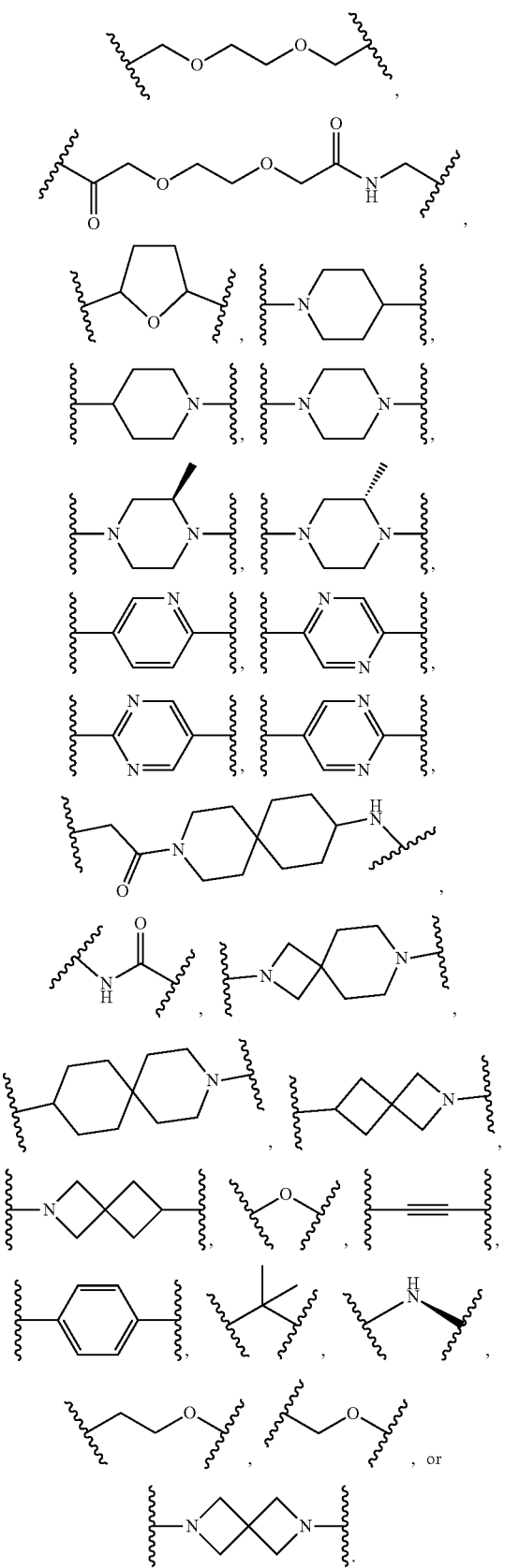

Preferably $L_2^{-1}$ in the compound of formula III is

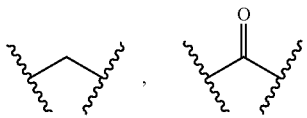

Preferably, in the five-membered-fused six-membered compound of formula II or III, $L_2^{-1}$-$L_2^{-2}$ is

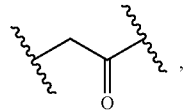 [SMILES: *CC(*)=O]

$L_2^{-3}$, $L_2^{-4}$, $L_2^{-5}$, $L_2^{-6}$, and $L_2^{-7}$ are independently absent,

unsubstituted

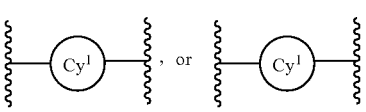

substituted by one or more than one $L_1^{1-2}$, and ring $Cy^1$ is a 7- to 11-membered heterocyclic ring; the heteroatom of the 7- to 11-membered heterocyclic ring is N, and the number of heteroatoms is 1 or 2. In a certain preferred embodiment, in $L_2$, $R^c$ is H, unsubstituted $C_1$-$C_6$ alkyl, or $C_1$-$C_6$ alkyl substituted by one or more than one halogen. In a certain preferred embodiment, ring $Cy^3$ is an unsubstituted 5- to 6-membered heterocyclic ring or a 5- to 6-membered heterocyclic ring substituted by one or more than one $Cy^{3-1}$; the heteroatom of the 5- to 6-membered heterocyclic ring is N, S, or O, and the number of heteroatoms is 1.

In a certain preferred embodiment, each $Cy^{3-1}$ is independently oxo.

In a certain preferred embodiment, ring $Cy^4$ is unsubstituted 5- to 8-membered heterocycloalkyl or 5- to 8-membered heterocycloalkyl substituted by one or more than one $Cy^{4-1}$; the heteroatom of the 5- to 8-membered heterocyclic ring is selected from one or more than one of N, S, and O, and the number of heteroatoms is 1, 2, or 3.

In a certain preferred embodiment, each $Cy^{4-1}$ is independently $C_1$-$C_6$ alkyl, hydroxyl, or oxo.

In a certain preferred embodiment, ring $Cy^5$ is an unsubstituted 5- to 6-membered heterocyclic ring or a 5- to 6-membered heterocyclic ring substituted by one or more than one $Cy^{5-1}$; the heteroatom of the 5- to 6-membered heterocyclic ring is N, S, or O, and the number of heteroatoms is 1.

In a certain preferred embodiment, each $Cy^{5-1}$ is hydroxyl.

In a certain preferred embodiment, ring $Cy^6$ is an unsubstituted benzene ring.

In a certain preferred embodiment, ring $Cy^7$ is an unsubstituted 5- to 6-membered heteroaromatic ring or a 5- to 6-membered heteroaromatic ring substituted by one or more than one Cy$^{7-1}$; the heteroatom of the 5- to 6-membered heteroaromatic ring is N, S, or O, and the number of heteroatoms is 2.

In a certain preferred embodiment, each Cy$^{7-1}$ is independently $C_1$-$C_6$ alkyl, for example, methyl.

In a certain preferred embodiment, each R$^5$ is independently halogen, for example, fluorine.

In a certain preferred embodiment, L$_3$ is unsubstituted

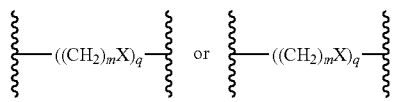

substituted by one or more than one L$_3^{-1}$; wherein m is an integer from 1 to 4, q is an integer from 1 to 6, and X is absent; L$_3^{-1}$ is independently unsubstituted $C_1$-$C_6$ alkyl, for example, methyl.

In a certain preferred embodiment, the five-membered-fused six-membered compound of formula II is a compound of formula II-a, II-b, II-c, II-d, II-e, II-f, II-g, II-h, II-i, or II-j:

II-a

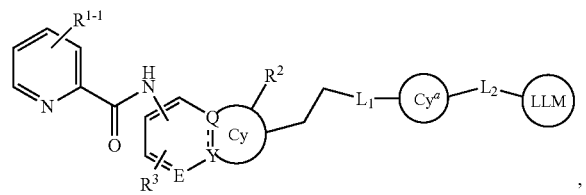

,

II-b

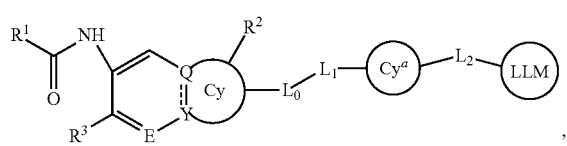

,

II-c

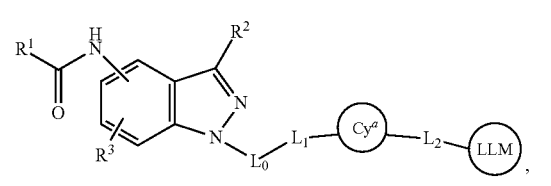

,

II-d

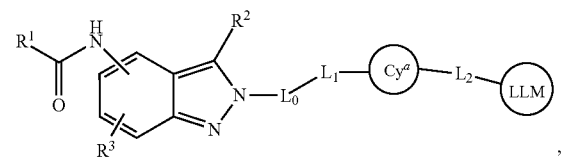

,

II-e

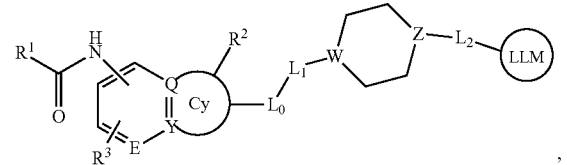

,

-continued

II-f

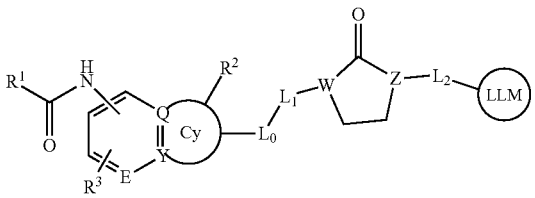

,

II-g

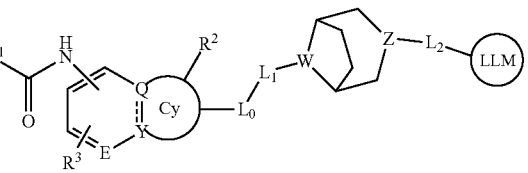

,

II-h

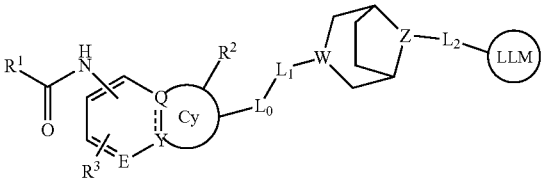

,

II-i

, or

II-j

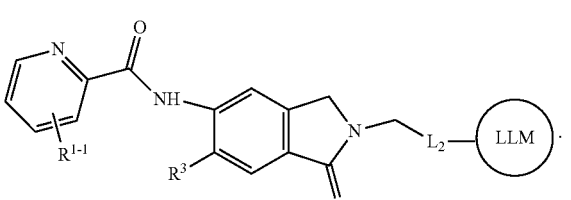

.

In a certain preferred embodiment, the five-membered-fused six-membered compound of formula III is a compound of formula III-a:

III-a

In a certain preferred embodiment, LLM is O or
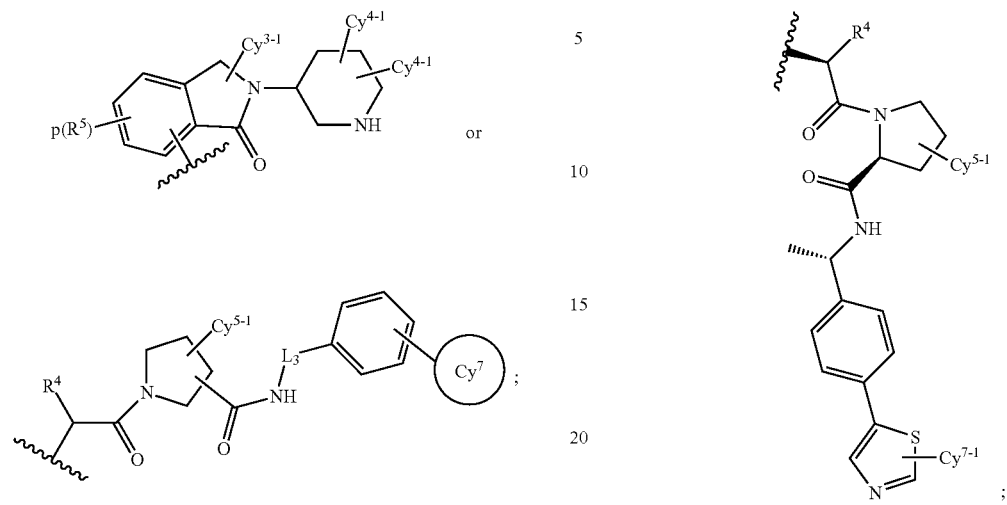
preferably
p is 0 or 1,
p is 0 or 1, or
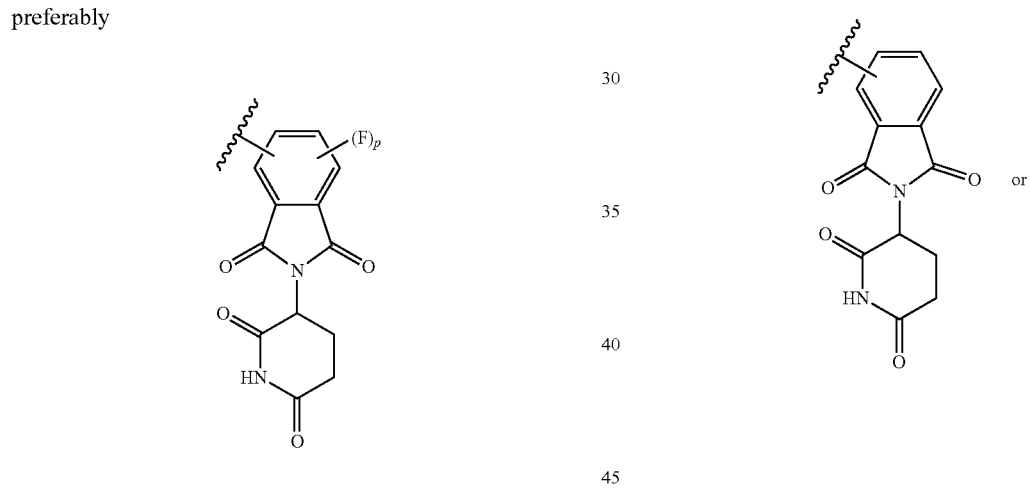
more preferably
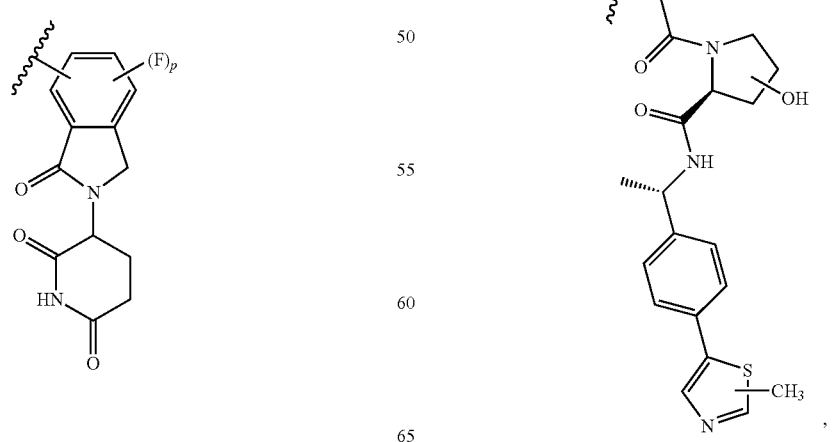

for example,
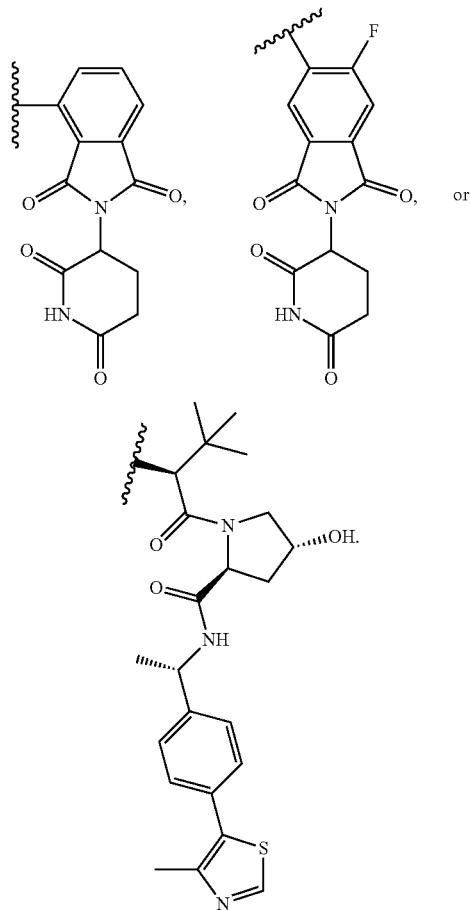
In a certain preferred embodiment, ring Cy$^a$ is
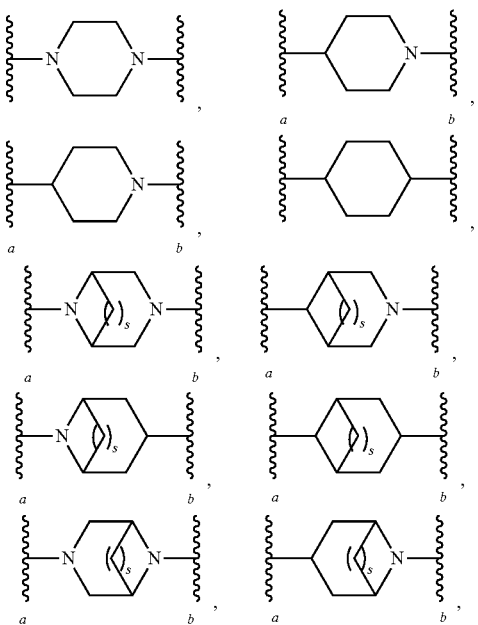
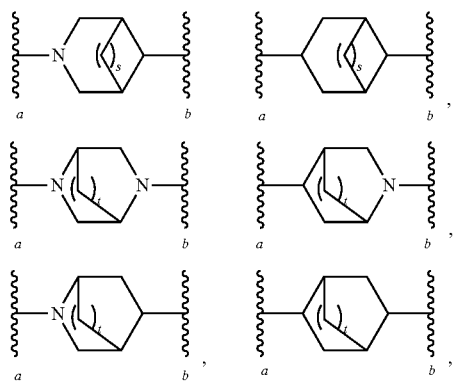
-continued
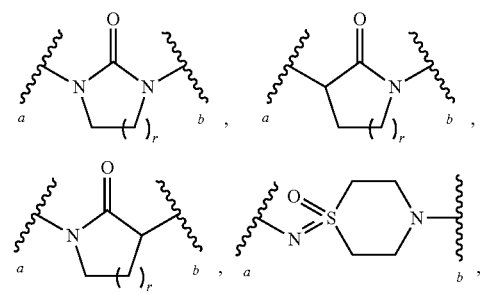
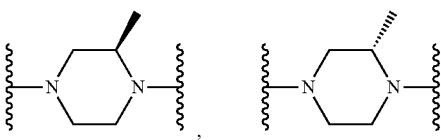
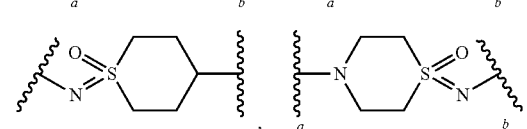
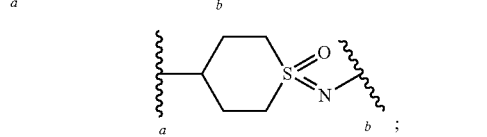
wherein r is 1 or 2; s is 1 or 2; t is 1 or 2; the a end is attached to $L_1$, and b is attached to $L_2$; preferably
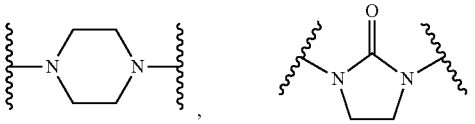
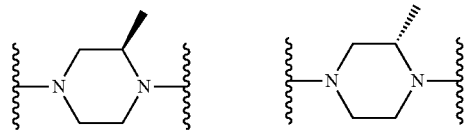
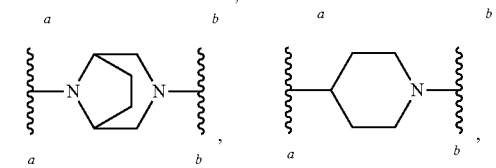

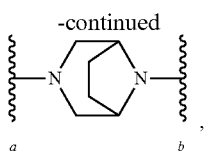

the a end is attached to $L_1$, and b is attached to $L_2$; more preferably

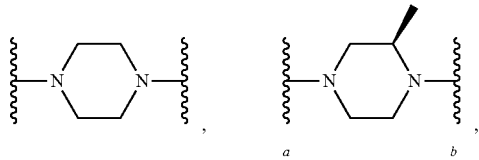

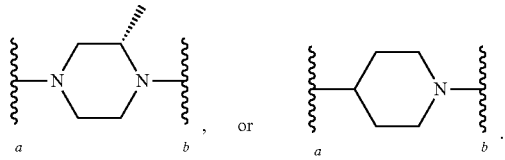

In a certain preferred embodiment, $R^1$ is

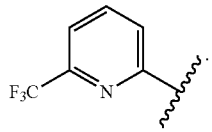

In a certain preferred embodiment, $R^3$ is methoxy, isopropoxy, difluoromethoxy, trifluoromethoxy, bromine, or

In a certain preferred embodiment,

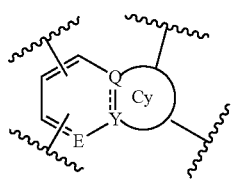

is

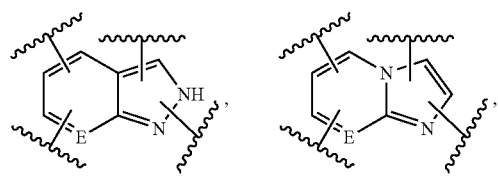

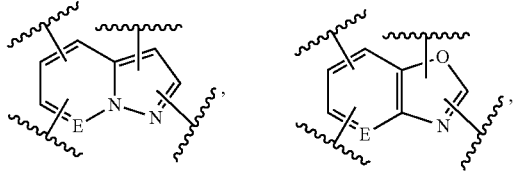

for example,

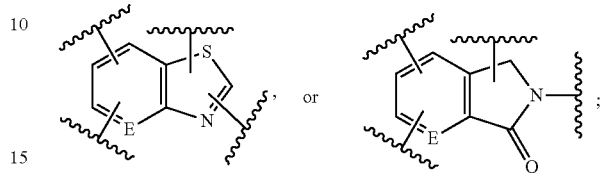

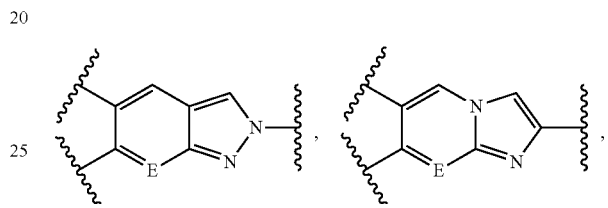

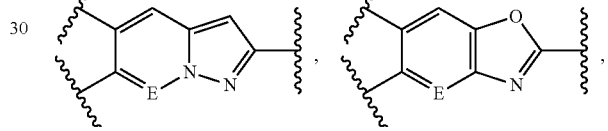

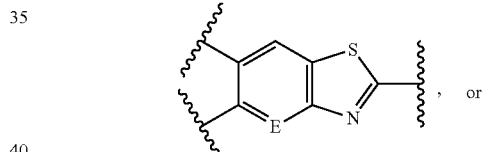

In a certain preferred embodiment, in the five-membered-fused six-membered compound of formula II,

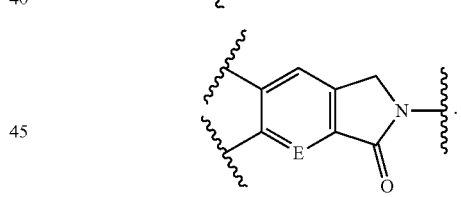

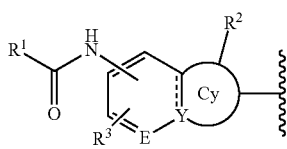

is
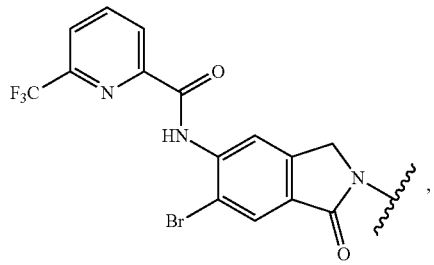,
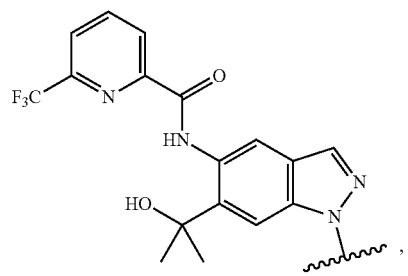,
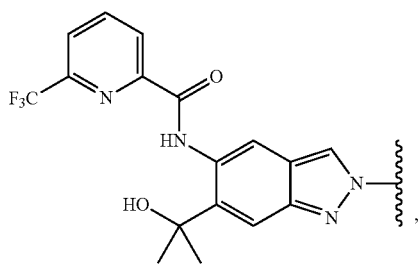,
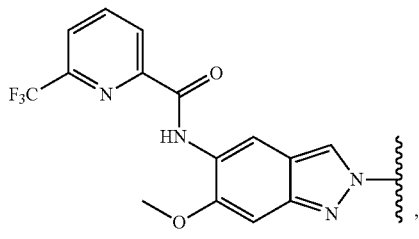,
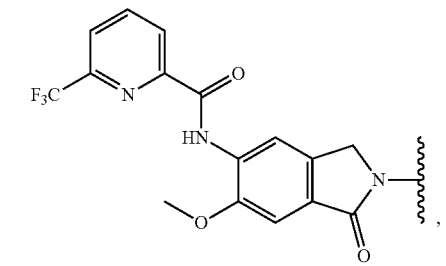,
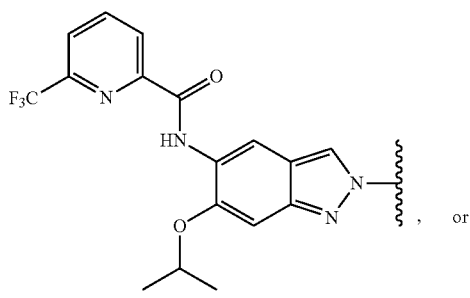, or
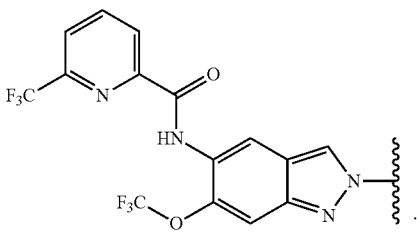 [SMILES: *n1cc2cc(NC(=O)c3cccc(C(F)(F)F)n3)c(OC(F)(F)F)cc2n1].
In a certain preferred embodiment, in the compound of formula III,
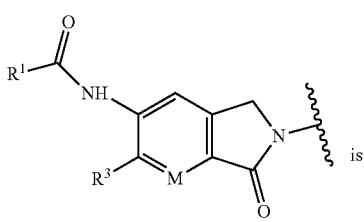 is
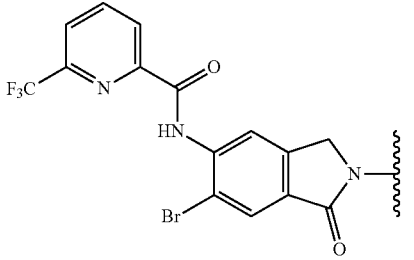 or
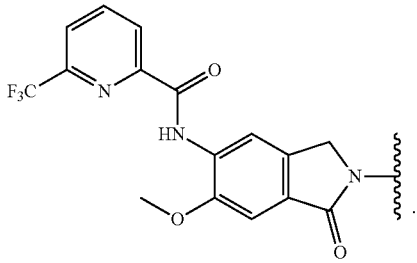.
In a certain preferred embodiment, $L_1$ is —CH$_2$— or —CH$_2$CH$_2$—.
In a certain preferred embodiment, L is —CH$_2$—, —CH$_2$CH$_2$—, or
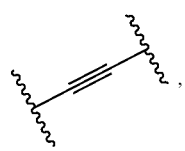 [SMILES: *C#C*],
more preferably —CH$_2$—.
In a certain preferred embodiment, $L_0$ is —CH$_2$— or —CH$_2$CH$_2$—.
In a certain preferred embodiment, $L_0$ is —CH$_2$— or —CH$_2$CH$_2$—, more preferably —CH$_2$—.

In a certain preferred embodiment, L$_2$ is absent,
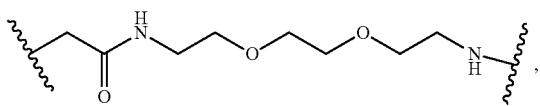
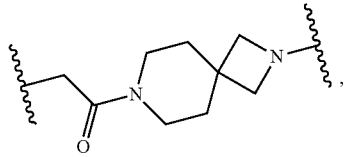
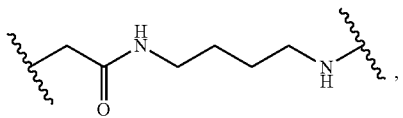
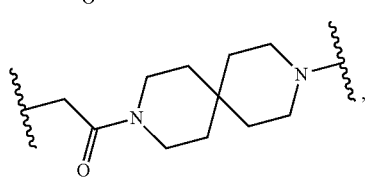
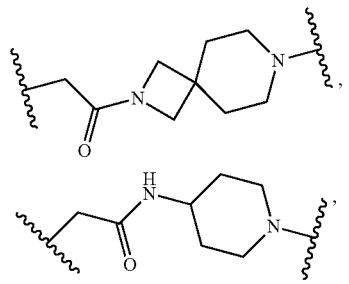
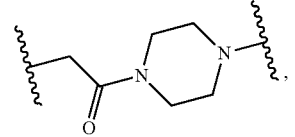
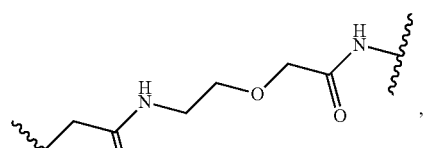
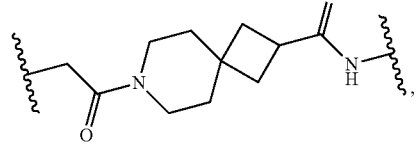
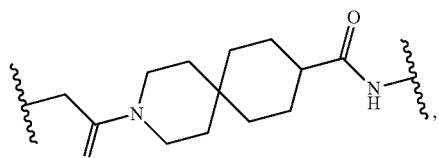
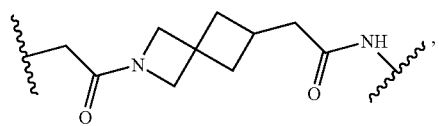
-continued
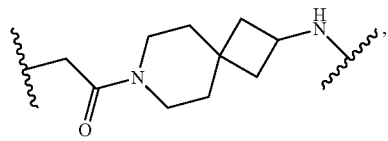
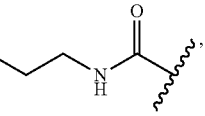
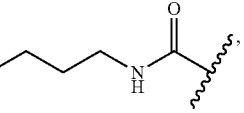
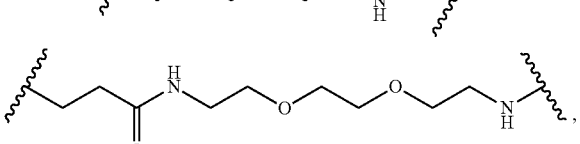
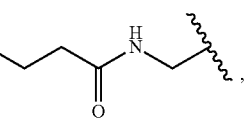
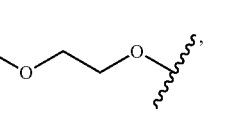
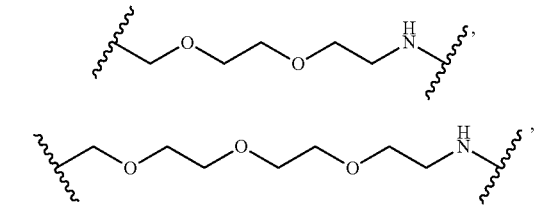
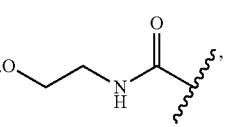
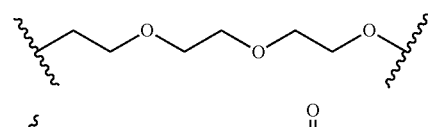
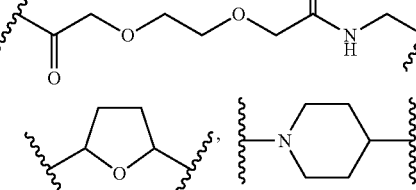
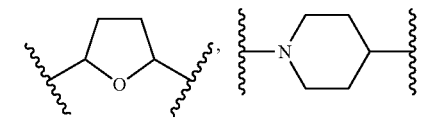
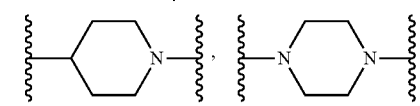
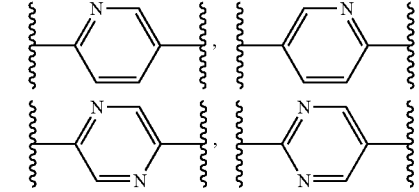

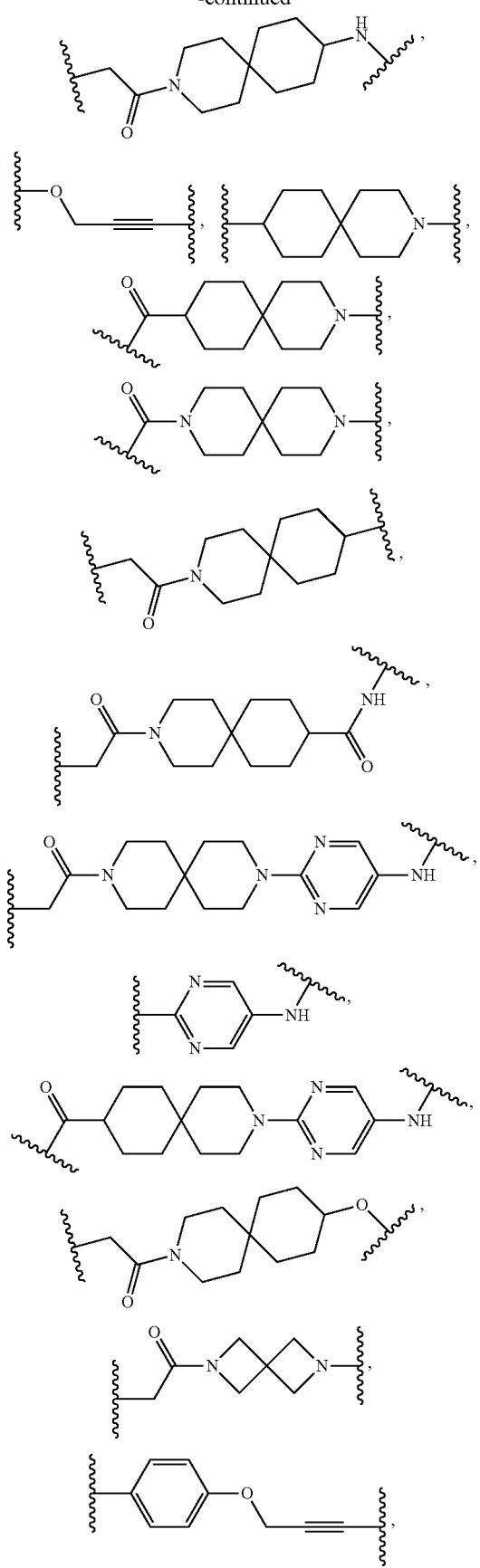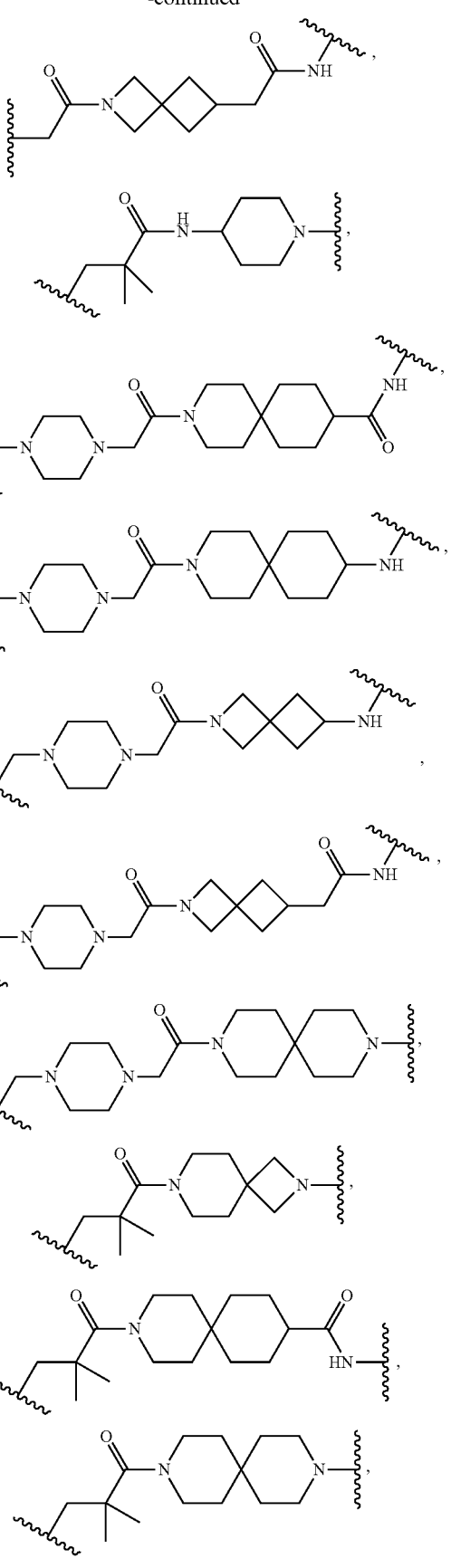

-continued
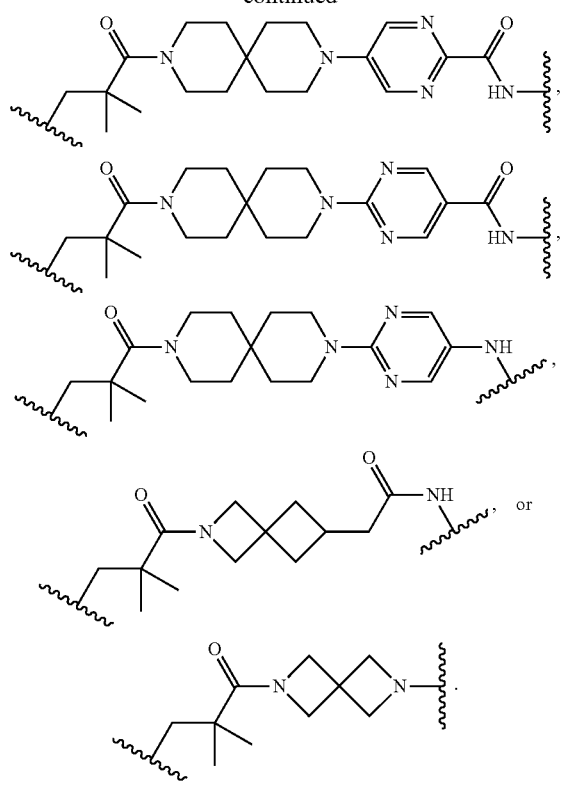
Preferably, L₂ is
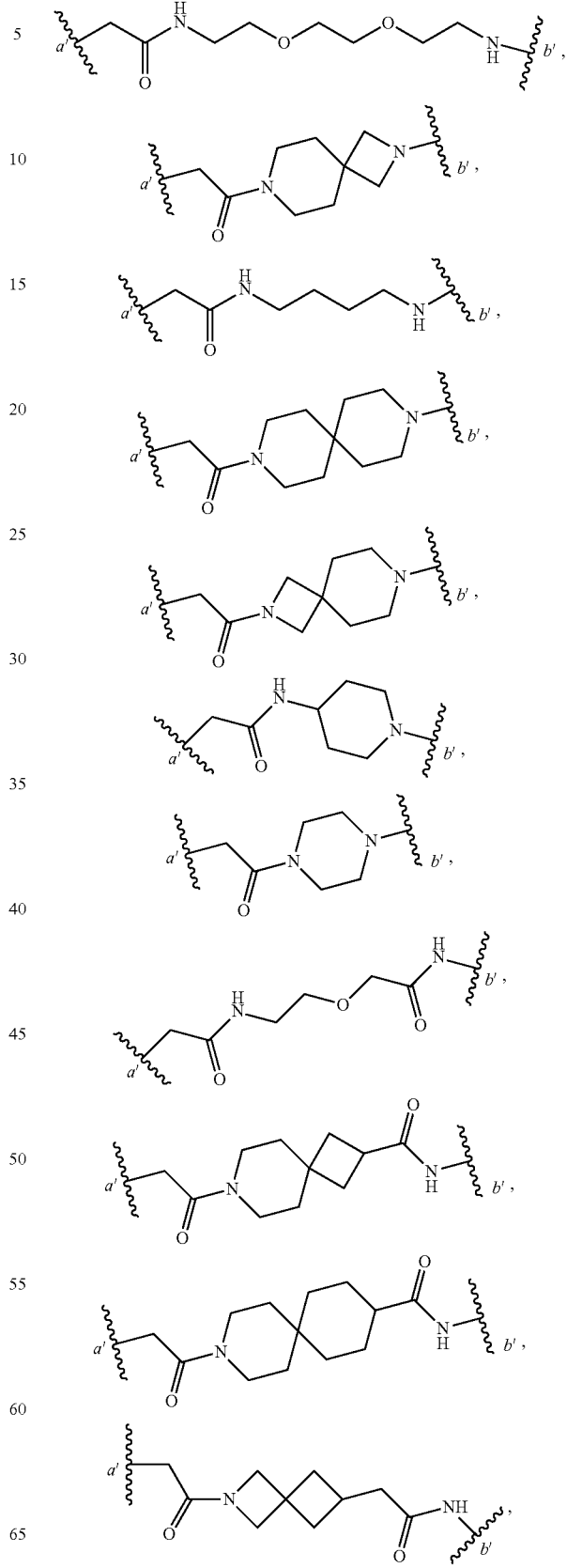
In a certain preferred embodiment, L₂ is absent,
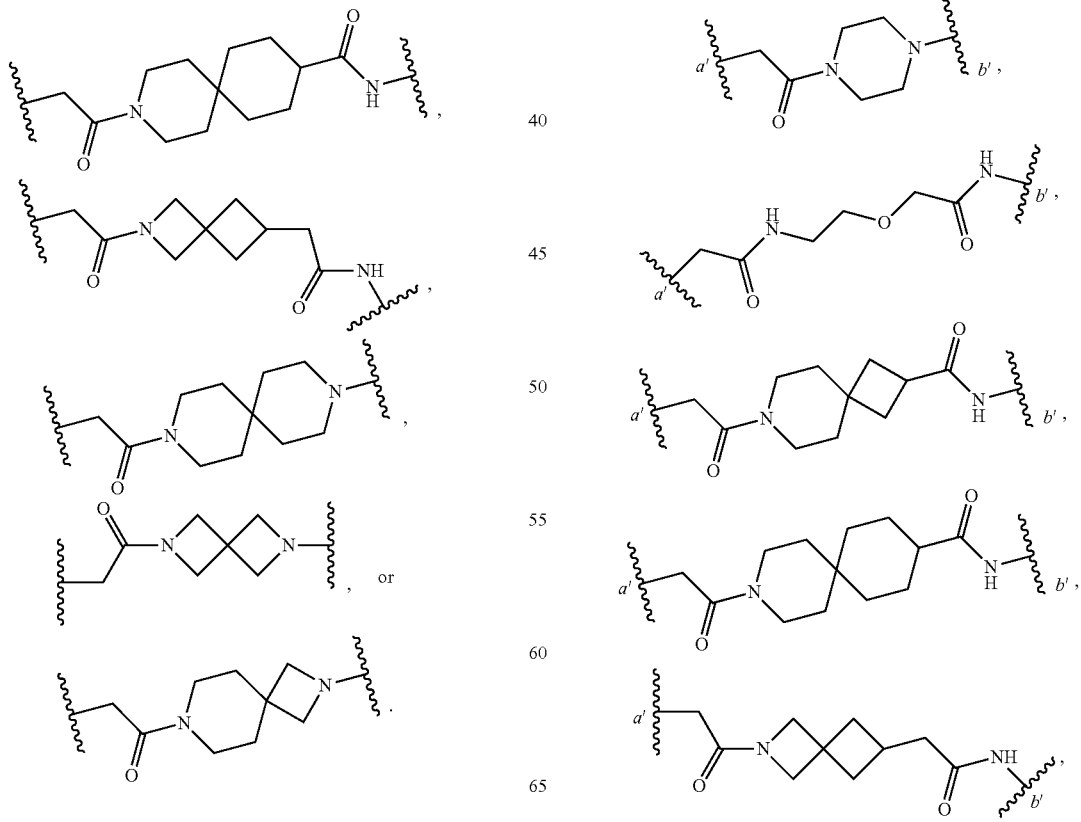

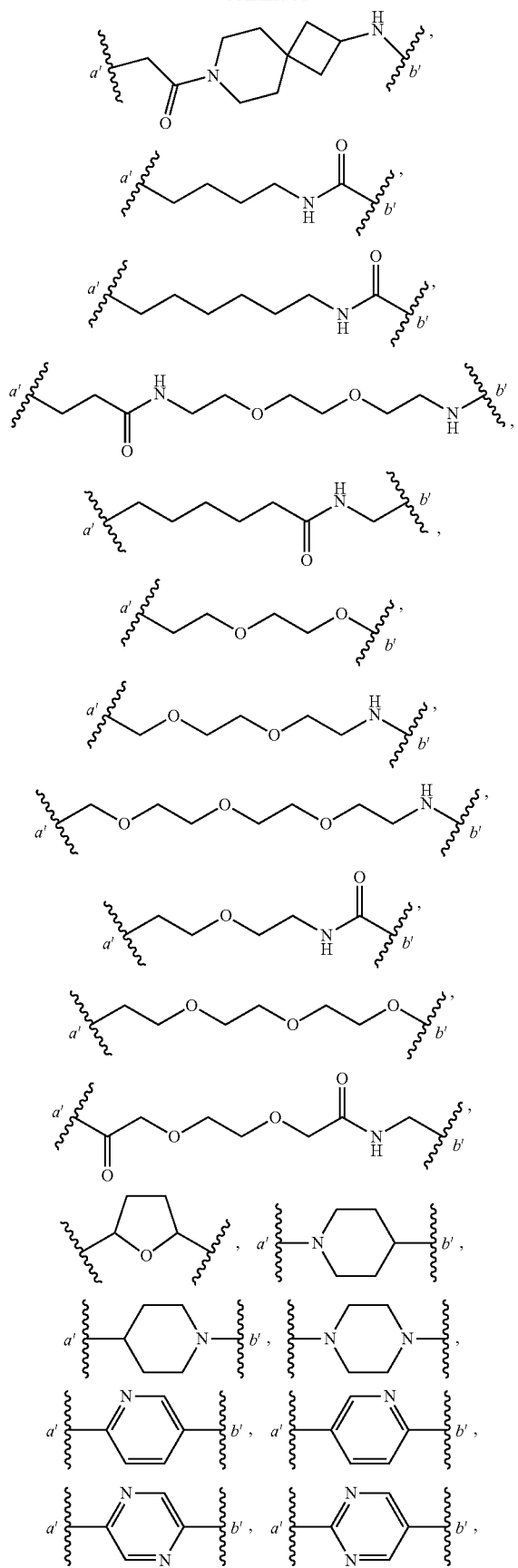

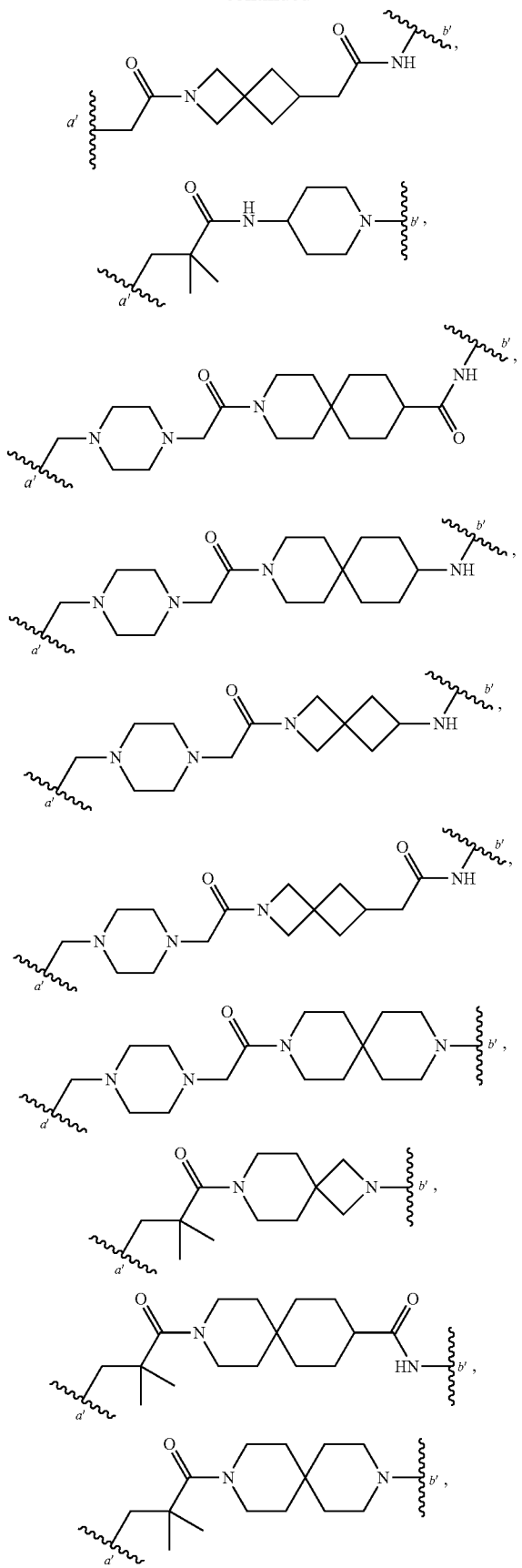
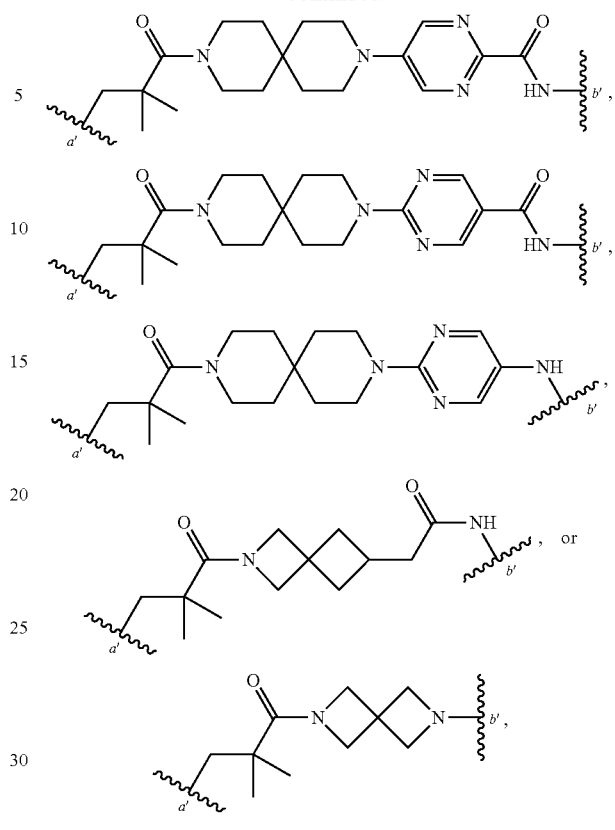
the a' end is attached to Cy$^a$ or
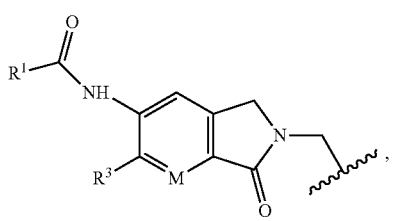
and the b' end is attached to LLM.
Preferably, L$_2$ is
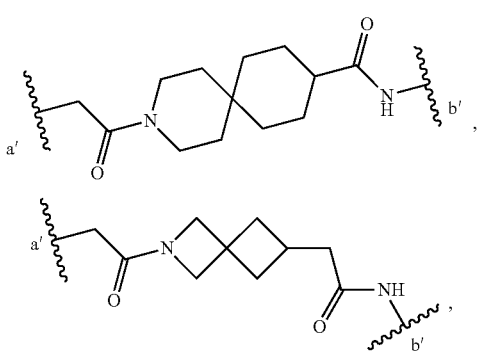

-continued

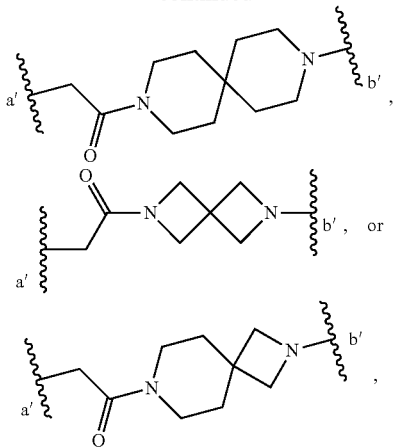

the a' end is attached to Cy$^a$ or

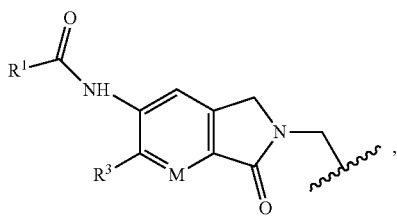

and the b' end is attached to LLM.

In a certain preferred embodiment, ring Cy is a 5-membered heteroaromatic ring, the heteroatom of the 5-membered heteroaromatic ring is N, and the number of heteroatoms is 1 or 2.

In a certain preferred embodiment, $R^1$ is unsubstituted 5- to 6-membered heteroaryl or 5- to 6-membered heteroaryl substituted by one or more than one $R^{1-1}$, the heteroatom of the 5- to 6-membered heteroaryl is N, and the number of heteroatoms is 1 or 2.

In a certain preferred embodiment, each $R^{1-1}$ is independently unsubstituted $C_1$-$C_6$ alkyl or $C_1$-$C_6$ alkyl substituted by one or more than one $R^{1-1-4}$.

In a certain preferred embodiment, each $R^{1-1-4}$ is independently halogen.

In a certain preferred embodiment, $R^3$ is unsubstituted $C_1$-$C_6$ alkoxy, $C_1$-$C_6$ alkoxy substituted by one or more than one $R^{3-7}$, unsubstituted $C_1$-$C_6$ alkyl, or $C_1$-$C_6$ alkyl substituted by one or more than one $R^{3-4}$.

In a certain preferred embodiment, when $R^3$ is unsubstituted $C_1$-$C_6$ alkyl or $C_1$-$C_6$ alkyl substituted by one or more than one $R^{3-4}$, ring $Cy^1$ is an 11-membered heterocyclic ring, the heteroatom of the 11-membered heterocyclic ring is N, and the number of heteroatoms is 1 or 2.

In a certain preferred embodiment, each $R^{3-4}$ is independently hydroxyl.

In a certain preferred embodiment, ring Cy$^a$ is

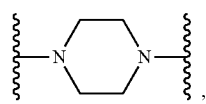

-continued

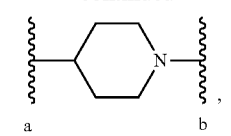

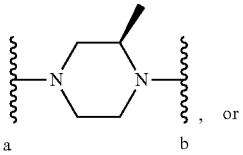

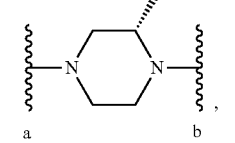

the a end is attached to $L_1$, and b is attached to $L_2$.

In a certain preferred embodiment, $L_3$ is unsubstituted

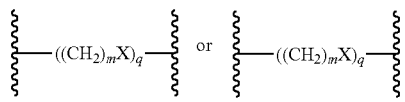

substituted by one or more than one $L_3^{-1}$; wherein m is an integer from 1 to 4, q is an integer from 1 to 6, and X is absent; $L_3^{-1}$ is independently unsubstituted $C_1$-$C_6$ alkyl.

In a certain preferred embodiment, $L_2$ is -$L_2^{-1}$-$L_2^{-2}$-$L_2^{-3}$-$L_2^{-4}$-$L_2^{-5}$-$L_2^{-6}$-$L_2^{-7}$; $L_2^{-1}$-$L_2^{-2}$ is

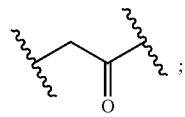 [SMILES: *CC(*)=O]

$L_2^{-3}$, $L_2^{-4}$, $L_2^{-5}$, $L_2^{-6}$, and $L_2^{-7}$ are independently absent,

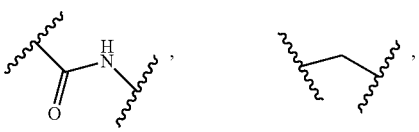

unsubstituted

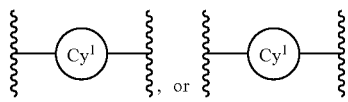

or substituted by one or more than one $L_1^{1-2}$, and ring $Cy^1$ is a 7- to 11-membered heterocyclic ring; the heteroatom of the 7- to 11-membered heterocyclic ring is N, and the number of heteroatoms is 1 or 2.

In a certain preferred embodiment, ring Cy¹ is

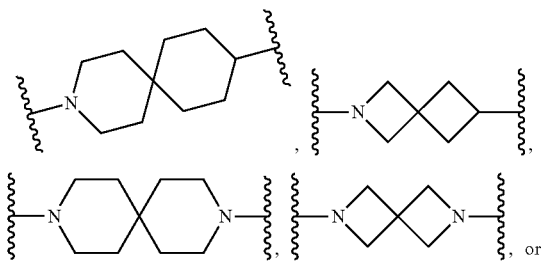

In a certain preferred embodiment, when Cy$^a$ is

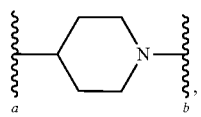

the a end is attached to L₁, b is attached to L₂, and ring Cy¹ is

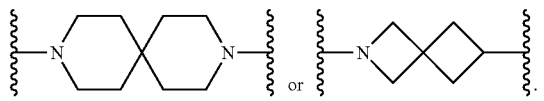

In a certain preferred embodiment, L₂ is

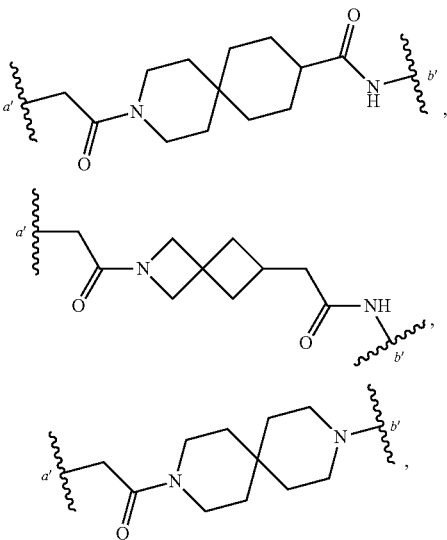

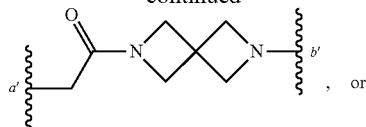

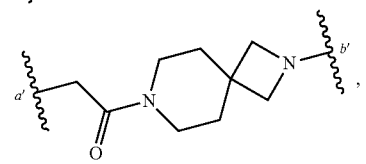

the a' end is attached to Cy$^a$ or

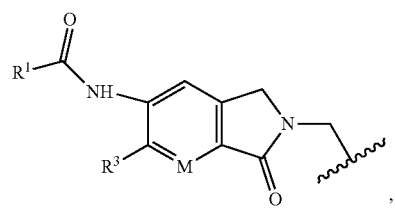

and the b' end is attached to LLM.

In a certain preferred embodiment, in the five-membered-fused six-membered compound of formula II, ring Cy is a 5-membered heteroaromatic ring, the heteroatom of the 5-membered heteroaromatic ring is N, and the number of heteroatoms is 1 or 2;

∥ is ∥;

Q is C;

E is CH;

Y is C;

R¹ is unsubstituted 5- to 6-membered heteroaryl or 5- to 6-membered heteroaryl substituted by one or more than one R$^{1-1}$, the heteroatom of the 5- to 6-membered heteroaryl is N, and the number of heteroatoms is 1 or 2;

each R$^{1-1}$ is independently unsubstituted $C_1$-$C_6$ alkyl or $C_1$-$C_6$ alkyl substituted by one or more than one R$^{1-1-4}$;

each R$^{1-1-4}$ is independently halogen;

R² is hydrogen;

R³ is unsubstituted $C_1$-$C_6$ alkoxy, $C_1$-$C_6$ alkoxy substituted by one or more than one R$^{3-7}$, unsubstituted $C_1$-$C_6$ alkyl, or $C_1$-$C_6$ alkyl substituted by one or more than one R$^{3-4}$;

each R$^{3-4}$ is independently hydroxyl;

L₁ is —CH₂—;

L₀ is —CH₂—;

ring Cy$^a$ is

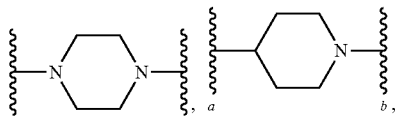

-continued

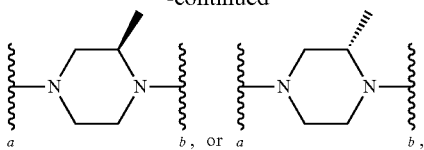

the a end is attached to $L_1$, and b is attached to $L_2$;

ring $Cy^3$ is an unsubstituted 5- to 6-membered heterocyclic ring or a 5- to 6-membered heterocyclic ring substituted by one or more than one $Cy^{3-1}$; the heteroatom of the 5- to 6-membered heterocyclic ring is N, S, or O, and the number of heteroatoms is 1;

each $Cy^{3-1}$ is independently oxo;

ring $Cy^4$ is unsubstituted 5- to 8-membered heterocycloalkyl or 5- to 8-membered heterocycloalkyl substituted by one or more than one $Cy^{4-1}$; the heteroatom of the 5- to 8-membered heterocyclic ring is selected from one or more than one of N, S, and O, and the number of heteroatoms is 1, 2, or 3;

each $Cy^{4-1}$ is independently oxo;

ring $Cy^5$ is an unsubstituted 5- to 6-membered heterocyclic ring or a 5- to 6-membered heterocyclic ring substituted by one or more than one $Cy^{5-1}$; the heteroatom of the 5- to 6-membered heterocyclic ring is N, S, or O, and the number of heteroatoms is 1;

each $Cy^{5-1}$ is hydroxyl;

ring $Cy^6$ is an unsubstituted benzene ring;

ring $Cy^7$ is an unsubstituted 5- to 6-membered heteroaromatic ring or a 5- to 6-membered heteroaromatic ring substituted by one or more than one $Cy^{7-1}$; the heteroatom of the 5- to 6-membered heteroaromatic ring is N, S, or O, and the number of heteroatoms is 2;

each $Cy^{7-1}$ is independently $C_1$-$C_6$ alkyl;

each $R^5$ is independently halogen;

$L_3$ is unsubstituted

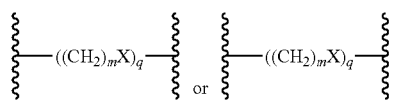

substituted by one or more than one $L_3^{-1}$; wherein m is an integer from 1 to 4, q is an integer from 1 to 6, and X is absent; $L_3^{-1}$ is independently unsubstituted $C_1$-$C_6$ alkyl;

$L_2$ is -$L_2^{-1}$-$L_2^{-2}$-$L_2^{-3}$-$L_2^{-4}$-$L_2^{-5}$-$L_2^{-6}$-$L_2^{-7}$; $L_2^{1}$-$L_2^{-2}$ is

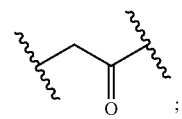 [SMILES: *CC(*)=O]

$L_2^{-3}$, $L_2^{-4}$, $L_2^{-5}$, $L_2^{-6}$, and $L_2^{-7}$ are independently absent,

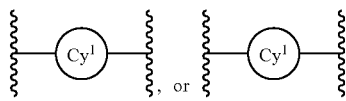

unsubstituted

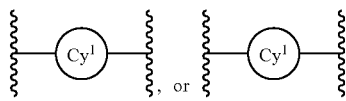

substituted by one or more than one $L_1^{1-2}$, and ring $Cy^1$ is a 7- to 11-membered heterocyclic ring; the heteroatom of the 7- to 11-membered heterocyclic ring is N, and the number of heteroatoms is 1 or 2;

when $R^3$ is unsubstituted $C_1$-$C_6$ alkyl or $C_1$-$C_6$ alkyl substituted by one or more than one $R^{3-4}$, ring $Cy^1$ is an 11-membered heterocyclic ring, the heteroatom of the 11-membered heterocyclic ring is N, and the number of heteroatoms is 1 or 2;

when $Cy^a$ is

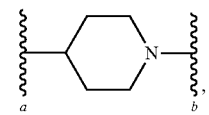

ring $Cy^1$ is

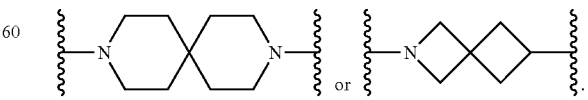

In a certain preferred embodiment, the five-membered-fused six-membered compound of formula II is any one of the following compounds:

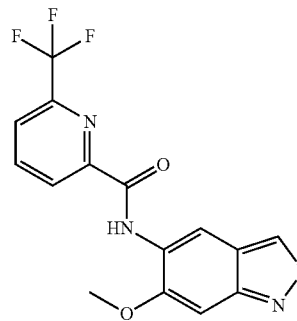
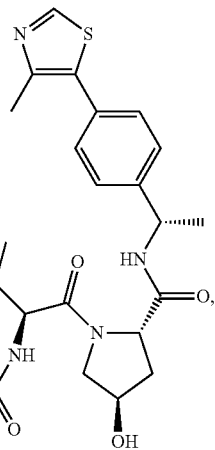
III-29
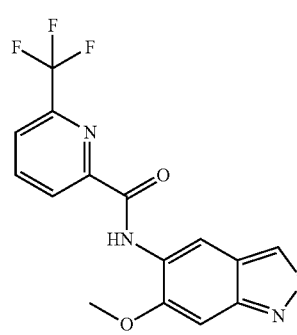
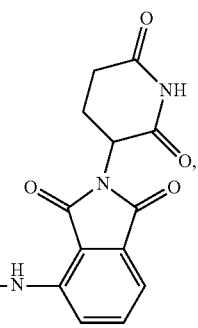
III-30
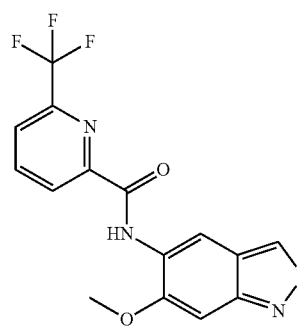
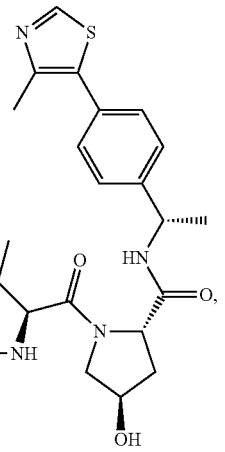
III-31

III-34
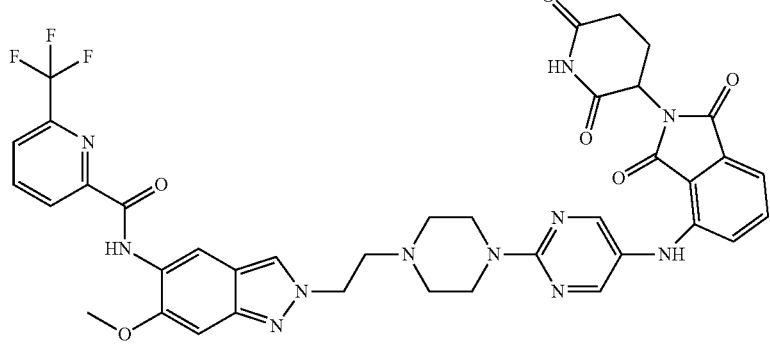
III-35
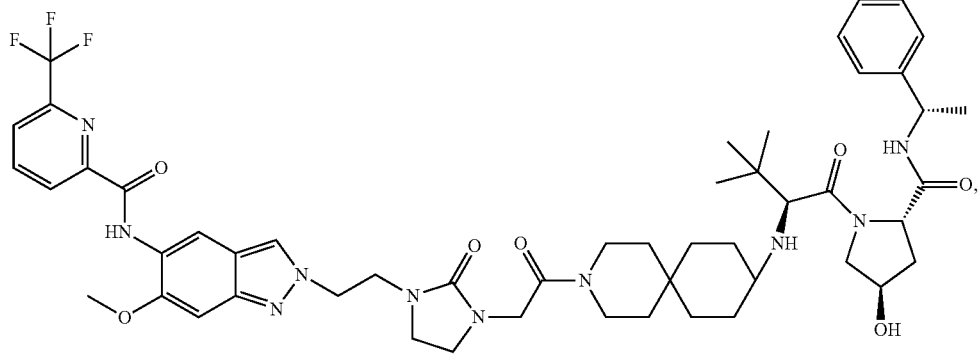
III-36
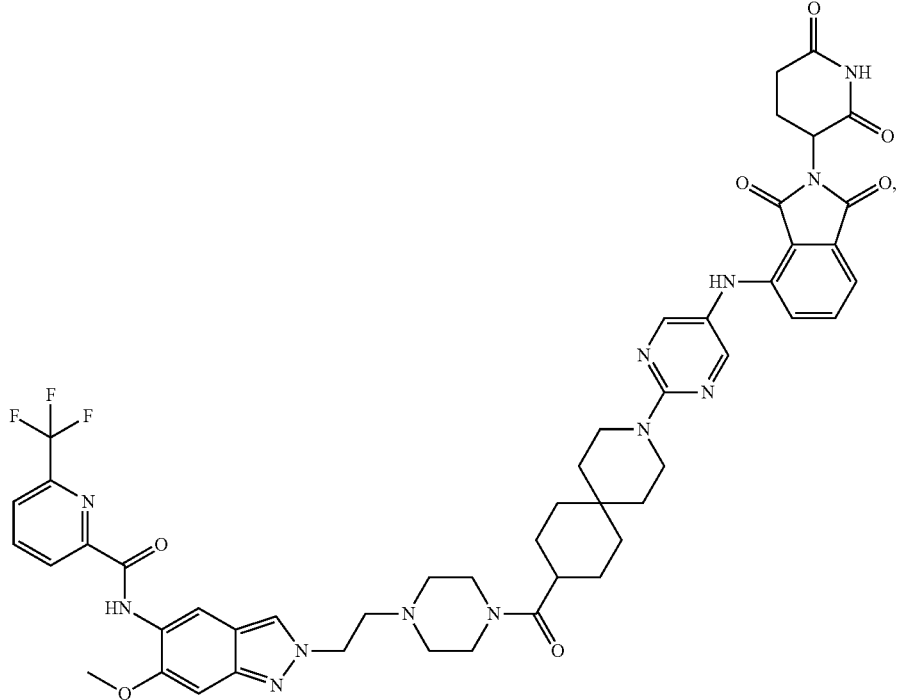

III-2
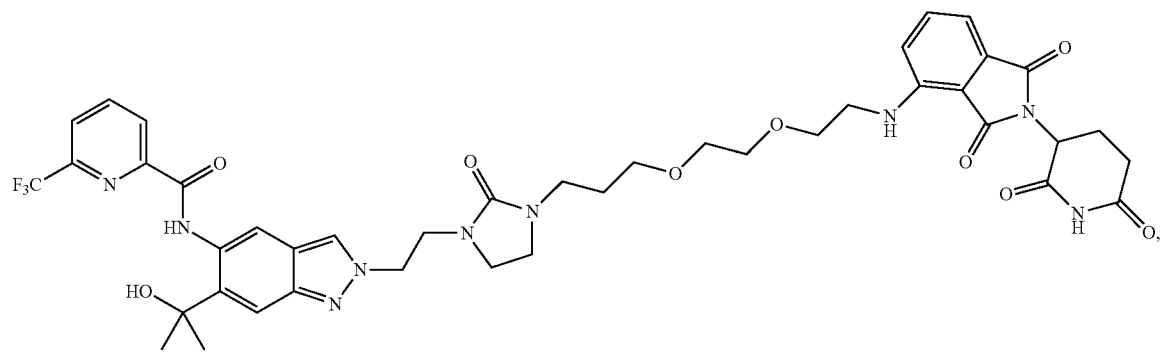
III-5
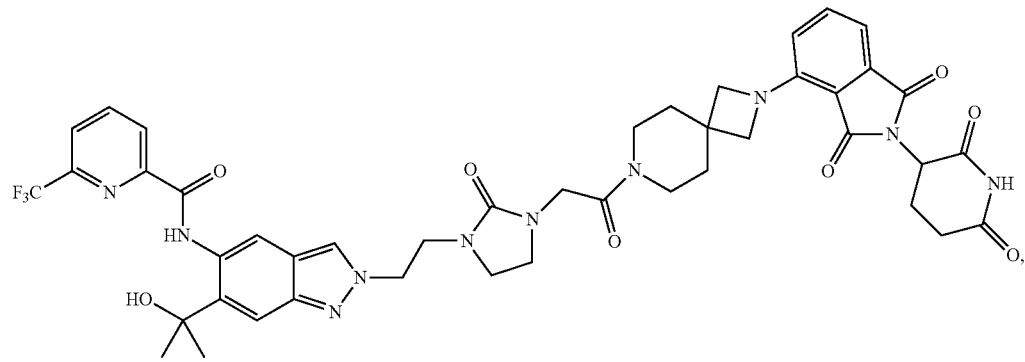
III-10
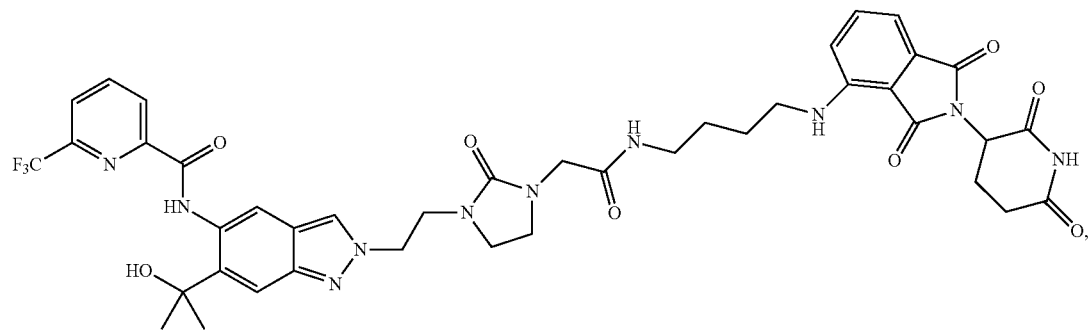
III-11
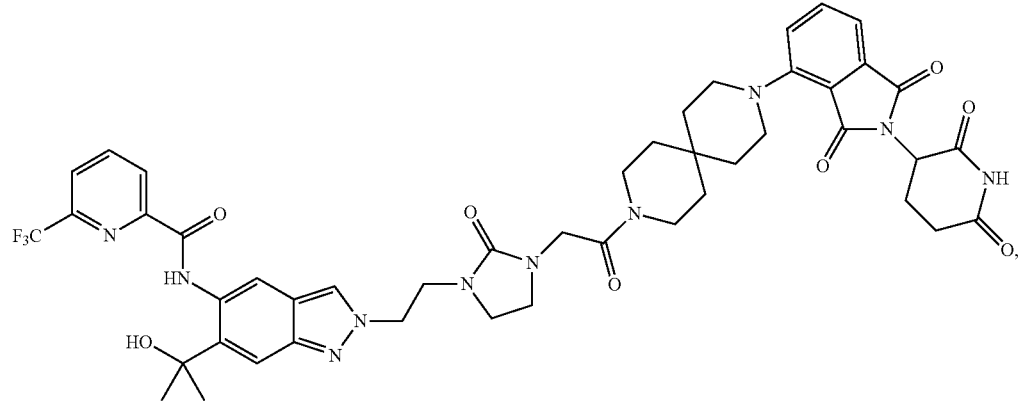

III-12
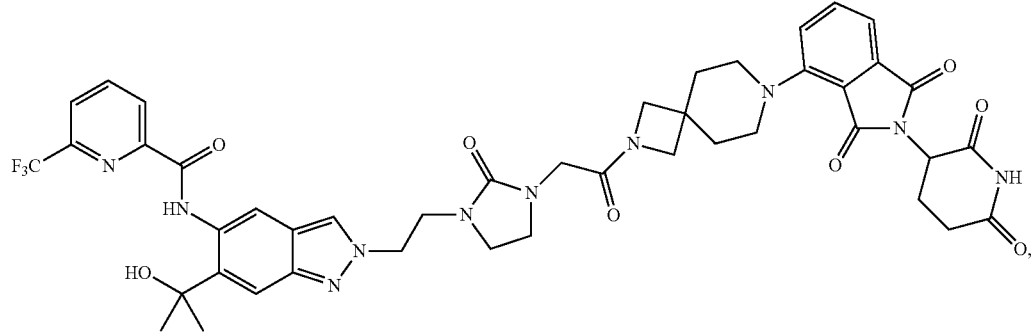
III-13
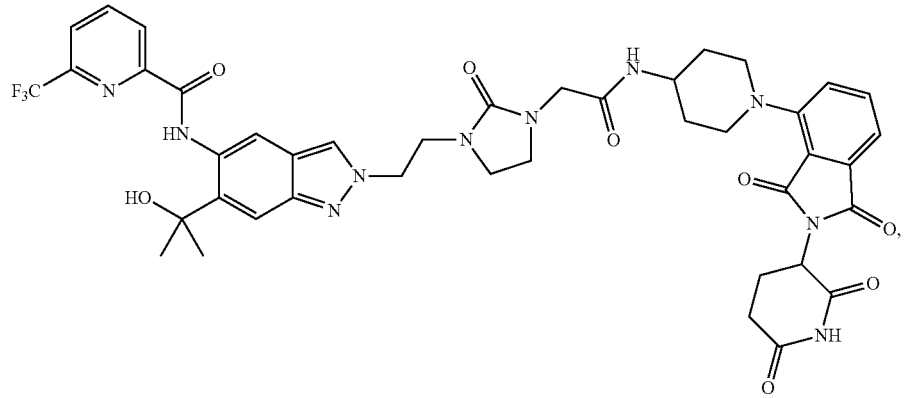
III-14
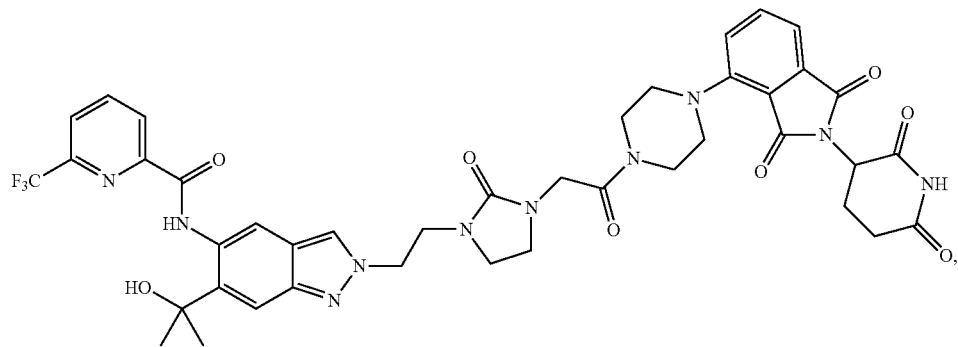
III-15
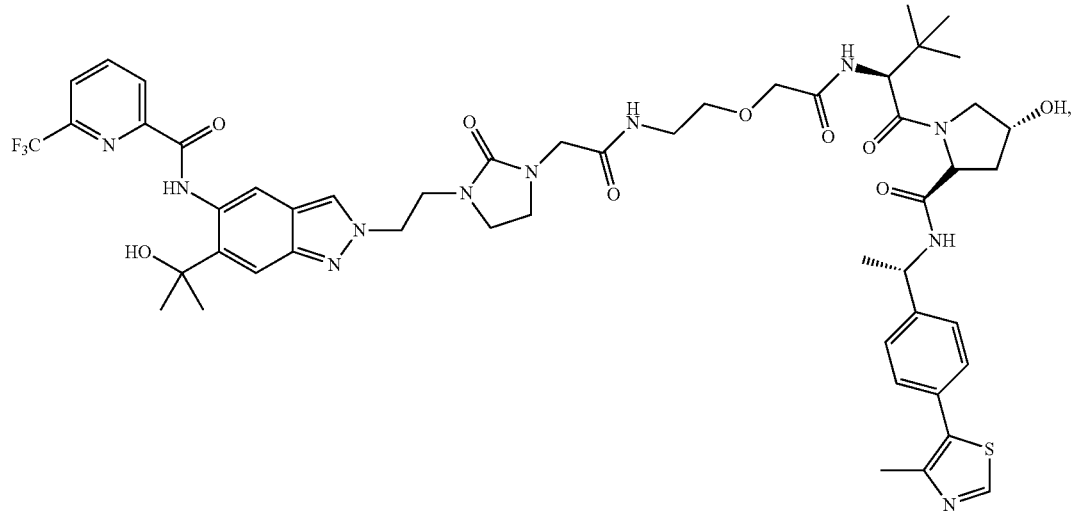

III-16
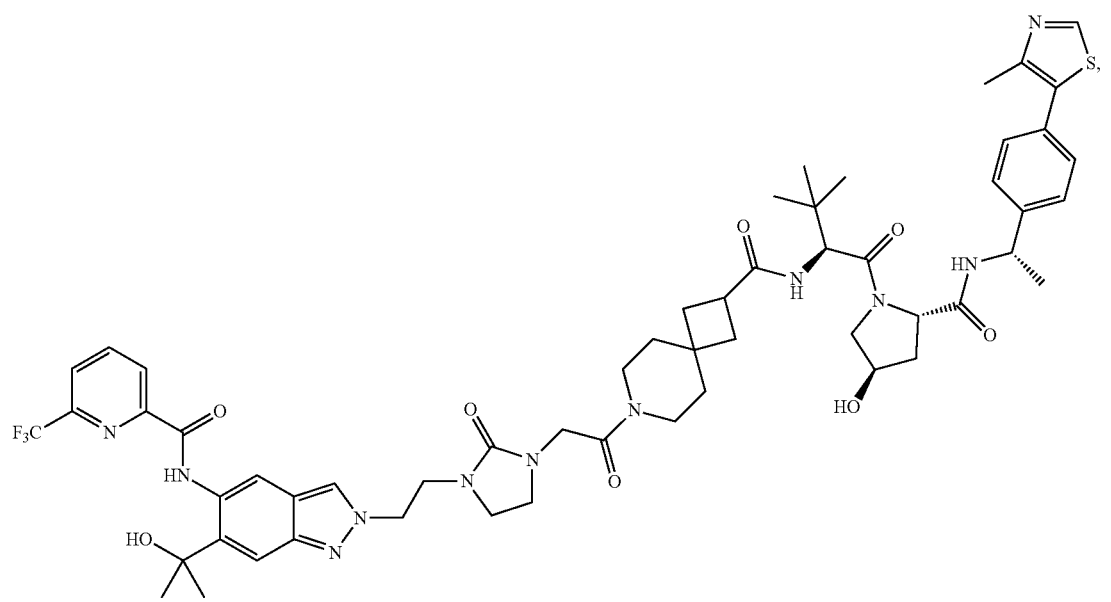
III-17
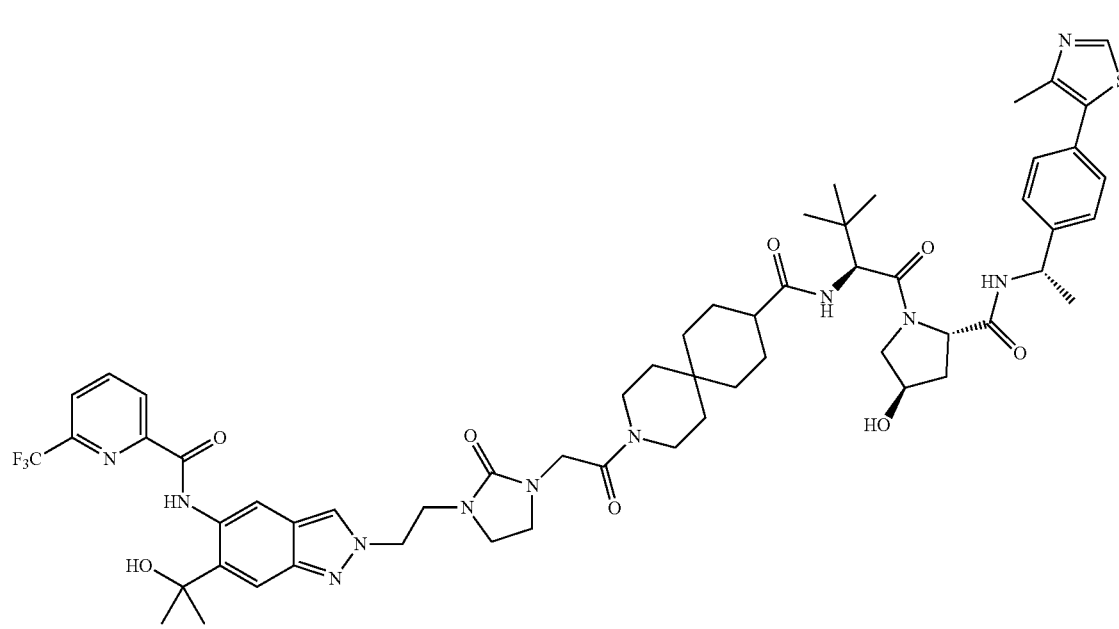
III-18
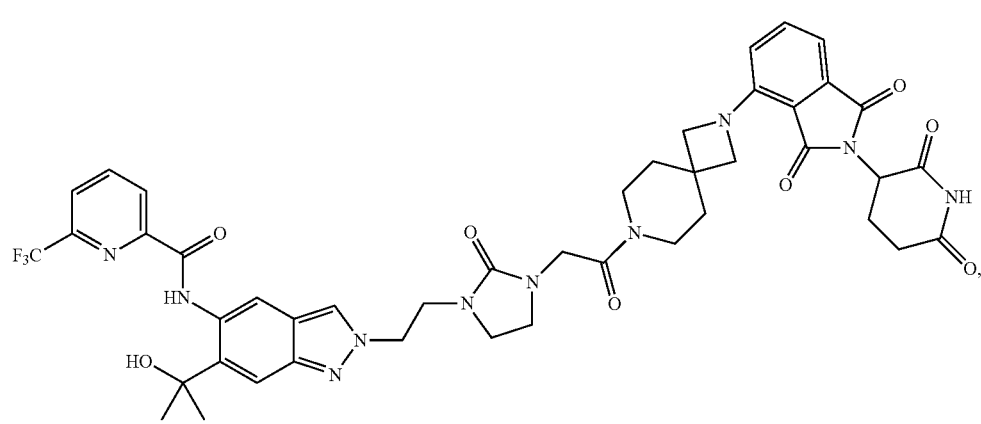

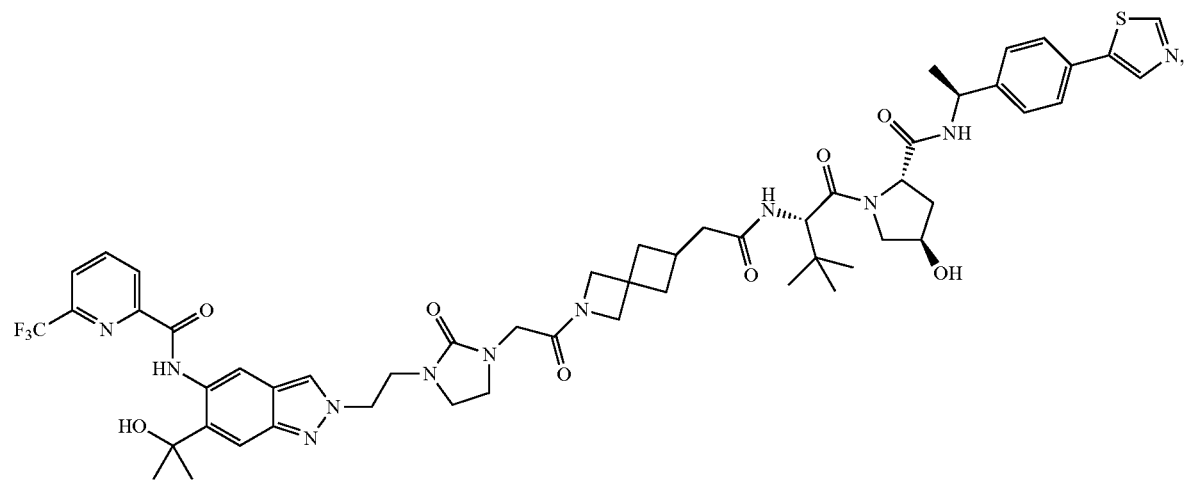
III-19
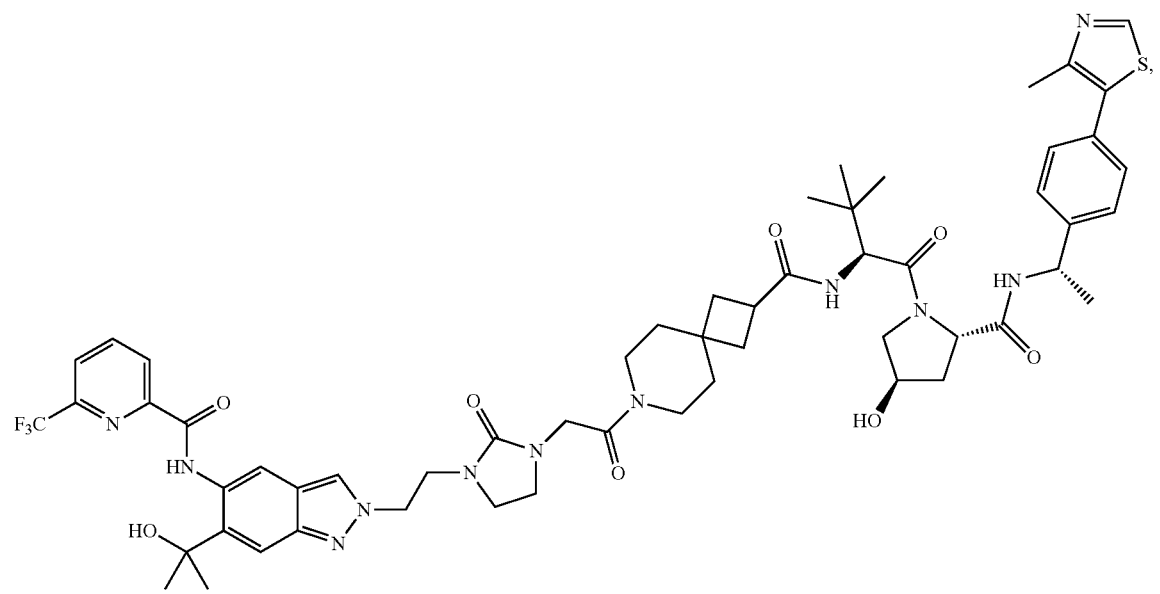
III-20

-continued
III-21
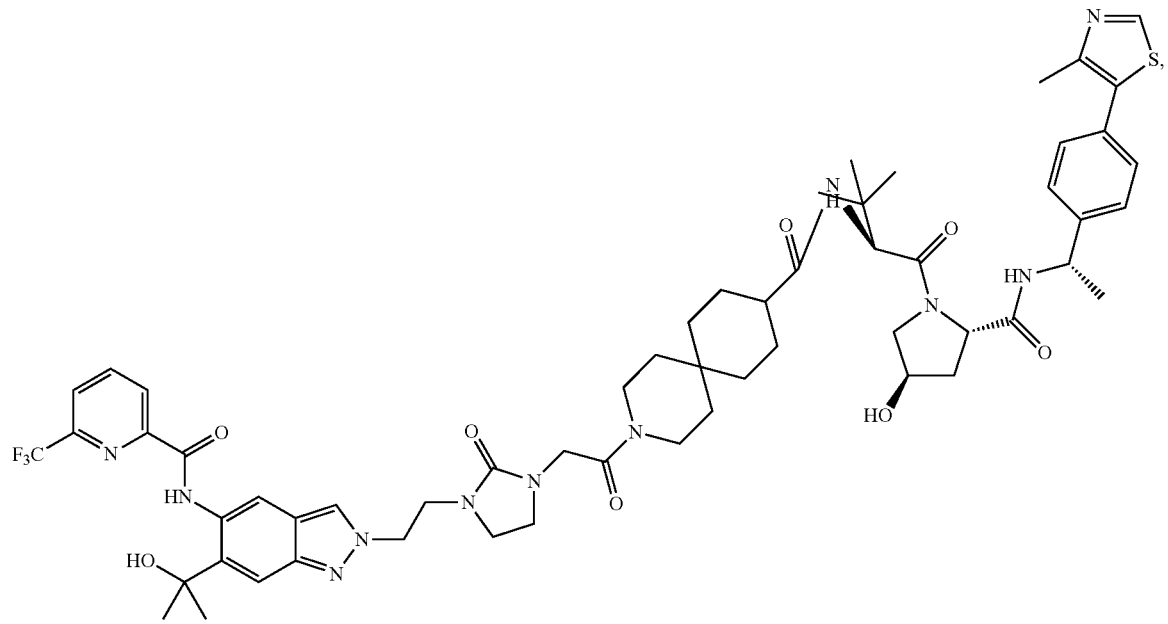
III-22
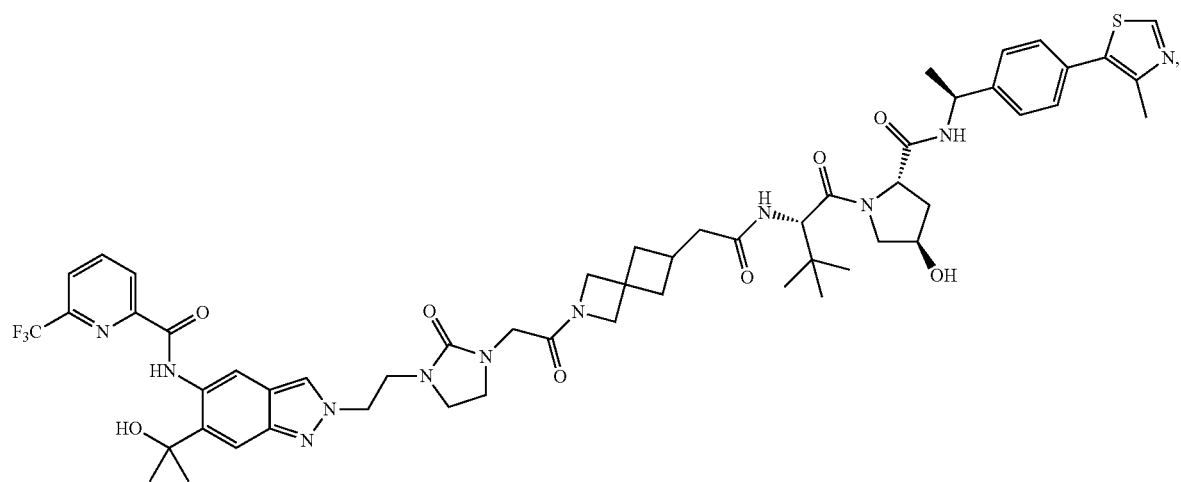
III-23
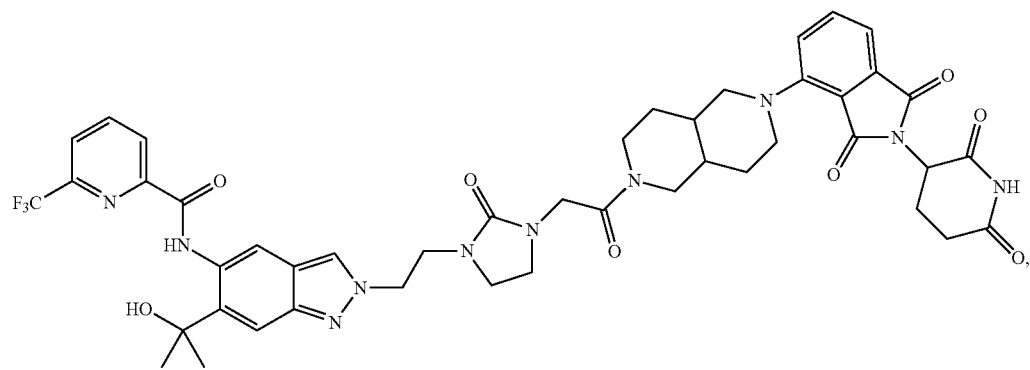

III-28
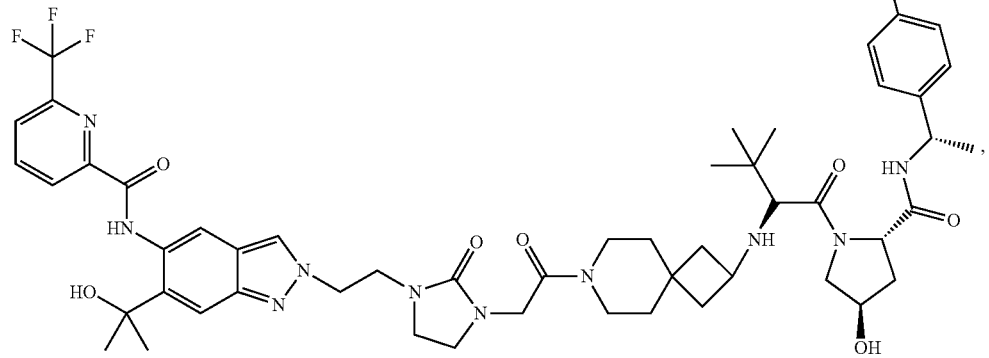
III-38
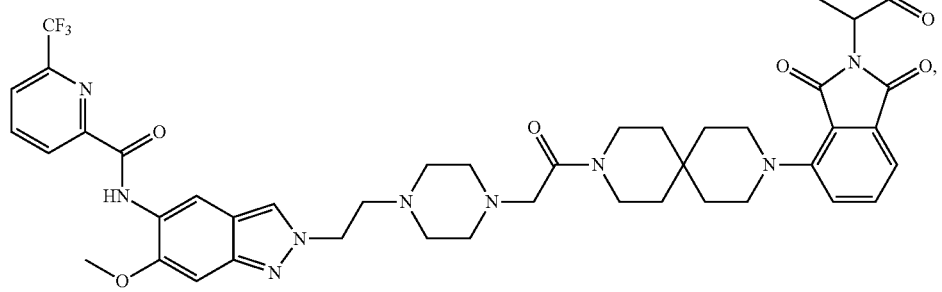
III-39
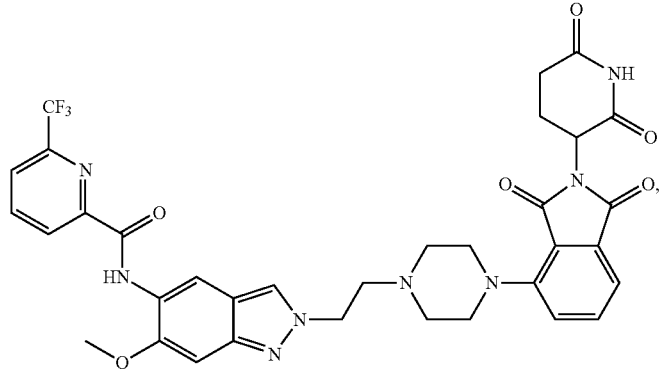
III-40
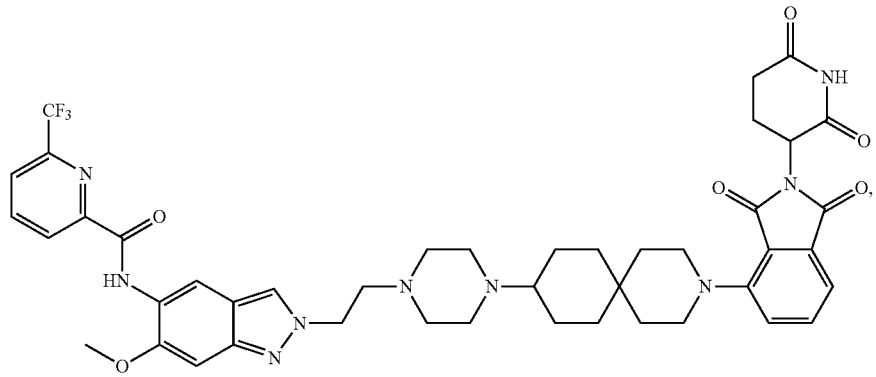

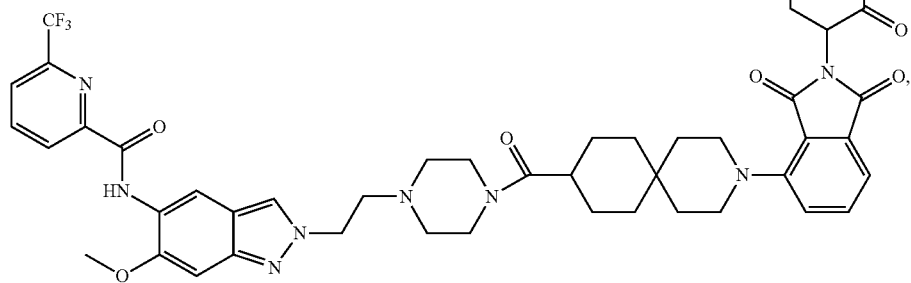
III-41
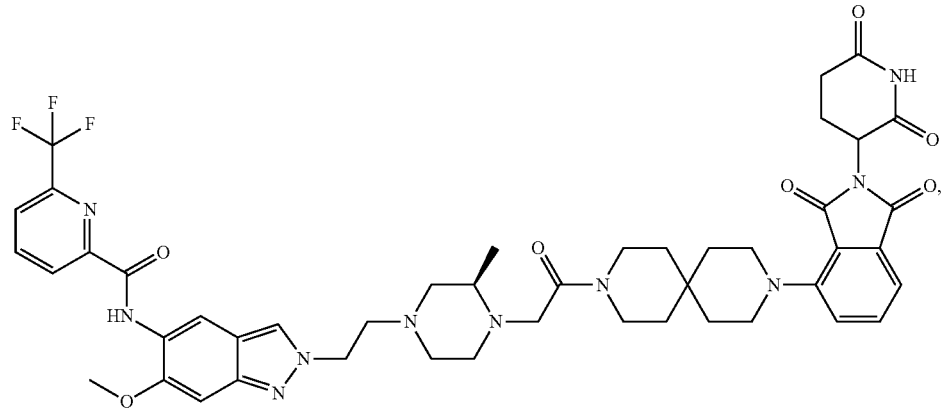
III-45
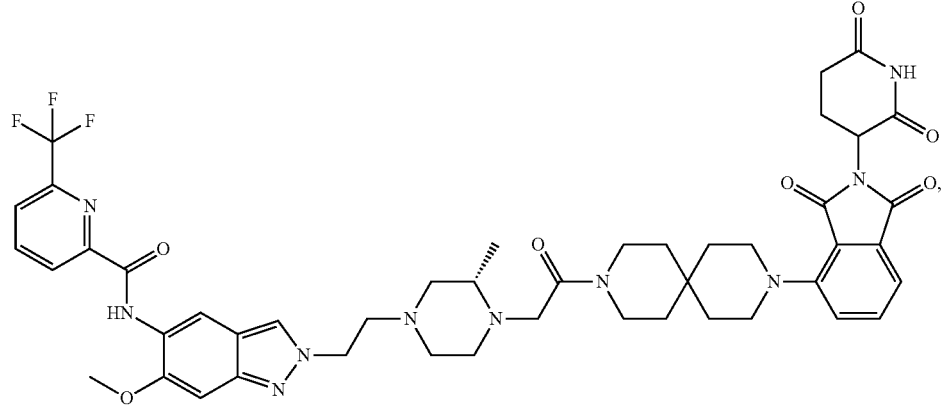
III-46

-continued
III-47
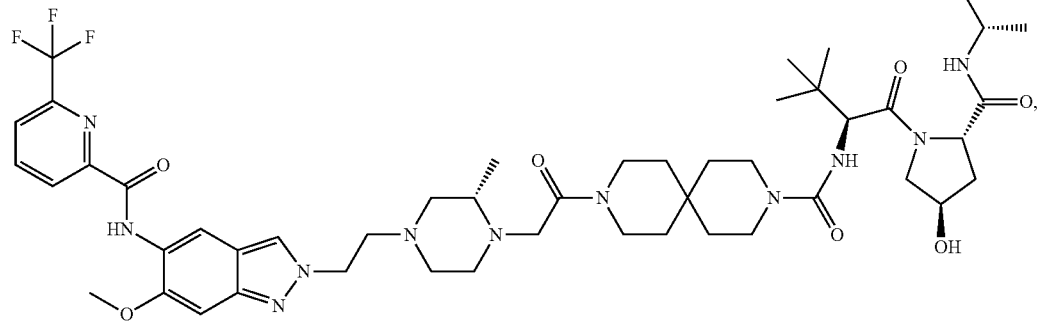
III-48
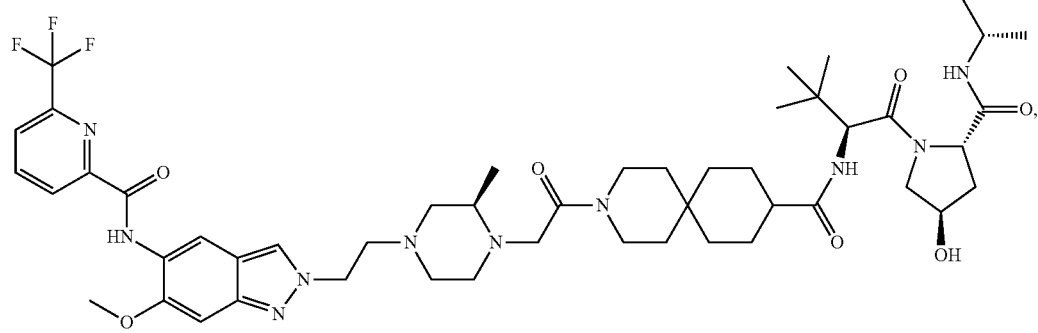
III-50
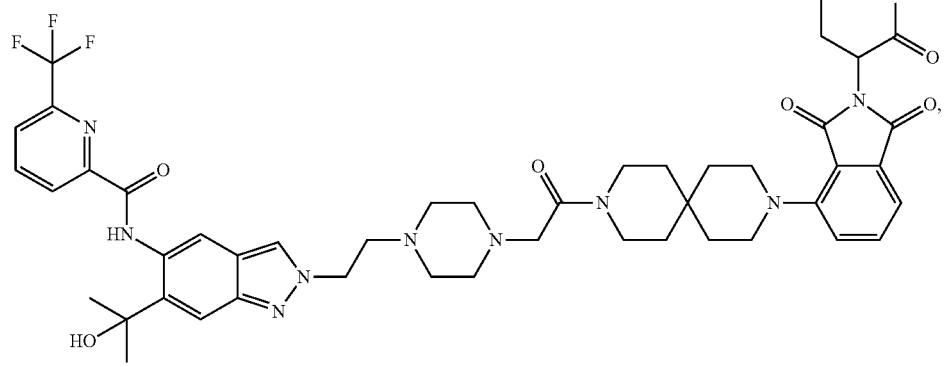

-continued
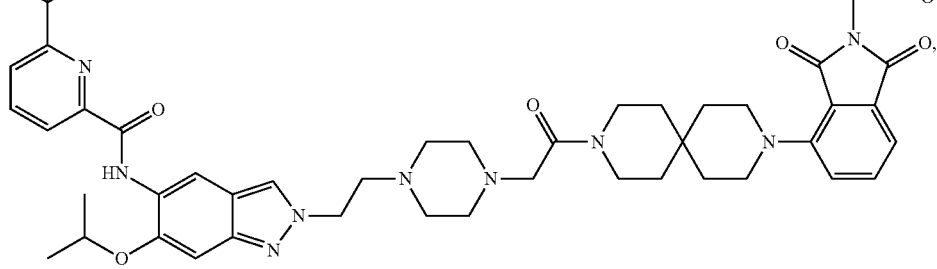
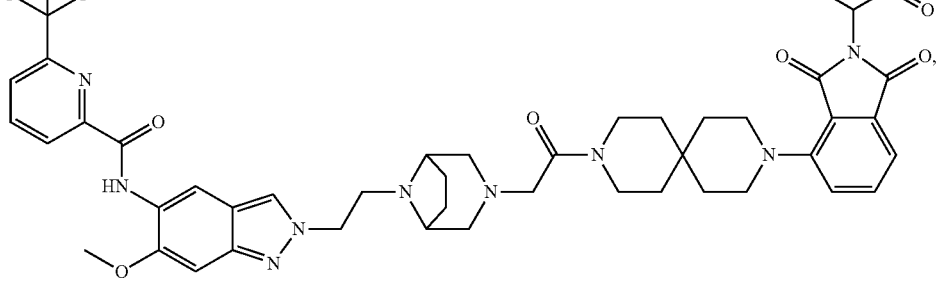
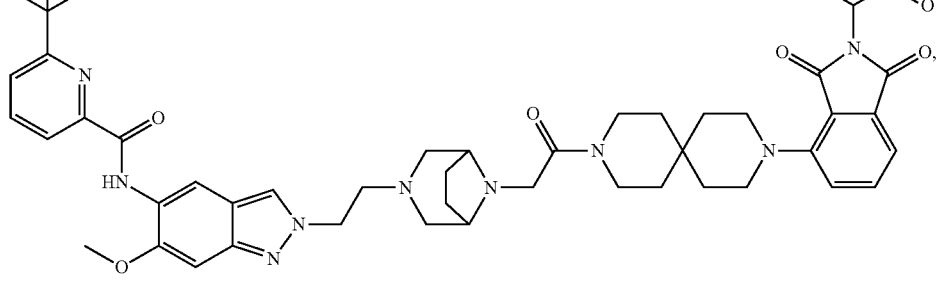
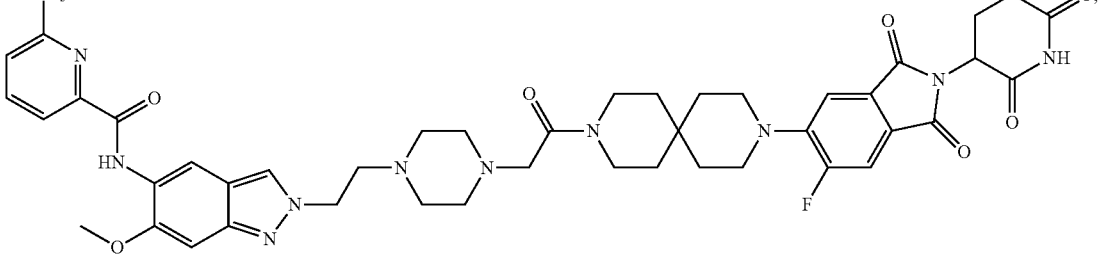

III-56
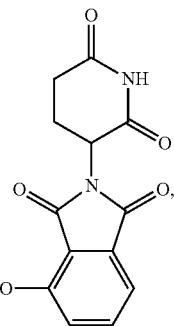
III-57
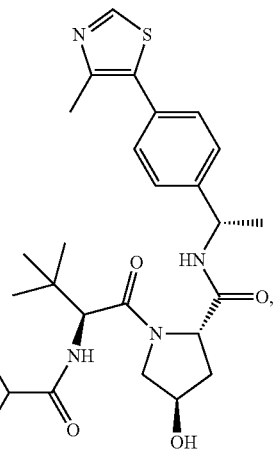
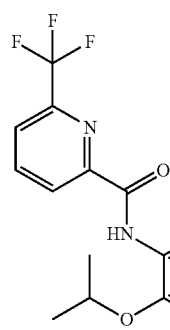
III-60
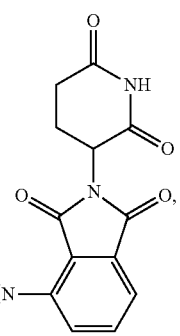
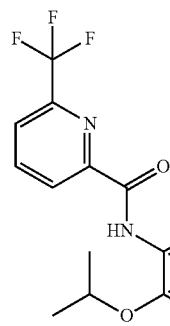

III-61
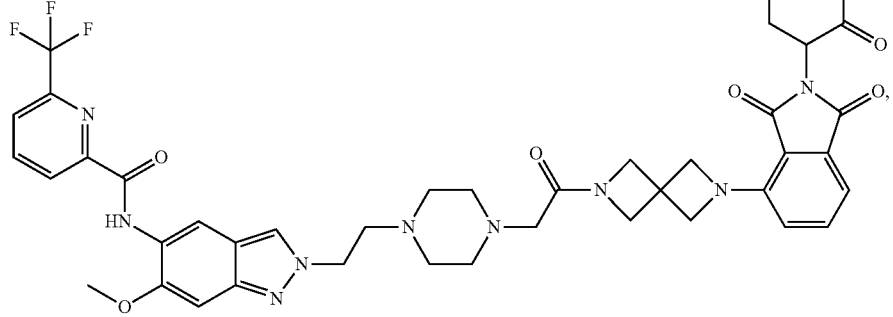
III-62
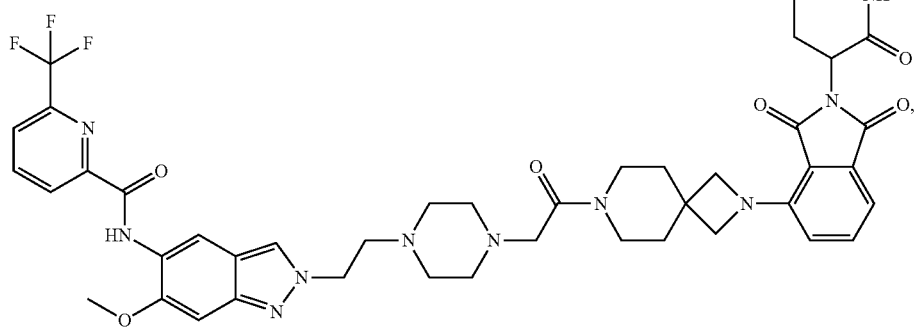
III-63
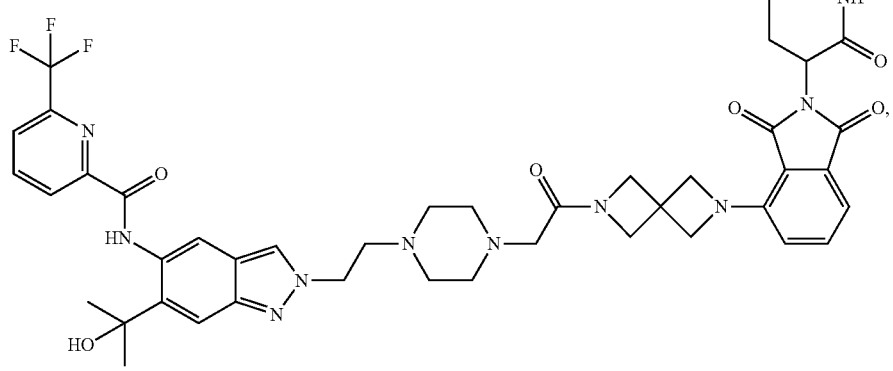
III-65
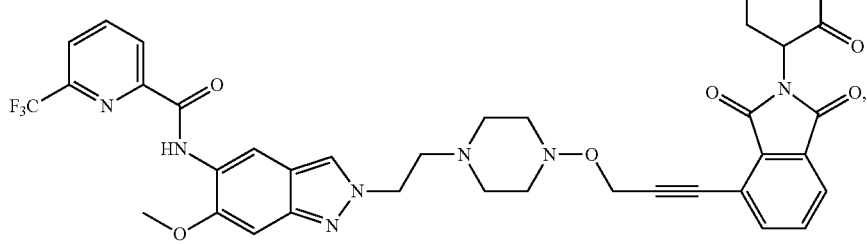

III-66
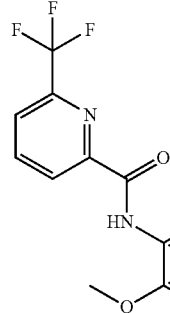 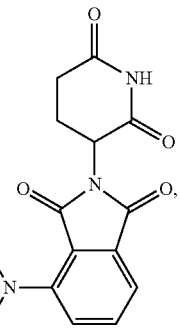
III-67
 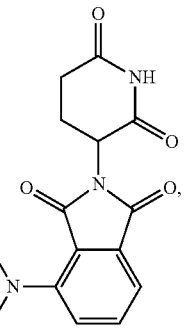
III-68
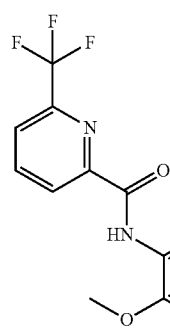 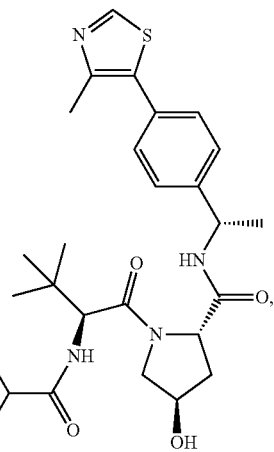

III-69
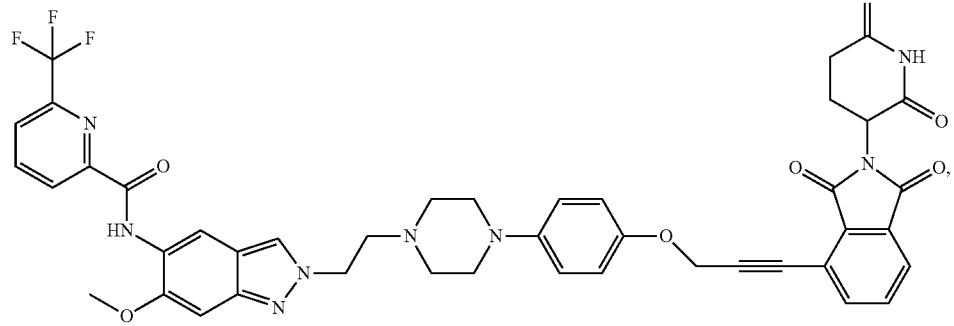
III-70
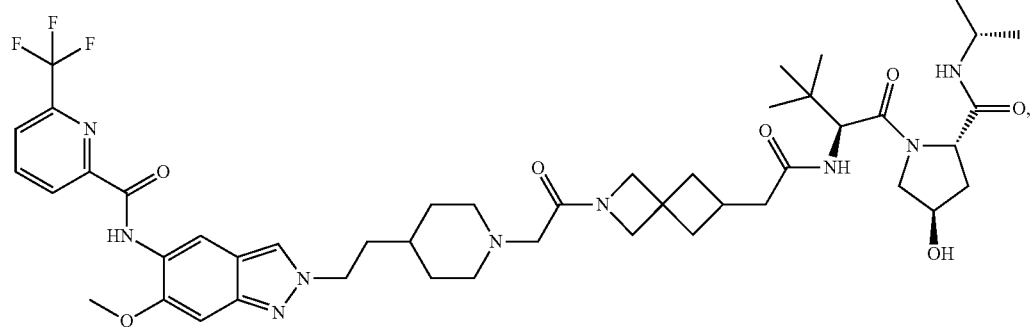
III-71
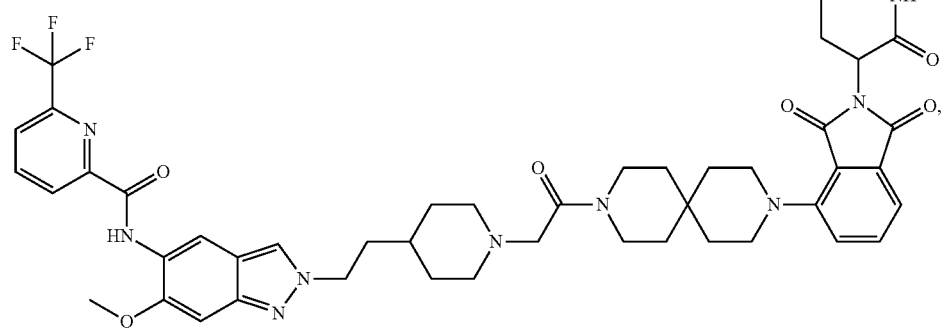

III-72
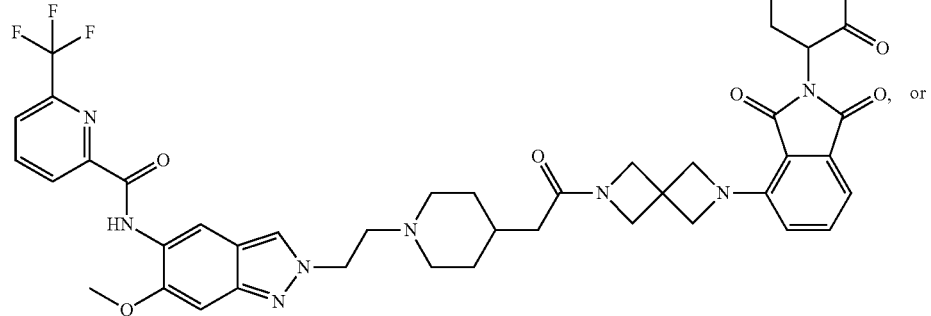
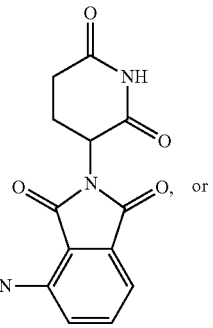
III-73
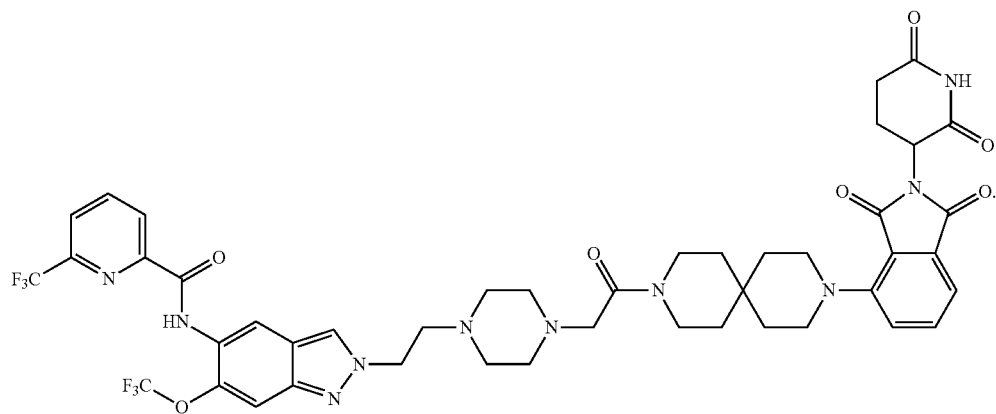
In a certain preferred embodiment, the compound of formula III is any one of the following compounds:
III-1
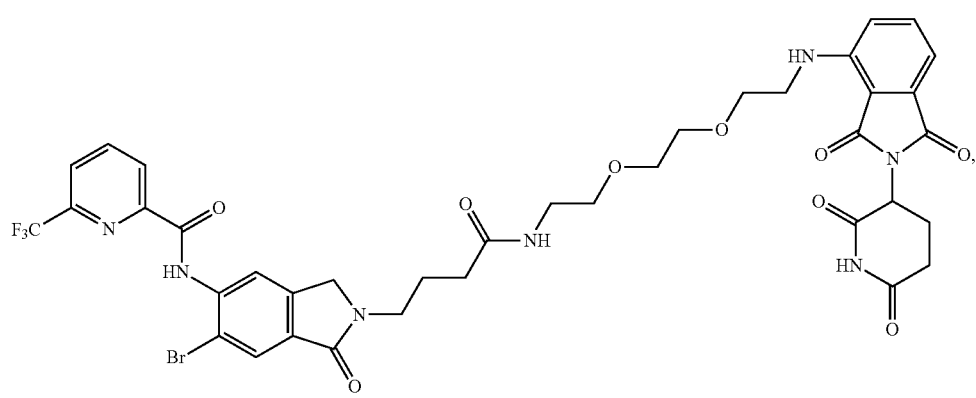

-continued
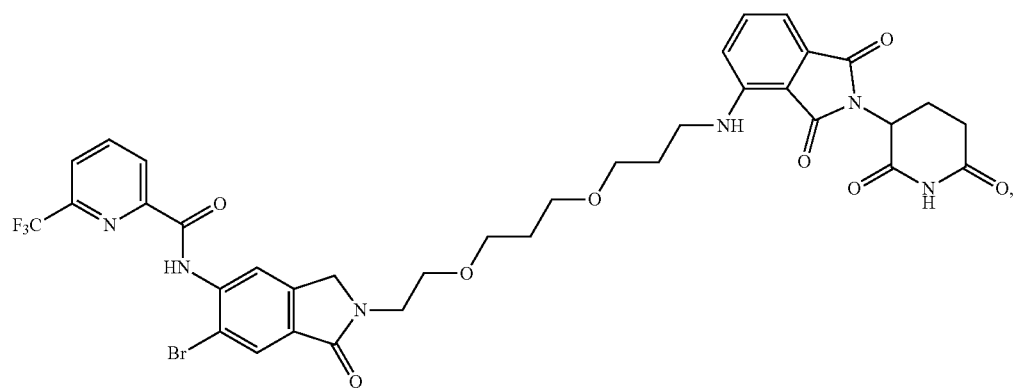
III-3
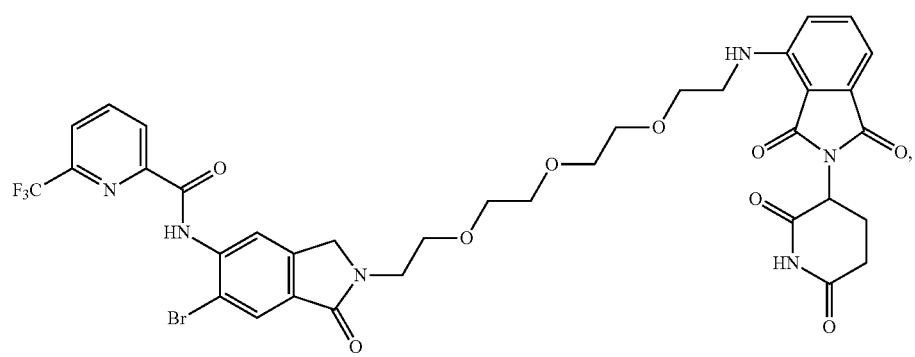
III-4
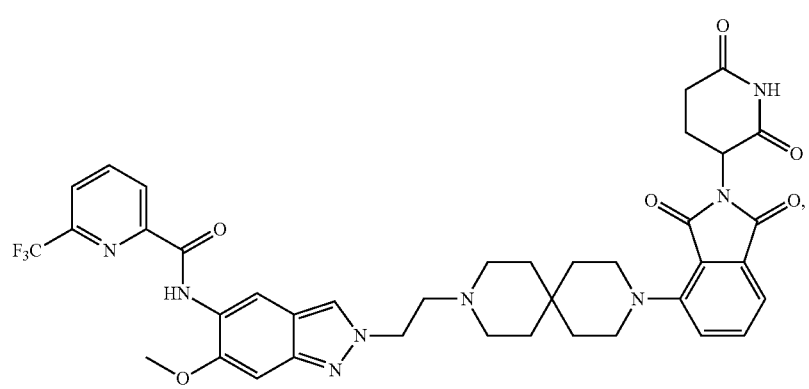
III-24
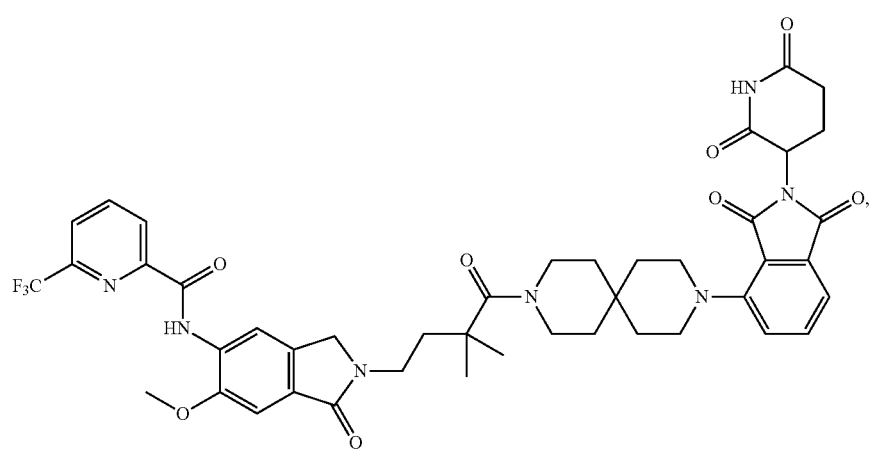
III-25

III-26
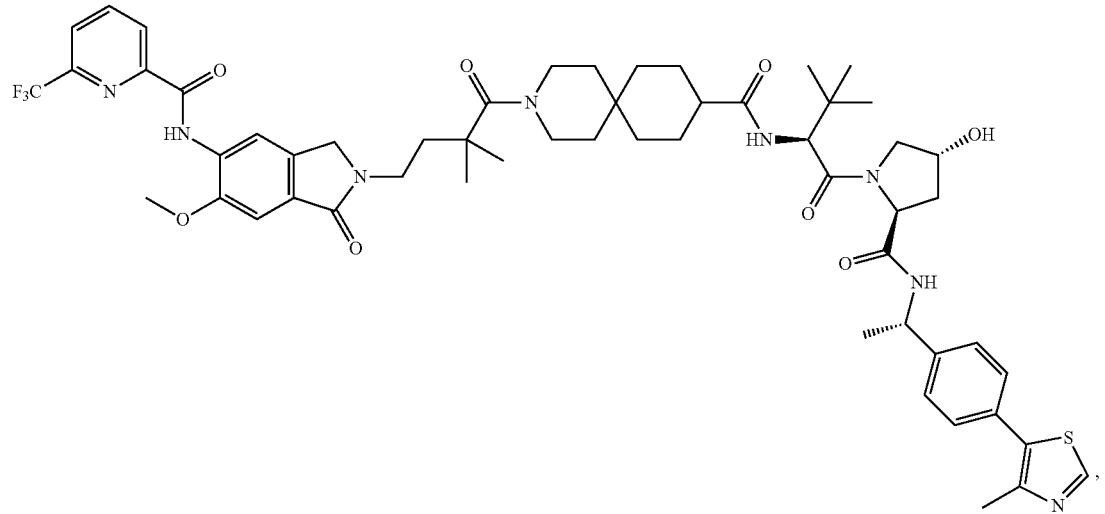
III-27
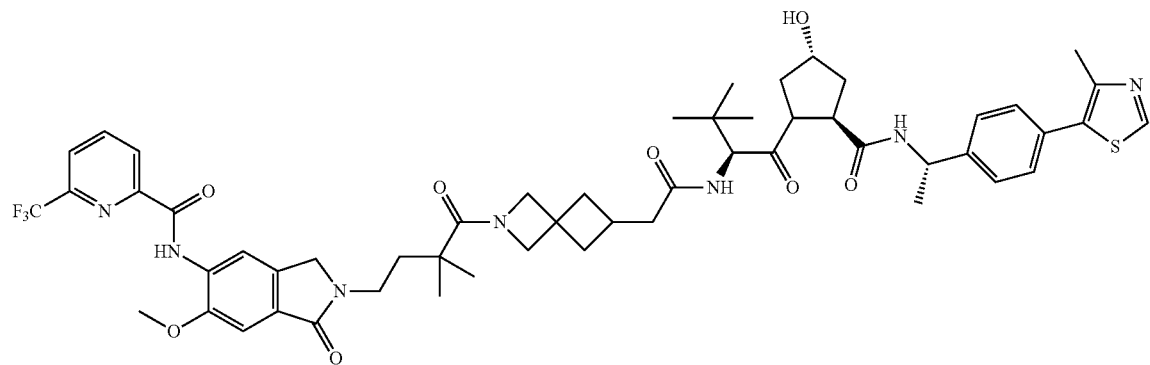
III-32
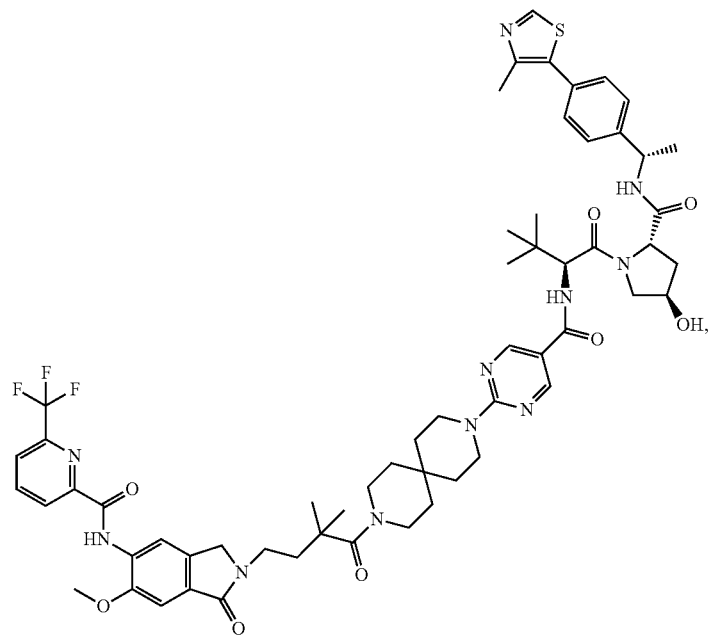

-continued
III-33
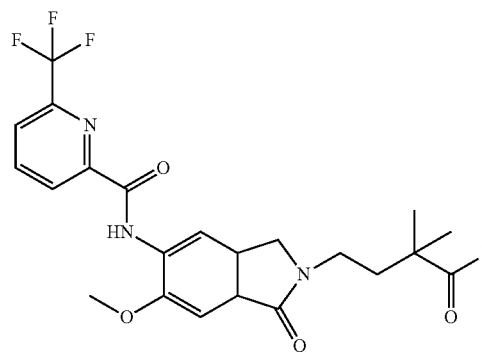
III-36
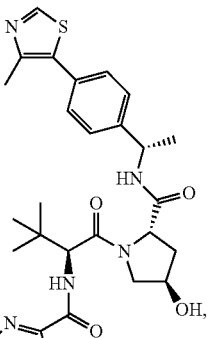
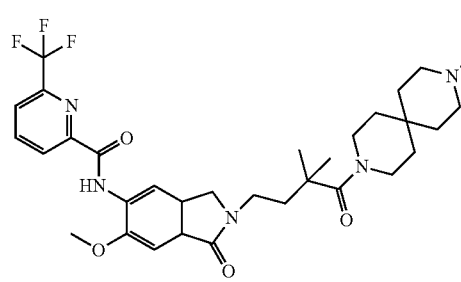
III-41
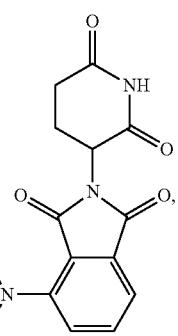
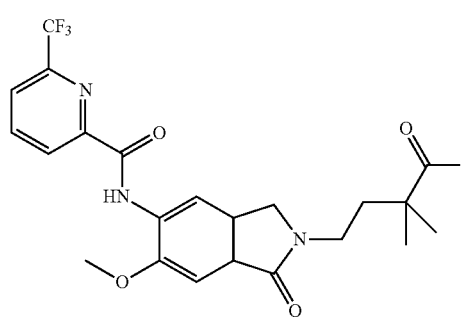

III-43
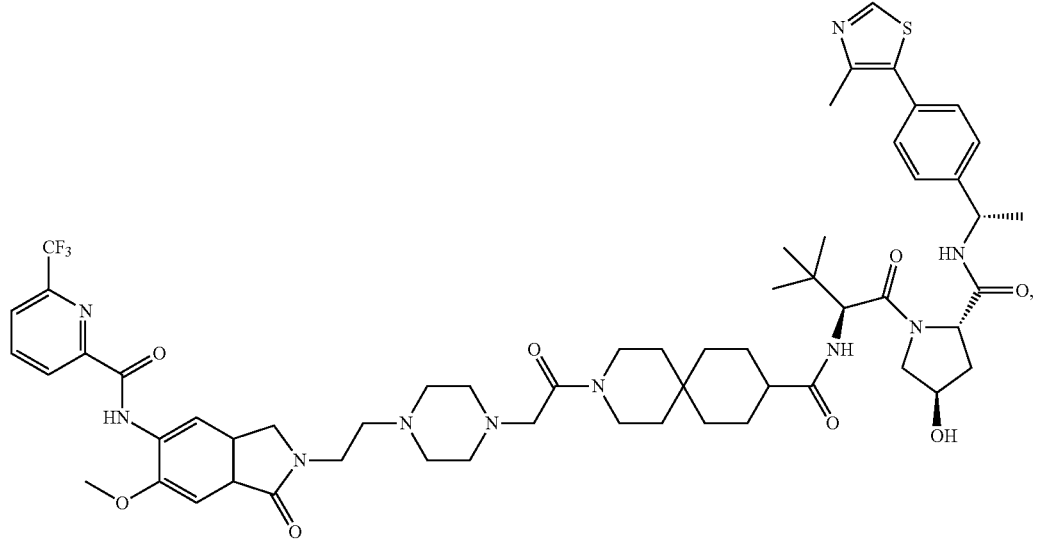
III-44
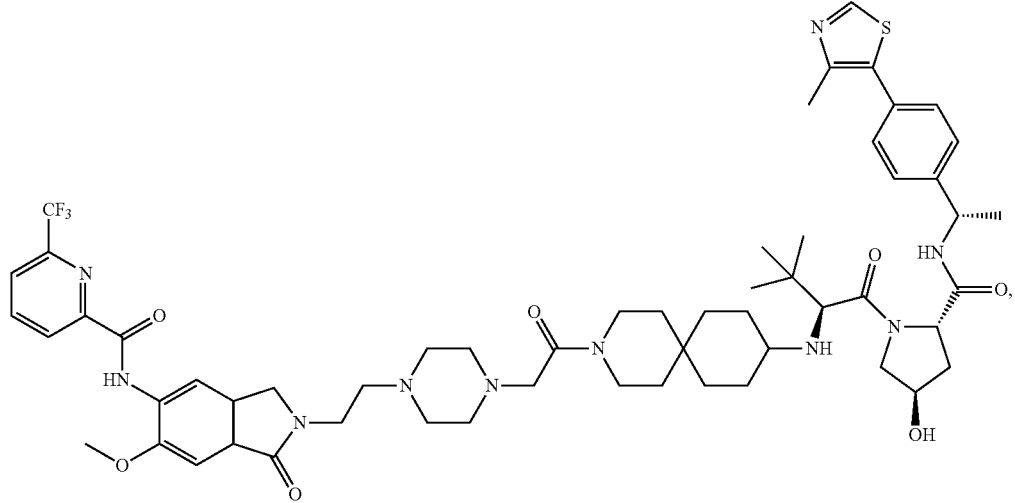
III-49
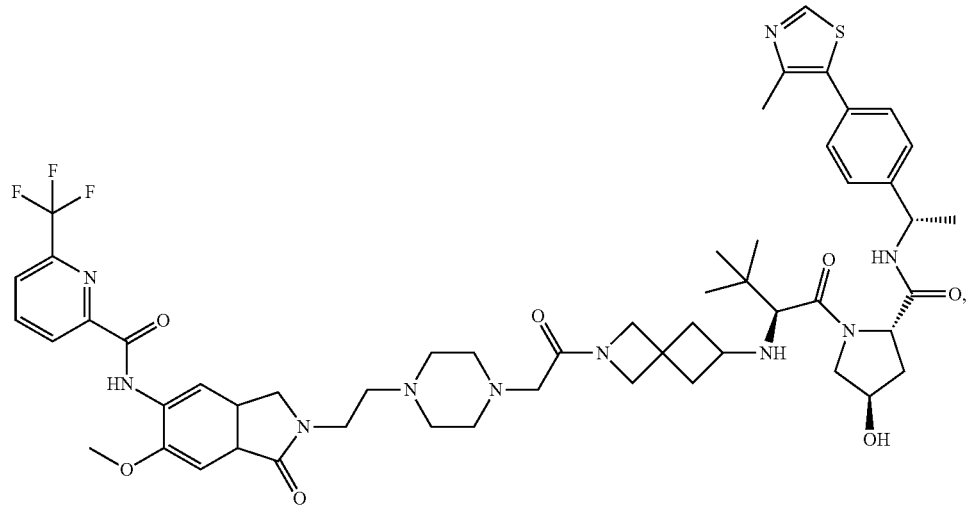

III-52
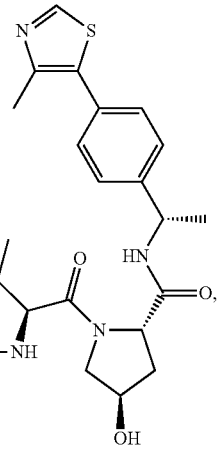
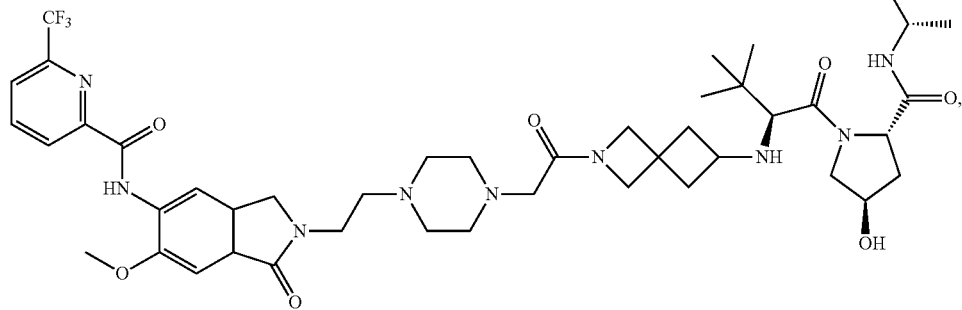
III-58
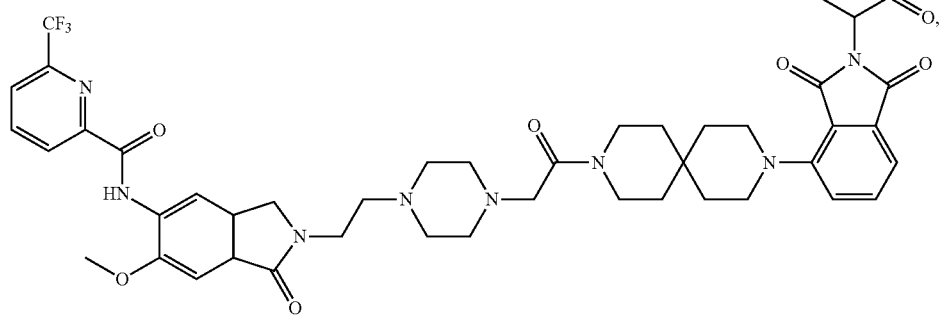
III-59
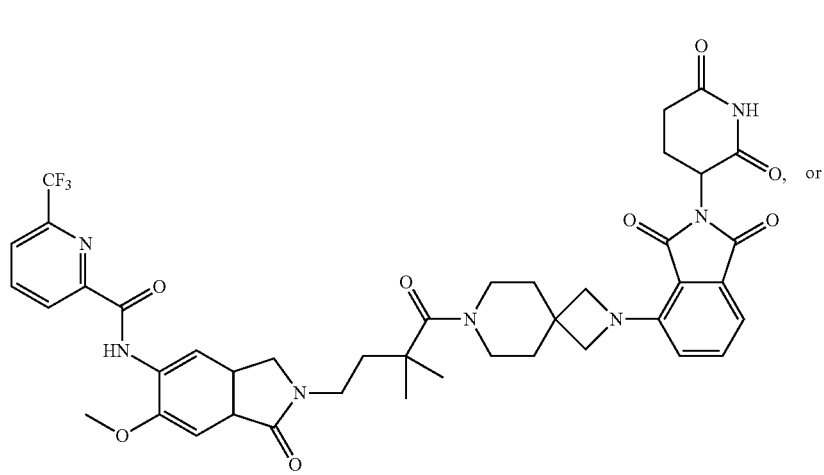

-continued

III-64

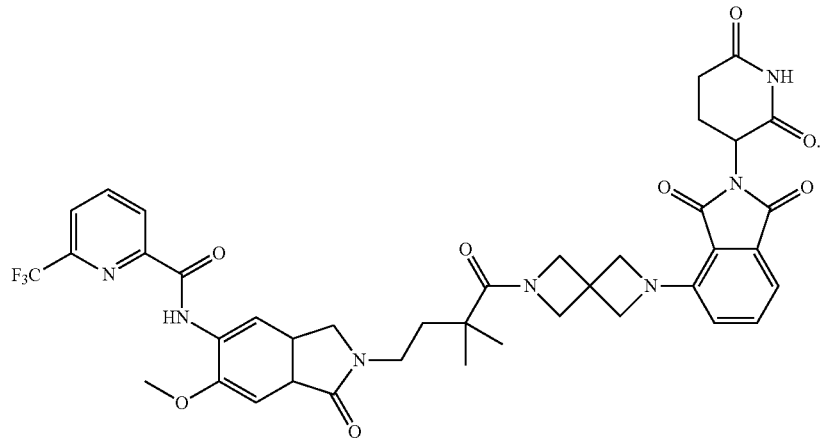

The present disclosure also provides a preparation method for the five-membered-fused six-membered compound of formula II or III,
the preparation method for the compound of formula II comprises: a compound of formula II-A and a compound of formula II-B undergo a condensation reaction in a solvent with the presence of a base and a condensing agent to obtain the compound of formula II;

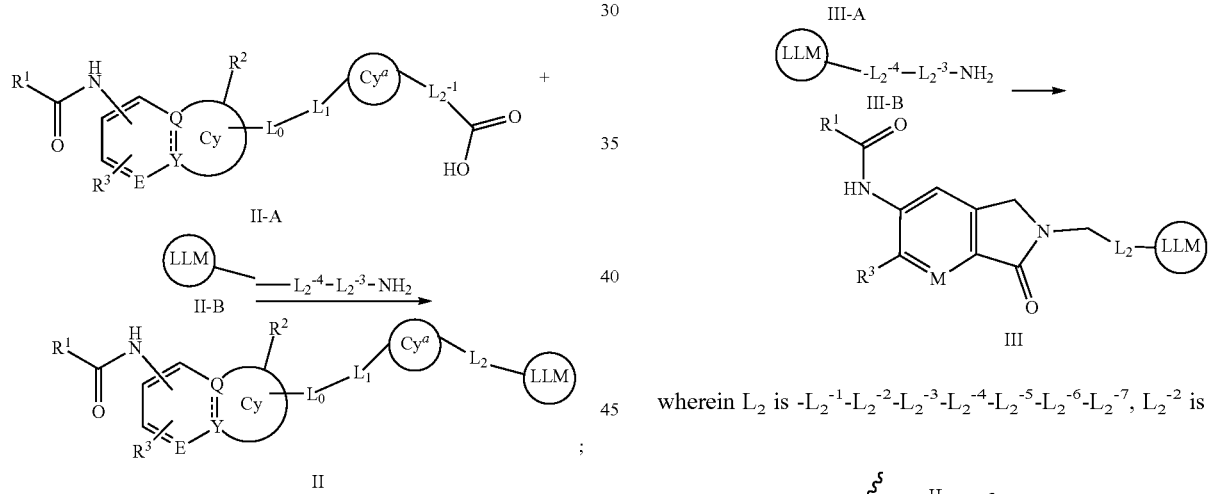

wherein $L_2$ is $-L_2^{-1}-L_2^{-2}-L_2^{-3}-L_2^{-4}-L_2^{-5}-L_2^{-6}-L_2^{-7}$, $L_2^{-2}$ is

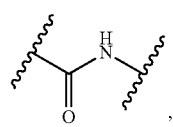

and E, Y, Q, $R^1$, $R^2$, $R^3$, ring Cy, $L_0$, $L_1$, $L_2^{-1}$, $L_2^{-3}$, $L_2^{-4}$, $L_2^{-5}$, $L_2^{-6}$, $L_2^{-7}$, and LLM are as defined above;
the preparation method for the compound of formula III comprises: a compound of formula III-A and a compound of formula III-B undergo a condensation reaction in a solvent with the presence of a base and a condensing agent to obtain the compound of formula III;

wherein $L_2$ is $-L_2^{-1}-L_2^{-2}-L_2^{-3}-L_2^{-4}-L_2^{-5}-L_2^{-6}-L_2^{-7}$, $L_2^{-2}$ is and M, $R^1$, $R^2$, $R^3$, ring Cy, $L_1$, $L_2^{-1}$, $L_2^{-3}$, $L_2^{-4}$, $L_2^{-5}$, $L_2^{-6}$, $L_2^{-7}$, and LLM are as defined above.

In the condensation reaction, the solvent is a conventional solvent for such reactions in the art, preferably an amide solvent, and more preferably DMF, such as anhydrous DMF.

In the present disclosure, the amount of the solvent is that of a conventional solvent in the art. Preferably, the volume molar ratio of the solvent to the compound of formula II-A or the compound of formula III-A is (30 to 10):1 mL/mmol, such as 15:1 mL/mmol or 20:1 mL/mmol.

In the present disclosure, the base is a conventional base for such reactions in the art, preferably a nitrogen-containing organic base, such as N,N-diisopropylethylamine.

In the present disclosure, the amount of the base is that of a conventional base in the art. Preferably, the molar ratio of the base to the compound of formula II-A or the compound of formula III-A is (1 to 10):1, such as 2:1, 3:1, or 5:1.

In the present disclosure, the condensing agent is a condensing agent for such reactions in the art, preferably a phosphate condensing agent, such as bromo-tris-pyrrolidino-phosphonium hexafluorophosphate or 2-(7-azabenzotriazol-1-yl)-N,N,N',N'-tetramethyluronium hexafluorophosphate.

In the present disclosure, the amount of the condensing agent is that of a conventional condensing agent in the art. Preferably, the molar ratio of the condensing agent to the compound of formula II-A or the compound of formula III-A is (1 to 2):1, such as 1:1, 1.2:1, 1.3:1, or 1.5:1.

In the present disclosure, the reaction temperature of the condensation reaction is a conventional reaction temperature in the art, preferably −10° C. to 50° C., such as room temperature.

The present disclosure also provides a pharmaceutical composition comprising a substance Z and a pharmaceutical excipient, wherein the substance Z is the compound of formula II or I or the pharmaceutically acceptable salt thereof.

The present disclosure also provides a use of a substance Z in the manufacture of an IRAK4 degrading agent and a medicament for the treatment and/or prevention of a Myd88-related disease and/or an IRAK4-related disease, wherein the substance Z is the compound of formula II or III or the pharmaceutically acceptable salt thereof.

The present disclosure also provides a method for the treatment and/or prevention of a Myd88-related disease and/or an IRAK4-related disease, comprising administering an effective amount of a substance Z to a patient, wherein the substance Z is the compound of formula II or III or the pharmaceutically acceptable salt thereof.

In a certain preferred embodiment, the IRAK4-related disease comprises one or more than one of an autoimmune disease, an inflammatory disease, a tumor, a cardiovascular disease, and a central nervous system disease.

In a certain preferred embodiment, the autoimmune disease comprises psoriasis and rheumatoid arthritis.

In a certain preferred embodiment, the inflammatory disease comprises ulcerative colitis.

In a certain preferred embodiment, the tumor may be a hematological tumor and a solid tumor.

In a certain preferred embodiment, the hematological tumor comprises large B-cell lymphoma and acute and chronic lymphocytic leukemia.

In a certain preferred embodiment, the solid tumor comprises intestinal cancer and skin cancer caused by MYD88 mutations.

In a certain preferred embodiment, the cardiovascular disease comprises stroke and atherosclerosis.

In a certain preferred embodiment, the central nervous system disease comprises primary central nervous system lymphoma.

Unless otherwise specified, the terms used in the present disclosure have the following meanings:

The terms "compound" and "pharmaceutically acceptable salt", if the tautomer exists, may exist in the form of tautomers or mixtures thereof, preferably in the form of predominantly more stable tautomers.

If a linkage group is expressed as "absent", the structures on both sides of the linkage group are directly attached by a single bond, such as -A-B-C-, when B is absent, -A-B-C- is -A-C-.

The term "|" means presence or absence.

The term "oxo" refers to the substitution of hydrogen or lone pair of electrons on a non-oxygen atom by oxygen. For example,

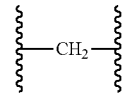

is oxo-substituted to

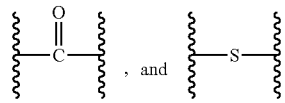

is oxo-substituted to

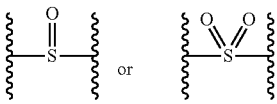

The term "halogen" refers to fluorine, chlorine, bromine, or iodine.

The term "cycloalkyl" refers to a saturated monocyclic group consisting only of carbon atoms with a specified number of carbon atoms (e.g., $C_3$ to $C_{10}$). The monocycloalkyl includes, but is not limited to, cyclopropyl, cyclobutyl, cyclopentyl, cyclohexyl, etc.

The term "alkyl" refers to a straight or branched alkyl group with a specified number of carbon atoms (e.g., $C_1$ to $C_6$). The alkyl includes, but is not limited to, methyl, ethyl, n-propyl, isopropyl, n-butyl, tert-butyl, isobutyl, sec-butyl, n-pentyl, n-hexyl, etc.

The term "heterocycloalkyl" refers to a cyclic group with a specified number of ring atoms (e.g., 3- to 8-membered), a specified number of heteroatoms (e.g., 1, 2, or 3), and a specified type of heteroatom (one or more than one of N, O, and S), wherein the heteroatom may be attached to other groups as an linkage group, or may not be attached to other groups (e.g., piperidinyl may be

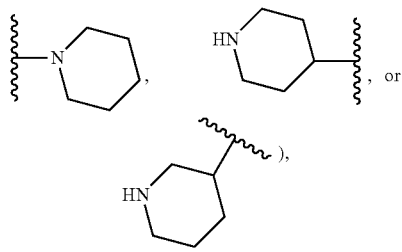

and it is a monocyclic ring, a fused ring, a bridged ring, or a spiro ring, and each ring is saturated. The heterocycloalkyl includes, but is not limited to, azetidinyl, tetrahydropyrrolyl, tetrahydrofuryl, morpholinyl, piperidinyl, etc.

The term "heterocyclic ring" refers to a cyclic group with a specified number of ring atoms (e.g., 3- to 12-membered), a specified number of heteroatoms (e.g., 1, 2, or 3), and a specified type of heteroatom (one or more than one of N, O, and S), wherein the heteroatom may be attached to other groups as an linkage group, or may not be attached to other groups (e.g., the piperidine ring may be

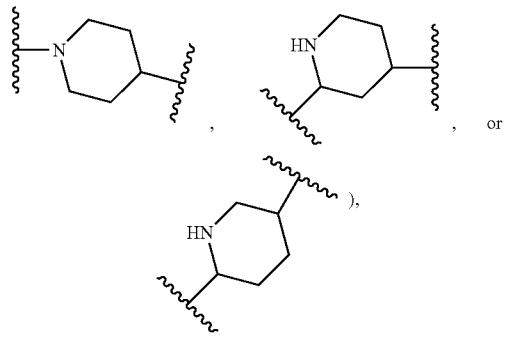

and it is a monocyclic ring, a fused ring, a bridged ring, or a spiro ring, and each ring is saturated. The heterocyclic ring includes, but is not limited to, an azetidine ring, a tetrahydropyrrole ring, a tetrahydrofuran ring, a morpholine ring, and a piperidinyl ring.

The term "heteroaryl" refers to a cyclic group with a specified number of ring atoms (e.g., 5- to 9-membered), a specified number of heteroatoms (e.g., 1, 2, or 3), and a specified type of heteroatom (one or more than one of N, O, and S), which is a monocyclic ring or a polycyclic ring, and at least one ring is aromatic (in accordance with Huckel's rule). The heteroaryl is attached to other moieties in the molecule through an aromatic ring or a non-aromatic ring. The heteroaryl includes, but is not limited to, furyl, pyrrolyl, thienyl, pyrazolyl, imidazolyl, oxazolyl, thiazolyl, pyridyl, pyrimidinyl, indolyl, etc.

The term "heteroaromatic ring" refers to a cyclic group with a specified number of ring atoms (e.g., 5- to 9-membered), a specified number of heteroatoms (e.g., 1, 2, or 3), and a specified type of heteroatom (one or more than one of N, O, and S), which is a monocyclic ring or a polycyclic ring, and at least one ring is aromatic (in accordance with Huckel's rule). The heteroaromatic ring is attached to other moieties in the molecule through an aromatic ring or a non-aromatic ring. The heteroaromatic ring includes, but is not limited to, a furan ring, a pyrrole ring, a thiophene ring, a pyrazole ring, an imidazole ring, an oxazole ring, a thiazole ring, a pyridine ring, a pyrimidine ring, an indole ring, etc.

The term "aryl" refers to a cyclic group consisting carbon atoms only with a specified number of carbon atoms (e.g., $C_6$ to $C_{10}$), which is a monocyclic ring or a polycyclic ring, and at least one ring is aromatic (in accordance with Huckel's rule). The aryl is attached to other moieties in the molecule through aromatic rings or non-aromatic rings. The aryl includes, but is not limited to, phenyl, naphthyl.

The term "aromatic ring" refers to a cyclic group consisting carbon atoms only with a specified number of carbon atoms (e.g., $C_6$ to $C_{10}$), which is a monocyclic ring or a polycyclic ring, and at least one ring is aromatic (in accordance with Huckel's rule). The aromatic ring is attached to other moieties in the molecule through aromatic rings or non-aromatic rings. The aromatic ring includes, but is not limited to, phenyl, naphthyl.

The "—" at the end of a group means that the group is attached to other moieties in the molecule through this site. For example, $CH_3$—C(=O)— refers to acetyl.

The "

" in a structural moiety means that the structural moiety is attached to other moieties in the molecule through this site. For example,

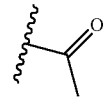

refers to acetyl.

The term "more than one" refers to 2, 3, 4, or 5.

When any variable (such as group $R^{1-1}$) appears multiple times in the definition of a compound, their definitions are independent of each other and do not affect each other. For example, $C_6$-$C_{10}$ aryl substituted by 3 $R^{1-1}$ groups means that the $C_6$-$C_{10}$ aryl will be substituted by 3 $R^{1-1}$ groups, and the definitions of the 3 $R^{1-1}$ groups are independent of each other and do not affect each other.

The substituents such as heterocyclic ring, aromatic ring, heteroaryl, aryl, heterocycloalkyl, alkoxy, alkyl, and cycloalkyl described in the present disclosure may also be referred to as sub-heterocyclic ring, sub-aromatic ring, heteroarylene, arylene, heterocycloalkylene, alkyleneoxy, alkylene, and cycloalkylene, when used as a linkage unit to attach the different components of the compound, respectively.

The term "pharmaceutically acceptable salt" refers to a salt obtained by reacting a compound with a pharmaceutically acceptable (relatively nontoxic, safe, and suitable for use by a patient) acid or base. When the compound contains a relatively acidic functional group, a base addition salt can be obtained by contacting the free form of the compound with a sufficient amount of a pharmaceutically acceptable base in a suitable inert solvent. The pharmaceutically acceptable base addition salt includes, but is not limited to, a sodium salt, a potassium salt, a calcium salt, an aluminum salt, a magnesium salt, a bismuth salt, an ammonium salt, etc. When the compound contains a relatively basic functional group, an acid addition salt can be obtained by contacting the free form of the compound with a sufficient amount of a pharmaceutically acceptable acid in a suitable inert solvent. The pharmaceutically acceptable acid addition salt includes, but is not limited to, hydrochloride, acetate, trifluoroacetate, sulfate, methanesulfonate, etc. For details, see *Handbook of Pharmaceutical Salts: Properties, Selection, and Use* (P. Heinrich Stahl, 2002).

The term "solvate of a pharmaceutically acceptable salt" refers to a substance formed by combining a compound with a pharmaceutically acceptable (relatively nontoxic, safe, and suitable for use by a patient) acid or base, and a solvent (including, but not limited to, water, methanol, ethanol, etc.), wherein the pharmaceutically acceptable salt has the same meaning as the term "pharmaceutically acceptable salt" above, and the solvent is stoichiometric or non-stoichiometric. The solvate of a pharmaceutically acceptable salt includes, but is not limited to, hydrochloride monohydrate.

The term "pharmaceutical excipient" refers to the excipient and additive used in the production of drugs and preparation of prescriptions, and is all substances other than active ingredients included in pharmaceutical preparations. For details, see the *Pharmacopoeia of the People's Republic of China* (2020 edition) or *Handbook of Pharmaceutical EMcipients* (Raymond C Rowe, 2009).

The term "treatment" refers to any of the following: (1) alleviating one or more than one biological manifestation of a disease; (2) interfering with one or more than one point in the biological cascade that causes the disease; (3) slowing the progression of one or more than one biological manifestation of a disease.

The term "prevention" refers to reducing the risk of developing a disease.

The term "patient" refers to any animal, preferably a mammal, most preferably a human, that has been or is about to be treated. The mammal includes, but is not limited to, a cattle, horse, sheep, pig, cat, dog, mouse, rat, rabbit, guinea pig, monkey, human, etc.

As used in the specifications and claims, the singular form "a", "an" and "the" includes plural references unless the context clearly dictates otherwise.

On the basis of not violating common sense in the art, the above preferred conditions can be combined arbitrarily to obtain preferred examples of the present disclosure.

The reagent and raw material used in the present disclosure are all commercially available.

The positive and progressive effect of the present disclosure is that the compound of the present disclosure has an inhibitory or/and degrading effect on IRAK4, and are capable of near-complete degradation of the IRAK4 protein at a low drug concentration. The compound of the present disclosure can also inhibit the scaffolding function of the Myddosome complex. The compound of the present disclosure has potential clinical application value and is expected to be applied to various IRAK4-related immune diseases and various hematological diseases and solid tumors caused by MYD88 mutations.

DETAILED DESCRIPTION OF THE INVENTION

The present disclosure is further illustrated below by means of examples, but the present disclosure is not limited to the scope of the examples. The experimental methods for which specific conditions are not indicated in the following examples are selected according to conventional methods and conditions, or according to the product instructions.

Example III-1: Synthesis of (III-1)

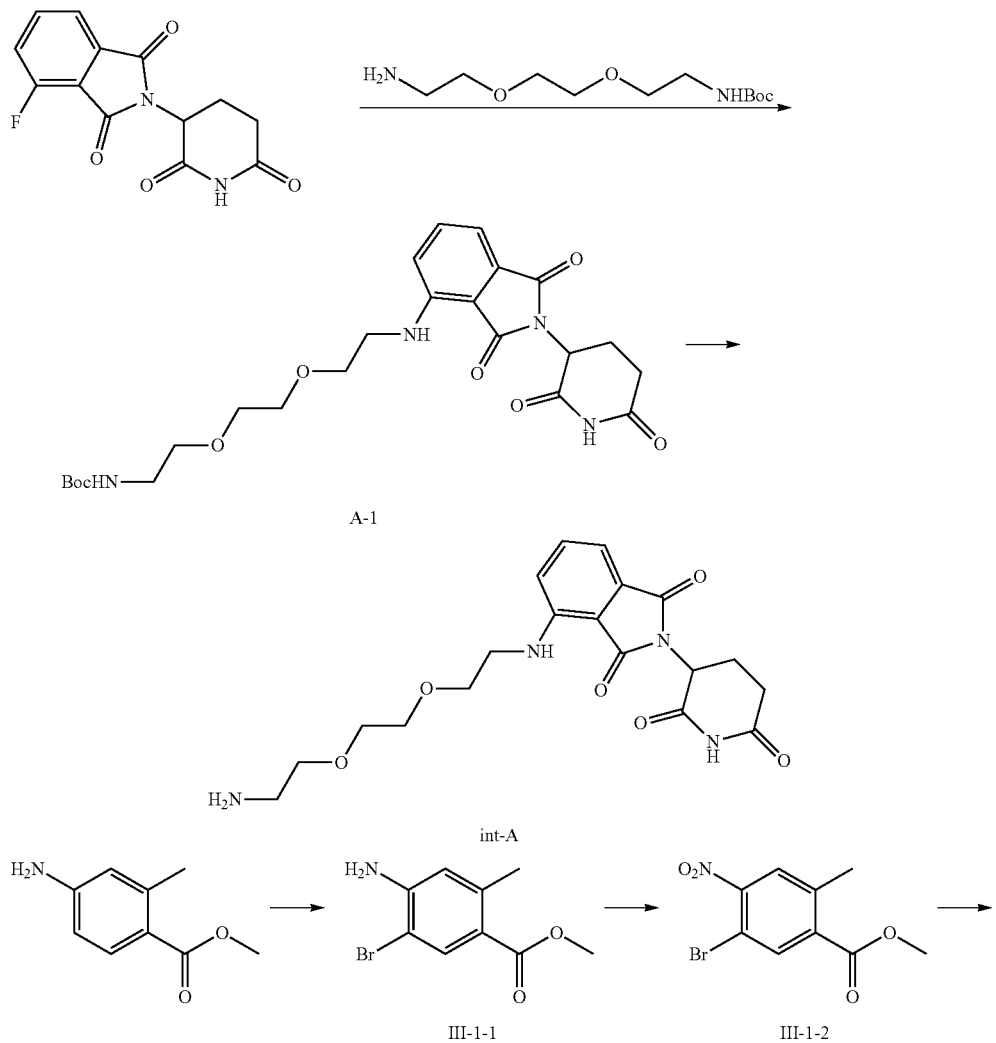

-continued
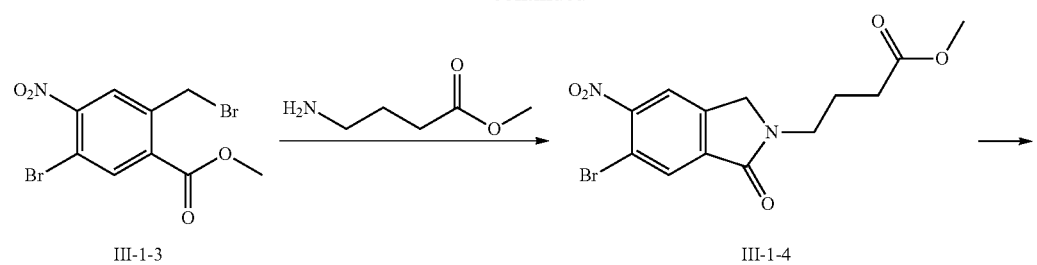
III-1-3 → III-1-4
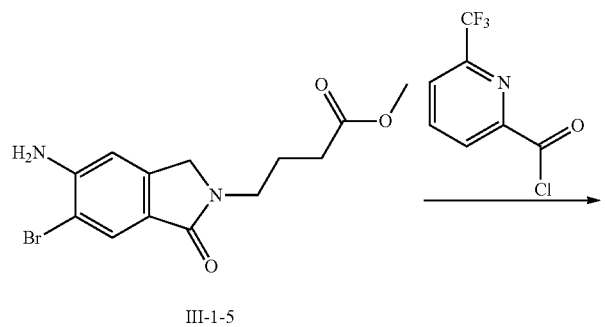
III-1-5
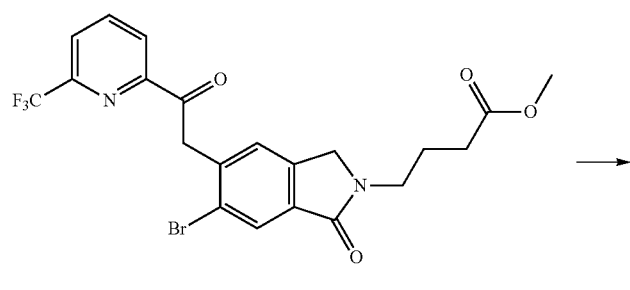
III-1-6
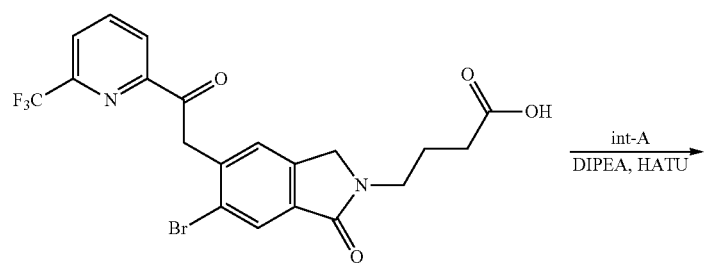
III-1-7

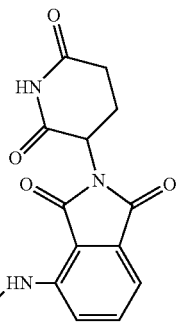
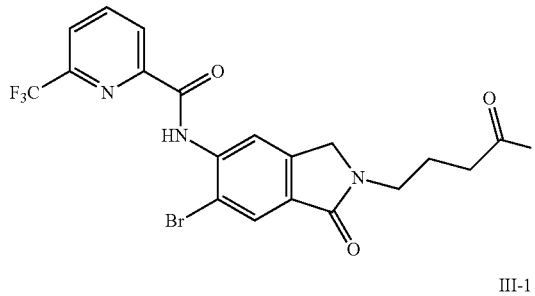

III-1

Step 1: Synthesis of (A-1)

2-(2,6-Dioxopiperidin-3-yl)-4-fluoroisoindoline-1,3-dione (224 mg, 0.81 mmol), tert-butyl (2-(2-(2-aminoethoxy)ethoxy)ethylcarbamate (242 mg, 0.97 mmol), DIPEA (N,N-diisopropylethyl amine, 186 mg, 1.45 mmol), and DMSO (dimethyl sulfoxide, 3 mL) were added to a reaction flask, and the reaction mixture was heated to 100° C. and reacted for 2 hours. The reaction mixture was directly purified by C18 column chromatography and eluted with (MeCN (acetonitrile)/$H_2O$+1‰ HCOOH) to obtain product A-1 (326 mg, yield: 79.8%) as a yellow solid. MS (ESI) m/z: 505.2 $[M+H]^+$.

Step 2: Synthesis of (int-A)

A-1 (65 mg, 0.13 mmol) was added to a mixture (3 mL of anhydrous DCM (dichloromethane) and 1.5 mL of TFA (trifluoroacetic acid)), then the reaction mixture was stirred at room temperature for 30 minutes, and the solvent was subjected to rotary evaporation until dryness to obtain crude product int-A (70 mg), which was directly used in the next reaction step. MS (ESI) m/z: 405.1 $[M+H]^+$.

Step 3: Synthesis of (III-1-1)

Methyl 5-amino-2-methylbenzoate (10 g, 60.54 mmol) and DMF (N,N-dimethylformamide, 150 mL) were added to a reaction flask, and the reaction mixture was stirred until clarified. NBS (N-bromosuccinimide, 13 g, 72.64 mmol) was slowly added thereto at room temperature, and the reaction mixture was stirred and reacted at room temperature until the reaction was complete. The reaction mixture was added with 500 mL of distilled water to precipitate a product, and filtered. The filter cake was washed with water, and dried under vacuum to obtain product III-1-1 (13.6 g, yield: 92%) as a white solid. MS (ESI) m/z: 243.9 $[M+H]^+$.

Step 4: Synthesis of (III-1-2)

A mixture of III-1-1 (13.6 g, 55.74 mmol), KI (925 g, 5.574 mmol), and acetonitrile (100 mL) was heated to 80° C. under nitrogen atmosphere, and TBHP (tert-butyl hydroperoxide, 50 g, 557.4 mmol) was slowly added dropwise thereto. After the addition was completed, the system was stirred and reacted at 80° C. overnight until the reaction was complete. The reaction mixture was cooled to room temperature, distilled under reduced pressure to remove the solvent, and added with ethyl acetate. The organic phase was washed with saturated brine, dried over anhydrous sodium sulfate, filtered, and distilled under reduced pressure to remove the solvent to obtain a crude product. The crude product was purified by silica gel column chromatography (mobile phase: 0 to 10% ethyl acetate/petroleum ether) to obtain product III-1-2 (6 g, yield: 39.4%) as a white solid. MS (ESI) m/z: 273.9 $[M+H]^+$.

Step 5: Synthesis of (III-1-3)

A solution of III-1-2 (6 g, 21.98 mmol), AIBN (azobisisobutyronitrile, 360.93 mg, 2.2 mmol), and acetonitrile (90 mL) was added to a reaction flask under nitrogen atmosphere. The reaction mixture was heated to 75° C., and stirred and reacted for 6 hours until the reaction was complete. The reaction mixture was cooled to room temperature, distilled under reduced pressure to remove the solvent, added with ethyl acetate, and washed with saturated brine. The organic phase was dried over anhydrous sodium sulfate, filtered, and distilled under reduced pressure to remove the solvent to obtain a crude product. The crude product was purified by silica gel column chromatography (mobile phase: 0 to 10% ethyl acetate/petroleum ether) to obtain product III-1-3 (5 g, yield: 64.4%) as a white solid. MS (ESI) m/z: 351.8 $[M+H]^+$.

Step 6: Synthesis of (III-1-4)

A solution of III-1-3 (200 mg, 0.57 mmol), methyl 4-aminobutanoate (176 mg, 1.7 mmol), triethylamine (173 mg, 1.7 mmol), and methanol (3 mL) was added to a reaction flask under nitrogen atmosphere. The reaction mixture was heated to 70° C., stirred and reacted for 2 hours until the reaction was complete, and subjected to rotary evaporation until dryness to obtain a crude product. The crude product was slurried with petroleum ether/ethyl acetate=10/1, and filtered to obtain product III-1-4 (140 mg, yield: 69.6%) as a white solid. MS (ESI) m/z: 359.1 $[M+H]^+$.

Step 7: Synthesis of (III-1-5)

III-1-4 (140 mg, 0.31 mmol), iron powder (78 mg, 1.4 mmol), ammonium chloride (53 mg, 1.1 mmol), and a mixed solvent (1.5 mL of ethanol and 0.3 mL of water) were added to a reaction flask. The reaction mixture was heated to 80° C., and stirred and reacted for 2 hours until the reaction was complete. The reaction mixture was filtered, and the filtrate was subjected to rotary evaporation until dryness under reduced pressure, added with ethyl acetate, and washed with saturated brine. The organic phase was dried over anhydrous sodium sulfate, filtered, and distilled under reduced pressure to remove the solvent to obtain a crude product. The crude product was purified by silica gel column chromatography (mobile phase: 0 to 70% ethyl acetate/petroleum ether) to obtain product III-1-5 (95 mg, yield: 96.77%) as a white solid. MS (ESI) m/z: 329.1 [M+H]⁺.

Step 8: Synthesis of (III-1-6)

A solution of III-1-5 (3 mL) was added to a reaction flask under nitrogen atmosphere, then 6-(trifluoromethyl)pyridine-2-carbonyl chloride (122 mg, 0.64 mmol) was slowly added thereto at 0° C., and the reaction mixture was stirred and reacted at room temperature for 1 hour until the reaction was complete. The reaction mixture was added with ethyl acetate, and washed four times with citric acid. The organic phase was dried over anhydrous sodium sulfate, filtered, and distilled under reduced pressure to remove the solvent to obtain a crude product. The crude product was purified by C18 column chromatography (mobile phase: 0 to 60% water/acetonitrile) to obtain product III-1-6 (140 mg, yield: 96.66%) as a white solid. MS (ESI) m/z: 502.1 [M+H]⁺.

Step 9: Synthesis of (III-1-7)

LiOH (10 mg, 0.4 mmol) was added to a mixture of III-1-6 (100 mg, 0.2 mmol) in CH₃OH (4 mL), THF (4 mL), and H₂O (2 mL), and the reaction mixture was stirred and reacted at room temperature for 2 hours until the reaction was complete. The reaction mixture was subjected to rotary evaporation until dryness under reduced pressure, added with ethyl acetate, washed with saturated ammonium chloride solution, dried over anhydrous sodium sulfate, filtered, and distilled under reduced pressure to remove the solvent to obtain a crude product. The crude product was purified by C18 column chromatography (mobile phase: 0 to 60% water/acetonitrile) to obtain product III-1-7 (63 mg, yield: 65%) as a white solid. MS (ESI) m/z: 486.2 [M+H]⁺.

Step 10: Synthesis of (III-1)

III-1-7 (50 mg, 0.1 mmol), DIPEA (60 mg, 0.45 mmol), HATU (2-(7-azabenzotriazol-1-yl)-N,N,N',N'-tetramethyluronium hexafluorophosphate, 50 mg, 0.13 mmol), and DMF (2 mL) were added to a reaction flask. The reaction mixture was stirred at room temperature for 30 minutes, added with int-A, and reacted at room temperature for 1 hour. The reaction mixture was directly purified by C18 column chromatography and eluted with (MeCN/H₂O+10‰ HCOOH) to obtain product III-1 (43 mg, yield: 50%) as a yellow solid. MS (ESI) m/z: 874.5 [M+H]⁺, ¹H NMR (500 MHz, DMSO-d₆) δ 11.10 (s, 1H), 10.68 (s, 1H), 8.65 (s, 1H), 8.49 (d, J=7.5 Hz, 1H), 8.44 (t, J=8.0 Hz, 1H), 8.28 (d, J=7.5 Hz, 1H), 7.95 (s, 1H), 7.87 (t, J=5.5 Hz, 1H), 7.59-7.51 (m, 1H), 7.10 (d, J=8.5 Hz, 1H), 7.00 (d, J=6.0 Hz, 1H), 6.57 (t, J=5.0 Hz, 1H), 5.05 (dd, J=13.0, 5.5 Hz, 1H), 4.50 (s, 2H), 3.60 (t, J=5.5 Hz, 2H), 3.57-3.53 (m, 2H), 3.47-3.50 (m, 4H), 3.41-3.45 (m, 2H), 3.15 (dd, J=11.5, 5.7 Hz, 2H), 2.93-2.83 (m, 1H), 2.51-2.61 (m, 4H), 2.08-2.11 (m, 2H), 2.01-2.03 (m, 1H), 1.89-1.76 (m, 2H).

Example III-2: Synthesis of (III-2)

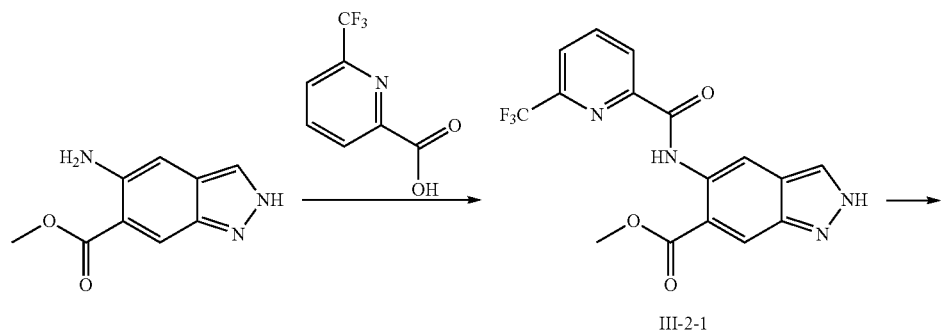

III-2-1

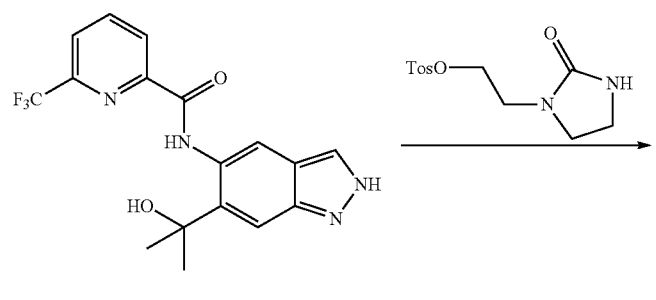

III-2-2

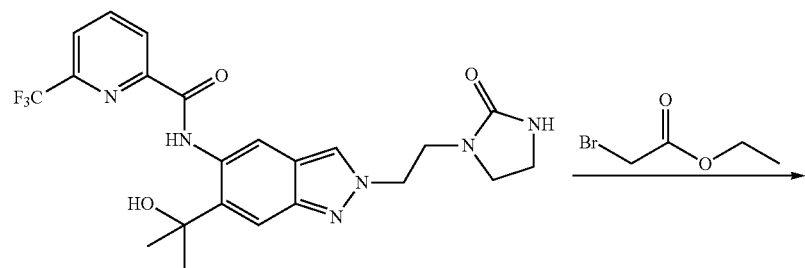
III-2-3
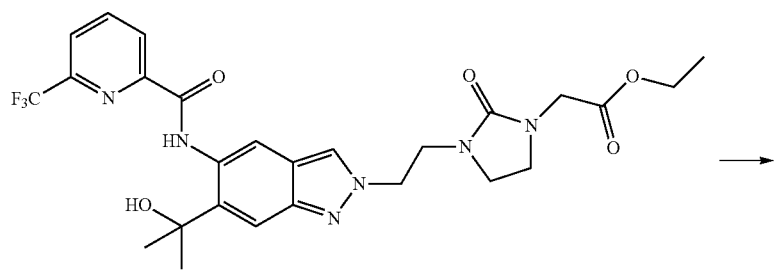
III-2-4
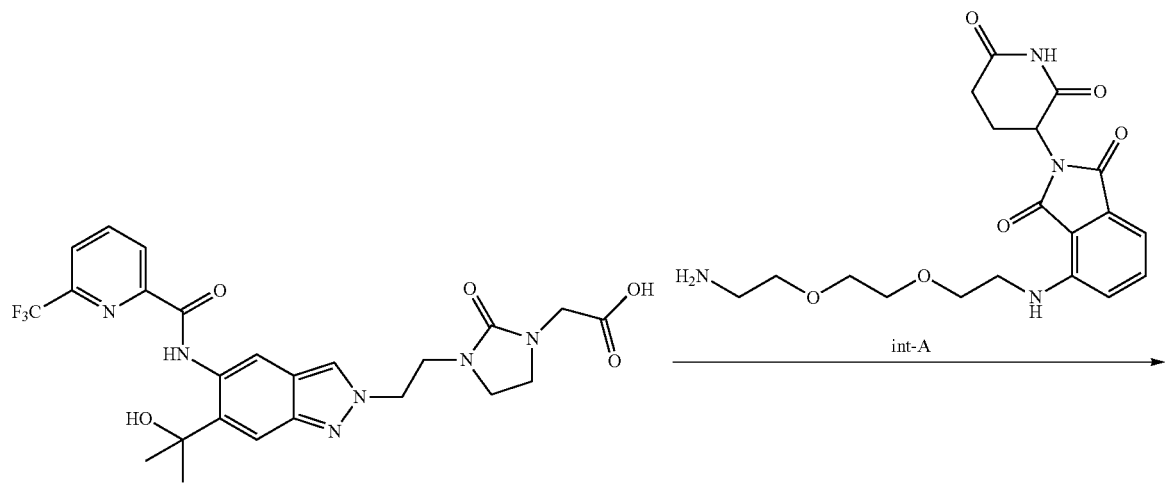
III-2-5

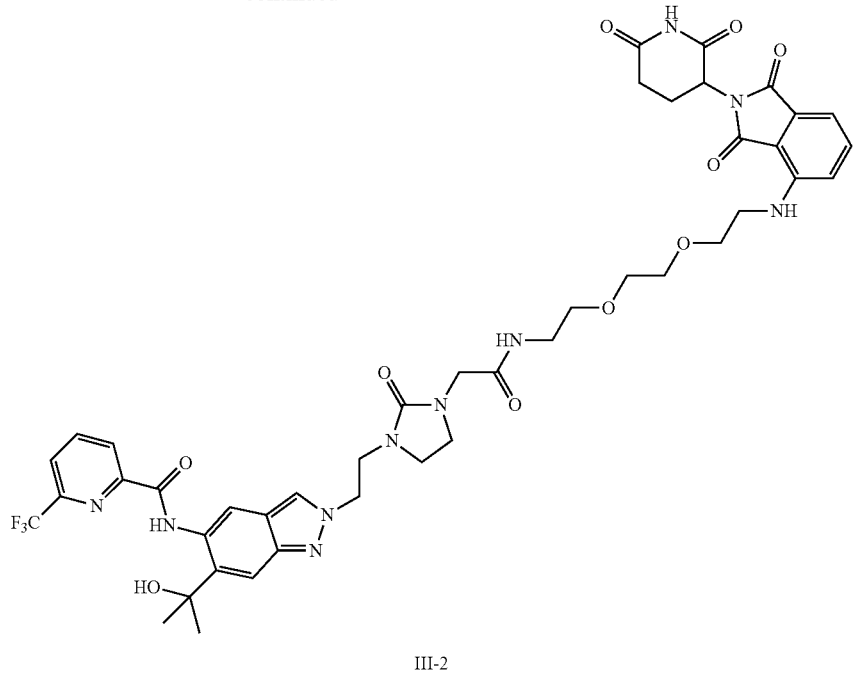 [SMILES: CC(C)(O)c1cc2nn(CCN3CCN(CC(=O)NCCOCCOCCNc4cccc5c4C(=O)N(C4CCC(=O)NC4=O)C5=O)C3=O)cc2cc1NC(=O)c1cccc(C(F)(F)F)n1 ; "III-2"]

III-2

Step 1: Synthesis of (III-2-1)

Methyl 5-amino-2H-indazole-6-carboxylate (5 g, 26 mmol) was dissolved in tetrahydrofuran solution (50 mL), then DIPEA (27 g, 209 mmol) was slowly added dropwise thereto, and $T_3P$ (propylphosphonic anhydride, 25 g, 78.6 mmol) was added thereto. The reaction mixture was then added with 6-(trifluoromethyl)picolinic acid (7.5 g, 39 mmol). After the dropwise addition was completed, the reaction mixture was stirred at room temperature for 16 hours. The reaction system was added with water to precipitate a large amount of solid, which was filtered and then dried under vacuum to obtain product III-2-1 (9.3 g, yield: 98%) as a light yellow solid.

MS (ESI) m/z: 365.3 [M+H]$^+$.

Step 2: Synthesis of (III-2-2)

III-2-1 (9.3 g, 25.5 mmol) was dissolved in anhydrous THF (tetrahydrofuran, 100 mL), and LiCl (5.4 g, 128 mmol) was weighed and added to the reaction system. The reaction mixture was replaced with nitrogen three times, added with MeMgCl (10 mL) under an ice-water bath, and reacted for 3 hours until the reaction was complete. The reaction mixture was distilled under reduced pressure to remove half of the solvent, added with 10 mL of water to quench under an ice bath, stirred at 0° C. for 10 minutes, and extracted twice with ethyl acetate. The organic phase was dried over anhydrous sodium sulfate, filtered, and subjected to rotary evaporation until dryness to obtain crude product III-2-2 (9.2 g, yield: 98.9%). MS (ESI) m/z: 365.1 [M+H]$^+$.

Step 3: Synthesis of (III-2-3)

III-2-2 (100 mg, 0.27 mmol) was dissolved in toluene (1.5 mL), and DIPEA (177 mg, 13.7 mmol) was added to the reaction mixture. 2-(2-oxoimidazolidin-1-yl)ethyl 4-methylbenzenesulfonate (91 mg, 0.33 mmol) was then weighed, and the reaction mixture was heated to 110° C. and reacted for 2 hours until the reaction was complete. The reaction mixture was cooled, distilled under reduced pressure to remove the solvent, and extracted twice with ethyl acetate. The organic phase was dried over anhydrous sodium sulfate, and the crude product was purified by silica gel column chromatography to obtain product III-2-3 (43 mg, yield: 33%) as a light yellow solid. MS (ESI) m/z: 477.2 [M+H]$^+$.

Step 4: Synthesis of (III-2-4)

III-2-3 (68 mg, 0.143 mmol) was weighed and dissolved in DMF (1 mL), then NaH (10 mg, 0.429 mmol) was slowly added thereto under an ice bath, and the reaction mixture was stirred for 30 minutes under an ice bath. The reaction system was then added with ethyl 2-bromoacetate (47 mg, 0.286 mmol), naturally warmed to 25° C., and stirred for 2 hours until the reaction was complete. The reaction mixture was distilled under reduced pressure to remove the solvent, and extracted with ethyl acetate. The organic phase was dried over anhydrous sodium sulfate, and the crude product was purified by silica gel column chromatography to obtain product III-2-4 (45 mg, 0.08 mmol, yield: 56%) as a white solid. MS (ESI) m/z: 563.2 [M+H]$^+$.

Step 5: Synthesis of (III-2-5)

III-2-4 (45 mg, 0.08 mmol) was weighed and dissolved in methanol/water=1/1 (1 mL), then LiOH (4 mg, 0.167 mmol) was added thereto, and the reaction mixture was stirred and reacted at room temperature for 2 hours until the reaction was complete. The reaction mixture was distilled under reduced pressure to remove the solvent, and extracted with ethyl acetate. The organic phase was dried over anhydrous sodium sulfate, and the crude product was purified by silica gel column chromatography to obtain product III-2-5 (40 mg, yield: 94%) as a light yellow solid. MS (ESI) m/z: 535.2 [M+H]$^+$.

Step 6: Synthesis of (III-2)

III-2-5 (40 mg, 0.075 mmol) was dissolved in DMF (1 mL), then HATU (42.7 mg, 0.112 mmol, 1.5 eq) and DIPEA (29 mg, 0.225 mmol, 3 eq) were weighed, and the reaction mixture was stirred and reacted at room temperature for 30 minutes. The reaction system was then added with int-A (39.3 mg, 0.097 mmol, 1.3 eq), and stirred and reacted at room temperature for 2 hours until the reaction was complete. The reaction system was purified by C18 column chromatography and lyophilized to obtain product III-2 (36 mg, yield: 52%) as a light yellow solid. MS (ESI) m/z: 921.3 [M+H]+, 1H NMR (500 MHz, DMSO-d6) δ: 12.36 (s, 1H), 8.73 (s, 1H), 8.45 (d, J=8.0 Hz, 1H), 8.41 (s, 2H), 8.39-8.34 (m, 2H), 8.16 (d, J=8.0 Hz, 1H), 7.94 (t, J=6.0 Hz, 1H), 7.63-7.50 (m, 3H), 7.14 (d, J=8.5 Hz, 1H), 7.03 (d, J=7.0 Hz, 1H), 6.60 (t, J=5.5 Hz, 2H), 5.98 (s, 2H), 5.06 (dd, J=12.5, 5.0 Hz, 1H), 4.52 (t, J=6.0 Hz, 2H), 3.67-3.58 (m, 7H), 3.57-3.53 (m, 2H), 3.47-3.52 (m, 3H), 3.46-3.32 (m, 5H), 3.26-3.17 (m, 6H), 3.11-3.04 (m, 2H), 1.63 (s, 6H).
Example III-3: Synthesis of (III-3)
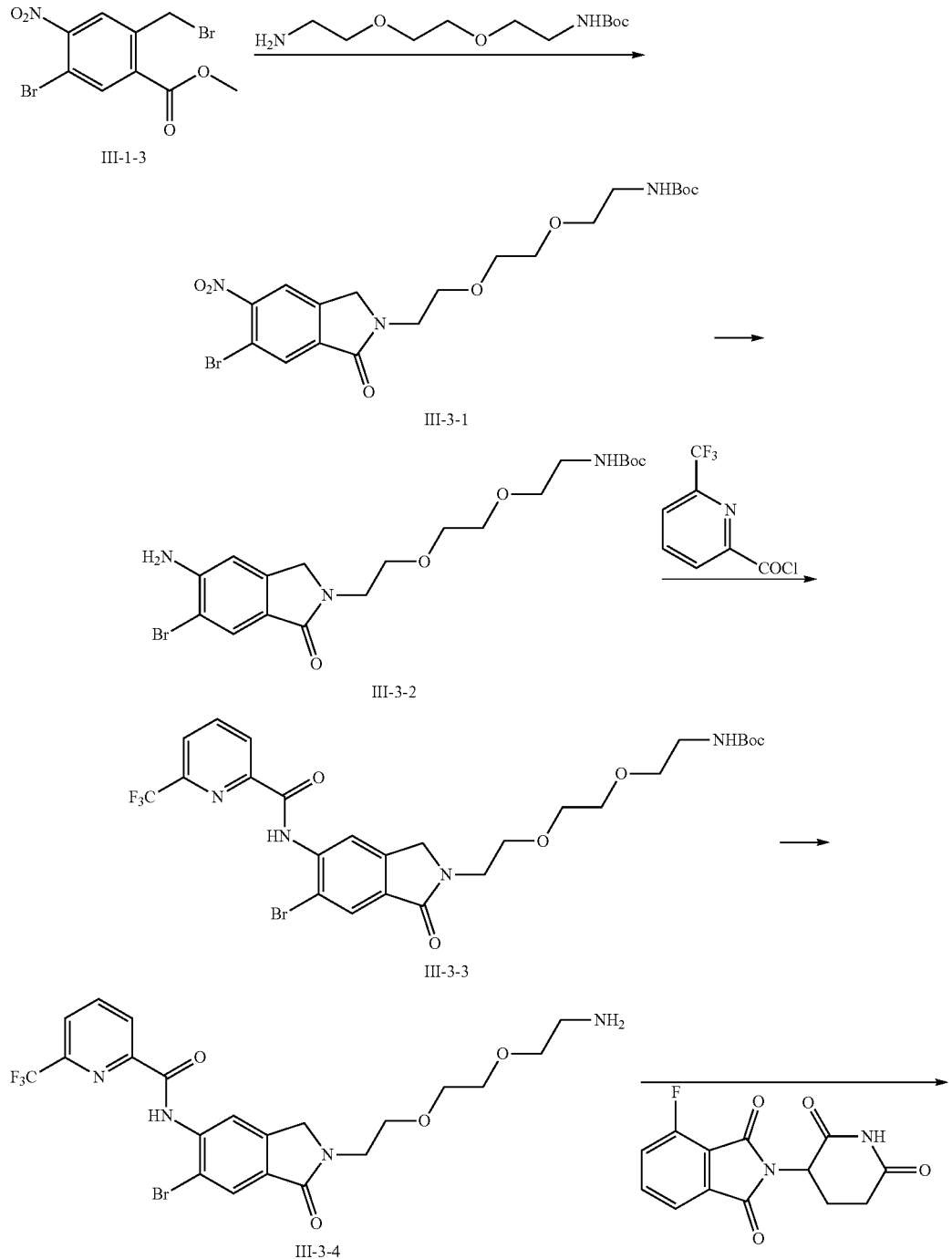

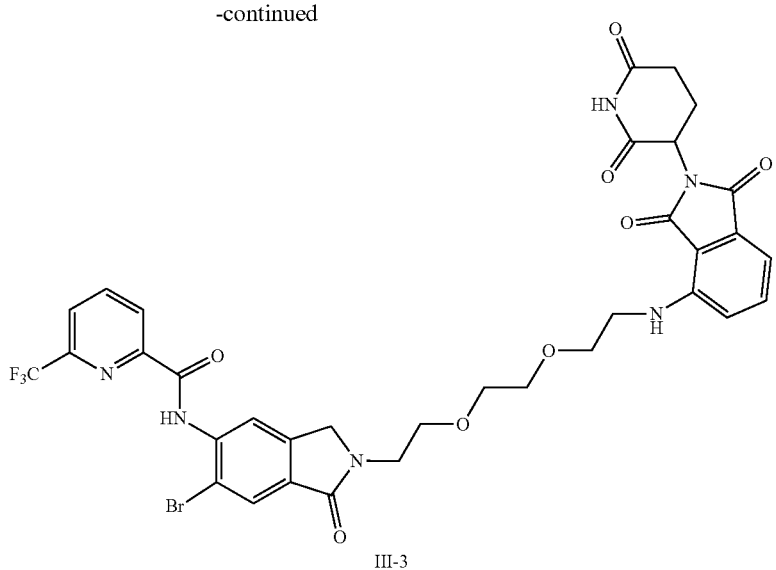

III-3

Step 1: Synthesis of (III-3-1)

III-1-3 (212 mg, 0.60 mmol), tert-butyl (2-(2-aminoethoxy)ethoxy)carbamate (350 mg, 1.4 mmol), triethylamine (183 mg, 1.80 mmol), and methanol (5 mL) were added to a reaction flask, and the reaction mixture was heated to reflux and reacted for 5 hours. The reaction mixture was cooled, added with water to quench, and extracted with ethyl acetate. The organic phase was dried over anhydrous sodium sulfate, filtered, and concentrated. The crude product was purified by silica gel column chromatography (dichloromethane/methanol) to obtain product III-3-1 (269 mg, yield: 92%) as a light yellow liquid, MS (ESI) m/z: 488.2 [M+H]$^+$.

Step 2: Synthesis of (III-3-2)

III-3-1 (269 mg, 0.55 mmol), iron powder (92 mg, 1.65 mmol), ammonium chloride (88 mg, 1.65 mmol), and ethanol/water (3:1, 8 mL) were added to a reaction flask, and the reaction mixture was heated to 90° C. and reacted for 3 hours. The reaction mixture was cooled, added with water to quench, and extracted with ethyl acetate. The organic phase was dried over anhydrous sodium sulfate, filtered, and concentrated. The crude product was purified by silica gel column chromatography (dichloromethane/methanol) to obtain product III-3-2 (236 mg, yield: 94%) as a light yellow liquid, MS (ESI) m/z: 458.2 [M+H]$^+$.

Step 3: Synthesis of (III-3-3)

III-3-2 (236 mg, 0.52 mmol), 6-(trifluoromethyl)picolinoyl chloride (164 mg, 0.78 mmol), DIPEA (336 mg, 2.60 mmol), and dichloromethane (5 mL) were added to a reaction flask, and the reaction mixture was heated to 40° C. and reacted for 2 hours. The reaction mixture was cooled, added with water to quench, and extracted with ethyl acetate. The organic phase was dried over anhydrous sodium sulfate, filtered, and concentrated. The crude product was purified by silica gel column chromatography (dichloromethane/methanol) to obtain product III-3-3 (38 mg, yield: 12%) as a light yellow liquid, MS (ESI) m/z: 631.4 [M+H]$^+$.

Step 4: Synthesis of (III-3-4)

III-3-3 (38 mg, 0.06 mmol) was dissolved in dichloromethane (2 mL), and then trifluoroacetic acid (1 mL) was added thereto. The reaction mixture was stirred at 25° C. for 1 hour until the reaction was complete. The reaction mixture was distilled under reduced pressure to remove the solvent, and the crude product was azeotroped twice with dichloromethane to obtain product III-3-4 (42 mg, crude product), MS (ESI) m/z: 531.1 [M+H]$^+$.

Step 5: Synthesis of (III-3)

The crude product III-3-4 (42 mg) was dissolved in DMF (1 mL), and DIPEA (78 mg, 0.60 mmol) and 2-(2,6-dioxopiperidin-3-yl)-4-fluoroisoindoline-1,3-dione (250 mg, 0.90 mmol) were added to the reaction mixture. The reaction mixture was stirred at 95° C. for 2 hours. After the reaction was stopped, the reaction mixture was cooled to room temperature, and directly purified by C18 column chromatography and eluted with (MeCN/H$_2$O+1‰ HCOOH) to obtain product III-3 (12 mg, yield: 25%) as a yellow solid, MS (ESI) m/z: 787.3 [M+H]$^+$. $^1$H NMR (500 MHz, DMSO-d$_6$) δ: 11.04 (s, 1H), 10.55 (s, 1H), 8.57 (s, 1H), 8.46 (d, J=14.0 Hz, 2H), 8.28 (d, J=5.0 Hz, 1H), 7.90 (s, 1H), 7.45 (t, J=8.0 Hz, 1H), 7.00 (d, J=8.0 Hz, 1H), 6.88 (d, J=7.0 Hz, 1H), 6.46 (s, 1H), 5.07-5.00 (m, 1H), 4.57 (s, 2H), 3.71-3.65 (m, 4H), 3.62-3.55 (m, 6H), 2.93-2.84 (m, 1H), 2.63-2.52 (m, 2H), 2.08-2.02 (m, 1H), 1.25-1.19 (m, 2H).

Example III-4: Synthesis of (III-4)

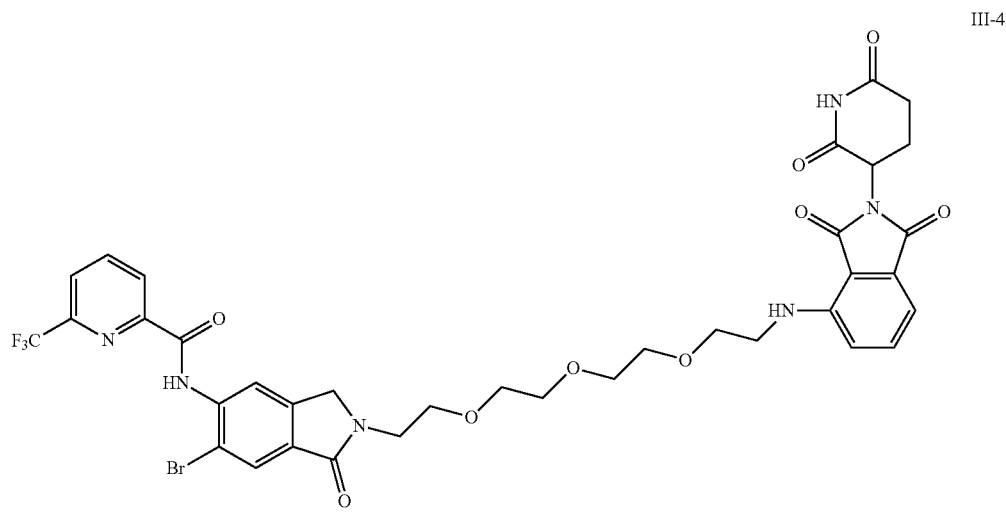 [SMILES: O=C1CCC(N2C(=O)c3cccc(NCCOCCOCCOCCN4Cc5cc(NC(=O)c6cccc(C(F)(F)F)n6)c(Br)cc5C4=O)c3C2=O)C(=O)N1]

Referring to example 3 for the synthesis procedure by replacing tert-butyl (2-(2-aminoethoxy)ethoxy)carbamate in step 1 with tert-butyl (2-(2-(2-aminoethoxy)ethoxy)ethoxy)carbamate, product III-4 (16 mg) was finally obtained, MS (ESI) m/z: 831.3 [M+H]$^+$. $^1$H NMR (500 MHz, DMSO-d$_6$) δ: 11.09 (s, 1H), 10.64 (s, 1H), 8.65 (s, 1H), 8.46 (dq, J=15.5, 8.0 Hz, 2H), 8.26 (d, J=7.5 Hz, 1H), 7.95 (s, 1H), 7.54-7.45 (m, 1H), 7.05 (t, J=8.0 Hz, 1H), 6.96 (t, J=6.5 Hz, 1H), 6.53 (t, J=5.5 Hz, 1H), 5.03 (dd, J=13.0, 5.5 Hz, 1H), 4.58 (s, 2H), 3.66-3.64 (m, 4H), 3.59 (t, J=5.5 Hz, 2H), 3.56-3.52 (m, 6H), 3.42-3.38 (m, 2H), 2.94-2.83 (m, 1H), 2.64-2.55 (m, 2H), 2.08-1.99 (m, 1H), 1.26-1.18 (m, 2H).

Example III-5: Synthesis of (III-5)

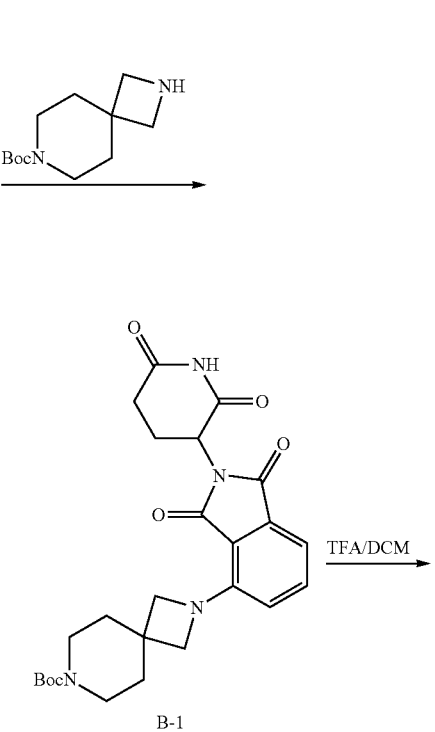

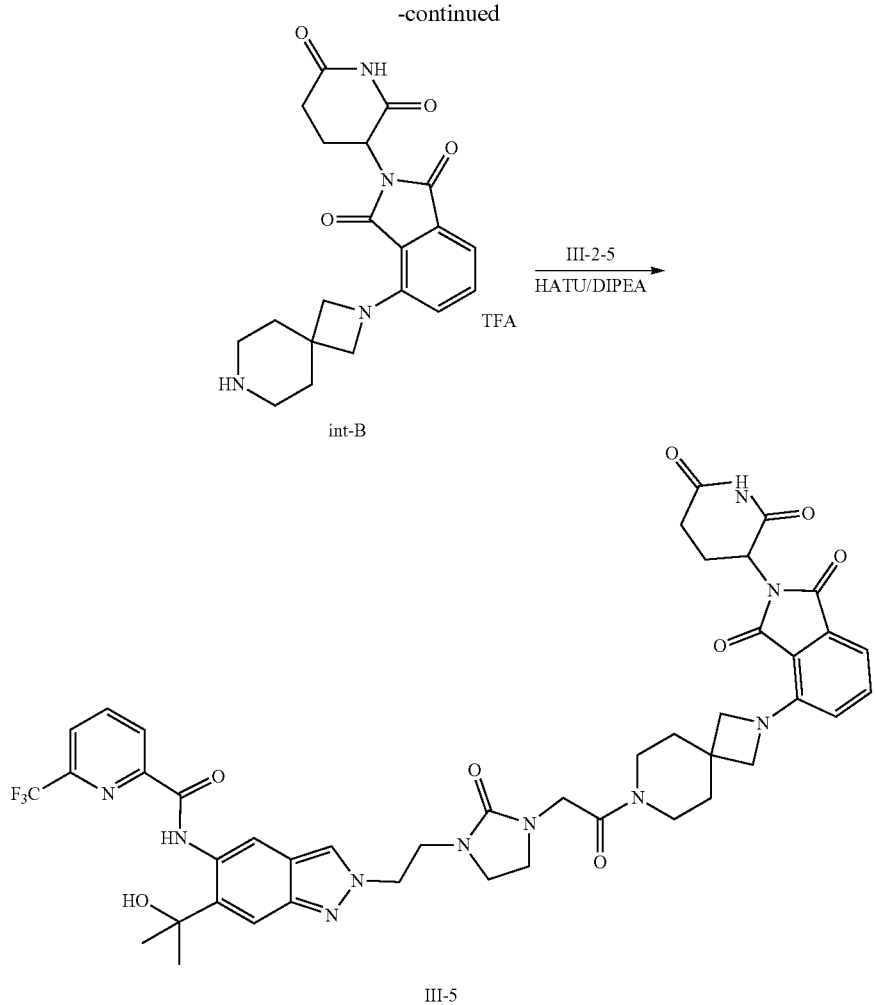

Step 1: Synthesis of (B-1)

2-(2,6-Dioxopiperidin-3-yl)-4-fluoroisoindoline-1,3-dione (200 mg, 0.72 mmol), tert-butyl 2,7-diazaspiro[3.5]nonane-7-carboxylate (197 mg, 0.86 mmol), and DIPEA (187 mg, 1.4 mmol) were dissolved in 2 mL of DMSO. The reaction mixture was stirred and reacted for 2 hours, and directly purified by C18 column chromatography to obtain product A-1 (251 mg, yield: 72%) as a light yellow solid, MS (ESI) m/z: 483.2 [M+H]+.

Step 2: Synthesis of (int-B)

B-1 (251 mg, 0.52 mmol) was dissolved in 3 mL of DCM, and TFA (549 mg, 4.82 mmol) was added thereto. The reaction mixture was stirred and reacted for 1 hour, and subjected to rotary evaporation until dryness to obtain crude product int-B (195 mg, crude product), MS (ESI) m/z: 383.1 [M+H]+.

Step 3: Synthesis of (III-5)

III-2-5 (40 mg, 0.075 mmol) was dissolved in DMF (1 mL), then HATU (42.7 mg, 0.112 mmol) and DIPEA (29 mg, 0.225 mmol) were weighed, and the reaction mixture was stirred and reacted at room temperature for 30 minutes. The reaction system was then added with int-B (39.3 mg, 0.097 mmol), and stirred and reacted at room temperature for 2 hours until the reaction was complete. The reaction system was purified by C18 column chromatography and lyophilized to obtain product III-5 (36 mg, yield: 520%) as a light yellow solid. MS (ESI) m/z: 899.3 [M+H]+, H NMR ((500 MHz, DMSO-$d_6$) δ: 12.35 (s, 1H), 11.07 (s, 1H), 8.73 (s, 1H), 8.43 (d, J=7.5 Hz, 1H), 8.36 (dd, J=6.0 Hz, 2H), 8.15 (d, J=7.5 Hz, 1H), 7.60 (s, 1H), 7.57-7.51 (m, 1H), 7.09 (d, J=7.0 Hz, 1H), 6.76 (d, J=8.5 Hz, 1H), 5.96 (s, 1H), 5.04 (dd, J=5.5 Hz, 1H), 4.53 (t, J=5.5 Hz, 2H), 3.971-3.90 (m, 5H), 3.65 (t, J=5.5 Hz, 2H), 3.38-3.44 (m, 4H), 3.29-3.24 (m, 3H), 3.15-3.05 (m, 2H), 2.923-2.82 (m, 1H), 2.62-2.54 (m, 2H), 2.02-1.93 (3, 1H), 1.77-1.68 (m, 4H), 1.63 (s, 6H).

Referring to example III-2 and example III-5, the following products can finally be synthesized:

| Molecule ID | MS (ESI) m/z: [M + H]+ | 1H NMR |
|---|---|---|
| III-10 | 861.3 | (500 MHz, DMSO-$d_6$) δ: 12.36 (s, 1H), 11.10 (s, 1H), 8.73 (s, 1H), 8.45 (d, J = 7.5 Hz, 1H), 8.37 (d, J = 9.0 Hz, 2H), 8.16 (d, J = 7.5 Hz, 1H), 7.92 (s, 1H), 7.57 (dd, J = 8.0 Hz, 2H), 7.09 (d, J = 8.0 Hz, 1H), 7.01 (d, J = 6.5 Hz, 1H), 6.55 |

| Molecule ID | MS (ESI) m/z: [M + H]+ | 1H NMR |
|---|---|---|
| | | (s, 1H), 5.97 (s, 1H), 5.05 (dd, J = 7.5 Hz, 1H), 4.53 (s, 2H), 3.61-3.66 (m, 3H), 3.32-3.27 (m, 3H), 3.25-3.21 (m, 2H), 3.10 (d, J = 6.5 Hz, 3H), 2.88-2.82 (m, 1H), 2.64-2.59 (m, 2H), 2.03-1.98 (m, 1H), 1.63 (s, 6H), 1.49-1.44 (m, 2H). |
| III-11 | 927.3 | (500 MHz, DMSO-d$_6$) δ: 12.36 (s, 1H), 11.09 (s, 1H), 8.73 (s, 1H), 8.44 (d, J = 7.5 Hz, 1H), 8.40-8.32 (m, 2H), 8.15 (d, J = 7.5 Hz, 1H), 7.67 (t, J = 7.5 Hz, 1H), 7.60 (s, 1H), 7.35-7.29 (m, 2H), 7.26-7.01 (m, 2H), 5.96 (s, 1H), 5.08 (dd, J = 5.0 Hz, 1H), 4.53 (t, J = 5.5 Hz, 2H), 3.92 (s, 2H), 3.65-3.61 (m, 3H), 3.46-3.41 (m, 2H), 3.30-3.22 (m, 6H), 3.15-3.06 (m, 3H), 2.92-2.83 (m, 1H), 2.65-2.56 (m, 2H), 2.06-1.95 (m, 2H), 1.63 (s, 6H), 1.48-1.42 (m, 4H), 1.31-1.22 (m, 6H), 1.18 (t, J = 7.0 Hz, 1H). |
| III-12 | 899.3 | (500 MHz, DMSO-d$_6$) δ: 12.35 (s, 1H), 11.07 (s, 1H), 8.73 (s, 1H), 8.43 (d, J = 7.5Hz, 1H), 8.36 (dd, J = 6.0Hz, 2H), 8.15 (d, J = 7.5 Hz, 1H), 7.60 (s, 1H), 7.57-7.51 (m, 1H), 7.09 (d, J = 7.0 Hz, 1H), 6.76 (d, J = 8.5 Hz, 1H), 5.96 (s, 1H), 5.04 (dd, J = 5.5 Hz, 1H), 4.53 (t, J = 5.5 Hz, 2H), 3.94 (d, J = 13.0 Hz, 5H), 3.65 (t, J = 5.5 Hz, 2H), 3.45-3.41 (m, 4H), 3.29-3.24 (m, 3H), 3.15-3.05 (m, 2H), 2.92-2.82 (m, 1H), 2.58 (dd, J = 15.0 Hz, 2H), 1.99 (t, J = 6.0 Hz, 1H), 1.75 (d, J = 5.0 Hz, 2H), 1.72-1.66 (m, 2H), 1.63 (s, 6H). |
| III-13 | 873.3 | (500 MHz, DMSO-d$_6$) δ: 12.36 (s, 1H), 11.10 (s, 1H), 8.73 (s, 1H), 8.43 (d, J = 7.5 Hz, 1H), 8.36 (dd, J = 6.0 Hz, 2H), 8.15 (d, J = 7.5 Hz, 1H), 7.63-7.54 (m, 2H), 7.22 (d, J = 8.5 Hz, 1H), 7.04 (d, J = 7.0 Hz, 1H), 6.25 (d, J = 8.0 Hz, 1H), 5.97 (s, 1H), 5.05 (dd, J =5.0 Hz, 1H), 4.53 (t, J = 6.0 Hz, 2H), 4.25 (d, J = 12.0 Hz, 1H), 3.94 (s, 2H), 3.83-3.75 (m, 2H), 3.66-3.62 (m, 2H), 3.31-3.25 (m, 3H), 3.17-3.07 (m, 3H), 2.94-2.75 (m, 3H), 2.64-2.56 (m, 1H), 2.06-1.98 (m, 1H), 1.97-1.91 (m, 2H), 1.63 (s, 6H), 1.48-1.42 (m, 1H), 1.36-1.31 (m, 1H). |
| III-14 | 859.3 | (500 MHz, DMSO-d$_6$) δ: 12.36 (s, 1H), 11.10 (s, 1H), 8.73 (s, 1H), 8.44 (d, J = 7.5 Hz, 1H), 8.37 (dd, J = 6.0 Hz, 2H), 8.16 (d, J = 7.5 Hz, 1H), 7.74-7.67 (m, 1H), 7.60 (s, 1H), 7.38 (d, J = 7.5 Hz, 1H), 7.33 (d, J = 8.5 Hz, 1H), 5.97 (s, 1H), 5.11 (dd, J = 5.5 Hz, 1H), 4.53 (t, J = 6.0 Hz, 2H), 4.00 (s, 2H), 3.67-3.58 (m, 6H), 3.31-3.25 (m, 6H), 3.15-3.09 (m, 2H), 2.93-2.83 (m, 1H), 2.08-1.99 (m, 1H), 1.63 (s, 6H). |

Example III-15: Synthesis of (III-15)

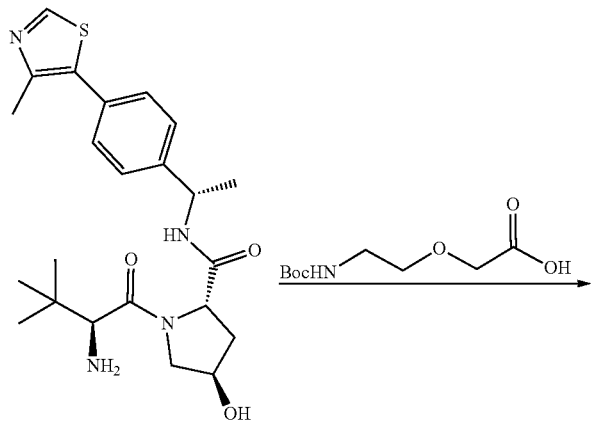

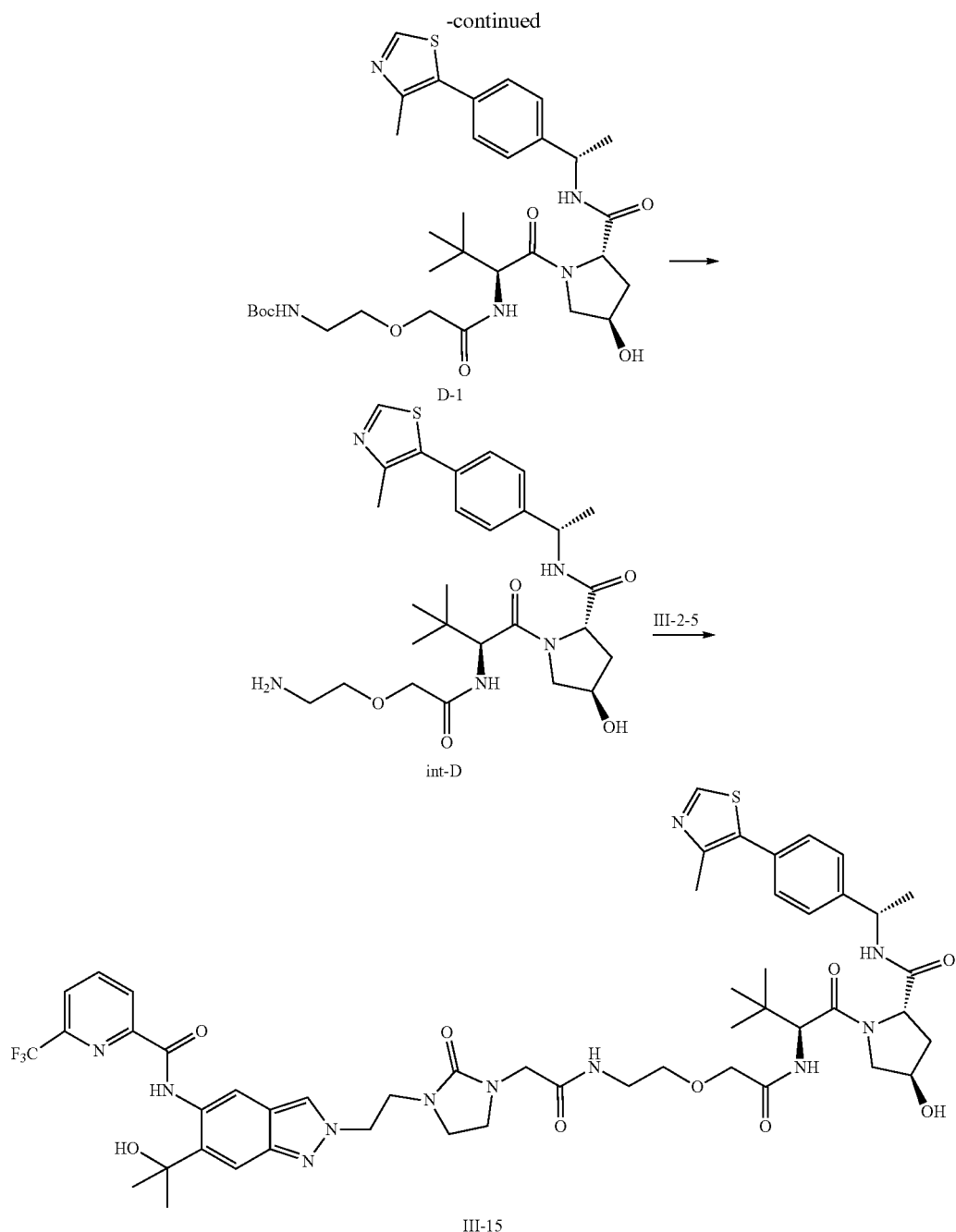

Step 1: Synthesis of (D-1)

(2S,4R)-1-((S)-2-amino-3,3-dimethylbutanoyl)-4-hydroxy-N-((S)-1-(4-(4-methylthiazol-5-yl)phenyl)ethyl)pyrrolidine-2-carboxamide (200 mg, 0.45 mmol), 2-(2-(((tert-butoxycarbonyl)amino)ethoxy)acetic acid (127 mg, 0.86 mmol), DIPEA (174 mg, 1.4 mmol), and HATU (257 mg, 0.67 mmol) were dissolved in 2 mL of DMF. The reaction mixture was stirred and reacted for 2 hours, and directly purified by C18 column chromatography and eluted with (MeCN/H$_2$O+1‰ HCOOH) to obtain product D-1 (197 mg, yield: 68%) as a white solid, MS (ESI) m/z: 646.3 [M+H]$^+$.

Step 2: Synthesis of (int-D)

D-1 (196 mg, 0.29 mmol) was dissolved in 3 mL of DCM, and TFA (549 mg, 4.82 mmol) was added thereto. The reaction mixture was stirred and reacted for 1 hour, and subjected to rotary evaporation until dryness to obtain crude product int-D (163 mg, crude product). MS (ESI) m/z: 546.2 [M+H]$^+$.

Step 3: Synthesis of (III-15)

III-2-5 (40 mg, 0.075 mmol) was dissolved in DMF (1 mL), then HATU (42.7 mg, 0.112 mmol) and DIPEA (29 mg, 0.225 mmol) were added thereto, and the reaction mixture was stirred and reacted at room temperature for 30 minutes. The reaction system was then added with int-D (53 mg, 0.097 mmol), and stirred and reacted at room temperature for 2 hours until the reaction was complete. The reaction mixture was directly purified by C18 column chromatography and eluted with (MeCN/H$_2$O+1‰ HCOOH) to obtain product III-15 (27.8 mg, yield: 35) as a white solid, MS (ESI) m/z: 1062.4 [M+H]+, 1H NMR (500 MHz, DMSO-d6) δ: 12.37 (s, 1H), 8.98 (s, 1H), 8.73 (s, 1H), 8.45 (dd, J=7.5, 3.1 Hz, 2H), 8.40-8.32 (m, 2H), 8.16 (d, J=7.5 Hz, 1H), 7.59 (s, 1H), 7.43-7.41 (m, 3H), 7.39-7.33 (m, 2H), 5.98 (s, 1H), 5.16 (s, 1H), 4.93-4.84 (m, 1H), 4.60-4.49 (m, 3H), 4.43 (t, J=8.0 Hz, 1H), 4.28 (s, 1H), 3.97-3.91 (m, 2H), 3.69-3.63 (m, 4H), 3.62-3.56 (m, 2H), 3.53-3.47 (m, 3H), 3.29-3.25 (m, 5H), 3.10 (t, J=8.0 Hz, 2H), 2.44 (s, 3H), 2.07-1.95 (m, 2H), 1.83-1.70 (m, 1H), 1.62 (s, 6H), 1.37-1.32 (m, 2H), 0.93 (s, 9H).

Referring to example III-15, the following products can finally be synthesized:

| Molecule ID | MS (ESI) m/z: [M + H]+ | 1H NMR |
|---|---|---|
| III-16 | 1112.5 | (500 MHz, DMSO-d6) δ: 12.37 (s, 1H), 8.99 (s, 1H), 8.73 (s, 1H), 8.46 (d, J = 7.5 Hz, 1H), 8.41-8.34 (m, 3H), 8.17 (d, J = 7.5 Hz, 1H), 7.65 (t, J = 10.0Hz, 1H), 7.60 (s, 1H), 7.44 (d, J = 8.0 Hz, 2H), 7.38 (d, J = 8.0 Hz, 2H), 5.97 (s, 1H), 5.15-5.11 (m, 1H), 4.92-4.87 (m, 1H), 4.54-4.50 (m, 3H), 4.42 (t, J = 8.0 Hz, 1H), 4.29 (s, 1H), 3.90 (d, J = 8.0 Hz, 2H), 3.68-3.56 (m, 4H), 3.31-3.17 (m, 5H), 3.11-3.07 (m, 2H), 2.46 (s, 3H), 2.05-1.90 (m, 3H), 1.87-1.75 (m, 3H), 1.63 (s, 6H), 1.55-1.45 (m, 4H), 1.37 (d, J = 7.0 Hz, 4H), 0.92 (s, 9H). |
| III-17 | 1140.5 | (500 MHz, DMSO-d6) δ: 12.37 (s, 1H), 8.99 (s, 1H), 8.72 (s, 1H), 8.45 (d, J = 7.5Hz, 1H), 8.37 (t, J = 10.0 Hz, 3H), 8.16 (d, J = 7.5 Hz, 1H), 7.87-7.78 (m, 1H), 7.60 (s, 1H), 7.43 (d, J = 8.0 Hz, 2H), 7.38 (d, J = 8.0 Hz, 2H), 5.97 (s, 1H), 5.11 (s, 1H), 4.97-4.86 (m, 2H), 4.57-4.47 (m, 4H), 4.41 (t, J = 8.0 Hz, 1H), 4.27 (s, 1H), 4.10 (s, 1H), 4.04-3.98 (m, 1H), 3.86 (s, 1H), 3.82-3.74 (m, 2H), 3.66-3.54 (m, 7H), 3.26-3.22 (m, 3H), 3.11-3.03 (m, 2H), 2.45 (s, 3H), 2.41-2.30 (m, 3H), 2.27-2.16 (m, 4H), 2.05-1.96 (m, 2H), 1.92-1.74 (m, 4H), 1.63 (s, 6H), 1.37 (d, J = 7.0 Hz, 3H), 0.92 (s, 9H). |
| III-19 | 1098.5 | (500 MHz, DMSO-d6) δ: 10.50 (s, 1H), 8.98 (s, 1H), 8.69 (s, 1H), 8.47 (d, J = 7.5 Hz, 1H), 8.42 (d, J = 7.9 Hz, 1H), 8.39-8.37 (m, 1H), 8.34 (s, 1H), 8.22 (d, J = 7.8 Hz, 1H), 7.65-7.61 (m, 1H), 7.45-7.35 (m, 5H), 7.17 (s, 1H), 5.32 (t, J = 4.9 Hz, 2H), 5.11 (d, J = 3.0 Hz, 1H), 4.94-4.88 (m, 2H), 4.50 (d, J = 9.5 Hz, 2H), 4.48-4.44 (m, 2H), 4.44-4.39 (m, 2H), 4.28 (br, 1H), 3.99 (s, 3H), 3.90 (d, J = 7.9 Hz, 2H), 3.63-3.59 (m, 4H), 3.09 (br, 3H), 2.45 (s, 3H), 2.03-2.00 (m, 3H), 2.00-1.98 (m, 2H), 1.82-1.78 (m, 2H), 1.47-1.44 (m, 3H), 1.37 (d, J = 7.0 Hz, 4H), 0.92 (s, 9H). |

Example III-18: Synthesis of (III-18)

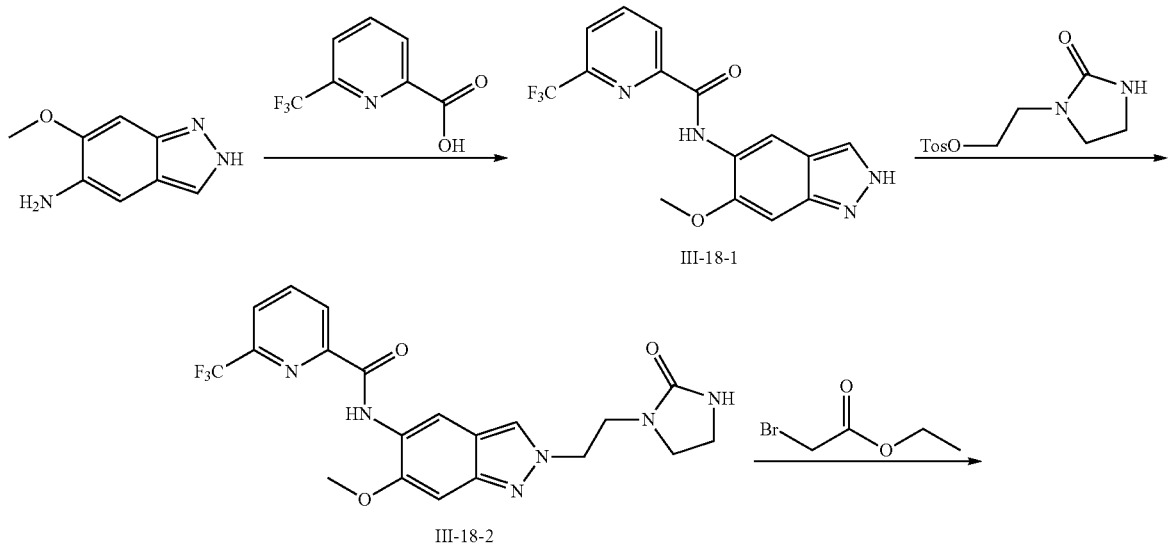

-continued

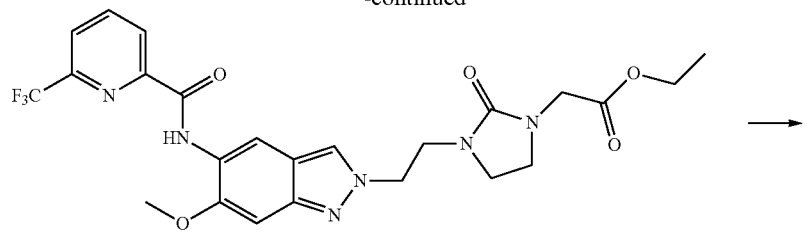

III-18-3

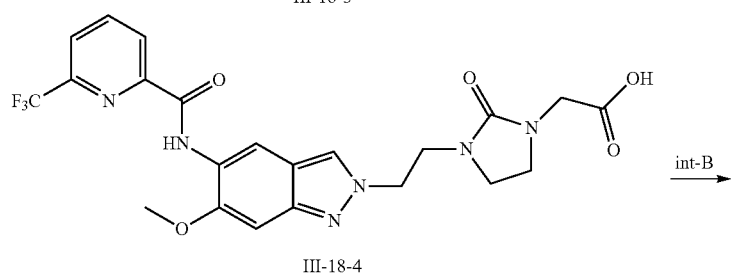

III-18-4

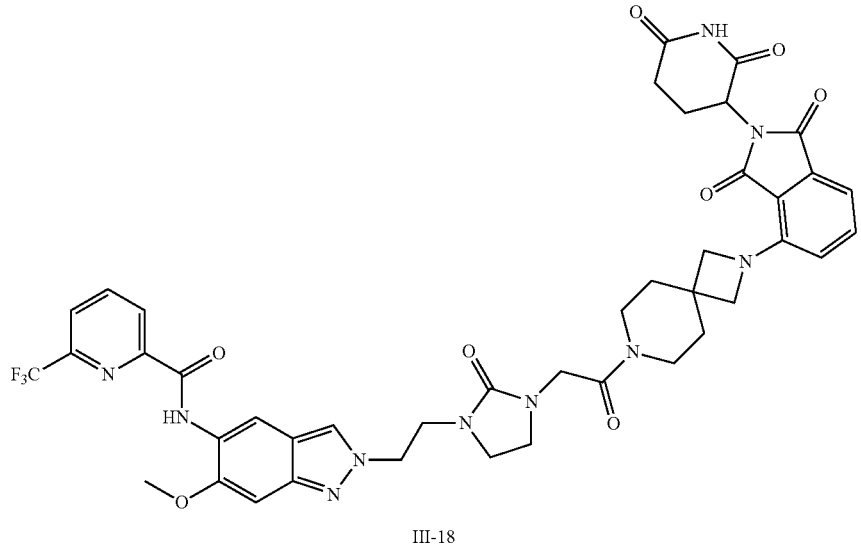

III-18

Step 1: Synthesis of (III-18-1)

6-Methoxy-2H-indazol-5-amine (1 g, 6 mmol) was dissolved in tetrahydrofuran solution (50 mL), then DIPEA (4.6 g, 36 mmol) was slowly added dropwise thereto, and $T_3P$ (3.9 g, 12 mmol) was added thereto. The reaction mixture was then added with 6-(trifluoromethyl)picolinic acid (1.4 g, 7 mmol). After the dropwise addition was completed, the reaction mixture was stirred at room temperature for 16 hours. The reaction system was added with water to precipitate a large amount of solid, which was filtered and then dried under vacuum to obtain product III-18-1 (1.96 g, yield: 95%) as a light yellow solid, MS (ESI) m/z: 337.1 [M+H]$^+$.

Step 2: Synthesis of (III-18-2)

III-18-1 (100 mg, 5.8 mmol) was weighed and dissolved in toluene (2 mL), and DIPEA (192 mg, 1.49 mmol) was added to the reaction mixture. Ethyl 2-(2-oxopyrrolidin-1-yl)benzenesulfonate (96 mg, 0.36 mmol) was then weighed, and the reaction mixture was heated to 110° C. and reacted for 2 hours until the reaction was complete. The reaction mixture was cooled, subjected to rotary evaporation under reduced pressure to remove the solvent, and extracted with ethyl acetate. The organic phase was dried over anhydrous sodium sulfate, and the crude product was purified by silica gel column chromatography to obtain product III-18-2 (123 mg, yield: 92%) as a light yellow solid, MS (ESI) m/z: 449.2 [M+H]$^+$.

Step 3: Synthesis of (III-18-3)

III-18-2 (123 mg, 0.27 mmol) was weighed and dissolved in DMF (2 mL), then NaH (20 mg, 0.824 mmol) was slowly added thereto under an ice bath, and the reaction mixture was stirred for 30 minutes under an ice bath. The reaction system was then added with ethyl 2-bromoacetate (92 mg, 0.55 mmol), naturally warmed, and reacted for 2 hours until the reaction was complete. The reaction mixture was subjected to rotary evaporation under reduced pressure to remove the solvent, and extracted with ethyl acetate. The organic phase was dried over anhydrous sodium sulfate, and the crude product was purified by silica gel column chromatography to obtain product III-18-3 (75 mg, yield: 51%) as a white solid, MS (ESI) m/z: 535.2 [M+H]$^+$.

Step 4: Synthesis of (III-18-4)

III-18-3 (75 mg, 0.14 mmol) was weighed and dissolved in methanol:water=1:1 (1 mL), then LiOH (6.7 mg, 0.28 mmol) was added thereto, and the reaction mixture was stirred and reacted at room temperature for 2 hours until the reaction was complete. The reaction mixture was subjected to rotary evaporation under reduced pressure to remove the solvent, and extracted with ethyl acetate. The organic phase was dried over anhydrous sodium sulfate, and the crude product was purified by silica gel column chromatography to obtain product III-18-4 (68 mg, yield: 95%) as a light yellow solid, MS (ESI) m/z: 507.1 [M+H]⁺.

Step 5: Synthesis of (III-18)

III-18-4 (68 mg, 0.134 mmol) was dissolved in DMF (1 mL), then HATU (76.6 mg, 0.202 mmol) and DIPEA (51.8 mg, 0.4 mmol) were weighed, and the reaction mixture was stirred and reacted at room temperature for 30 minutes. The reaction system was then added with int-B (63 mg, 0.165 mmol), and stirred and reacted at room temperature for 2 hours until the reaction was complete. The reaction mixture was purified by C18 column chromatography to obtain product III-18 (36 mg, yield: 31%) as a yellow solid, MS (ESI) m/z: 871.5 [M+H]⁺, ¹H NMR (500 MHz, DMSO-d₆) δ: 11.07 (s, 1H), 10.48 (s, 1H), 8.69 (s, 1H), 8.46-8.41 (m, 1H), 8.41-8.36 (m, 1H), 8.34 (s, 1H), 8.20 (d, J=7.7 Hz, 1H), 7.57-7.51 (m, 1H), 7.18 (s, 1H), 7.07 (d, J=7.0 Hz, 1H), 6.74 (d, J=8.6 Hz, 1H), 5.32 (t, J=4.8 Hz, 1H), 5.04 (dd, J=12.8, 5.5 Hz, 1H), 4.48 (t, J=5.8 Hz, 2H), 3.99 (s, 3H), 3.93 (s, 4H), 3.64 (t, J=5.8 Hz, 2H), 3.44-3.40 (m, 3H), 3.28-3.23 (m, 3H), 3.14-3.08 (m, 2H), 2.92-2.80 (m, 2H), 2.03-1.97 (m, 3H), 1.74-1.65 (m, 4H).

Referring to example III-18, the following products can finally be synthesized:

| Molecule ID | MS (ESI) m/z: [M + H]⁺ | ¹H NMR |
| --- | --- | --- |
| III-20 | 1084.5 | (500 MHz, DMSO-d₆) δ: 10.50 (s, 1H), 8.98 (s, 1H), 8.69 (s, 1H), 8.47 (d, J = 7.5 Hz, 1H), 8.43-8.37 (m, 2H), 8.34 (s, 1H), 8.22 (d, J = 7.8 Hz, 1H), 7.65-7.59 (m, 1H), 7.46-7.35 (m, 4H), 7.17 (s, 1H), 6.66 (s, 2H), 5.32 (t, J = 4.9 Hz, 2H), 5.11 (d, J = 3.0 Hz, 1H), 4.97-4.84 (m, 3H), 4.56-4.44 (m, 4H), 4.43-4.39 (m, 1H), 4.28 (br, 1H), 3.99 (s, 3H), 3.90 (d, J = 7.9 Hz, 2H), 3.64-3.58 (m, 4H), 3.09 (br, 2H), 2.45 (s, 3H), 2.03-1.96 (m, 6H), 1.83-1.78 (m, 2H), 1.51-1.42 (m, 5H), 1.37 (d, J = 7.0 Hz, 4H), 0.92 (s, 9H). |
| III-21 | 1112.5 | (500 MHz, DMSO-d₆) δ: 10.50 (s, 1H), 8.98 (s, 1H), 8.69 (s, 1H), 8.47 (d, J = 7.8 Hz, 1H), 8.43-8.33 (m, 3H), 8.22 (d, J = 7.6 Hz, 1H), 7.65 (t, J = 10.1 Hz, 1H), 7.48-7.34 (m, 4H), 7.17 (s, 1H), 5.11 (br, 1H), 4.94-4.88 (m, 1H), 4.51-4.45 (m, 3H), 4.42 (t, J = 8.1 Hz, 1H), 4.28 (br, 1H), 3.99 (s, 3H), 3.90 (d, J = 7.5 Hz, 2H), 3.65-3.57 (m, 4H), 3.29-3.23 (m, 3H), 3.12-3.06 (m, 2H), 2.45 (s, 3H), 2.04-1.98 (m, 1H), 1.83-1.75 (m, 1H), 1.68 (d, J = 11.1 Hz, 2H), 1.57-1.43 (m, 5H), 1.37 (d, J = 7.0 Hz, 2H), 1.29-1.20 (m, 5H), 1.15 (d, J = 6.2 Hz, 2H), 1.12-1.02 (m, 3H), 0.93 (s, 9H). |
| III-22 | 1070.5 | (500 MHz, DMSO-d₆) δ: 11.07 (s, 1H), 10.48 (s, 1H), 8.69 (s, 1H), 8.44 (d, J = 7.8 Hz, 1H), 8.38 (t, J = 7.8 Hz, 1H), 8.34 (s, 1H), 8.20 (d, J = 7.7 Hz, 1H), 7.57-7.51 (m, 1H), 7.18 (s, 1H), 7.07 (d, J = 7.0 Hz, 1H), 6.74 (d, J = 8.6 Hz, 1H), 5.32 (t, J = 4.8 Hz, 1H), 5.04 (dd, J = 12.8, 5.5 Hz, 1H), 4.48 (t, J = 5.8 Hz, 2H), 3.99 (s, 3H), 3.93 (br, 4H), 3.64 (t, J = 5.8 Hz, 2H), 3.44-3.40 (m, 3H), 3.28-3.24 (m, 3H), 3.13-3.08 (m, 2H), 2.93-2.80 (m, 2H), 2.03-1.97 (m, 3H), 1.74-1.65 (m, 4H). |
| III-23 | 899.3 | (500 MHz, DMSO-d₆) δ: 11.07 (s, 1H), 10.49 (s, 1H), 8.69 (s, 1H), 8.45 (d, J = 7.7 Hz, 1H), 8.39 (t, J = 7.8 Hz, 1H), 8.34 (s, 1H), 8.20 (d, J = 7.8 Hz, 1H), 7.70-7.63 (m, 1H), 7.31 (dd, J = 7.7, 5.0 Hz, 2H), 7.17 (s, 1H), 5.08 (dd, J = 12.7, 5.5 Hz, 1H), 4.48 (t, J = 5.9 Hz, 2H), 3.99 (s, 3H), 3.92 (s, 2H), 3.63 (t, J = 5.8 Hz, 2H), 3.49-3.43 (m, 3H), 3.28-3.20 (m, 6H), 3.14-3.08 (m, 2H), 2.92-2.82 (m, 1H), 2.65-2.53 (m, 3H), 2.05-1.97 (m, 1H), 1.70-1.56 (m, 4H), 1.51-1.38 (m, 4H). |
| III-28 | 1056.5 | (500 MHz, DMSO-d₆) δ: 10.50 (s, 1H), 8.98 (s, 1H), 8.69 (s, 1H), 8.47 (d, J = 7.7 Hz, 1H), 8.43-8.36 (m, 2H), 8.34 (s, 1H), 8.24-8.21 (m, 1H), 7.45-7.34 (m, 4H), 7.17 (s, 1H), 5.04 (br, 1H), 4.92-4.88 (m, 1H), 4.50-4.43 (m, 3H), 4.28 (br, 1H), 3.99 (s, 3H), 3.89 (d, J = 4.0 Hz, 2H), 3.64-3.58 (m, 2H), 3.55-3.46 (m, 4H), 3.28-3.23 (m, 6H), 3.13-3.04 (m, 4H), 2.91 (s, 1H), 2.45 (s, 3H), 2.04-1.96 (m, 3H), 1.79-1.75 (m, 1H), 1.48-1.40 (m, 4H), 1.23 (s, 1H), 1.09-1.02 (m, 1H), 0.89 (s, 9H). |
| III-35 | 1085.4 | (500 MHz, DMSO-d₆) δ 10.50 (s, 1H), 8.99 (s, 1H), 8.69 (s, 1H), 8.47 (d, J = 7.5 Hz, 1H), 8.43-8.36 (m, 2H), 8.34 (s, 1H), 8.26 (s, 1H), 8.22 (d, J = 7.5 Hz, 1H), 7.44 (d, J = 8.0 Hz, 2H), 7.37 (d, J = 8.5 Hz, 2H), 7.18 (s, 1H), 4.94-4.88 (m, 1H), 4.50-4.46 (m, 3H), 4.28 (s, 1H), 3.99 (s, 3H), 3.89 (d, J = 7.5 Hz, 2H), 3.63-3.60 (m, 3H), 3.38 (s, 2H), 3.29-3.26 (m, 4H), 3.11-3.08 (m, 3H), 2.82-2.80 (m, 1H), 2.46 (s, 3H), 2.16-2.14 (m, 1H), 2.06-1.98 (m, 1H), 1.83-1.76 (m, 1H), 1.6-1.59 (m, 3H), 1.41-1.38 (m, 2H), 1.37-1.35 (m, 3H), 1.35-1.34 (m, 1H), 1.22-1.20 (m, 3H), 1.12-1.02 (m, 4H), 0.90 (s, 9H). |
| III-29 | 1112.5 | (500 MHz, DMSO-d₆) δ: 10.50 (s, 1H), 8.99 (br, 1H), 8.69 (s, 1H), 8.47 (d, J = 7.8 Hz, 1H), 8.42-8.39 (m, 1H), 8.37 (d, J = 5.2 Hz, 1H), 8.31 (s, 1H), 8.22 (d, J = 7.7 Hz, 1H), 7.67 (dd, |

| Molecule ID | MS (ESI) m/z: [M + H]+ | 1H NMR |
|---|---|---|
| | | J = 8.9, 3.5 Hz, 1H), 7.46-7.35 (m, 4H), 7.15 (s, 1H), 5.12 (br, 1H), 4.95-4.90 (m, 1H), 4.56-4.35 (m, 5H), 4.28 (s, 1H), 3.98 (s, 3H), 3.63-3.53 (m, 3H), 3.48-3.42 (m, 5H), 3.07 (s, 2H), 2.82 (t, J = 6.3 Hz, 2H), 2.45 (s, 3H), 2.44-2.27 (m, 7H), 2.03-1.98 (m, 1H), 1.81-1.75 (m, 1H), 1.68 (d, J = 12.1 Hz, 2H), 1.59-1.42 (m, 6H), 1.30 (s, 1H), 1.23 (s, 1H), 1.19 (br, 1H), 1.14-0.98 (m, 3H), 0.93 (s, 9H). |
| III-31 | 1070.5 | (500 MHz, DMSO-$d_6$) δ: 10.50 (s, 1H), 8.98 (s, 1H), 8.68 (s, 1H), 8.47 (d, J = 7.8 Hz, 1H), 8.43-8.36 (m, 2H), 8.31 (s, 1H), 8.22 (d, J = 7.7 Hz, 1H), 7.81 (t, J = 9.9 Hz, 1H), 7.45-7.34 (m, 4H), 7.15 (s, 1H), 5.11 (br, 1H), 4.93-4.89 (m, 1H), 4.50 (d, J = 9.5 Hz, 1H), 4.47-4.38 (m, 2H), 4.27 (br, 1H), 4.15 (s, 1H), 4.07-4.03 (m, 1H), 3.98 (s, 3H), 3.83 (s, 1H), 3.80-3.68 (m, 2H), 3.61-3.55 (m, 2H), 2.89 (d, J = 1.9 Hz, 1H), 2.84-2.80 (m, 2H), 2.45 (s, 3H), 2.40-2.31 (m, 6H), 2.29-2.14 (m, 5H), 2.01 (s, 2H), 1.92-1.74 (m, 5H), 1.23 (s, 2H), 0.92 (s, 9H). |
| III-30 | 992.4 | (500 MHz, DMSO-$d_6$) δ: 11.13 (s, 1H), 10.50 (s, 1H), 8.69 (s, 1H), 8.47 (d, J = 7.8 Hz, 1H), 8.41 (t, J = 7.8 Hz, 1H), 8.34 (s, 2H), 8.32 (s, 1H), 8.22 (d, J = 7.8 Hz, 1H), 8.16 (s, 1H), 7.56-7.50 (m, 1H), 7.19-7.11 (m, 2H), 6.95 (d, J = 8.6 Hz, 1H), 5.32 (t, J = 4.8 Hz, 1H), 5.11 (dd, J = 12.8, 5.3 Hz, 1H), 4.46 (t, J = 6.2 Hz, 2H), 3.99 (s, 3H), 3.80-3.75 (m, 3H), 3.55-3.49 (m, 3H), 3.10 (s, 2H), 2.83 (t, J = 6.3 Hz, 2H), 2.41-2.35 (m, 3H), 2.09-2.04 (m, 1H), 2.03-1.95 (m, 4H), 1.52-1.48 (m, 4H), 1.23 (s, 9H). |

Example III-24: Synthesis of (III-24)

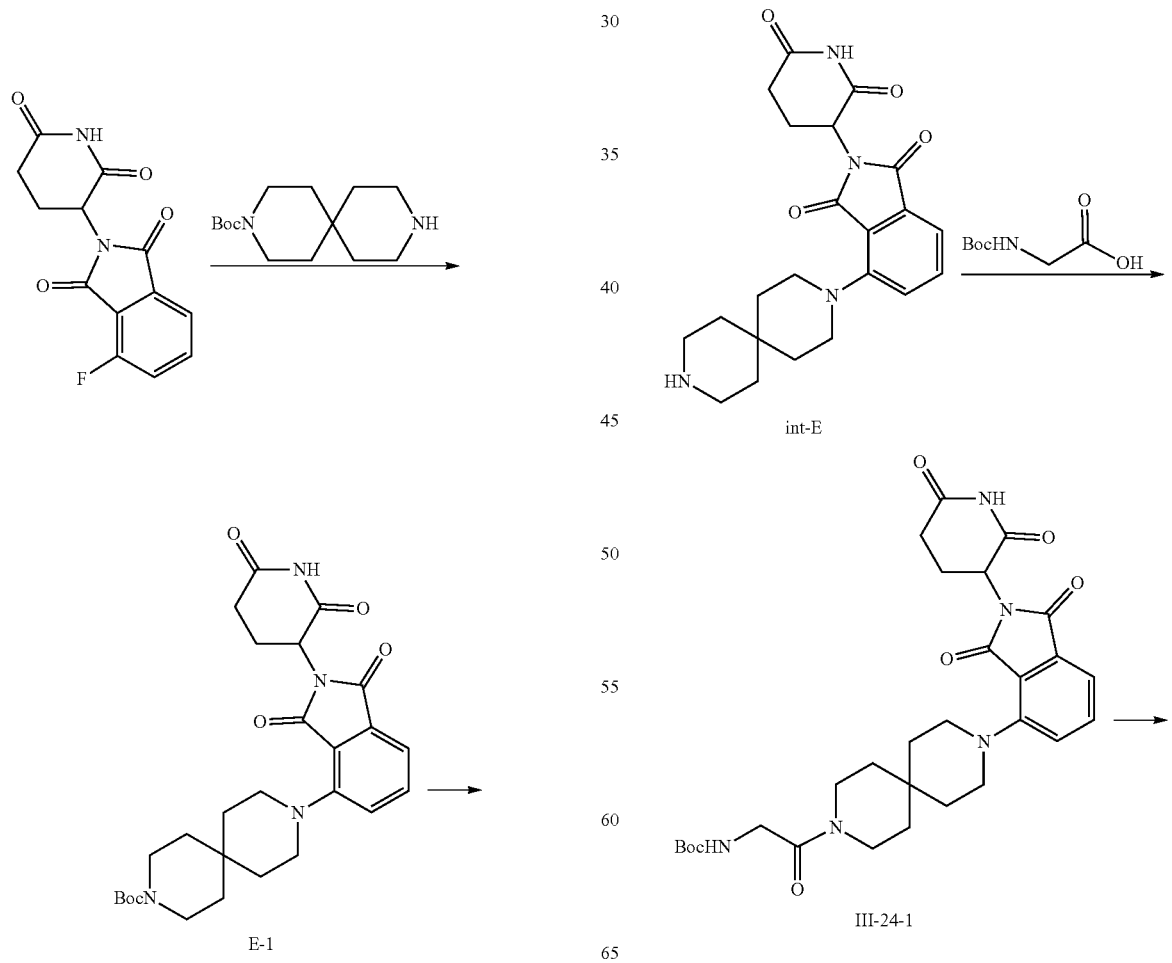

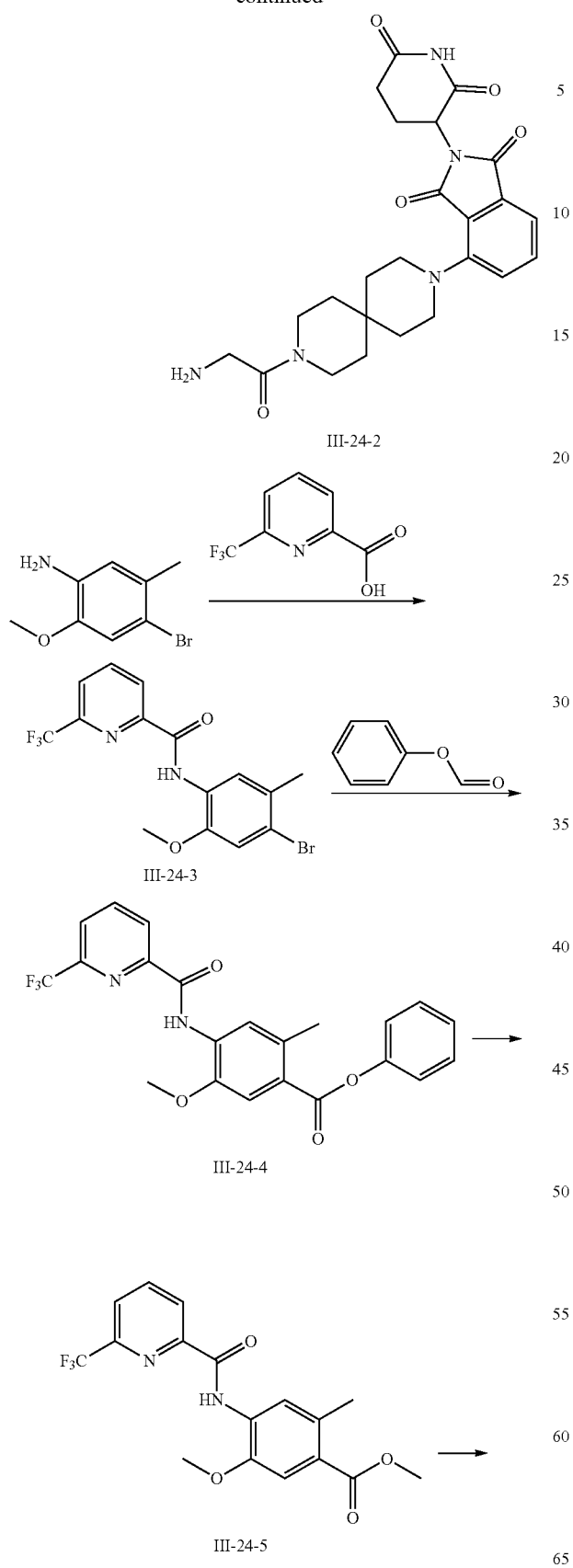

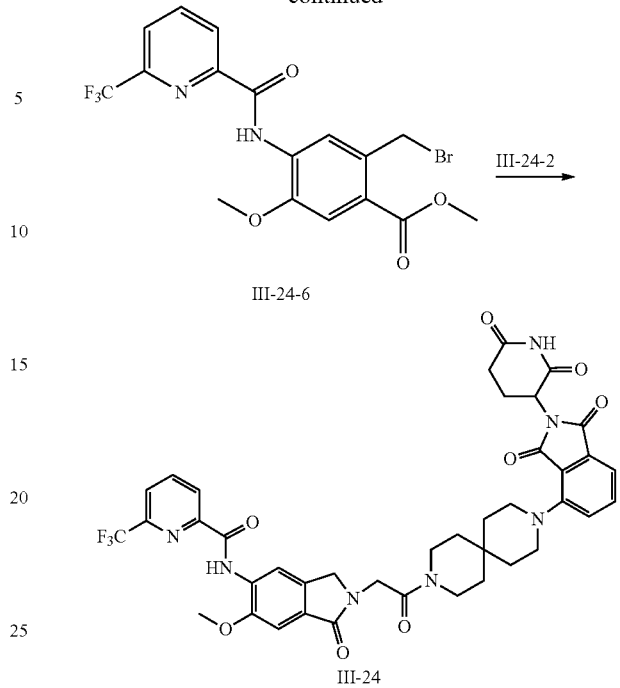

Step 1: Synthesis of (E-1)

2-(2,6-Dioxopiperidin-3-yl)-4-fluoroisoindoline-1,3-dione (200 mg, 0.72 mmol), tert-butyl 3,9-diazaspiro[5.5]undecane-3-carboxylate (220 mg, 0.86 mmol), and DIPEA (187 mg, 1.4 mmol) were dissolved in 2 mL of DMSO. The reaction mixture was stirred and reacted for 2 hours until the reaction was complete, and purified by C18 column chromatography to obtain product E-1 (246 mg, yield: 67%) as a light yellow solid, MS (ESI) m/z: 511.2 [M+H]$^+$.

Step 2: Synthesis of (int-E)

E-1 (100 mg, 0.19 mmol) was added to a mixture of TFA (1 mL) and DCM (2 mL). The reaction mixture was stirred at room temperature for 30 minutes until the reaction was complete, and subjected to rotary evaporation until dryness to remove the solvent to obtain crude product int-E (108 mg, crude product), MS (ESI) m/z: 411.2 [M+H]$^+$.

Step 3: Synthesis of (III-24-1)

2-(tert-Butoxycarbonylamino)acetic acid (44.60 mg, 0.25 mmol), HATU (96.81 mg, 0.25 mmol), and DIPEA (50.63 mg, 0.4 mmol) were added to DMF (1.5 mL), and the reaction mixture was stirred at room temperature for 30 minutes. Then int-E (80.39 mg, 0.2 mmol) was added thereto, and the reaction mixture was reacted at room temperature for 1 hour until the reaction was complete. The reaction mixture was directly purified by C18 column chromatography and eluted with (MeCN/H$_2$O+1‰ HCOOH) to obtain product III-24-1 (110 mg, yield: 98.94%) as a white solid, MS (ESI) m/z: 568.2 [M+H]$^+$.

Step 4: Synthesis of (III-24-2)

III-24-1 (110 mg, 0.2 mmol) was added to a mixture of TFA (1.5 mL) and DCM (3 mL). The reaction mixture was stirred at room temperature for 30 minutes, and subjected to rotary evaporation until dryness to remove the solvent to obtain crude product III-24-2 (120 mg, crude product), MS (ESI) m/z: 468.2 [M+H]$^+$.

Step 5: Synthesis of (III-24-3)

4-Bromo-2-methoxy-5-methyl-aniline (1 g, 4.63 mmol), 6-(trifluoromethyl)pyridine-2-carboxylic acid (1.06 g, 5.55 mmol), DIPEA (1.20 g, 9.26 mmol, 1.61 mL), and anhydrous THF (15 mL) were added to a reaction flask under nitrogen atmosphere, and the reaction mixture was cooled to 0° C. T$_3$P (2.95 g, 9.26 mmol) was slowly added dropwise thereto, and the reaction mixture was stirred at 25° C. for 1 hour. The reaction mixture was added with H$_2$O (60 mL) to precipitate a product, and filtered. The filter cake was washed with water, and dried under vacuum under reduced pressure to obtain product III-24-3 (1.77 g, yield: 98.16%) as a white solid, MS (ESI) m/z: 389.00 [M+H]$^+$.

Step 6: Synthesis of (III-24-4)

III-24-3 (1.77 g, 4.54 mmol), phenyl formate (1.1 g, 9.08 mmol), Pd(OAc)$_2$ (palladium acetate, 101 mg, 0.45 mmol), P(t-Bu)$_3$·HBF$_4$ (tri-tert-butylphosphine tetrafluoroborate, 516.4 mg, 1.78 mmol), Et$_3$N (triethylamine, 917.08 mg, 9.08 mmol), and acetonitrile (3 mL) were added to a reaction flask under nitrogen atmosphere, and the reaction mixture was heated to 80° C. and reacted overnight. The reaction mixture was cooled to room temperature and filtered, and the filtrate was subjected to rotary evaporation under reduced pressure to remove the solvent. The reaction mixture was then added with ethyl acetate, and washed twice with saturated brine. The organic phase was dried over anhydrous sodium sulfate, filtered, and distilled under reduced pressure to remove the solvent to obtain a crude product. The crude product was purified by C18 column chromatography (mobile phase: 0 to 60% water/acetonitrile) to obtain product III-24-4 (1.3 g, yield: 70%) as a white solid, MS (ESI) m/z: 431.1 [M+H]$^+$.

Step 7: Synthesis of (III-24-5)

III-24-4 (1.3 g, 3.2 mmol), potassium carbonate (1.77 g, 12.8 mmol), and methanol (4 mL) were added to a reaction flask, and the reaction mixture was reacted at room temperature for 2 hours. The reaction mixture was added with water to precipitate a product, and filtered. The filter cake was washed with water, and dried under reduced pressure to obtain a crude product, which was purified by C18 column chromatography (mobile phase: 0 to 60% water/acetonitrile) to obtain product III-24-5 (900 mg, yield: 75%) as a white solid, MS (ESI) m/z: 369.1 [M+H]$^+$.

Step 8: Synthesis of (III-24-6)

III-24-5 (900 mg, 2.4 mmol), NBS (512.6 mg, 2.88 mmol), and AIBN (39 mg, 0.24 mmol) were added to a reaction flask under nitrogen atmosphere, and the reaction mixture was heated to 80° C. and reacted for 5 hours. The reaction mixture was cooled and filtered, and the filtrate was added with H$_2$O, extracted with EA (ethyl acetate), dried over anhydrous Na$_2$SO$_4$, filtered, and concentrated under vacuum under reduced pressure to provide a crude product. The crude product was purified by C18 column chromatography and eluted with (MeCN/H$_2$O+1‰ HCOOH) to obtain desired product III-24-6 (802 mg, yield: 76%) as a white solid, MS (ESI) m/z: 447.1 [M+H]$^+$.

Step 9: Synthesis of (III-24)

III-24-6 (40 mg, 0.9 mmol), III-24-2 (120 mg), DIPEA (13.27 mg, 0.1 mmol), and MeCN (3 mL) were added to a reaction flask, and the reaction mixture was stirred at room temperature for 1 hour until the reaction was complete. The reaction mixture was directly purified by C18 column chromatography and eluted with (MeCN/H$_2$O+1‰ HCOOH) to obtain product III-24 (10 mg, yield: 36.44%) as a yellow solid, MS (ESI) m/z: 802.2 [M+H]$^+$, $^1$H NMR (500 MHz, DMSO-d$_6$) δ: 11.10 (s, 1H), 10.59 (s, 1H), 8.66 (s, 1H), 8.48 (d, J=7.6 Hz, 1H), 8.43 (t, J=7.8 Hz, 1H), 8.25 (d, J=7.7 Hz, 1H), 7.71-7.67 (m, 1H), 7.40 (s, 1H), 7.34 (dd, J=16.2, 7.8 Hz, 2H), 5.09 (dd, J=12.7, 5.5 Hz, 1H), 4.46 (d, J=8.2 Hz, 4H), 4.03 (s, 3H), 3.54-3.48 (m, 6H), 3.33-3.23 (m, 6H), 1.72-1.63 (m, 4H), 1.57 (br, 2H), 1.48 (br, 2H).

Example III-25: Synthesis of (III-25)

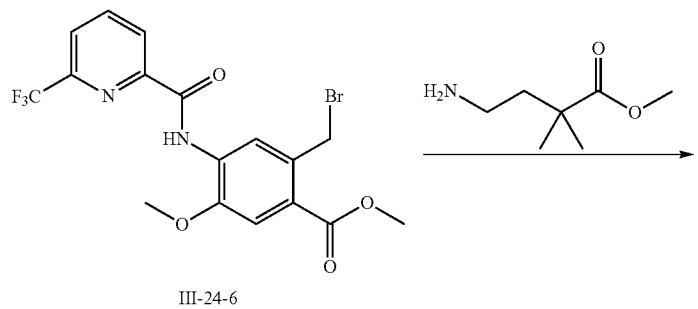

III-24-6

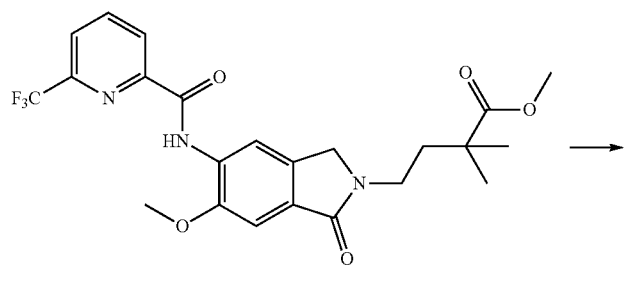

III-25-1

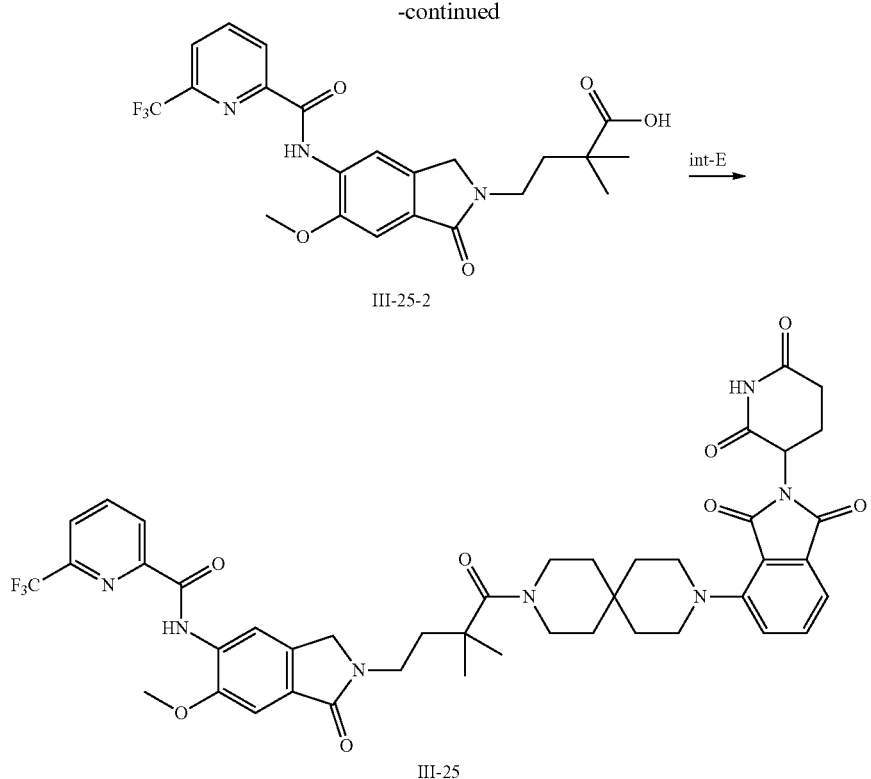

Step 1: Synthesis of (III-25-1)

Methyl 4-amino-2,2-dimethylbutanoate (29.01 mg, 0.2 mmol) and DIPEA (34.68 mg, 0.03 mmol) were added to a solution of III-24-6 (30 mg, 0.07 mmol) in acetonitrile (2.06 mL), and the reaction mixture was reacted at 25° C. for 3 hours. The reaction mixture was purified by C18 column chromatography and eluted with (MeCN/H$_2$O+1‰ HCOOH) to obtain desired product III-25-1 (0.022 g, yield: 67.92%) as a white solid. MS (ESI) m/z: 480.2 [M+H]$^+$.

Step 2: Synthesis of (III-25-2)

III-25-1 (220 mg, 0.46 mmol) was added to a mixture of THF (4 mL) and H$_2$O (2 mL), then LiOH (32.97 mg, 1.38 mmol) was added thereto at room temperature, and the reaction mixture was stirred at room temperature for 2 hours. The reaction mixture was subjected to rotary evaporation under reduced pressure to remove the solvent, added with 2 mol/L hydrochloric acid to adjust the pH to about 3, extracted with ethyl acetate, and subjected to rotary evaporation until dryness to remove the solvent to obtain a crude product. The crude product was purified by C18 column chromatography (mobile phase: 0 to 60% water/acetonitrile) to obtain product III-25-2 (145 mg, yield: 67.9%) as a white solid, MS (ESI) m/z: 466.1 [M+H]$^+$.

Step 3: Synthesis of (III-25)

III-25-2 (48 mg, 0.1 mmol), DIPEA (66.65 mg, 0.52 mmol), HATU (50.98 mg, 0.13 mmol), and DMF (2 mL) were added to a reaction flask, and the reaction mixture was stirred at room temperature for 30 minutes. Then int-E (51 mg, 0.1 mmol) was added thereto, and the reaction mixture was reacted at room temperature for 1 hour. The reaction mixture was directly purified by C18 column chromatography and eluted with (MeCN/H$_2$O+1‰ HCOOH) to obtain product III-25 (50 mg, yield: 52.78%) as a yellow solid, MS (ESI) m/z: 858.3 [M+H]$^+$, $^1$H NMR (500 MHz, DMSO-d$_6$) δ: 11.10 (s, 1H), 10.56 (s, 1H), 8.64 (s, 1H), 8.48 (d, J=7.8 Hz, 1H), 8.42 (t, J=7.8 Hz, 1H), 8.25 (d, J=7.7 Hz, 1H), 7.72-7.64 (m, 1H), 7.36 (s, 1H), 7.36-7.28 (m, 2H), 5.09 (dd, J=12.7, 5.5 Hz, 1H), 4.47 (s, 2H), 4.02 (s, 3H), 3.64-3.53 (m, 4H), 3.51-3.46 (m, 2H), 3.30-3.23 (m, 4H), 2.93-2.82 (m, 1H), 2.64-2.53 (m, 2H), 2.06-1.99 (m, 1H), 1.96-1.87 (m, 2H), 1.72-1.60 (m, 4H), 1.56-1.44 (m, 4H), 1.27 (s, 6H).

Referring to example III-25, the following products can finally be synthesized:

| Molecule ID | MS (ESI) m/z: [M + H]$^+$ | $^1$H NMR |
|---|---|---|
| III-26 | 1071.5 | (500 MHz, DMSO-d$_6$) δ: 10.56 (s, 1H), 8.99 (s, 1H), 8.64 (s, 1H), 8.48 (d, J = 7.7 Hz, 1H), 8.43 (d, J = 7.8 Hz, 1H), 8.41-8.38 (m, 1H), 8.25 (d, J = 7.7 Hz, 1H), 7.67 (d, J = 9.2 Hz, 1H), 7.47-7.37 (m, 1H), 7.35 (s, 1H), 5.12 (br, 1H), 4.95-4.88 (m, 1H), 4.50 (d, J = 9.3 Hz, 1H), 4.45 (s, 2H), 4.42 (t, J = 8.1 Hz, 1H), 4.28 (br, 1H), 4.01 (s, 3H), 3.62-3.55 (m, 2H), 3.51-3.45 (m, 6H), 2.46 (s, 3H), 2.39-2.29 (m, 1H), 2.06-1.98 (m, 1H), 1.94-1.86 (m, 2H), |

-continued

| Molecule ID | MS (ESI) m/z: [M + H]+ | 1H NMR |
|---|---|---|
| III-27 | 1029.5 | 1.83-1.75 (m, 1H), 1.71 (d, J = 11.3 Hz, 2H), 1.58-1.42 (m, 6H), 1.38 (d, J = 7.0 Hz, 3H), 1.30-1.26 (m, 2H), 1.25 (s, 6H), 1.08 (br, J = 4.3 Hz, 2H), 0.93 (s, 9H). (500 MHz, DMSO-$d_6$) δ: 10.57 (s, 1H), 8.99 (d, J = 1.9 Hz, 1H), 8.63 (s, 1H), 8.48 (d, J = 7.9 Hz, 1H), 8.46-8.37 (m, 2H), 8.25 (d, J = 7.7 Hz, 1H), 7.80 (d, J = 9.2 Hz, 1H), 7.46-7.41 (m, 2H), 7.40-7.36 (m, 2H), 7.35 (s, 1H), 5.12 (br, 1H), 4.95-4.89 (m, 1H), 4.50 (d, J = 9.1 Hz, 1H), 4.42 (s, 3H), 4.28 (br, 1H), 4.02 (d, J = 1.6 Hz, 3H), 3.61-3.57 (m, 2H), 3.53-3.45 (m, 4H), 2.45 (d, J = 1.8 Hz, 3H), 2.39-2.32 (m, 2H), 2.26 (br, 1H), 2.21-2.05 (m, 3H), 2.05-1.98 (m, 1H), 1.90-1.73 (m, 5H), 1.37 (d, J = 6.8 Hz, 3H), 1.30-1.21 (m, 1H), 1.15 (s, 6H), 0.92 (s, 9H). |
| III-33 | 951.3 | (500 MHz, DMSO-$d_6$) δ: 11.13 (s, 1H), 10.57 (s, 1H), 8.65 (s, 1H), 8.48 (d, J = 7.8 Hz, 1H), 8.45-8.40 (m, 1H), 8.34 (s, 2H), 8.25 (d, J = 7.6 Hz, 1H), 8.17 (s, 1H), 7.57-7.51 (m, 1H), 7.37 (s, 1H), 7.17 (d, J = 7.0 Hz, 1H), 6.96 (d, J = 8.5 Hz, 1H), 5.11 (dd, J = 12.7, 5.3 Hz, 1H), 4.47 (s, 2H), 4.03 (s, 3H), 3.83-3.73 (m, 4H), 3.61-3.52 (m, 4H), 3.51-3.47 (m, 2H), 2.94-2.87 (m, 1H), 2.64-2.59 (m, 1H), 2.09-2.04 (m, 1H), 2.03-1.95 (m, 1H), 1.94-1.87 (m, 2H), 1.57-1.45 (m, 8H), 1.27 (s, 6H). |
| III-32 | 1150.5 | (500 MHz, DMSO-$d_6$) δ: 10.57 (s, 1H), 8.99 (s, 1H), 8.80 (s, 2H), 8.64 (s, 1H), 8.48 (d, J = 7.8 Hz, 1H), 8.44-8.40 (m, 2H), 8.25 (d, J = 7.6 Hz, 1H), 8.03 (d, J = 9.0 Hz, 1H), 7.48-7.37 (m, 5H), 7.36 (s, 1H), 5.15 (br, 1H), 4.96-4.90 (m, 1H), 4.73 (d, J = 9.0 Hz, 1H), 4.48-4.45 (m, 2H), 4.31 (br, 1H), 4.03 (s, 3H), 3.87-3.80 (m, 4H), 3.70-3.65 (m, 2H), 3.59-3.52 (m, 4H), 3.50-3.46 (m, 2H), 2.46 (s, 3H), 2.05-1.97 (m, 2H), 1.94-1.88 (m, 2H), 1.83-1.78 (m, 1H), 1.54-1.47 (m, 8H), 1.38 (d, J = 6.9 Hz, 3H), 1.26 (s, 6H), 1.02 (s, 9H). |
| III-36 | 1151.7 | (500 MHz, DMSO-$d_6$) δ 10.57 (s, 1H), 8.99 (s, 1H), 8.64 (s, 1H), 8.58 (s, 2H), 8.49-8.47 (m, 2H), 8.42 (t, J = 8.0 Hz, 1H), 8.32 (d, J = 7.5 Hz, 1H), 8.25 (d, J = 7.5 Hz, 1H), 7.45 (d, J = 8.0 Hz, 2H), 7.40-7.37 (d, J = 8.0 Hz, 2H), 7.36 (s, 1H), 5.17 (s, 1H), 4.94-4.90 (m, 1H), 4.69-4.67 (m, 1H), 4.46 (d, J = 7.0 Hz, 2H), 4.30 (s, 1H), 4.02 (s, 3H), 3.65-3.63 (m, 2H), 3.57-3.55 (m, 4H), 3.50-3.48 (m, 3H), 3.45-3.42 (m, 4H), 2.46 (s, 3H), 2.10-2.05 (m, 1H), 1.93-1.88 (m, 2H), 1.82-1.76 (m, 1H), 1.62-1.59 (m, 4H), 1.50-1.48 (m, 4H), 1.39 (d, J = 7.0 Hz, 3H), 1.27 (s, 6H), 0.99 (s, 9H). |

Example III-51: Synthesis of (III-51)

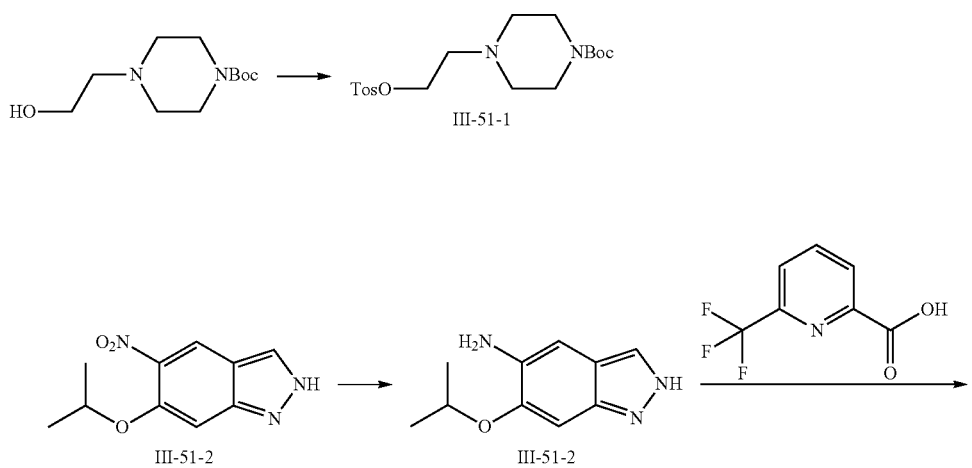

-continued
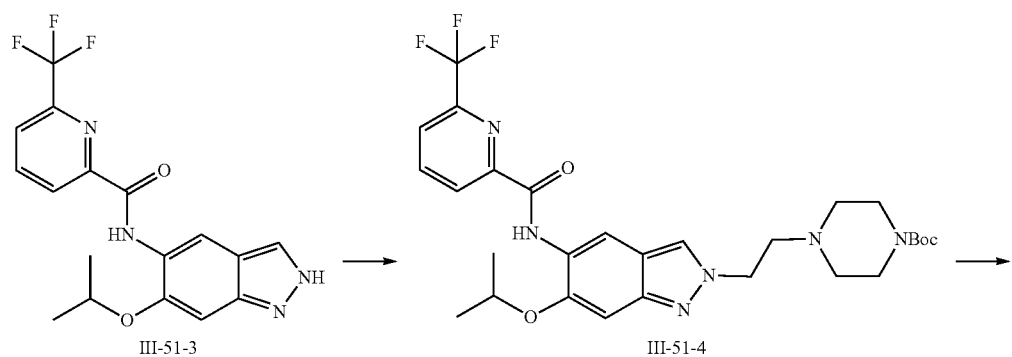
III-51-3 → III-51-4
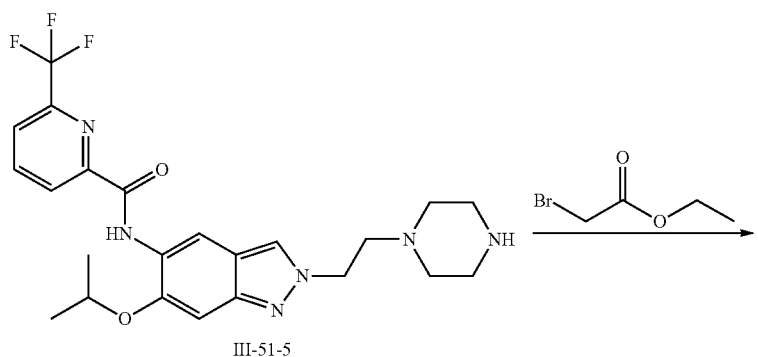
III-51-5
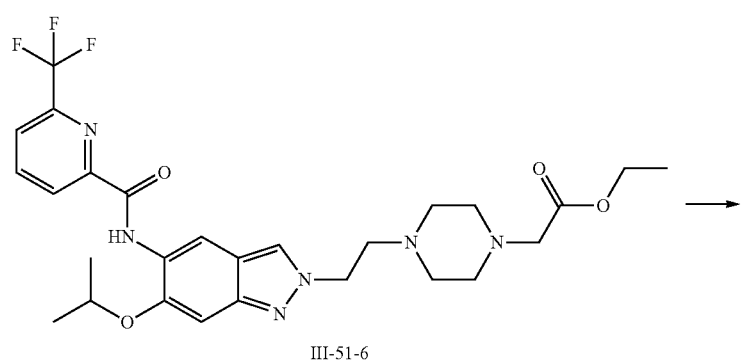
III-51-6
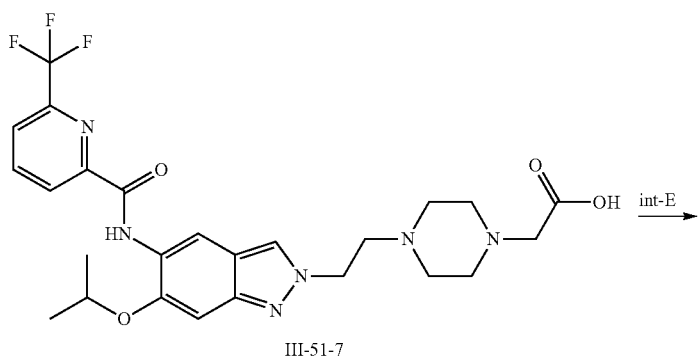
III-51-7

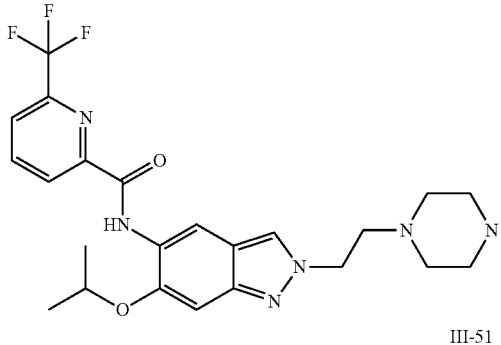 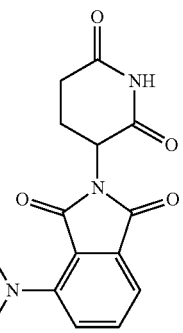

III-51

Step 1: Synthesis of (III-51-1)

A mixture of tert-butyl 4-(2-hydroxyethyl)piperazine-1-carboxylate (600 mg, 2.61 mmol), TEA (1.32 g, 13.03 mmol, 1.82 mL), 4-methylbenzenesulfonyl chloride (546.35 mg, 2.87 mmol), and DCM (5 mL) was stirred at 25° C. for 6 hours under nitrogen atmosphere until the reaction was complete. The reaction mixture was added with $H_2O$ (20 mL), stirred, and extracted with EA (15 mL×3). The combined organic phases were then washed with saturated brine (10 mL), dried over anhydrous $Na_2SO_4$, filtered, and concentrated under reduced pressure to obtain product III-51-1 (542 mg, crude product) as a light yellow oil, MS (ESI) m/z: 358.5 [M+H]+.

Step 2: Synthesis of (III-51-2)

A mixture of 6-isopropoxy-5-nitro-2H-indazole (500 mg, 2.26 mmol), wet Pd/C (55 mg, purity: 10%), and MeOH (15 mL) was stirred at 25° C. for 24 hours under hydrogen atmosphere until the reaction was complete. The reaction mixture was filtered, then the filter cake was washed with MeOH (10 mL×3), and the filtrate was concentrated under reduced pressure to obtain product III-51-2 (331 mg, yield: 76.58%) as a yellow solid, MS (ESI) m/z: 192.2 [M+H]+.

Step 3: Synthesis of (III-51-3)

A mixture of III-51-2 (300 mg, 1.57 mmol), 6-(trifluoromethyl)pyridine-2-carboxylic acid (359.77 mg, 1.88 mmol), PyBOP (979.66 mg, 1.86 mmol), DIPEA (405.50 mg, 3.14 mmol, 546.50 µL), and DMF (5 mL) was stirred at 25° C. for 6 hours under nitrogen atmosphere until the reaction was complete. The reaction mixture was added with $H_2O$ (50 mL), stirred, and extracted with EA (50 mL×3). The combined organic phases were washed with saturated brine (50 mL), dried over anhydrous $Na_2SO_4$, filtered, and concentrated under reduced pressure to obtain product III-51-3 (421 mg, crude product) as a brown solid, MS (ESI) m/z: 365.1 [M+H]+.

Step 4: Synthesis of (III-51-4)

A mixture of III-51-3 (500 mg, 1.37 mmol), DIPEA (354.74 mg, 2.74 mmol, 478.09 L), III-51-1 (527.68 mg, 1.38 mmol), and toluene (10 mL) was stirred at 110° C. for 2 hours under nitrogen atmosphere until the reaction was complete. The reaction mixture was added with $H_2O$ (30 mL), and extracted with EA (50 mL×3). The combined organic phases were washed with saturated brine (10 mL), dried over anhydrous $Na_2SO_4$, filtered, and concentrated under reduced pressure to obtain a crude product. The crude product was purified by silica gel column chromatography to obtain product III-51-4 (142 mg, yield: 17.94%) as a brown solid, MS (ESI) m/z: 577.2 [M+H]+.

Step 5: Synthesis of (III-51-5)

A mixture of III-51-4 (142 mg, 246.27 µmol), DCM (3 mL), and HCl-dioxane solution (4 M, 0.5 mL) was stirred at 25° C. for 2 hours until the reaction was complete. The reaction mixture was filtered, and the filter cake was washed with DCM (10 mL×3) and dried under vacuum under reduced pressure to obtain product III-51-5 (100 mg, yield: 85.22%, hydrochloride) as a white solid, MS (ESI) m/z: 477.2 [M+H]+.

Step 6: Synthesis of (III-51-6)

A mixture of III-51-5 (100 mg, 209.87 µmol), DIPEA (27.12 mg, 2090.87 µmol, 36.55 L), ethyl 2-bromoacetate (42.06 mg, 251.84 µmol, 27.93 µL), and DMF (2 mL) was stirred at 25° C. for 2 hours under nitrogen atmosphere until the reaction was complete. The reaction mixture was added with $H_2O$ (20 mL), and extracted with EA (30 mL×3). The combined organic phases were washed with saturated brine (10 mL), dried over anhydrous $Na_2SO_4$, filtered, and concentrated under reduced pressure to obtain product III-51-6 (85 mg, crude product) as a yellow solid, MS (ESI) m/z: 563.2 [M+H]+.

Step 7: Synthesis of (III-51-7)

A mixture of III-51-6 (85 mg, 151.09 µmol), lithium hydroxide (18.09 mg, 755.44 mol), methanol (3 mL), and $H_2O$ (1.5 mL) was stirred at 25° C. for 3 hours under nitrogen atmosphere until the reaction was complete. The reaction mixture was added with $H_2O$ (5 mL), acidified to adjust the pH to about 6 with stirring, and concentrated under vacuum to remove the organic solution to obtain an aqueous phase. The aqueous phase was purified by reverse phase C18 column chromatography to obtain product III-51-7 (36 mg, yield: 44.58%) as a yellow solid, MS (ESI) m/z: 535.3 [M+H]+.

Step 8: Synthesis of (III-51)

A mixture of III-51-7 (30 mg, 56.12 µmol), int-E (27.64 mg, 67.35 µmol), HATU (25.61 mg, 67.35 µmol), DIPEA (14.51 mg, 112.25 µmol, 19.55 µL), and DMF (2 mL) was stirred at 25° C. for 2 hours until the reaction was complete. The reaction mixture was added with $H_2O$ (10 mL), and extracted with EA (10 mL×3). The combined organic phases were washed with saturated brine (10 mL), dried over anhydrous $Na_2SO_4$, filtered, and concentrated under reduced pressure to obtain a crude product, which was purified by preparative thin-layer chromatography (DCM:MeOH=20:1) to obtain product III-51 (13 mg, yield: 23.47%) as a yellow solid, MS (ESI) m/z: 927.5 [M+H]+. 1H NMR (500 MHz, DMSO-d₆) δ 11.11 (s, 1H), 10.74 (s, 1H), 8.72 (s, 1H), 8.45 (d, J=8.0 Hz, 1H), 8.40 (t, J=8.0 Hz, 1H), 8.31 (s, 1H), 8.22 (d, J=7.5 Hz, 1H), 7.67 (t, J=8.0 Hz, 1H), 7.34-7.31 (m, 2H), 7.18 (s, 1H), 5.09 (dd, J=12.5, 5.5 Hz, 1H), 4.87-4.82 (m, 1H), 4.45 (t, J=7.0 Hz, 2H), 3.50-3.44 (m, 4H), 3.29-3.25 (m, 4H), 3.10 (s, 2H), 2.91-2.83 (m, 4H), 2.63-2.53 (m, 4H), 2.42-2.36 (m, 4H), 2.03-1.96 (m, 2H), 1.66-1.64 (m, 4H), 1.51-1.49 (m, 2H), 1.42-1.52-1.38 (m, 8H).

Referring to examples III-2, III-18, III-25, and III-51, the following products can finally be synthesized:

| Molecule ID | MS (ESI) m/z: [M + H]⁺ | ¹H NMR |
|---|---|---|
| III-38 | 899.5 | (500 MHz, DMSO-d₆) δ 11.11 (s, 1H), 10.50 (s, 1H), 8.69 (s, 1H), 8.46 (d, J = 8.0 Hz, 1H), 8.40 (t, J = 8.0 Hz, 1H), 8.32 (s, 1H), 8.22 (d, J = 7.5 Hz, 1H), 7.67 (t, J = 7.5 Hz, 1H), 7.35-7.31 (m, 2H), 7.15 (s, 1H), 5.09 (dd, J = 12.5, 5.5 Hz, 1H), 4.46 (t, J = 6.0 Hz, 2H), 3.98 (s, 3H), 3.53-3.43 (m, 4H), 3.30-3.25 (m, 4H), 3.10 (s, 2H), 2.89-2.80 (m, 3H), 2.63-2.54 (m, 2H), 2.49-2.33 (m, 7H), 2.05-1.97 (m, 2H), 1.68-1.61(m, 4H), 1.52-1.38 (m, 4H). |
| III-39 | 705.5 | (500 MHz, DMSO-d₆) δ 11.10 (s, 1H), 10.51 (s, 1H), 8.70 (s, 1H), 8.47 (d, J = 7.5 Hz, 1H), 8.41 (t, J = 7.5 Hz, 1H), 8.36 (s, 1H), 8.22 (d, J = 7.5 Hz, 1H), 7.69 (t, J = 7.5 Hz, 1H), 7.36-7.32 (m, 2H), 7.17 (s, 1H), 5.09 (dd, J = 12.5, 5.5 Hz, 1H), 4.53 (t, J = 6.0 Hz, 2H), 3.99 (s, 3H), 3.31-3.25 (m, 4H), 2.94-2.76 (m, 3H), 2.68-2.60 (m, 4H), 2.59-2.51 (m, 2H), 2.04-1.99 (m, 1H). |
| III-40 | 856.6 | (500 MHz, DMSO-d₆) δ 11.10 (s, 1H), 10.51 (s, 1H), 8.69 (s, 1H), 8.47 (d, J = 7.5 Hz, 1H), 8.41 (t, J = 7.5 Hz, 1H), 8.35 (s, 1H), 8.23 (d, J = 7.5 Hz, 1H), 7.67 (t, J = 7.5 Hz, 1H), 7.34-7.30 (m, 2H), 7.16 (s, 1H), 5.09 (dd, J = 12.5, 5.5 Hz, 1H), 4.46 (t, J = 6.0 Hz, 2H), 3.99 (s, 3H), 3.55-3.41 (m, 4H), 3.31-3.26 (m, 4H), 2.88-2.81 (m, 3H), 2.66-2.55 (m, 3H), 2.48-2.32 (m, 6H), 2.07-1.92 (m, 3H), 1.75-1.47 (m, 8H). |
| III-41 | 804.5 | (500 MHz, DMSO-d₆) δ 11.09 (s, 1H), 10.56 (s, 1H), 8.64 (s, 1H), 8.48 (d, J = 8.0 Hz, 1H), 8.42-8.38 (m, 2H), 8.25 (d, J = 7.5 Hz, 1H), 7.69-7.66 (t, J = 7.5 Hz, 1H), 7.39-7.32 (m, 3H), 5.09 (dd, J = 12.5, 5.5 Hz, 1H), 4.45 (s, 2H), 4.01 (s, 3H), 3.72-3.67 (m, 3H), 2.94-2.84 (m, 4H), 2.04-1.95 (m, 4H), 1.82-1.71 (m, 6H), 1.16 (s, 6H). |
| III-42 | 884.6 | (500 MHz, DMSO-d₆) δ 11.10 (s, 1H), 10.50 (s, 1H), 8.70 (s, 1H), 8.46 (d, J = 7.5 Hz, 1H), 8.40 (t, J = 7.5 Hz, 1H), 8.35 (s, 1H), 8.22 (d, J = 7.5 Hz, 1H), 7.66 (t, J = 7.5 Hz, 1H), 7.35-7.30 (m, 2H), 7.15 (s, 1H), 5.09 (dd, J = 12.5, 5.5 Hz, 1H), 4.49 (t, J = 6.0 Hz, 2H), 4.03 (s, 3H), 3.48-3.40 (m, 5H), 3.27-3.25 (m, 4H), 2.92-2.83 (m, 3H), 2.65-2.52 (m, 4H), 2.41 (s, 4H), 2.05-2.00 (m, 1H), 1.74-1.72 (m, 2H), 1.66-1.62 (m, 2H), 1.56-1.42 (m, 6H). |
| III-43 | 1127.5 | (500 MHz, DMSO-d₆) δ 10.58 (s, 1H), 8.99 (s, 1H), 8.65 (s, 1H), 8.49 (d, J = 8.0 Hz, 1H), 8.45-8.39 (m, 2H), 8.26 (d, J = 7.5 Hz, 1H), 7.69 (d, J = 9.5 Hz, 1H), 7.44-7.42 (m, 2H), 7.39-7.37 (m, 3H), 5.33-5.31 (m, 1H), 5.12 (d, J = 3.5 Hz, 1H), 4.93-4.90 (m, 1H), 4.57-4.51 (m, 3H), 4.43-4.39 (m, 1H), 4.02 (s, 3H), 3.69-3.54 (m, 4H), 3.45-3.40 (m, 2H), 3.11-3.08 (m, 2H), 2.45 (s, 3H), 2.41-2.28 (m, 4H), 2.02-1.96 (m, 4H), 1.85-1.74 (m, 2H), 1.69-1.65 (m, 2H), 1.55-1.51 (m, 3H), 1.46 (s, 4H), 1.37 (d, J = 7.0 Hz, 4H), 1.28-1.26 (m, 3H), 1.09-1.01 (m, 4H), 0.93 (s, 9H). |
| III-44 | 1099.3 | (500 MHz, DMSO-d₆) δ 10.57 (s, 1H), 8.98 (s, 1H), 8.64 (s, 1H), 8.48 (d, J = 8.0 Hz, 1H), 8.45-8.36 (m, 2H), 8.25 (d, J = 8.0 Hz, 1H), 7.49-7.34 (m, 5H), 5.33-5.30 (m, 1H), 5.06-5.02 (m, 1H), 4.94-4.88 (m, 1H), 4.53-4.48 (m, 3H), 4.29-4.27 (m, 1H), 4.02 (s, 3H), 3.67-3.59 (m, 2H), 3.56-3.43 (m, 4H), 3.12-3.04 (m, 3H), 2.45 (s, 3H), 2.41-2.29 (m, 4H), 2.23-2.11 (m, 2H), 2.07-1.96 (m, 2H), 1.87-1.74 (m, 2H), 1.72-1.54 (m, 4H), 1.52-1.40 (m, 3H), 1.37 (d, J = 7.0 Hz, 3H), 1.34-1.28 (m, 2H), 1.26-1.17 (m, 4H), 1.16-1.00 (m, 4H), 0.90 (s, 9H). |
| III-45 | 913.3 | (500 MHz, DMSO-d₆) δ 11.18 (s, 1H), 10.55 (s, 1H), 8.74 (s, 1H), 8.51 (d, J = 7.5 Hz, 1H), 8.45 (t, J = 7.5 Hz, 1H), 8.37 (s, 1H), 8.27 (d, J = 7.5 Hz, 1H), 7.72 (t, J =7.5 Hz, 1H), 7.39-7.36 (m, 2H), 7.20 (s, 1H), 5.15 (dd, J = 12.5, 5.5 Hz, 1H), 4.51 (t, J = 6.0 Hz, 2H), 4.03 (s, 3H), 3.71-3.50 (m, 4H), 3.35-3.28 (m, 4H), 2.98-2.81 (m, 4H), 2.79-2.72 (m, 2H), 2.70-2.61 (m, 2H), 2.50-2.40 (m, 1H), 2.35-2.20 (m, 2H), 2.12-1.95 (m, 3H), 1.70-1.66 (m, 4H), 1.63-1.45 (m, 4H), 1.43-1.38 (m, 1H), 1.03 (d, J = 6.0 Hz, 3H). |
| III-46 | 913.5 | (500 MHz, DMSO-d₆) δ 11.19 (s, 1H), 10.56 (s, 1H), 8.75 (s, 1H), 8.52 (d, J = 7.5 Hz, 1H), 8.46 (t, J = 7.5 Hz, 1H), 8.38 (s, 1H), 8.28 (d, J = 7.5 Hz, 1H), 7.73 (t, J = 7.5 Hz, |

| Molecule ID | MS (ESI) m/z: [M + H]+ | 1H NMR |
|---|---|---|
| | | 1H), 7.42-7.35 (m, 2H), 7.21 (s, 1H), 5.15 (dd, J = 12.0, 5.5 Hz, 1H), 4.48 (t, J = 6.0 Hz, 2H), 4.04 (s, 3H), 3.72-3.49 (m, 4H), 3.37-3.29 (m, 4H), 2.99-2.82 (m, 4H), 2.80-2.73 (m, 2H), 2.68-2.59 (m, 2H), 2.51-2.39 (m, 1H), 2.39-2.21 (m, 2H), 2.14-1.92 (m, 3H), 1.71-1.68 (m, 4H), 1.64-1.46 (m, 4H), 1.45-1.40 (m, 1H), 1.09 (d, J = 6.0 Hz, 3H). |
| III-47 | 1126.5 | (500 MHz, DMSO-$d_6$) δ 10.51 (s, 1H), 8.99 (s, 1H), 8.69 (s, 1H), 8.47 (d, J = 7.5 Hz, 1H), 8.43-8.39 (m, 2H), 8.31 (s, 1H), 8.23 (d, J = 7.5 Hz, 1H), 7.69 (dd, J = 8.5, 4.0 Hz, 1H), 7.41 (d, J = 8.0 Hz, 2H), 7.39 (d, J = 8.0 Hz, 2H), 7.15 (s, 1H), 5.12 (s, 1H), 4.95-4.88 (m, 1H), 4.54-4.39 (m, 4H), 4.32-4.25 (m, 1H), 3.99 (s, 3H), 3.61-3.45 (m, 4H), 2.83-2.74 (m, 3H), 2.72-2.60 (m, 3H), 2.46 (s, 3H), 2.41-2.30 (m, 2H), 2.27-2.15 (m, 2H), 2.05-1.94 (m, 3H), 1.80-1.72 (m, 2H), 1.65-1.60 (m, 1H), 1.57-1.42 (m, 7H), 1.38 (d, J = 7.0 Hz, 3H), 1.32-1.28 (m, 2H), 1.12-1.03 (m, 3H), 0.99-0.95 (m, 3H), 0.94 (s, 9H). |
| III-48 | 1126.5 | (500 MHz, DMSO-$d_6$) δ 10.50 (s, 1H), 8.99 (s, 1H), 8.69 (s, 1H), 8.47 (d, J = 7.5 Hz, 1H), 8.42-8.39 (m, 2H), 8.31 (s, 1H), 8.23 (d, J = 7.5 Hz, 1H), 7.70 (dd, J = 8.5, 4.0 Hz, 1H), 7.44-7.37(m, 4H), 7.15 (s, 1H), 5.12 (s, 1H), 4.93-4.89 (m, 1H), 4.51-4.42 (m, 4H), 4.30-4.26 (m, 1H), 3.98 (s, 3H), 3.60-3.45 (m, 4H), 2.81-2.74 (m, 3H), 2.71-2.60 (m, 3H), 2.45 (s, 3H), 2.39-2.16 (m, 4H), 2.03-1.95 (m, 3H), 1.80-1.73 (m, 2H), 1.64-1.41 (m, 8H), 1.37 (d, J = 7.0 Hz, 3H), 1.33-1.28 (m, 2H), 1.12-1.03 (m, 3H), 0.99-0.95 (m, 3H), 0.93 (s, 9H). |
| III-49 | 1043.5 | (500 MHz, DMSO-$d_6$) δ 10.58 (s, 1H), 8.99 (s, 1H), 8.65 (s, 1H), 8.48 (d, J = 8.0 Hz, 1H), 8.44-8.39 (m, 2H), 8.26 (d, J = 8.0 Hz, 1H), 7.45-7.35 (m, 5H), 5.31 (s, 1H), 5.07 (s, 1H), 4.92-4.88 (m, 1H), 4.52 (s, 2H), 4.47-4.43 (m, 1H), 4.29-4.04 (m, 3H), 4.02 (s, 3H), 3.84-3.69 (m, 3H), 3.62-3.47 (m, 4H), 2.92-2.89 (m, 4H), 2.45 (s, 3H), 2.32-2.28 (m, 3H), 2.07-1.97 (m, 2H), 1.79-1.72 (m, 2H), 1.40-1.33 (m, 4H), 1.26-1.19 (m, 7H), 0.89 (s, 9H). |
| III-50 | 927.6 | (500 MHz, DMSO-$d_6$) δ 12.37 (s, 1H), 11.11 (s, 1H), 8.72 (s, 1H), 8.45 (d, J = 8.0 Hz, 1H), 8.39-8.33 (m, 2H), 8.16 (d, J = 7.5 Hz, 1H), 7.67 (t, J = 7.5 Hz, 1H), 7.57 (s, 1H), 7.34-7.31 (m, 2H), 5.97 (s, 1H), 5.09 (dd, J = 13.0, 5.5 Hz, 1H), 4.52-4.48 (m, 2H), 3.50-3.37 (m, 6H), 3.28-3.21 (m, 4H), 3.10 (s, 2H), 2.83-2.85 (m, 3H), 2.67-2.55 (m, 4H), 2.40-2.32 (s, 4H), 2.07-1.99 (m, 1H), 1.62-1.65 (m, 10H), 1.51-1.48 (m, 2H), 1.43-1.39 (m, 2H). |
| III-52 | 1085.5 | (500 MHz, DMSO-$d_6$) δ 10.61 (s, 1H), 9.05 (s, 1H), 8.69 (s, 1H), 8.53-8.45 (m, 3H), 8.30 (d, J = 7.5 Hz, 1H), 7.91 (t, J = 10.0 Hz, 1H), 7.50-7.40 (m, 5H), 5.20 (s, 1H), 4.99-4.95 (m, 1H), 4.60-4.53 (m, 3H), 4.47 (t, J = 8.0 Hz, 1H), 4.35-4.30 (m, 1H), 4.21 (s, 1H), 4.15-4.11 (m, 1H), 4.07 (s, 3H), 3.91 (s, 1H), 3.85-3.79 (m, 1H), 3.74-3.61 (m, 4H), 3.08-3.02 (m, 2H), 2.56 (s, 3H), 2.45-2.39 (m, 2H), 2.33-2.18 (m, 4H), 2.11-1.99 (m, 2H), 1.95-1.80 (m, 4H), 1.59-1.49 (m, 1H), 1.43 (d, J = 7.0 Hz, 3H), 1.35-1.27 (m, 6H), 0.98 (s, 9H). |
| III-53 | 925.5 | (500 MHz, DMSO-$d_6$) δ 11.13 (s, 1H), 10.51 (s, 1H), 8.70 (s, 1H), 8.46 (d, J = 7.5 Hz, 1H), 8.40 (t, J = 7.5 Hz, 1H), 8.32 (s, 1H), 8.23 (d, J = 7.5 Hz, 1H), 7.67 (t, J = 8.0 Hz, 1H), 7.35-7.31 (m, 2H), 7.15 (s, 1H), 5.10 (dd, J = 12.5, 5.5 Hz, 1H), 4.40 (t, J = 6.0 Hz, 2H), 3.98 (s, 3H), 3.61-3.55 (m, 2H), 3.47-3.43 (m, 3H), 3.30-3.25 (m, 4H), 3.12-3.05 (m, 4H), 2.92-2.84 (m, 1H), 2.79 (t, J = 6.0 Hz, 2H), 2.63-2.54 (m, 3H), 2.27-2.25 (m, 2H), 2.05-1.98 (m, 1H), 1.75-1.69 (m, 2H), 1.68-1.62 (m, 4H), 1.58-1.49 (m, 4H), 1.44-1.38 (m, 2H). |
| III-54 | 925.6 | (500 MHz, DMSO-$d_6$) δ 11.12 (s, 1H), 10.51 (s, 1H), 8.70 (s, 1H), 8.47 (d, J = 7.5 Hz, 1H), 8.41 (t, J = 7.5 Hz, 1H), 8.34 (s, 1H), 8.23 (d, J = 8.0 Hz, 1H), 7.68 (t, J = 7.5 Hz, 1H), 7.37-7.28 (m, 2H), 7.15 (s, 1H), 5.09 (dd, J = 12.5, 5.0 Hz, 1H), 4.41 (t, J = 6.0 Hz, 2H), 3.99 (s, 3H), 3.54-3.50 (m, 2H), 3.45-3.42 (m, 3H), 3.29-3.24 (m, 4H), 3.08-3.01 (m, 4H), 2.91-2.83 (m, 1H), 2.78 (t, J = 6.0 Hz, 2H), 2.62-2.56 (m, 1H), 2.49-2.45 (m, 2H), 2.22-2.20 (m, 2H), 2.06-1.98 (m, 1H), 1.82-1.75 (m, 2H), 1.69-1.60 (m, 6H), 1.55-1.50 (m, 2H), 1.45-1.38 (m, 2H). |

-continued

| Molecule ID | MS (ESI) m/z: [M + H]+ | 1H NMR |
|---|---|---|
| III-55 | 917.6 | (500 MHz, DMSO-d$_6$) δ 11.15 (s, 1H), 10.50 (s, 1H), 8.69 (s, 1H), 8.46 (d, J = 7.5 Hz, 1H), 8.40 (t, J = 7.5 Hz, 1H), 8.32 (s, 1H), 8.22 (d, J = 7.5 Hz, 1H), 7.71 (d, J = 11.5 Hz, 1H), 7.44 (d, J = 7.5 Hz, 1H), 7.15 (s, 1H), 5.11 (dd, J = 13.0, 5.5 Hz, 1H), 4.46 (t, J = 6.0 Hz, 2H), 3.98 (s, 3H), 3.51-3.48 (m, 2H), 3.46-3.41 (m, 3H), 3.24-2.21 (m, 4H), 3.12 (s, 2H), 2.93-2.82 (m, 3H), 2.62-2.53 (m, 4H), 2.48-2.31 (m, 5H), 2.07-2.00 (m, 1H), 1.64-1.59 (m, 4H), 1.52-1.47 (m, 2H), 1.43-1.38 (m, 2H). |
| III-56 | 914.6 | (500 MHz, DMSO-d$_6$) δ 11.13 (s, 1H), 10.50 (s, 1H), 8.69 (s, 1H), 8.47 (d, J = 8.0 Hz, 1H), 8.41 (t, J = 7.5 Hz, 1H), 8.32 (s, 1H), 8.22 (d, J = 7.5 Hz, 1H), 7.75 (t, J = 7.5 Hz, 1H), 7.57 (d, J = 7.5 Hz, 1H), 7.44 (d, J = 7.0 Hz, 1H), 7.15 (s, 1H), 5.09 (dd, J = 12.5, 5.5 Hz, 1H), 4.78-4.69 (m, 1H), 4.46 (t, J = 6.0 Hz, 2H), 3.99 (s, 3H), 3.48-3.39 (m, 4H), 3.33-3.30 (m, 2H), 3.12 (s, 2H), 2.93-2.80 (m, 3H), 2.63-2.52 (m, 2H), 2.49-2.34 (m, 6H), 2.07-2.00 (m, 1H), 1.87-1.79 (m, 2H), 1.73-1.60 (m, 4H), 1.48-1.41 (m, 2H), 1.39-1.30 (m, 4H). |
| III-57 | 1140.6 | (500 MHz, DMSO-d$_6$) δ 10.73 (s, 1H), 8.98 (s, 1H), 8.72 (s, 1H), 8.46 (d, J = 8.0 Hz, 1H), 8.43-8.37 (m, 2H), 8.30 (s, 1H), 8.22 (dd, J = 7.5, 1.0 Hz, 1H), 7.68 (dd, J = 9.5, 3.5 Hz, 1H), 7.43 (d, J = 8.0 Hz, 2H), 7.37 (d, J = 8.5 Hz, 2H), 7.18 (s, 1H), 4.94-4.82 (m, 2H), 4.49-4.27 (m, 4H), 3.60-3.55 (m, 2H), 3.45-3.39 (m, 4H), 3.31-3.20 (m, 6H), 3.08 (s, 2H), 2.81 (t, J = 6.5 Hz, 2H), 2.45 (s, 3H), 2.40-2.27 (m, 5H), 2.02-1.97 (m, 1H), 1.69-1.67 (m, 2H), 1.55-1.43 (m, 6H), 1.41 (d, J = 6.0 Hz, 6H), 1.38-1.35 (m, 4H), 1.29-1.23 (m, 2H), 1.09-1.03 (m, 2H), 0.93 (s, 9H). |
| III-58 | 914.6 | (500 MHz, DMSO-d$_6$) δ 11.11 (s, 1H), 10.57 (s, 1H), 8.65 (s, 1H), 8.48 (d, J = 8.0 Hz, 1H), 8.42 (t, J = 8.0 Hz, 1H), 8.26 (dd, J = 8.0, 1.0 Hz, 1H), 7.68 (t, J = 8.0 Hz, 1H), 7.37-7.31 (m, 3H), 5.09 (dd, J = 13.0, 5.5 Hz, 1H), 4.52 (s, 2H), 4.02 (s, 3H), 3.63 (t, J = 6.0 Hz, 2H), 3.55-3.49 (m, 2H), 3.47-3.43 (m, 2H), 3.30-3.25 (m, 4H), 3.10 (s, 2H), 2.93-2.82 (m, 2H), 2.64-2.51 (m, 4H), 2.44-2.34 (m, 4H), 2.10-1.85 (m, 4H), 1.69-1.59 (m, 4H), 1.54-1.48 (m, 2H), 1.44-1.39 (m, 2H). |
| III-59 | 830.6 | (500 MHz, DMSO-d$_6$) δ 11.10 (s, 1H), 10.57 (s, 1H), 8.65 (s, 1H), 8.48 (d, J = 8.0 Hz, 1H), 8.43 (t, J = 8.0 Hz, 1H), 8.26 (dd, J = 8.0, 1.0 Hz, 1H), 7.58 (t, J = 8.0 Hz, 1H), 7.37 (s, 1H), 7.12 (d, J = 7.0 Hz, 1H), 6.79 (d, J = 7.5 Hz, 1H), 5.06 (dd, J = 12.5, 5.5 Hz, 1H), 4.47 (s, 2H), 4.03 (s, 3H), 4.00-3.97 (m, 2H), 3.58-3.50 (m, 4H), 3.48 (t, J = 6.5 Hz, 2H), 2.93-2.83 (m, 2H), 2.65-2.56 (m, 2H), 2.05-1.95 (m, 2H), 1.92 (t, J = 8.0 Hz, 2H), 1.75 (t, J = 6.0 Hz, 4H), 1.26 (s, 6H). |
| III-60 | 871.5 | (500 MHz, DMSO-d$_6$) δ 11.11 (s, 1H), 10.74 (s, 1H), 8.72 (s, 1H), 8.46 (d, J = 8.0 Hz, 1H), 8.41 (t, J = 8.0 Hz, 1H), 8.31 (s, 1H), 8.23 (dd, J = 8.0, 1.0 Hz, 1H), 7.58 (t, J = 8.0 Hz, 1H), 7.19 (s, 1H), 7.13 (d, J = 7.0 Hz, 1H), 6.79 (d, J = 8.5 Hz, 1H), 5.06 (dd, J = 12.5, 5.5 Hz, 1H), 4.87-4.82 (m, 1H), 4.45 (t, J = 6.5 Hz, 2H), 4.37 (s, 2H), 4.32 (s, 4H), 4.04 (s, 2H), 2.93 (s, 2H), 2.82 (t, J = 6.5 Hz, 2H), 2.59-2.53 (m, 3H), 2.45-2.34 (m, 8H), 2.02-1.96 (m, 1H), 1.39 (d, J = 6.0 Hz, 6H). |
| III-61 | 843.5 | (500 MHz, DMSO-d$_6$) δ 11.12 (s, 1H), 10.51 (s, 1H), 8.69 (s, 1H), 8.47 (d, J = 7.5 Hz, 1H), 8.41 (t, J = 7.5 Hz, 1H), 8.32 (s, 1H), 8.23 (d, J = 7.5 Hz, 1H), 7.58 (t, J = 8.0 Hz, 1H), 7.17-7.10 (m, 2H), 6.79 (d, J = 8.5 Hz, 1H), 5.06 (dd, J = 12.5, 5.5 Hz, 1H), 4.46 (t, J = 6.0 Hz, 2H), 4.37 (s, 2H), 4.33 (s, 4H), 4.05 (s, 2H), 3.98 (s, 3H), 2.94 (s, 2H), 2.89-2.79 (m, 3H), 2.66-2.54 (m, 2H), 2.47-2.31 (m, 6H), 2.03-1.94 (m, 3H). |
| III-62 | 871.5 | (500 MHz, DMSO-d$_6$) δ 11.18 (s, 1H), 10.57 (s, 1H), 8.76 (s, 1H), 8.53 (d, J = 7.5 Hz, 1H), 8.47 (t, J = 7.5 Hz, 1H), 8.39 (s, 1H), 8.29 (d, J = 7.5 Hz, 1H), 7.62 (t, J = 7.5 Hz, 1H), 7.22 (s, 1H), 7.17 (d, J = 7.0 Hz, 1H), 6.84 (d, J = 8.5 Hz, 1H), 5.11 (dd, J = 12.5, 5.5 Hz, 1H), 4.53 (t, J = 6.0 Hz, 2H), 4.05 (s, 3H), 4.03-3.98 (m, 2H), 3.55-3.51 (m, 2H), 3.51-3.49 (m, 2H), 3.45-3.37 (m, 3H), 3.18 (s, 2H), 2.98-2.87 (m, 3H), 2.72-2.59 (m, 2H), 2.56-2.36 (m, 7H), 2.08-2.03 (m, 1H), 1.87-1.79 (m, 2H), 1.76-1.69 (m, 2H). |

| Molecule ID | MS (ESI) m/z: [M + H]+ | 1H NMR |
|---|---|---|
| III-63 | 871.5 | (500 MHz, DMSO-d$_6$) δ 12.37 (s, 1H), 11.10 (s, 1H), 8.71 (s, 1H), 8.45 (d, J = 8.0 Hz, 1H), 8.39-8.33 (m, 2H), 8.17 (d, J = 8.0 Hz, 1H), 7.60-7.55 (m, 2H), 7.13 (d, J = 7.0 Hz, 1H), 6.79 (d, J = 8.0 Hz, 1H), 5.98 (s, 1H), 5.05 (dd, J = 13.0, 5.5 Hz, 1H), 4.50 (t, J = 6.5 Hz, 2H), 4.37 (s, 2H), 4.32 (s, 4H), 4.04 (s, 2H), 3.37-3.34 (m, 4H), 2.93 (s, 2H), 2.83 (t, J = 6.5 Hz, 2H), 2.61-2.56 (m, 3H), 2.42-2.33 (m, 4H), 2.00 (d, J = 5.5 Hz, 1H), 1.61 (s, 6H). |
| III-64 | 802.6 | (500 MHz, CD$_3$OD) δ 8.77 (s, 1H), 8.49 (d, J = 8.0 Hz, 1H), 8.32 (t, J = 8.0 Hz, 1H), 8.08 (d, J = 8.0 Hz, 1H), 7.53 (t, J = 7.5 Hz, 1H), 7.50 (s, 1H), 7.16 (d, J = 7.0 Hz, 1H), 6.75 (d, J = 8.5 Hz, 1H), 5.08 (dd, J = 12.5, 5.5 Hz, 1H), 4.73 (s, 2H), 4.63 (s, 3H), 4.48 (s, 2H), 4.45-4.36 (m, 2H), 4.36-4.23 (m, 2H), 4.11 (s, 2H), 3.78-3.65 (m, 4H), 2.81-2.64 (m, 2H), 1.99 (t, J = 6.0 Hz, 2H), 1.30 (s, 6H). |
| III-66 | 898.6 | (500 MHz, DMSO-d$_6$) δ 11.09 (s, 1H), 10.50 (s, 1H), 8.69 (s, 1H), 8.47 (d, J = 8.0 Hz, 1H), 8.41 (t, J = 7.5 Hz, 1H), 8.33 (s, 1H), 8.22 (d, J = 7.5 Hz, 1H), 7.68 (t, J = 7.5 Hz, 1H), 7.38-7.27 (m, 2H), 7.16 (s, 1H), 5.09 (dd, J = 12.5, 5.5 Hz, 1H), 4.39 (t, J = 6.5 Hz, 2H), 3.99 (s, 3H), 3.56-3.45 (m, 5H), 3.30-3.24 (m, 6H), 3.08 (s, 2H), 2.92-2.84 (m, 1H), 2.82-2.75 (m, 2H), 2.65-2.57 (m, 1H), 2.31-2.21 (m, 1H), 2.07-2.00 (m, 1H), 1.96-1.88 (m, 2H), 1.88-1.82 (m, 2H), 1.75-1.59 (m, 6H), 1.55-1.48 (m, 2H), 1.45-1.38 (m, 2H). |
| III-68 | 1111.5 | (500 MHz, DMSO-d$_6$) δ 10.50 (s, 1H), 8.99 (s, 1H), 8.69 (s, 1H), 8.47 (d, J = 7.5 Hz, 1H), 8.42-8.37 (m, 2H), 8.32 (s, 1H), 8.22 (d, J = 8.0 Hz, 1H), 7.69-7.63 (m, 1H), 7.44 (d, J = 8.0 Hz, 2H), 7.38 (d, J = 8.0 Hz, 2H), 7.16 (s, 1H), 5.12 (d, J = 3.0 Hz, 1H), 4.95-4.89 (m, 1H), 4.51 (d, J = 9.0 Hz, 1H), 4.45-4.37 (m, 3H), 4.32-4.26 (m, 1H), 3.99 (s, 3H), 3.63-3.55 (m, 2H), 3.11 (s, 2H), 2.86-2.74 (m, 2H), 2.46 (s, 3H), 2.36-2.29 (m, 1H), 2.07-1.91 (m, 3H), 1.91-1.75 (m, 4H), 1.73-1.66 (m, 4H), 1.60-1.43 (m, 6H), 1.38 (d, J = 7.0 Hz, 4H), 1.32-1.28 (m, 1H), 1.26-1.13 (m, 5H), 1.13-0.97 (m, 3H), 0.97-0.92 (m, 9H). |
| III-69 | 835.4 | (500 MHz, DMSO-d$_6$) δ 11.20 (s, 1H), 10.55 (s, 1H), 8.74 (s, 1H), 8.51 (d, J = 7.5 Hz, 1H), 8.46 (t, J = 7.5 Hz, 1H), 8.40 (s, 1H), 8.27 (dd, J = 7.5, 1.0 Hz, 1H), 7.98 (dd, J = 5.5, 3.0 Hz, 1H), 7.94-7.88 (m, 2H), 7.21 (s, 1H), 7.02 (d, J = 9.0 Hz, 2H), 6.95 (d, J = 9.0 Hz, 2H), 5.20 (dd, J = 12.5, 5.0 Hz, 1H), 5.08 (s, 2H), 4.56 (t, J = 6.0 Hz, 2H), 4.04 (s, 3H), 3.06 (t, J = 5.0 Hz, 4H), 2.97-2.93 (m, 2H), 2.69-2.57 (m, 6H), 2.13-2.01 (m, 2H). |
| III-70 | 1069.5 | (500 MHz, DMSO-d$_6$) δ 10.50 (s, 1H), 8.98 (s, 1H), 8.68 (s, 1H), 8.47 (d, J = 7.5 Hz, 1H), 8.42-8.37 (m, 2H), 8.32 (s, 1H), 8.22 (d, J = 7.5 Hz, 1H), 7.81 (t, J = 9.0 Hz, 1H), 7.43 (d, J = 8.0 Hz, 2H), 7.38 (d, J = 8.0 Hz, 2H), 7.16 (s, 1H), 5.13 (d, J = 3.0 Hz, 1H), 4.94-4.89 (m, 1H), 4.51 (d, J = 9.5 Hz, 1H) 4.44-4.36 (m, 3H), 4.30-4.26 (m, 1H), 4.15 (s, 1H), 4.07 (q, J = 8.5 Hz, 1H), 3.98 (s, 3H), 3.83 (s, 1H), 3.75 (q, J = 10.0 Hz, 1H), 3.62-3.56 (m, 2H), 2.88 (s, 2H), 2.76-2.72 (m, 2H), 2.45 (s, 3H), 2.40-2.33 (m, 2H), 2.28-2.14 (m, 4H), 2.04-1.99 (m, 1H), 1.93-1.79 (m, 8H), 1.68-1.64 (m, 2H), 1.38 (d, J = 7.0 Hz, 4H), 0.93 (s, 9H). |
| III-73 | 953.7 | (500 MHz, DMSO-d$_6$) δ 11.06 (s, 1H), 10.49 (s, 1H), 8.68 (s, 1H), 8.46 (d, J = 8.0 Hz, 1H), 8.40 (t, J = 8.0 Hz, 1H), 8.31 (s, 1H), 8.21 (dd, J = 8.0, 1.1 Hz, 1H), 7.57 (d, J = 7.5 Hz, 1H), 7.16-7.12 (m, 2H), 6.78 (d, J = 7.5 Hz, 1H), 5.05 (dd, J = 13.0, 5.5 Hz, 1H), 4.44 (t, J = 6.5 Hz, 2H), 4.32-4.27 (m, 6H), 4.02-3.98 (m, 5H), 2.89-2.79 (m, 5H), 2.65-2.51 (m, 4H), 2.47-2.45 (m, 2H), 2.01-1.93 (m, 6H), 1.62-1.57 (m, 4H). |

Example III-65: Synthesis of (III-65)
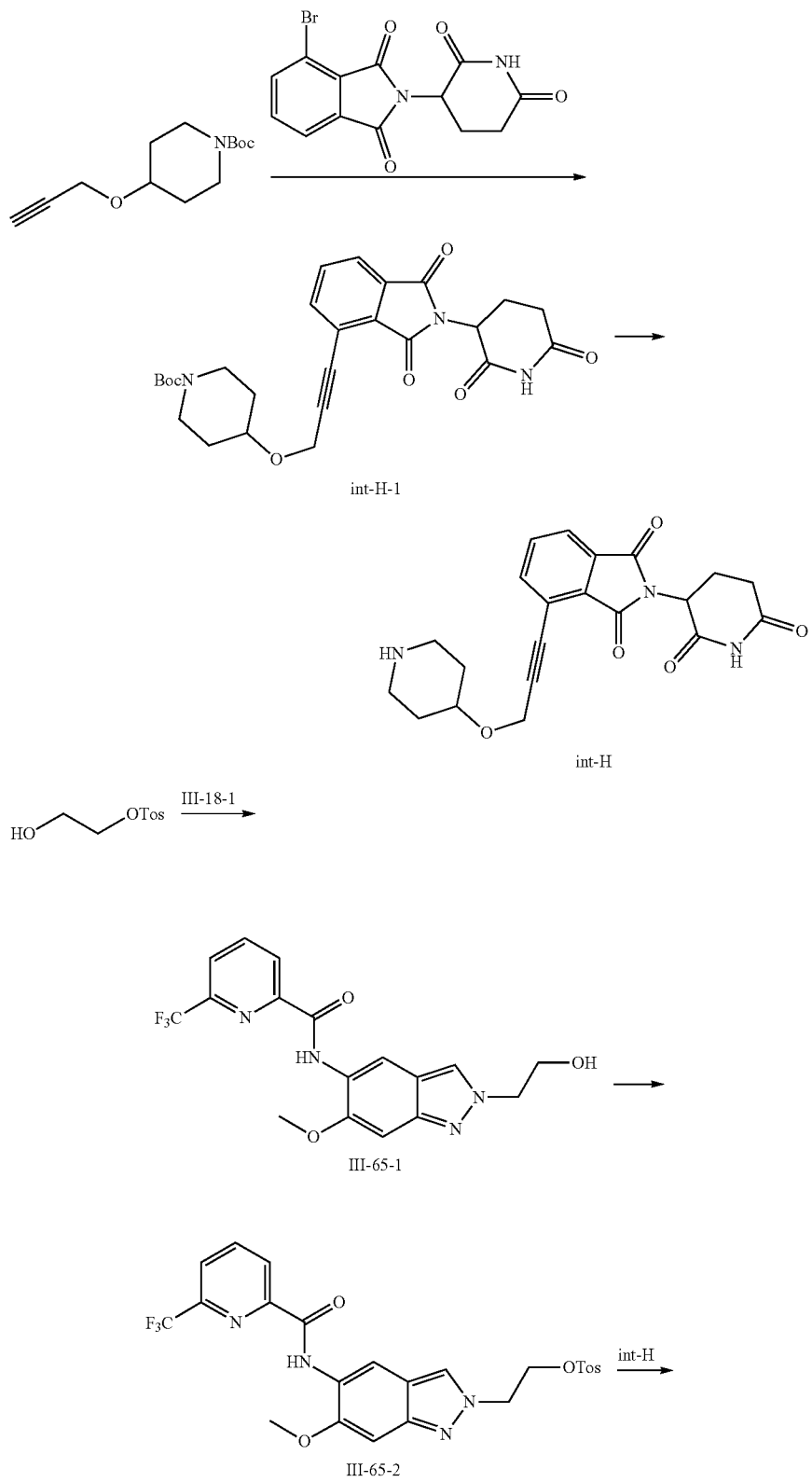

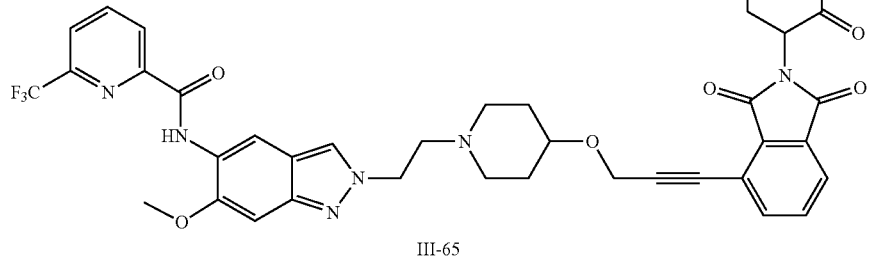

III-65

Step 1: Synthesis of (int-H-1)

4A molecular sieve (100 mg) was added to a solution of 4-bromo-2-(2,6-dioxo-3-piperidinyl)isoindole-1,3-dione (500 mg, 1.48 mmol), tert-butyl 4-prop-2-ynyloxy)piperidine-1-carboxylate (532.39 mg, 2.22 mmol), CuI (28.25 mg, 148.31 μmol, 5.03 μL), PdCl$_2$(PPh$_3$)$_2$ (104.10 mg, 148.31 μmol), Cs$_2$CO$_3$ (1.93 g, 5.93 mmol), and DMF (5 mL), and the reaction mixture was heated to 85° C. under nitrogen atmosphere and reacted for 2 hours until the reaction was complete. The reaction mixture was cooled to room temperature, then diluted with water (30 mL), and extracted with ethyl acetate (20 mL×3). The combined organic phases were washed with saturated brine (30 mL), dried over anhydrous sodium sulfate, filtered, and concentrated under vacuum. The crude product was purified by preparative thin-layer chromatography to obtain product int-H-1 (300 mg, yield: 40.82%) as a yellow solid, MS (ESI) m/z: 496.2 [M+H]$^+$.

Step 2: Synthesis of (int-H)

int-H-1 (40 mg, 80.72 μmol) was dissolved in DCM (2 mL), then TFA (1 mL) was added thereto, and the reaction mixture was stirred at 25° C. for 1 hour until the reaction was complete. The reaction mixture was repeatedly concentrated under reduced pressure to obtain product int-H (50 mg, crude product, TFA salt) as a yellow oil, which was directly used in the next reaction step, MS (ESI) m/z: 396.1 [M+H]$^+$.

Step 3: Synthesis of (III-65-1)

III-18-1 (200 mg, 594.76 μmol), hydroxymethyl 4-methylbenzenesulfonate (144.33 mg, 713.72 μmol), DIPEA (153.74 mg, 1.19 mmol, 207.19 μL), and toluene (4 mL) were added to a reaction flask, and the reaction mixture was heated to 110° C. and reacted for 4 hours until the reaction was complete. The reaction mixture was cooled to room temperature, and concentrated under reduced pressure to remove the solvent. The crude product was purified by preparative thin-layer chromatography to obtain product III-65-1 (170 mg, yield: 75.15%) as a white solid, MS (ESI) m/z: 381.3 [M+H]$^+$.

Step 4: Synthesis of (III-65-2)

4-Methylbenzenesulfonyl chloride (27.57 mg, 144.61 μmol) was added to a solution of III-65-1 (50 mg, 131.47 μmol), DMAP (1.61 mg, 13.15 μmol), TEA (26.61 mg, 262.94 mol, 36.65 μL), and DCM (3 mL) at 0° C. After the addition was completed, the reaction mixture was heated to 40° C. and reacted for 2 hours until the reaction was complete. The reaction mixture was directly purified by preparative thin-layer chromatography to obtain product III-65-2 (50 mg, yield: 71.15%) as a white solid, MS (ESI) m/z: 535.6 [M+H]$^+$.

Step 5: Synthesis of (III-65)

A mixture of III-65-2 (50 mg, 93.54 μmol), int-H (48.48 mg, 112.25 μmol, TFA salt), DIPEA (120.90 mg, 935.44 μmol, 162.94 μL), and ACN (2 mL) was heated to 80° C. and reacted for 2 hours until the reaction was complete. The reaction mixture was diluted with water (50 mL), and extracted with ethyl acetate (30 mL×3). The combined organic phases were washed with saturated brine (50 mL), dried over anhydrous sodium sulfate, filtered, and concentrated under vacuum. The crude product was subjected to reverse phase C18 silica gel column chromatography to obtain product III-65 (10 mg, yield: 13.69%) as a white solid, MS (ESI) m/z: 758.5 [M+H]$^+$. $^1$H NMR (500 MHz, DMSO-d$_6$) δ 11.14 (s, 1H), 10.49 (s, 1H), 8.69 (s, 1H), 8.47 (d, J=8.0 Hz, 1H), 8.41 (t, J=7.5 Hz, 1H), 8.31 (s, 1H), 8.22 (d, J=7.5 Hz, 1H), 7.93-7.86 (m, 3H), 7.15 (s, 1H), 5.14 (dd, J=13.0, 5.5 Hz, 1H), 4.49 (s, 2H), 4.45 (t, J=6.5 Hz, 2H), 3.98 (s, 3H), 3.70-3.64 (m, 1H), 2.93-2.81 (m, 3H), 2.78-2.68 (m, 2H), 2.65-2.54 (m 2H), 2.21 (t, J=9.0 Hz, 2H), 2.12-2.02 (m, 1H), 1.86-1.89 (m, 2H), 1.42-1.52 (m, 2H).

Example III-67: Synthesis of (III-67)

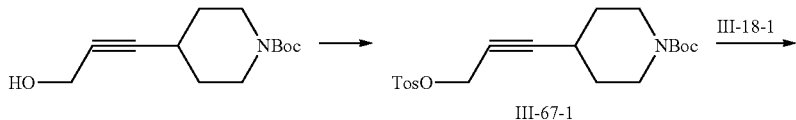

III-67-1

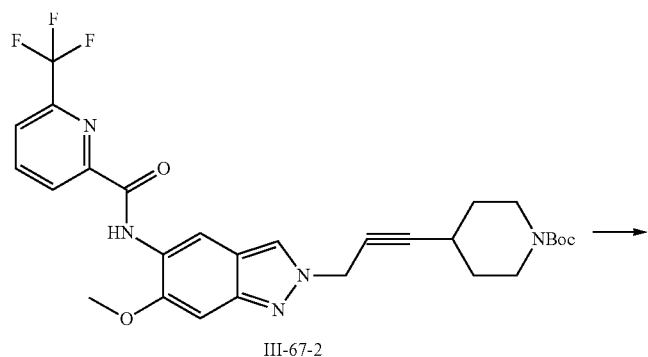
III-67-2
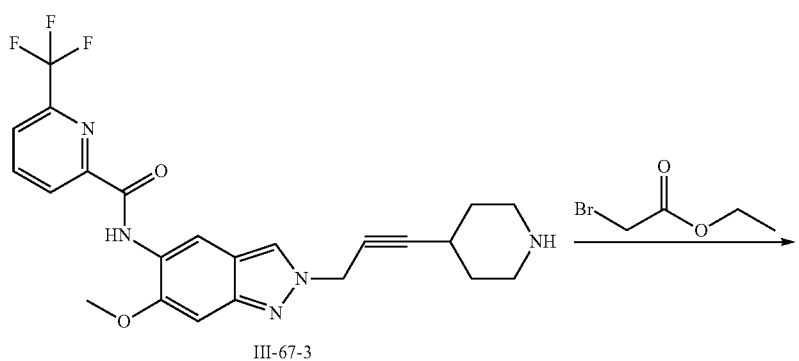
III-67-3
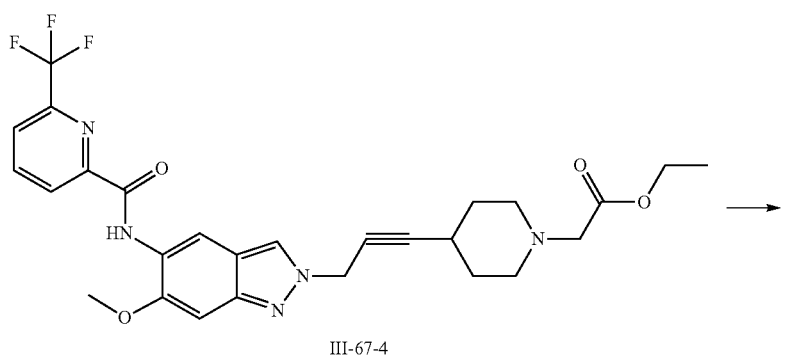
III-67-4
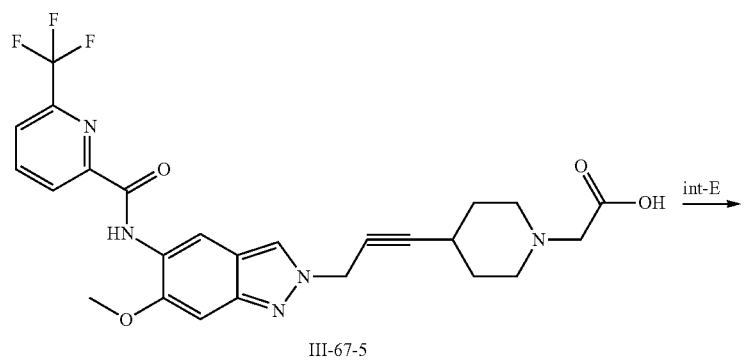
III-67-5

-continued

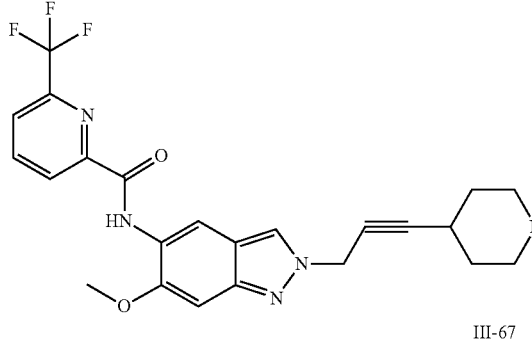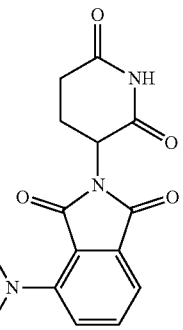

III-67

Step 1: Synthesis of (III-67-1)

A mixture of 4-methylbenzenesulfonyl chloride (286.80 mg, 1.50 mmol), tert-butyl 4-(3-hydroxyprop-1-ynyl)piperidine-1-carboxylate (0.3 g, 1.25 mmol), TEA (380.56 mg, 3.76 mmol, 524.18 µL), DMAP (15.32 mg, 125.36 µmol), and anhydrous DCM (3 mL) was stirred at 25° C. for 5 hours until the reaction was complete. The reaction mixture was diluted with water (30 mL), and extracted with DCM (20 mL×3). The combined organic phases were washed with saturated brine (50 mL), dried over anhydrous $Na_2SO_4$, filtered, and concentrated under reduced pressure to obtain product III-67-1 (0.5 g, crude product) as a white solid, MS (ESI) m/z: 394.3 [M+H]$^+$.

Step 2: Synthesis of (III-67-2)

III-18-1 (0.2 g, 594.76 µmol), III-67-1 (468.07 mg, 1.19 mmol), cesium carbonate (387.57 mg, 1.19 mmol), and anhydrous DMF (4 mL) were reacted at 90° C. for 2 hours. The reaction mixture was diluted with water (30 mL), and extracted with DCM (20 mL×3). The combined organic phases were washed with saturated brine (50 mL), dried over anhydrous $Na_2SO_4$, filtered, and concentrated under reduced pressure. The resulting crude product was purified by preparative thin-layer chromatography to obtain product III-67-2 (0.05 g, yield: 15.08%) as a brown solid, MS (ESI) m/z: 558.2 [M+H]$^+$.

Step 3: Synthesis of (III-67-3)

III-67-2 (0.1 g, 179.35 µmol) was dissolved in anhydrous DCM (2 mL), then the resulting mixture was stirred at 25° C., and TFA (40.90 mg, 358.70 µmol, 27.63 µL) was added dropwise thereto. After the dropwise addition was completed, the mixture was stirred for another 2 hours until the reaction was complete. The reaction mixture was directly concentrated to dryness under reduced pressure to obtain product III-67-3 (0.09 g, TFA salt crude product) as a brown oil, MS (ESI) m/z: 458.5 [M+H]$^+$.

Step 4: Synthesis of (III-67-4)

A mixture of III-67-3 (0.045 g, 98.37 µmol), ethyl 2-bromoacetate (24.64 mg, 147.56 mol, 16.36 µL), DIPEA (25.43 mg, 196.74 µmol, 34.27 µL), and anhydrous DMF (2 mL) was stirred at 25° C. for 3 hours until the reaction was complete. The reaction mixture was directly purified by reverse phase C18 silica gel column chromatography to obtain product III-67-4 (0.015 g, yield: 28.05%) as a white solid, MS (ESI) m/z: 544.5 [M+H]$^+$.

Step 5: Synthesis of (III-67-5)

A mixture of III-67-4 (0.015 g, 27.60 µmol), lithium hydroxide (2.64 mg, 110.39 mol), $H_2O$ (0.5 mL), and anhydrous THF (1.5 mL) was stirred at 25° C. for 1 hour until the reaction was complete. The reaction mixture was added with dilute HCl solution (4 M) to adjust the pH to 5 to 6 under an ice-water bath, and the resulting mixture was concentrated to dryness under reduced pressure to obtain product III-67-5 (0.01 g, crude product) as a white solid, MS (ESI) m/z: 516.3 [M+H]$^+$.

Step 6: Synthesis of (III-67)

A mixture of III-67-5 (0.01 g, 19.40 µmol), int-E (7.96 mg, 19.40 µmol), DIPEA (5.01 mg, 38.80 µmol, 6.76 µL), HATU (8.85 mg, 23.28 µmol), and anhydrous DMF (1 mL) was stirred at 25° C. for 2 hours under nitrogen atmosphere until the reaction was complete. The reaction mixture was diluted with water (10 mL), and extracted with EA (10 mL×3). The combined organic phases were washed with saturated brine (20 mL), dried over anhydrous $Na_2SO_4$, filtered, and concentrated under reduced pressure. The resulting crude product was purified by preparative thin-layer chromatography (DCM:MeOH=20:1) to obtain product III-67 (0.003 g, yield: 16.27%) as a yellow solid, MS (ESI) m/z: 908.5 [M+H]$^+$. $^1$H NMR (500 MHz, CD$_3$OD) δ 9.35 (s, 1H), 9.06 (s, 1H), 8.43 (d, J=8.0 Hz, 1H), 8.25 (t, J=8.0 Hz, 1H), 8.01 (dd, J=7.5, 1.0 Hz, 1H), 7.63-7.51 (m, 1H), 7.33 (s, 1H), 7.29-7.21 (m, 2H), 6.57 (d, J=2.0 Hz, 1H), 4.16 (s, 3H), 3.60-3.51 (m, 4H), 3.42 (s, 2H), 3.31-3.24 (m, 4H), 3.09-3.06 (m, 2H), 2.71-2.53 (m, 6H), 2.42-2.25 (m, 4H), 2.04-1.93 (m, 2H), 1.75-1.67 (m, 4H), 1.63-1.56 (m, 2H), 1.55-1.46 (m, 2H), 1.28 (s, 2H).

Example III-71: Synthesis of (III-71)

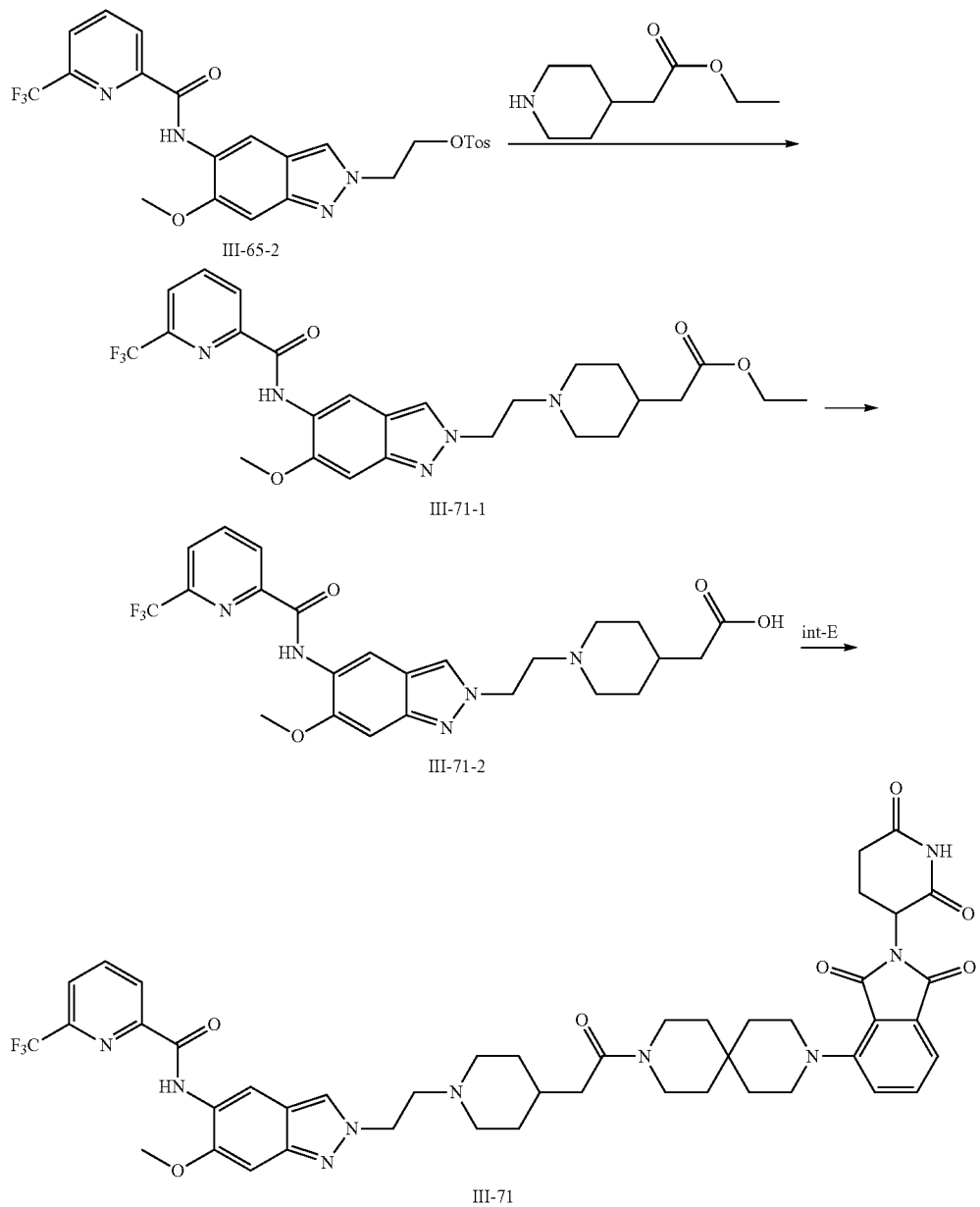

Step 1: Synthesis of (III-71-1)

A mixture of III-65-2 (100 mg, 187.09 μmol), ethyl 2-(4-piperidinyl)acetate (48.05 mg, 280.63 μmol), DIPEA (48.36 mg, 374.18 μmol, 65.17 μL), and anhydrous toluene (10 mL) was stirred at 100° C. for 16 hours under nitrogen atmosphere until the reaction was complete. The reaction mixture was cooled to 25° C., and then concentrated under reduced pressure to remove toluene. The residue was diluted with water (20 mL), and extracted with EA (20 mL×3). The combined organic phases were dried over anhydrous sodium sulfate, filtered, and concentrated to dryness under reduced pressure. The resulting crude product was purified by silica gel column chromatography (DCM:MeOH=20:1) to obtain product III-71-1 (47 mg, yield: 47.09%) as a yellow solid, MS (ESI) m/z: 534.2 [M+H]+.

Step 2: Synthesis of (III-71-2)

A mixture of III-71-1 (47 mg, 88.09 μmol), lithium hydroxide (10.55 mg, 440.45 mol), methanol (2 mL), and H₂O (1 mL) was stirred at 25° C. for 2 hours until the reaction was complete. The reaction mixture was concentrated under reduced pressure to remove methanol, and the residue was purified by reverse phase C18 column chromatography to obtain product III-71-2 (36 mg, yield: 80.85%) as a white solid, MS (ESI) m/z: 506.1 [M+H]+.

Step 3: Synthesis of (III-71)

A mixture of raw material III-71-2 (35 mg, 69.24 μmol), int-E (34.10 mg, 83.09 μmol), DIPEA (17.90 mg, 138.48 μmol, 24.12 μL), HATU (39.49 mg, 103.86 μmol), and DMF (2 mL) was stirred at 25° C. for 2 hours under nitrogen atmosphere until the reaction was complete. The reaction mixture was diluted with water (20 mL), and extracted with EA (20 mL×3). The combined organic phases were washed with saturated brine (20 mL), dried over anhydrous Na$_2$SO$_4$, filtered, and concentrated under reduced pressure. The resulting crude product was purified by preparative thin-layer chromatography to obtain product III-71 (26 mg, yield: 38.87%) as a yellow solid, MS (ESI) m/z: 898.7 [M+H]$^+$. $^1$H NMR (500 MHz, DMSO-d$_6$) δ 11.08 (s, 1H), 10.49 (s, 1H), 8.68 (s, 1H), 8.46 (d, J=8.0 Hz, 1H), 8.40 (t, J=8.0 Hz, 1H), 8.30 (s, 1H), 8.21 (dd, J=7.5, 1.0 Hz, 1H), 7.67 (t, J=8.0 Hz, 1H), 7.34-7.30 (m, 2H), 7.15 (s, 1H), 5.08 (dd, J=12.5, 5.5 Hz, 1H), 4.44 (t, J=6.5 Hz, 2H), 3.98 (s, 3H), 3.48-3.40 (m, 4H), 3.28-3.24 (m, 4H), 2.88-2.84 (m, 2H), 2.80 (t, J=6.5 Hz, 2H), 2.65-2.53 (m, 2H), 2.21 (d, J=6.5 Hz, 2H), 2.04-1.96 (m, 4H), 1.65-1.59 (m, 6H), 1.48-1.34 (m, 5H), 1.17-1.12 (m, 2H).

Referring to example III-71, the following product can finally be synthesized:

| Molecule ID | MS (ESI) m/z: [M + H]$^+$ | $^1$H NMR |
|---|---|---|
| III-72 | 842.6 | (500 MHz, DMSO-d$_6$) δ 11.06 (s, 1H), 10.49 (s, 1H), 8.68 (s, 1H), 8.46 (d, J = 8.0 Hz, 1H), 8.40 (t, J = 8.0 Hz, 1H), 8.31 (s, 1H), 8.21 (dd, J = 8.0, 1.0 Hz, 1H), 7.57 (t, J = 8.0 Hz, 1H), 7.16-7.11 (m, 2H), 6.78 (d, J = 7.5 Hz, 1H), 5.05 (dd, J = 13.0, 5.5 Hz, 1H), 4.44 (t, J = 6.5 Hz, 2H), 4.32 (s, 4H), 4.27 (s, 2H), 4.02 (s, 2H), 3.98 (s, 3H), 2.88-2.84 (m, 2H), 2.80 (t, J = 6.5 Hz, 2H), 2.65-2.52 (m, 2H), 2.02-1.93 (m, 6H), 1.63-1.57 (m, 4H), 1.36-1.32 (m, 1H). |

Application Examples

1. Evaluation of Compound Inhibition on Kinase Activity

Based on the experimental method of fluorescence microfluidic mobility shift assay, the IC$_{50}$ value of the compound for competitive binding of ATP to IRAK4 kinase was determined. The initial detection concentration of the compound was 10 µM, which was 4-fold serially diluted to 0.38 nM and assayed in duplicate. In this case, commercially available staurosporine was the standard control for the assay.

1.1. Information on Reagents and Consumables is as Follows:

| Name | Brand | Cat. No. |
|---|---|---|
| IRAK4 kinase | Carna | 09-145 |
| Substrate peptide FAM-P8 | GL Biochem | 112396 |
| Adenosine 5'-triphosphate disodium salt hydrate | Merck | A7699-1G |
| Dimethyl sulfoxide (DMSO) | Merck | D2650 |
| Ethylene diamine tetraacetic acid (EDTA) | Merck | E5134 |
| Staurosporine | Selleckchem | S1421 |
| 4-(2-Hydroxyethyl)-1-piperazineethanesulfonic acid (HEPES) | Gibco | 15630-080 |
| Polyethylene oxide lauroyl ether (Brij-35 solution) | Merck | 9002-92-0 |
| 1,4-Dithiothreitol (DTT) | Merck | D0632-20G |
| 0.2% Coating Reagent #3 | PerkinElmer | 760050 |
| 96-well plate | Corning | 3365 |
| 384-well plate | Corning | 3573 |

1.2. Experimental Methods

1) IRAK4 kinase was dissolved in kinase buffer (50 mM HEPES pH 7.5, 10 mM MgCl$_2$, 2 mM DDT, and 0.01% Brij-35) at a final concentration of 6 nM.

2) The substrate peptide FAM-P8 and ATP were dissolved in the above kinase buffer, and the final concentrations of the substrate peptide FAM-P8 and ATP for IRAK4 were 3 µM and 10 µM, respectively.

3) Compound dilution: The compound was first diluted to 50 µM, and then 4-fold serially diluted with DMSO. In this case, the solution without compound and kinase served as the blank control, corresponding to the "minimum value" shown below; the solution without compound but containing kinase, adenosine 5'-triphosphate disodium salt hydrate, DMSO, and the buffer served as the positive control, corresponding to the "maximum value" shown below.

4) Kinase reaction and termination: 10 µL of the kinase buffer was added to a 384-well plate containing 5 µL of the compound to be tested, and the mixture was incubated at room temperature for 10 minutes; another 10 µL of buffer containing the substrate peptide and adenosine 5'-triphosphate disodium salt hydrate was added to the 384-well plate, and after incubation at 28° C. for 1 hour, 25 µL of termination solution (100 mM HEPES pH 7.5, 50 mM EDTA, 0.2% Coating Reagent #3, and 0.015% Brij-35) was added to each well to terminate the reaction.

5) Data reading: CaliperEZ Reader II instrument was used to read the conversion rate data. Setting conditions: downstream voltage as −500 V, upstream voltage as −2250 V, base pressure as −0.5 PSI, and screening pressure as −1.2 PSI.

6) Data calculation: the conversion rate data was copied from CaliperEZ Reader II, and the conversion rate was converted into inhibition rate data. The calculation formula is as follows:

Inhibition percentage (%)=(maximum value−conversion rate)/(maximum value−minimum value)*100%

IC$_{50}$ values were fitted with XLFit excel add-in version 5.4.0.8.

Fitting Formula:

$Y = \text{Bottom} + (\text{Top} - \text{Bottom})/(1 + IC_{50}/X)^{\text{HillSlope}}$ The kinase activity data are shown in Tables 1 and 2.

TABLE 1

| Serial No. | IRAK4 IC$_{50}$ (nM) |
|---|---|
| III-1 | + |
| III-2 | +++ |
| III-3 | ++ |
| III-4 | ++ |
| III-5 | +++ |
| III-6 | +++ |
| III-7 | ++ |

TABLE 1-continued

| Serial No. | IRAK4 IC$_{50}$ (nM) |
|---|---|
| III-8 | ++ |
| III-9 | + |
| III-10 | +++ |
| III-11 | +++ |
| III-12 | +++ |
| III-13 | +++ |
| III-14 | +++ |
| III-15 | +++ |
| III-16 | +++ |
| III-17 | +++ |
| III-18 | +++ |
| III-19 | +++ |
| III-20 | +++ |
| III-21 | ++++ |
| III-22 | ++++ |
| III-23 | ++++ |
| III-24 | +++ |
| III-25 | +++ |
| III-26 | ++++ |
| III-27 | +++ |
| III-29 | ++++ |
| III-31 | ++++ |

IRAK4 assay: IC$_{50}$<100 nM: ++++; ≥100 nM, <1 µM: +++; ≥1 µM, <10 µM: ++; ≥10 µM: +

TABLE 2

| Serial No. | IRAK4 IC$_{50}$ (nM) | Serial No. | IRAK4 IC$_{50}$ (nM) | Serial No. | IRAK4 IC$_{50}$ (nM) |
|---|---|---|---|---|---|
| III-1 | + | III-2 | +++ | III-3 | ++ |
| III-4 | ++ | III-5 | +++ | III-10 | +++ |
| III-11 | +++ | III-12 | +++ | III-13 | +++ |
| III-14 | +++ | III-15 | +++ | III-16 | +++ |
| III-17 | +++ | III-18 | +++ | III-19 | ++ |
| III-20 | +++ | III-21 | ++++ | III-22 | ++++ |
| III-23 | ++++ | III-24 | +++ | III-25 | +++ |
| III-26 | ++++ | III-27 | +++ | III-28 | ++++ |
| III-29 | ++++ | III-30 | ++++ | III-31 | ++++ |
| III-32 | +++ | III-33 | +++ | III-35 | ++++ |
| III-36 | ++++ | III-38 | ++++ | III-39 | ++++ |
| III-40 | ++++ | III-41 | ++++ | III-42 | ++++ |
| III-43 | +++ | III-44 | +++ | III-45 | ++++ |
| III-46 | ++++ | III-47 | +++ | III-48 | ++++ |
| III-49 | +++ | III-50 | ++++ | III-51 | ++++ |
| III-52 | +++ | III-53 | ++++ | III-54 | ++++ |
| III-55 | ++++ | III-56 | ++++ | III-57 | ++++ |
| III-58 | +++ | III-59 | +++ | III-60 | ++++ |
| III-61 | ++++ | III-62 | ++++ | III-63 | ++++ |
| III-64 | +++ | III-65 | ++++ | III-66 | ++++ |
| III-67 | ++++ | III-68 | ++++ | III-69 | +++ |
| III-70 | ++++ | III-71 | ++++ | III-72 | ++++ |
| III-73 | +++ | | | | |

IRAK4 assay: IC$_{50}$<100 nM: ++++; ≥100 nM, <1 µM: +++; ≥1 µM, <10 µM: ++; ≥10 µM: +

2. LPS-Stimulated Cytokine Release in THP-1
2.1. Experimental Materials

| Product name | Supplier | Cat. No. |
|---|---|---|
| THP-1 | ATCC | TIB-202 |
| Dulbecco's Phosphate Buffered | Biosera | LM-S2041/500 |
| RPMI 1640 medium | Thermo Fisher | 11875119 |
| Fetal bovine serum (FBS) | Biological | 04-002-1A |
| Penicillin-Streptomycin Solution | Invitrogen | 15140122 |
| β-Mercaptoethanol | Merck | M3148 |
| Dimethyl sulfoxide (DMSO) | Sigma | D2650 |
| Lipopolysaccharide (LPS) | Thermo Fisher | tlrl-pb51ps |
| 96-well cell culture plate | Corning | 3799 |
| Human TNF-α Duoset ELISA Kit | R&D | DY210 |

2.2. Experimental Steps

THP-1 cells were cultured in suspension in RPMI 1640 complete medium (containing 10% serum, 1% penicillin-streptomycin, and 55 µM β-mercaptoethanol). THP-1 cells were collected, centrifuged at 350×g at room temperature to discard the supernatant, and resuspended in RPMI 1640 complete medium to a concentration of 2×10$^6$ cells per mL. THP-1 cells were spread into a 96-well plate at a concentration of 2×10$^5$ cells per well, and different concentrations of the compound to be tested were added thereto. The plate was incubated in a 37° C. cell culture incubator with 5% CO$_2$ for 60 minutes. 50 µL of LPS at a final concentration of 100 ng/mL was added to a 96-well plate, and incubated in a 37° C. cell culture incubator for 5 hours. The cell culture plate was then taken out from the incubator, and centrifuged at 350×g at low temperature for 5 minutes to collect 150 µL of the supernatant. Referring to the instructions in the Human TNF-α Duoset ELISA Kit, the level of TNF-α in the cell culture supernatant was detected.

Data on the inhibitory activity of cytokines (TNFα) against LPS-stimulated inflammatory responses in THP-1 cells are shown in Tables 3 and 4.

TABLE 3

| Serial No. | Inhibition IC$_{50}$ (nM) of cytokines (TNFα) against LPS-stimulated inflammatory responses in THP-1 cells |
|---|---|
| III-2 | + |
| III-7 | ++ |
| III-9 | ++ |
| III-10 | ++ |
| III-16 | ++ |
| III-17 | ++ |
| III-18 | ++ |
| III-19 | + |
| III-20 | ++ |
| III-22 | ++ |
| III-23 | ++ |
| III-24 | +++ |
| III-25 | ++ |
| III-26 | ++ |
| III-27 | +++ |

LPS/TNFα assay: IC$_{50}$<100 nM: ++++; ≥100 nM, <1 µM+++; ≥1 µM, <10 µM: ++; ≥10 µM: +

TABLE 4

| Serial No. | Inhibition IC$_{50}$ (nM) of cytokines (TNFα) against LPS-stimulated inflammatory responses in THP-1 cells | Serial No. | Inhibition IC$_{50}$ (nM) of cytokines (TNFα) against LPS-stimulated inflammatory responses in THP-1 cells | Serial No. | Inhibition IC$_{50}$ (nM) of cytokines (TNFα) against LPS-stimulated inflammatory responses in THP-1 cells |
|---|---|---|---|---|---|
| III-2 | + | III-5 | ++ | III-10 | ++ |
| III-11 | ++ | III-16 | ++ | III-17 | ++ |
| III-18 | ++ | III-19 | + | III-20 | ++ |
| III-21 | ++ | III-22 | ++ | III-23 | ++ |
| III-24 | +++ | III-25 | ++ | III-26 | ++ |
| III-27 | +++ | III-29 | ++ | III-30 | ++ |
| III-31 | ++ | III-35 | +++ | III-36 | ++ |

LPS/TNFα assay: IC$_{50}$<100 nM: ++++; ≥100 nM, <1 μM: +++; ≥1 μM, <10 μM: ++; ≥10 M: +

3. Detection of IRAK4 Protein Degradation in THP-1 Induced by PROTAC 3.1. Based on the experimental method of immunoblot, i.e., Western Blot, THP-1 cell samples processed by gel electrophoresis were stained with specific antibodies, and the degradation activity of the compounds on the IRAK4 protein in THP-1 cells was determined by analyzing the position of the staining and the depth of the staining. The detection concentrations of the compounds were 0 μM, 0.3 μM, 1 μM, and 3 μM, and the compounds were used to treat the cells for 8 hours, 16 hours, 24 hours, and 48 hours. In this case, glyceraldehyde-3-phosphate dehydrogenase (GAPDH) was the internal reference protein for the assay.

3.2. Information on Cells, Reagents, and Consumables is as Follows:

| Name | Brand | Cat. No. |
|---|---|---|
| THP-1 cells | ATCC | TIB-202 |
| RPMI 1640 medium | Gibco | 22400-089 |
| Fetal bovine serum (FBS) | ExCell Bio | FSP500 |
| Penicillin-Streptomycin Solution (P/S) | HyClone | SV30010 |
| Pierce ™ BCA Protein Assay Kit | Thermo Fisher | 23227 |
| RIPA lysis buffer | Merck | R0278 |
| Protease inhibitor (Complete Tablets EDTA-free, EASYpack) | Roche | 4693132001 |
| Phosphatase Inhibitor Cocktail 2 | Merck | P5726 |
| Phosphatase Inhibitor Cocktail 3 | Merck | P0044-5ML |
| Dimethyl sulfoxide (DMSO) | Merck | D2650 |
| NuPAGE ™ MOPS SDS Running Buffer (20×) | Invitrogen | NP0001 |
| Pierce ™ 20X TBS Tween ™ 20 Buffer | Thermo Fisher | 28360 |
| NuPAGE ™ 4 to 12% Bis-Tris, 1.5 mm, mini protein gel, 15-well | Invitrogen | NP0336BOX |
| 1,4-Dithiothreitol (DTT) | Invitrogen | P2325 |
| Bovine serum albumin (BSA) | Merck | B2064-100G |
| Difco ™ non-fat milk | BD Biosciences | 232100 |
| IBlot ™ 2 Transfer Stack, nitrocellulose, regular size | Invitrogen | IB23001 |
| NuPAGE ® LDS Sample Buffer (4×) | Invitrogen | NP0007 |
| PageRuler Prestained Protein Ladder | Thermo Fisher | 26616 |
| SuperSignal ™ West Femto Maximum Sensitivity Substrate | Thermo Fisher | 34095 |
| Anti-IRAK4 antibody | Abcam | ab5985 |
| Anti-Glyceraldehyde-3-Phosphate Dehydrogenase Antibody, clone 6C5, GAPDH | Merck | MAB374 |
| Goat Anti-Rabbit IgG H&L (HRP) | Abcam | ab205718 |
| Goat Anti-Mouse IgG H&L (HRP) | Abcam | ab205719 |

3.3. Equipment

| Equipment name | Brand | Model |
|---|---|---|
| Cell counter | Count start | IC1000 |
| Multi-Mode Microplate Reader | Molecular Device | Molecular Device Flexstation III |
| Life technologies iBlot2 Gel Transfer Device | IB 21001 | 31252173 |
| Image Quant LAS 4000 | 399699 | Image Quant LAS 4010 |

3.4. Reagent Preparation Method

Running buffer: 50 mL of MOPS SDS Running Buffer (20×) and 50 mL of 20×TBS Tween-20 buffer were diluted to 1 L with deionized water as running buffer;

5% non-fat milk (w/v): 5% non-fat milk was prepared by diluting 2.5 g of non-fat milk with 50 mL of 1×TBS Tween-20 buffer;

5% BSA (w/v): 5% BSA was prepared by diluting 2.5 g of BSA with 50 mL of 1×TBS Tween-20 buffer;

Anti-IRAK4 antibody was diluted at 1:1000 with 5% BSA to make primary antibody working solution;

Goat Anti-Rabbit IgG H&L (RP) was diluted at 1:2000 with 5% BSA to make secondary antibody working solution;

Goat Anti-Mouse IgG H&L (RP) was diluted at 1:2000 with 5% BSA to make secondary antibody working solution.

THP-1 cells were spread into a 6-well plate at a density of 1.5×10$^6$ cells per mL, and incubated in a 37° C. cell culture incubator with 5% CO$_2$ for 2 hours. The compound was diluted with DMSO to 0.6 mM, 0.2 mM, and 0.06 mM, respectively. 10 μL of compound solution was added to the corresponding wells, and the plate was incubated in the incubator for 16 hours, 24 hours, and 48 hours, respectively. The drug-treated THP-1 cells were collected from the wells, added with 120 μL of RIPA lysis buffer containing protease inhibitor, phosphatase inhibitor cocktail 2, and phosphatase inhibitor cocktail 3, and lysed on wet ice for 30 minutes. The cell lysate was then centrifuged at low temperature and high speed for 5 minutes, and the supernatant was collected. Referring to the instructions in the Pierce™ BCA Protein Assay Kit, the cell samples were tested for protein concentration.

The samples were adjusted to the same concentration using lysis buffer and NuPAGE® LDS sample buffer containing 1 M DTT. The samples were heated at 95° C. for 5 minutes and centrifuged at low temperature and high speed. 20 µL of prepared protein sample and 4 µL of PageRuler Prestained Protein Ladder were added to the gel wells. The mixture was electrophoresed at a voltage of 80 V for 0.5 hours, and then electrophoresed for another 1.5 hours after the voltage was adjusted to 120 V. The gel was removed and proteins in the gel were transferred to IBlot™ 2 Transfer Stack at a voltage of 20V. After successful membrane transfer, the bands were cut out at 65 kDa to 40 kDa and 40 kDa to 30 kDa, respectively. The membrane was blocked with 5% non-fat milk at room temperature for 1 hour. The membrane was washed three times with 1×TBST, and incubated with IRAK4 antibody working solution at 4° C. overnight. The IRAK4 antibody working solution was discarded, and the membrane was washed three times with 1×TBST. After the corresponding membrane was incubated with Goat Anti-Rabbit IgG H&L (HRP) working solution and Goat Anti-Mouse IgG H&L (HRP) working solution at room temperature for 1 hour, the antibody working solutions were discarded, and the membrane was washed three times with 1×TBST. Referring to the instructions in the SuperSignal™ West Femto Maximum Sensitivity Substrate Kit, the reagents in the kit were mixed in equal volume proportions to prepare a luminescent mixture, and the membrane was incubated for 1 minute and removed for exposure.

The Western Blot results 24 hours after administration at a drug concentration of 1 µM are shown in Table 5 or 6:

TABLE 5

| Serial No. | Western Blot results 24 hours after administration at a drug concentration of 1 µM |
|---|---|
| III-16 | <50% |
| III-17 | <25% |
| III-23 | <25% |
| III-27 | <25% |

WB assay: The results 24 hours after administration at 1 µM were divided into estimated <25%, <50%, <75%, and <100%.

TABLE 6

| Serial No. | Western Blot results 24 hours after administration at a drug concentration of 1 µM | Serial No. | Western Blot results 24 hours after administration at a drug concentration of 1 µM | Serial No. | Western Blot results 24 hours after administration at a drug concentration of 1 µM |
|---|---|---|---|---|---|
| III-5 | <25% | III-16 | 25 to 50% | III-17 | <25% |
| III-20 | 25 to 50% | III-21 | 50 to 75% | III-22 | 50 to 75% |
| III-23 | <25% | III-25 | 50 to 75% | III-26 | 50 to 75% |
| III-27 | <25% | III-28 | <25% | III-29 | 75 to 100% |
| III-30 | 25 to 50% | III-31 | 75 to 100% | III-35 | 25 to 50% |
| III-36 | 50 to 75% | III-38 | 50 to 75% | III-39 | <25% |
| III-40 | 50 to 75% | III-41 | <25% | III-42 | <25% |
| III-43 | 25 to 50% | III-45 | 50 to 75% | III-46 | 75 to 100% |
| III-47 | 75 to 100% | III-48 | 75 to 100% | III-49 | <25% |
| III-50 | 25 to 50% | III-51 | 50 to 75% | III-53 | 25 to 50% |
| III-54 | <25% | III-55 | 25 to 50% | III-56 | <25% |

TABLE 6-continued

| Serial No. | Western Blot results 24 hours after administration at a drug concentration of 1 µM | Serial No. | Western Blot results 24 hours after administration at a drug concentration of 1 µM | Serial No. | Western Blot results 24 hours after administration at a drug concentration of 1 µM |
|---|---|---|---|---|---|
| III-57 | 75 to 100% | III-60 | 50 to 75% | III-61 | 50 to 75% |
| III-62 | 50 to 75% | III-63 | <25% | III-65 | <25% |
| III-66 | 50 to 75% | III-67 | 50 to 75% | III-68 | 50 to 75% |
| III-69 | <25% | III-72 | 50 to 75% | III-70 | 75 to 100% |
| III-73 | 25 to 50% | | | | |

What is claimed is:

1. A five-membered-fused six-membered compound or a pharmaceutically acceptable salt thereof, wherein, the five-membered-fused six-membered compound is any one of the following compounds:

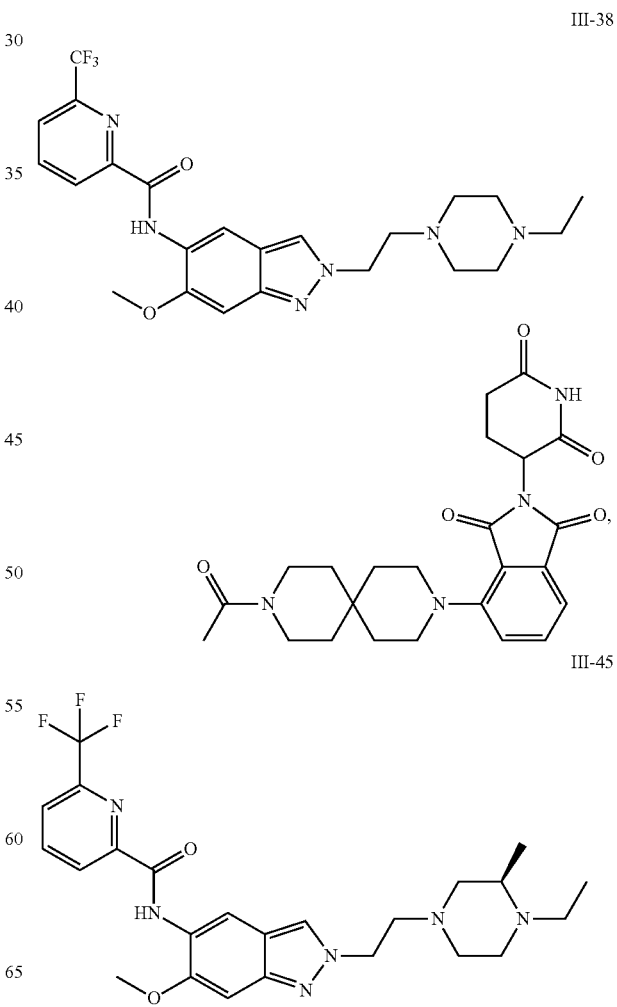

185
-continued
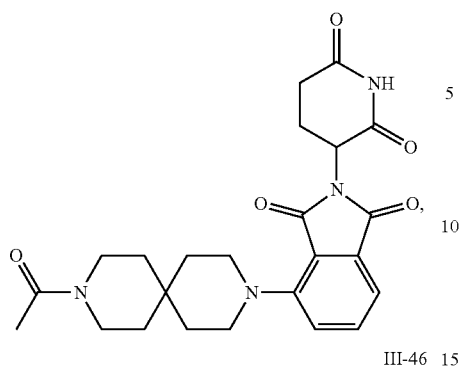
III-46
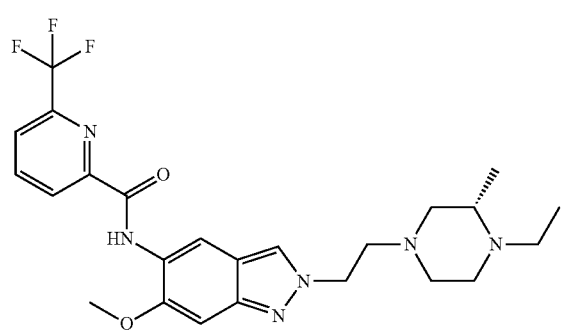
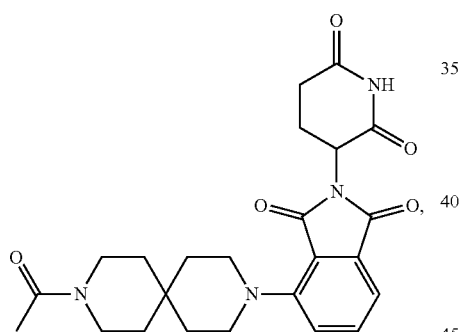
III-50
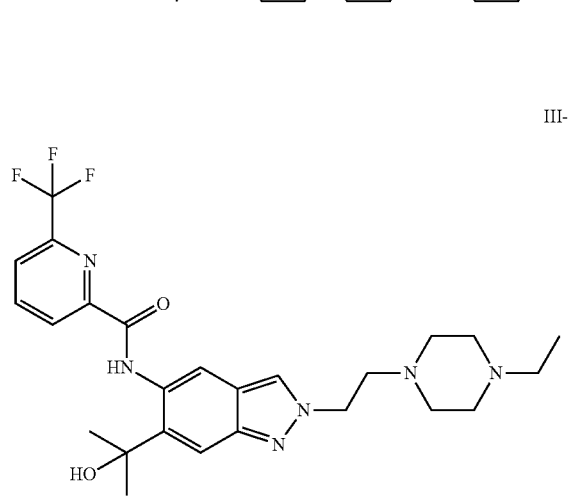
186
-continued
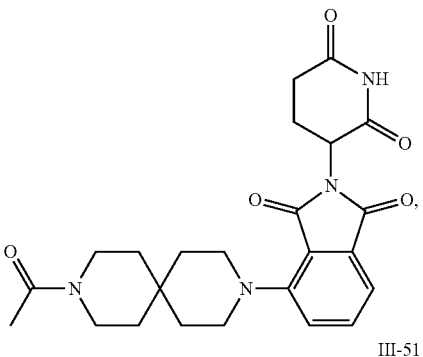
III-51
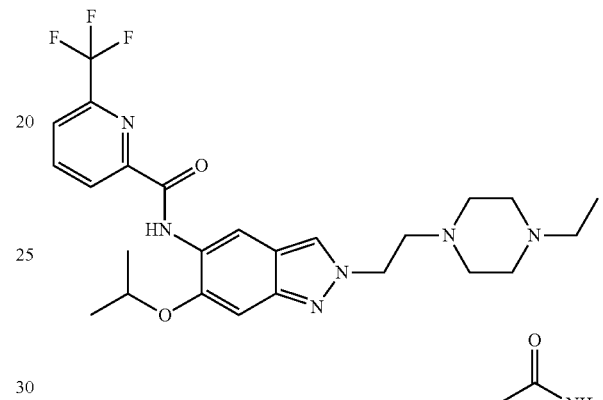
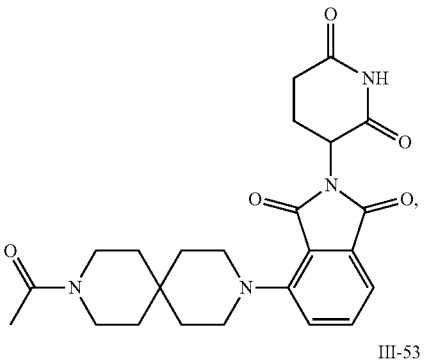
III-53
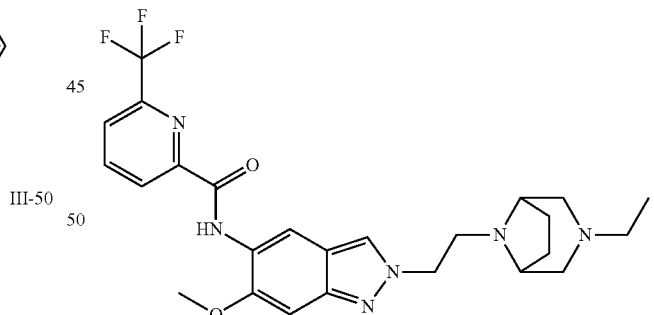
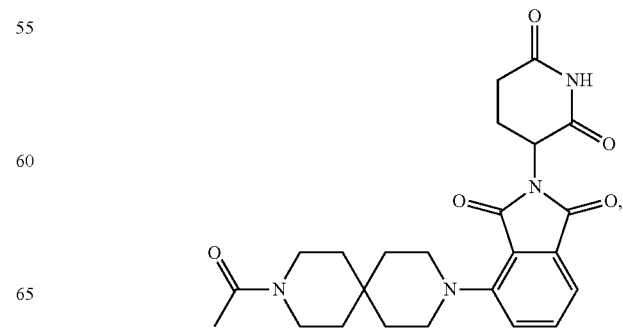

III-54
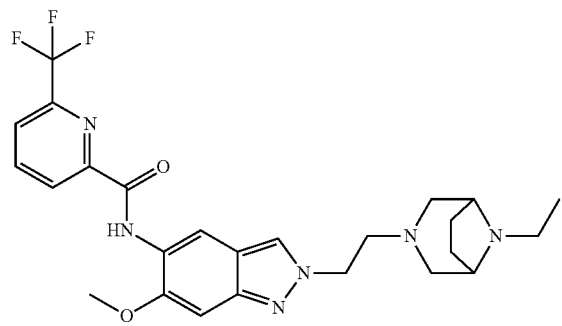
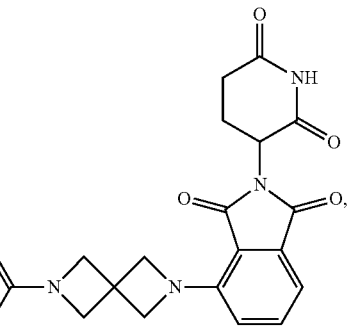
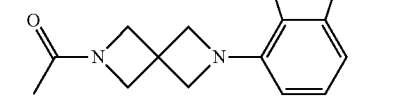
III-55
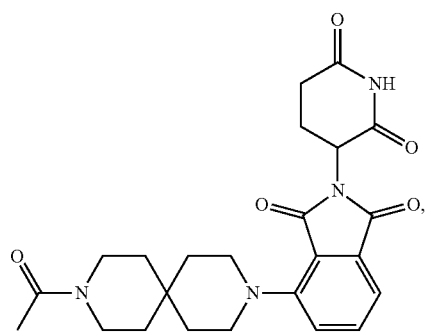
III-61
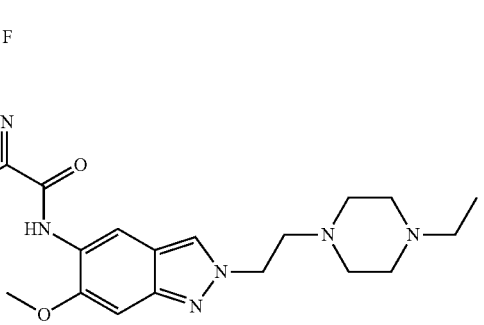
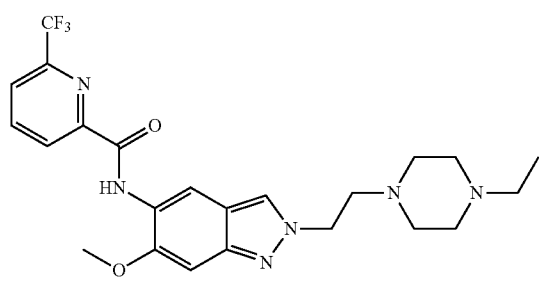
III-60
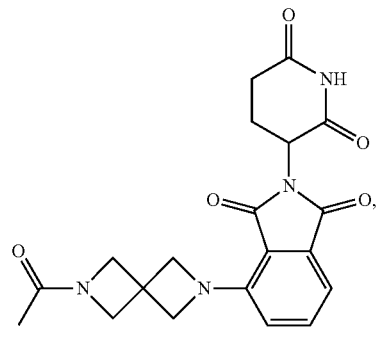
III-62
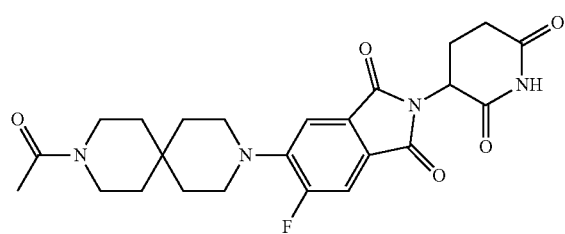
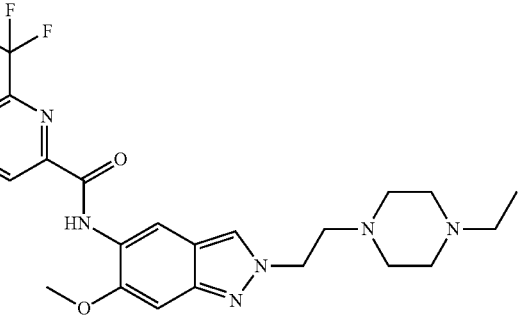
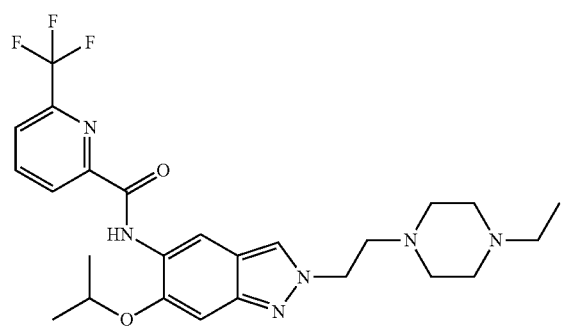
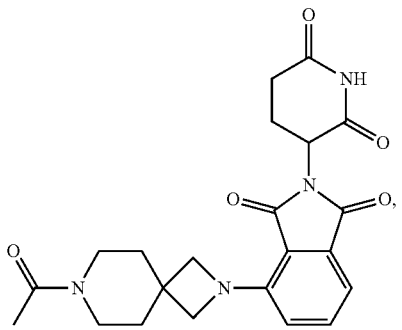

III-63
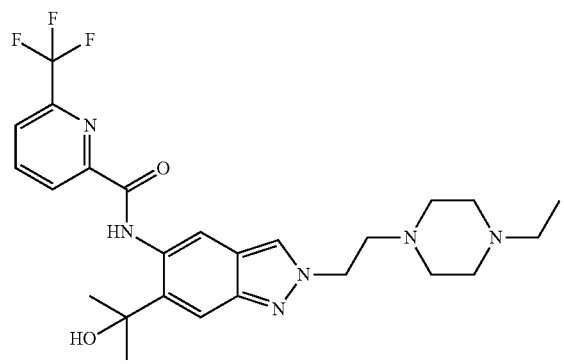
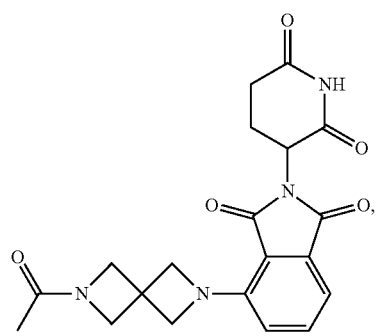
III-66
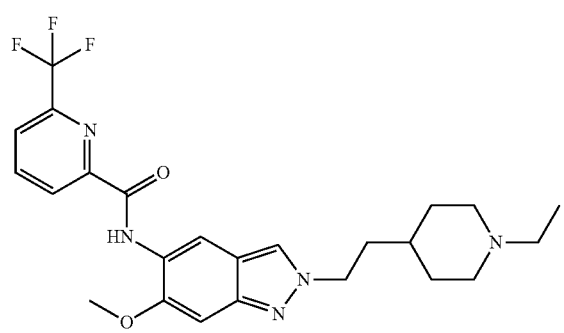
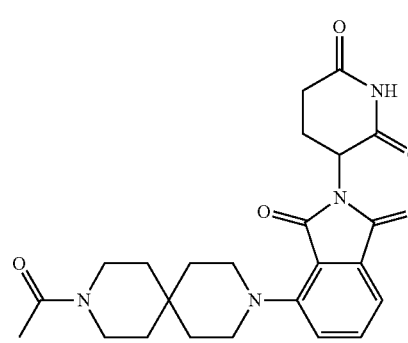
III-71
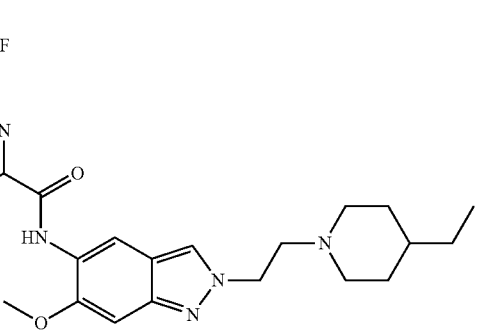
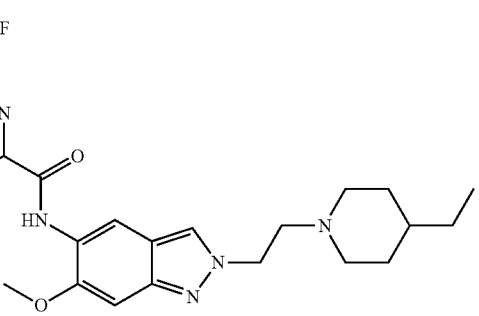
III-72
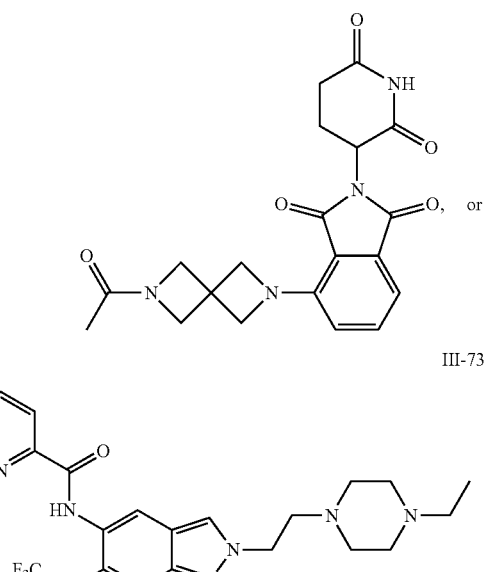
III-73

-continued

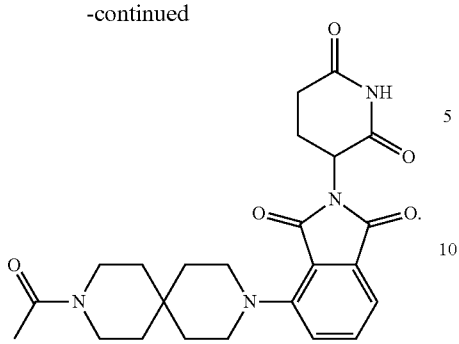

2. A pharmaceutical composition comprising a substance Z and a pharmaceutical excipient, wherein the substance Z is the five-membered-fused six-membered compound or the pharmaceutically acceptable salt thereof according to claim 1.

3. The five-membered-fused six-membered compound or the pharmaceutically acceptable salt thereof according to claim 1, wherein, the five-membered-fused six-membered compound is

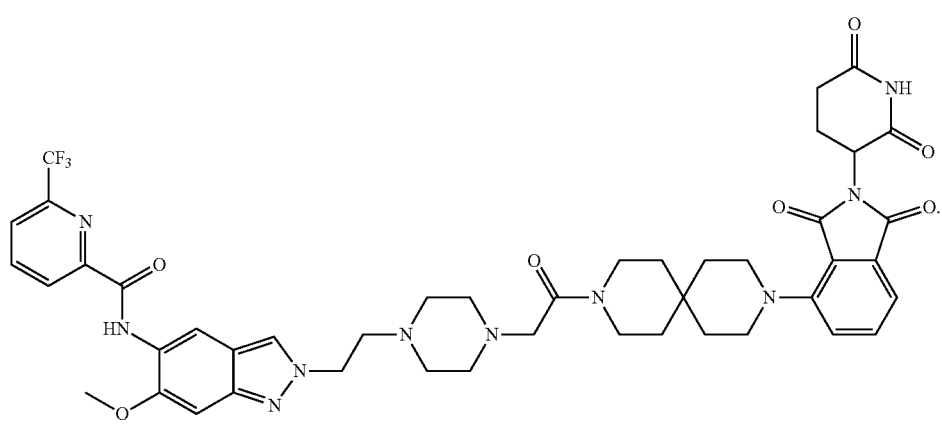

III-38

* * * * *